United States Patent
Hocutt et al.

(10) Patent No.: US 10,851,083 B2
(45) Date of Patent: *Dec. 1, 2020

(54) BENZOIMIDAZOLES AS PROLYL HYDROXYLASE INHIBITORS

(71) Applicant: Janssen Pharmaceutica NV, Beerse (BE)

(72) Inventors: Frances Meredith Hocutt, Seattle, WA (US); Barry Eastman Leonard, Jr., La Jolla, CA (US); Hillary M. Peltier, Evanston, CA (US); Victor K. Phuong, Los Angeles, CA (US); Michael H. Rabinowitz, San Diego, CA (US); Mark D. Rosen, San Diego, CA (US); Kyle T. Tarantino, Princeton, NJ (US); Hariharan Venkatesan, San Diego, CA (US); Lucy Xiumin Zhao, San Diego, CA (US)

(73) Assignee: Janssen Pharmaceutica NV (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/295,476

(22) Filed: Mar. 7, 2019

(65) Prior Publication Data

US 2019/0367486 A1    Dec. 5, 2019

Related U.S. Application Data

(63) Continuation of application No. 16/135,975, filed on Sep. 19, 2018, now abandoned, which is a continuation of application No. 15/695,958, filed on Sep. 5, 2017, now abandoned, which is a continuation of application No. 14/968,763, filed on Dec. 14, 2015, now abandoned, which is a continuation of application No. 14/732,332, filed on Jun. 5, 2015, now abandoned, which is a continuation of application No. 14/282,901, filed on May 20, 2014, now Pat. No. 9,073,923, which is a continuation of application No. 12/990,104, filed as application No. PCT/US2009/041902 on Apr. 28, 2009, now Pat. No. 8,759,345.

(60) Provisional application No. 61/048,531, filed on Apr. 28, 2008.

(51) Int. Cl.
| | |
|---|---|
| C07D 403/04 | (2006.01) |
| C07D 487/04 | (2006.01) |
| C07D 403/14 | (2006.01) |
| C07D 471/04 | (2006.01) |
| C07D 473/40 | (2006.01) |
| C07D 513/04 | (2006.01) |
| C07D 235/24 | (2006.01) |

(52) U.S. Cl.
CPC ......... *C07D 403/04* (2013.01); *C07D 235/24* (2013.01); *C07D 403/14* (2013.01); *C07D 471/04* (2013.01); *C07D 473/40* (2013.01); *C07D 487/04* (2013.01); *C07D 513/04* (2013.01)

(58) Field of Classification Search
CPC .......................... C07D 403/14; C07D 471/04
See application file for complete search history.

(56) References Cited

U.S. PATENT DOCUMENTS

| | | | |
|---|---|---|---|
| 6,093,730 A | 7/2000 | Weidmann et al. | |
| 6,974,813 B2 | 12/2005 | Hamanaka et al. | |
| 7,855,202 B2 | 12/2010 | Vidal Juan et al. | |
| 8,759,345 B2 * | 6/2014 | Hocutt ................ | C07D 403/04 514/234.5 |
| 8,865,713 B2 | 10/2014 | Hocutt et al. | |
| 2006/0199836 A1 | 9/2006 | Turtle et al. | |
| 2006/0276477 A1 | 12/2006 | Klaus et al. | |
| 2007/0299086 A1 | 12/2007 | Kawamoto et al. | |
| 2008/0171756 A1 | 7/2008 | Shaw et al. | |
| 2009/0239876 A1 | 9/2009 | Clements et al. | |
| 2014/0329873 A1 | 11/2014 | Sepassi et al. | |

FOREIGN PATENT DOCUMENTS

| | | |
|---|---|---|
| CN | 1289326 A | 3/2001 |
| DE | 3824658 A1 | 7/1988 |
| DE | 19746287 A1 | 4/1999 |
| DE | 10 2007 048447 A1 | 4/2009 |
| DE | 10 2007 049157 A1 | 4/2009 |

(Continued)

OTHER PUBLICATIONS

Vidal, et al. Document No. 146:401972, Apr. 12, 2007; retrieved from STN.*

(Continued)

Primary Examiner — Shawquia Jackson
(74) Attorney, Agent, or Firm — Mueting Raasch Group

(57) ABSTRACT

The present invention is directed to benzoimidazole compounds of the formula:

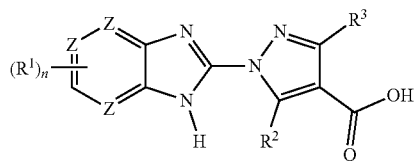

and enantiomers, diastereomers, racemates, and pharmaceutically acceptable salts thereof. Compounds of the present invention are useful in pharmaceutical compositions and methods for the treatment of disease states, disorders, and conditions modulated by prolyl hydroxylase activity.

4 Claims, No Drawings

(56) References Cited

FOREIGN PATENT DOCUMENTS

| | | | |
|---|---|---|---|
| EP | 0 266 940 A2 | 5/1988 | |
| JP | 2002 504546 A | 2/2002 | |
| JP | 2009 510152 A | 3/2009 | |
| JP | B60227260 | 10/2016 | |
| RU | 99113460/04 | 11/1997 | |
| WO | WO 92 22313 A1 | 12/1992 | |
| WO | WO 96 39384 A1 | 12/1996 | |
| WO | WO 98/23619 A1 | 6/1998 | |
| WO | WO 98 39343 A1 | 9/1998 | |
| WO | WO 99 43663 A1 | 9/1999 | |
| WO | WO-9943663 A1 * | 9/1999 | ........... A61K 31/428 |
| WO | WO 2004 052284 A2 | 6/2004 | |
| WO | WO 2004 052285 A2 | 6/2004 | |
| WO | WO 2004 108681 A1 | 12/2004 | |
| WO | WO 2005 012296 A1 | 2/2005 | |
| WO | WO 2005 012297 A1 | 2/2005 | |
| WO | WO 2005 063738 A1 | 7/2005 | |
| WO | WO 2006/114213 A1 | 11/2006 | |
| WO | WO 2007 038571 A2 | 4/2007 | |
| WO | WO 2007 039297 A1 | 4/2007 | |
| WO | WO 2007 070359 A2 | 6/2007 | |
| WO | WO 2007 090068 A2 | 8/2007 | |
| WO | WO 2007 103905 A2 | 9/2007 | |
| WO | WO 2007 136990 A2 | 11/2007 | |
| WO | WO 2007 150011 A2 | 12/2007 | |
| WO | WO 2008 067871 A1 | 6/2008 | |
| WO | WO 2008 082487 A2 | 7/2008 | |
| WO | WO 2008 089052 A2 | 7/2008 | |
| WO | WO 2008 033739 A2 | 9/2008 | |
| WO | WO 2008 130527 A1 | 10/2008 | |
| WO | WO 2008 130600 A2 | 10/2008 | |
| WO | WO 2008 137060 A1 | 11/2008 | |
| WO | WO 2008 137084 A2 | 11/2008 | |
| WO | WO 2009 073669 A1 | 6/2009 | |
| WO | WO 2009 086044 A1 | 7/2009 | |
| WO | WO 2009 086592 A1 | 7/2009 | |
| WO | WO 2009 089547 A1 | 7/2009 | |
| WO | WO 2009 108496 A1 | 9/2009 | |
| WO | WO 2009 108497 A1 | 9/2009 | |
| WO | WO 2009 108499 A1 | 9/2009 | |
| WO | WO 2009117269 A1 | 9/2009 | |
| WO | WO 2009/134750 A1 | 11/2009 | |

OTHER PUBLICATIONS

Abbott et al., "Stromal Cell-Derived Factor-1 [alpha] Plays a Critical Role in Stem Cell Recruitment to the Heart After Myocardial Infarction but Is Not Sufficient to Induce Homing in the Absence of Injury" 2004, *Circulation*, 110(21), pp. 3300-3305.
Al-Sheikh et al., "Disturbance in the HIF-1 alpha pathway associated with erythrocytosis: Further evidences brought by frameshift and nonsense mutations in the prolyl hydroxylase domain protein 2 (PHD2) gene" 2008, *Blood Cells Mol Dis.*, 40, pp. 160-165.
Aragones et al., "Deficiency or inhibition of oxygen sensor Phd1 induces hypoxia tolerance by reprogramming basal metabolism" 2008, *Nature Genetics*, 40(2), pp. 170-180.
Arcasoy, "The non-haematopoietic biological effects of erythropoietin", *British Journal of Haematology, 2008*, 141 (1), pp. 14-31.
Armellini et al."The effects of high altitude trekking on body composition and resting metabolic rate", *Hormone & Metabolic Research*, 1997, 29(9), pp. 458-461.
Bagshawe et al. "Antibody-Directed Enzyme Prodrug Therapy: A Review" *Drug Dev Res*, 1995, 34, pp. 220-230.
Berge, et al., "Pharmaceutical Salts", *J Pharm Sci.*, 1977, 66, pp. 1-19.
Bernaudin et al., "Normobaric hypoxia induces tolerance to focal permanent cerebral ischemia in association with an increased expression of hypoxia-inducible factor-1 and its target genes, erythropoietin and VEGF, in the adult mouse brain" 2002, *J Cereb Blood Flow Metab.*, 22(4), pp. 393-403.

Bernhardt et al., "Organ protection by hypoxia and hypoxia-inducible factors" 2007, *Methods Enzymol.*, 435, pp. 221-245.
Berra et al., "HIF prolyl-hydroxylase 2 is the key oxygen sensor setting low steady-state levels of HIF-1alpha in normoxia" 2003, *EMBO (European Molecular Biology Organization) Journal*, 22(16), pp. 4082-4090.
Bertolini et al. "A New Rational Hypothesis for the Pharmacophore of the Active Metabolite of Leflunomide, A Potent Immunosuppressive Drug" *J. Med. Chem.*, 1997, 40, pp. 2011-2016.
Bodor et al.,"Novel Approaches to the Design of Safer Drugs: Soft Drugs and Site-Specific Chemical Delivery Systems" *Adv Drug Res.* 1984, 13, 224-331.
Braliou et al., "2-Oxoglutarate-dependent oxygenases control hepcidin gene expression" 2008, *Journal of Hepatology*, 48 (5), pp. 801-810.
Breen, "VEGF in biological control" 2007, *J Cell Biochem.*, 102(6), pp. 1358-1367.
Bundgaard, Design of Prodrugs (Elsevier Press, 1985).
Cai et al., "Complete loss of ischaemic preconditioning-induced cardioprotection in mice with partial deficiency of HIF-1 alpha" 2008, *Cardiovasc Res.*, 77(3), pp. 463-470.
Carmeliet,"Manipulating angiogenesis in medicine" 2004, *J Intern Med.*, 255(5), pp. 538-561.
Carrière et al. "Mitochondrial Reactive Oxygen Species Control the Transcription Factor CHOP-10/GADD153 and Adipocyte Differentiation: A Mechanism for Hypdxia-Dependent Effect" 2004, *J Biol Chem.*, 279(39), pp. 40462-40469.
Chang et al "Age Decreases Endothelial Progenitor Cell Recruitment Through Decreases in Hypoxia-Inducible Factor 1 α Stabilization During Ischemia" Circulation 2007 vol. 116 pp. 2818-2829.
Ceradini et al., "Homing to hypoxia: HIF-1 as a mediator of progenitor cell recruitment to injured tissue" 2005, *Trends Cardiovasc Med.*, 15(2), pp. 57-63.
Ceradini et al., "Progenitor cell trafficking is regulated by hypoxic gradients through HIF-1 induction of SDF-1" 2004, *Nat Med.*, 10(8), pp. 858-864.
Chin et al. "Hypoxia-inducible factor 1alpha stabilization by carbon monoxide results in cytoprotective preconditioning" 2007, *Proc Natl Acad Sci. U.S.A.*, 104(12), pp. 5109-5114.
Collins-Cafiero "O-Nitroaniline Derivatives. Part 14. 1,2 Cyclisations Leading To Benzimidazole N-Oxides, N-Hydroxybenzimidazolones And N-Hydroxyquinoxaline-2,3-Diones: A Mechanistic Bordeline" Journal Of The Chemical Society Perkin Transactions—1 Organic And Bio Organic Chemistry 1997 vol. 9 pp. 1375-1384.
Crohns Disease Prevention, 2017, <http://www.webmd.com/ibd-crohns-disease/crohns-disease/tc/crohns-disease-prevention>.
Crohns Disease Cure, 2017, <http://www.healthline.com/health/crohns-disease/cure>.
Cummins et al, Laboratory Investigation, 2013, 93:378-83.
Darling et al., "'Postconditioning' the human heart: Multiple balloon inflations during primary angioplasty may confer cardioprotection." 2007, *Basic Res Cardiol.*, 2007, 102(3), pp. 274-278.
Das et al., "Molecular mechanism of preconditioning", *IUBMB Life*, 2008, 60(4), pp. 199-203.
Ebert et al. "Hypoxia and Mitochondrial Inhibitors Regulate Expression of Glucose Transporter-1 via Distinct Cis-acting Sequences" 1995, *J Biol Chem.*, 270(49), pp. 29083-29089.
Elson et al., "Induction of hypervascularity without leakage or inflammation in transgenic mice overexpressing hypoxia-inducible factor-1alpha" 2001, *Genes Dev.*, 15(19), pp. 2520-2532.
Epstein et al., "C. elegans EGL-9 and mammalian homologs define a family of dioxygenases that regulate HIF by prolyl hydroxylation" 2001, *Cell*, 107(1), pp. 43-54.
Feldser et al., "Reciprocal positive regulation of hypoxia-inducible factor 1alpha and insulin-like growth factor 2", *Cancer Res.* 1999 59 (16), pp. 3915-3918.
Firth et al. "Oxygen-regulated control elements in the phosphoglycerate kinase 1 and lactate dehydrogenase A genes: Similarities with the erythropoietin 3' enhancer" 1994, *Proc Natl Acad Sci. USA*, 91(14), pp. 6496-6500.
Fleisher et al. "Improved Oral Delivery: Solubility Limitations Overcome by the Use of Prodrugs" Advanced Drug Delivery Review, 1996, 19, pp. 115-130.

(56) References Cited

OTHER PUBLICATIONS

Floyd et al., "Effects of prolyl hydroxylase inhibitors on adipogenesis and hypoxia inducible factor 1 alpha levels under normoxic conditions" 2007, *J Cell Biochem.*, 101(6), pp. 1545-1557.
Fukuda et al., "HIF-1 regulates cytochrome oxidase subunits to optimize efficiency of respiration in hypoxic cells" 2007, *Cell*,129(1), pp. 111-122.
Greenwald et al. "Drug delivery systems. 2. Camptothecin 20-O-poly(ethylene glycol) ester transport forms" Journal of Medicinal Chemistry, 1996, 39(10), pp. 1938-1940.
Grosfeld et al."Hypoxia-inducible Factor 1 Transactivates the Human Leptin Gene Promoter" 2002, *J Biol Chem.*, 277(45), pp. 42953-42957.
Gustafsson et al., "Exercise-induced angiogenesis-related growth and transcription factors in skeletal muscle, and their modification in muscle pathology." *Frontiers in Bioscience*, 2001, 6, pp. D75-89.
Hirota et al "Targeting Hypoxia-Inducible Factor-1 (HIF-1) Signaling In Therapeutics: Implications For The Treatment Of Inflammatory Bowel Disease" Recent Patents On Inflammation And Allergy Drug Discovery 2009 vol. 3 pp. 1-16.
Hu et al., "Transplantation of hypoxia-preconditioned mesenchymal stem cells improves infarcted heart function via enhanced survival of implanted cells and angiogenesis", *Journal of Thoracic & Cardiovascular Surgery*, 2008 135(4), pp. 799-808.
Ivan et al. "Biochemical purification and pharmacological inhibition of a mammalian prolyl hydroxylase acting on hypoxia-inducible factor" *Proc Natl Acad Sci. USA*, 2002, 99(21), pp. 13459-13464.
Ivan et al., "HIF[alpha] Targeted for VHL-Mediated Destruction by Proline Hydroxylation: Implications for O2 Sensing" 2001, *Science*, 292(5516), pp. 464-468.
Jaakkola et al., "Targeting of HIF-[alpha] to the von Hippel-Lindau Ubiquitylation Complex by O2-Regulated Prolyl Hydroxylation" *Science*, 2001, 292(5516), pp. 468-472.
Kaelin, "Proline hydroxylation and gene expression" *Annu Rev Biochem.*, 2005, 74, pp. 115-128.
Kandeel et al., "Synthesis and Chemical Reactivity of Benzimidazol-2-YL Hydrazonyl Chlorides" *Polish Journal of Chemistry* (1983), 57(1-3), 327-31.
Ke et al., "Hypoxia-inducible factor-1 (HIF-1)", *Mol Pharmacol.* 2006, 70(5), pp. 1469-1480.
Kelly et al., "Cell type-specific regulation of angiogenic growth factor gene expression and induction of angiogenesis in nonischemic tissue by a constitutively active form of hypoxia-inducible factor 1", *Circ Res.*, 93(11), 2003, pp. 1074-1081.
Kim et al., "HIF-1-mediated expression of pyruvate dehydrogenase kinase: A metabolic switch required for cellular adaptation to hypoxia, *Cell Metab.*," 2006 3(3), pp. 177-185.
Kojima I et al.,"Protective role of hypoxia-inducible factor-2 alpha against ischemic damage and oxidative stress in the kidney" *J Am Soc Nephrol.*, 2007, 18 (4), pp. 1218-1226.
Larsen et al Design and Application of Prodrugs Design and Development Krogsgaard-Larsen et al eds Harwood Academic Publishers 1981.
LeCount et al., "Cyclisation of Heterocyclic Hydrazones Prepared from Dimethyl Acetyl-enedicarboxylate" *Journal of the Chemical Society, Perkin Transactions 1: Organic and Bio-Organic Chemistry* (1972-1999) (1974), (2), pp. 297-301.
Lee et al. "Hypox-inducible Factor-1 Mediates Transcriptional Activation of the Heme Oxygenase-1 Gene in Response to Hypoxia", *J Biol Chem.*, 1997, 272(9), pp. 5375-5381.
Ljublinskaya Et Al "A Mild Conversion Of The 2,4-Dinitrophenyl-Glycyl-Moiety To A Derivative of 6-Nitrobenzimidazol-1-Oxide" Tetrahedron Letters 1972 vol. 47 pp. 4511-4514.
Lin et al. "Differentiation Arrest by Hypoxia", *J Biol Chem.*, 2006, 281(31), pp. 30678-30683.
Lipunova et al., "Benzimidazol[1,2-a]pyrazol-1,5-c]quinazoline: a novel heterocyclic system" *Mendeleev Communications* 1996, 1 pp. 15-17.
Lipunova et al., "Synthesis and Cyclization of Derivatives of 3-Heterylhydrazino-2-polyfluorobenzoylacrylic Acid" *Russian Journal of Organic Chemistry* (Translation of Zhurnal Organicheskoi, Khimii) 1997, 33(10), pp. 1476-1486.
Liu et al., "Hypoxia Regulates Vascular Endothelial Growth Factor Gene Expression in Endothelial Cells: Identification of a 5 prime Enhancer", *Circ Res.*, 1995, 77(3), pp. 638-643.
Lok et al. "Identification of a Hypoxia Response Element in the Transferrin Receptor Gene", *J Biol Chem.*, 1999, 274(34), pp. 24147-24152.
Luttun et al., "Placental growth factor (PlGF) and its receptor Flt-1 (VEGFR-1): Novel therapeutic targets for angiogenic disorders" *Series Information: Annals of the New York Academy of Sciences*, 2002, 979, pp. 80-93.
Mace et al., "Sustained expression of Hif-1 alpha in the diabetic environment promotes angiogenesis and cutaneous wound repair", *Wound Repair Regen.*, 2007, 15(5), pp. 636-645.
Mallick et al., "Ischemia-Reperfusion Injury of the Intestine and Protective Strategies Against Injury", *Digestive Diseases & Sciences*, 2004, 49(9), pp. 1359-1377.
Metzen E. et al., "Intracellular localisation of human HIF-1alpha hydroxylases: Implications for oxygen sensing" *J Cell Sci.*, 2003,116, pp. 1319-1326.
Mukhopadhyay et al. "Role of Hypoxia-inducible Factor-1 in Transcriptional Activation of Ceruloplasmin by Iron Deficiency", *J Biol Chem.*, 2000, 275(28), pp. 21048-21054.
Murry et al. "Preconditioning with ischemia: a delay of lethal cell injury in ischemic myocardium", *Circulation*, 1986 74(5), pp. 1124-1136.
Nagai et al "Becaplermin: Recombinant Platelet Derived Growth Factor, a New Treatment for Healing Diabetic Foot Ulcers" Exp Opin Biol Ther 2002 vol. 2(2) pp. 211-218.
Natarajan et al., "Hypoxia inducible factor-1 upregulates adiponectin in diabetic mouse hearts and attenuates post-ischemic injury" 2008, J Cardiovasc Pharmacol., 51(2), pp. 178-187.
Natarajan et al., "Hypoxia inducible factor-1 activation by prolyl 4-hydroxylase-2 gene silencing attenuates myocardial ischemia reperfusion injury", *Circulation Res.*,2006, 98(1), pp. 133-140.
Nishiguchi, K. et al.,. "Sulfonyl Chloride Formatin from Thiol Derivatives by N-Chlorosuccinimide Mediated Oxidation" *Synthesis*, 2006, 24, pp. 4131-4134.
Pajusola et al., "Stabilized HIF-1alpha is superior to VEGF for angiogenesis in skeletal muscle via adeno-associated virus gene transfer" *FASEB Journal*, 2005, 19(10), pp. 1365-1367.
Papandreou et al., "HIF-1 mediates adaptation to hypoxia by actively downregulating mitochondrial oxygen consumption" *Cell Metab.*, 2006, 3(3), pp. 187-197.
Pasupathy et al., "Ischaemic preconditioning protects against ischaemia/reperfusion injury: emerging concepts" *European Journal of Vascular and Endovascular Surgery*, 2005, 29, pp. 106-115.
Paulekuhn, et al., "Trends in Active Pharmaceutical Ingredient Salt Selection based on Analysis of the Orange Book Database", *J. Med. Chem.*, 2007, 50:6665-72.
Percy et al. "A family with erythrocytosis establishes a role for prolyl hydroxylase domain protein 2 in oxygen homeostasis" *PNAS*, 2006, 103(3), pp. 654-659.
Peyssonnaux et al., "Critical role of HIF-1 alpha in keratinocyte defense against bacterial infection" *J Invest Dermatol.*, 2008 128(8), pp. 1964-1968.
Peyssonnaux et al., "HIF-1 alpha expression regulates the bactericidal capacity of phagocytes" *J Invest Dermatol.*, 2005, 115(7), pp. 1806-1815.
Peyssonnaux et al., "Regulation of iron homeostasis by the hypoxia-inducible transcription factors (HIFs)." *J Clin Invest.*, 2007, 117(7), pp. 1926-1932.
Pfander et al "HIF-1a Controls Extracellular Matrix Synthesis by Epiphyseal Chondrocytes" J Cell Sci 2003 116(9) pp. 1819-1826.
Povstyanoi et al., "2-hydrazino(alkylhydrazino)benzimidazole in reaction with 3-aroylpropanon-2-ic acids" *Ukrainskii Khimicheskii Zhurnal* (Russian Edition) (1990), 56(10), pp. 1089-1092.
Rastogi Et Al "Synthesis Of Benzimidazole-2-Carboxamides As Potential Anthelmintic Agents" Indian J. Chem 1979 vol. 18b pp. 464-467.
Regranex (Becaplermin) Label—Omj Pharmaceuticals Inc Revised Apr. 2010.

(56) References Cited

OTHER PUBLICATIONS

Robinson et al., "Mucosal protection by hypoxia-inducible factor prolyl hydroxylase inhibition" *Gastroenterology*, 2008, 134(1), pp. 145-155.

Rolfs et al. "Oxygen-regulated transferrin expression is mediated by hypoxia-inducible factor-1" *J Biol Chem.*,1997, 272(32), pp. 20055-20062.

Scheuermann et al., "Hypoxia-inducible factors Per/ARNT/Sim domains: structure and function" *Methods Enzymol.*, 2007, 435, pp. 3-24.

Schmid et al., "HIF-1 and p53: Communication of Transcription Factors under Hypoxia" Journal of Cellular & Molecular Medicine, 2004, 8(4), pp. 423-431.

Schultz et al., "Hypoxia and hypoxia-inducible factor-1 alpha promote growth factor-induced proliferation of human vascular smooth muscle cells" *Am J Physiol Heart Circ Physiol.*, 2006, 290(6), pp. H2528-H2534.

Semenza et al. "A nuclear factor induced by hypoxia via de novo protein synthesis binds to the human erythropoietin gene enhancer at a site required for transcriptional activation", , *Mol Cell Biol.*, 1992, 12(12), pp. 5447-5454.

Semenza et al., "Vasculogenesis, angiogenesis, and arteriogenesis: Mechanisms of blood vessel formation and remodeling", *J Cell Biochem.*, 102(4), 2007, pp. 840-847.

Semenza, "Hypoxia-inducible factor 1: Oxygen homeostasis and disease pathophysiology" *Trends in Molecular Medicine*, 2001, 7(8), pp. 345-350.

Semenza, "Oxygen-dependent regulation of mitochondrial respiration by hypoxia-inducible factor 1", *Biochem J.*, 405 (1), 2007, pp. 1-9.

Semenza, "Regulation of tissue perfusion in mammals by hypoxia-inducible factor 1." *Exp Physiol.*, 2007, 92(6), pp. 988-991.

Semenza, "Hypoxia-inducible factor 1 (HIF-1) Pathway" *Science's Stke (Signal Transduction Knowledge Environment )*2007, 407(cm8), pp. 1-3.

Senga et al., "Synthesis of Pyrazolo [1',5':1,2]-1,3,5-triazino[5,6-] benzimidazoles" *Journal of Heterocyclic Chemistry* 1975, 12(5):899-901.

Shan et al. "Prodrug strategies based on intramolecular cyclization reactions", *Journal of Pharmaceutical Sciences* 1997, 86(7), pp. 765-767.

Shaw, "Glucose metabolism and cancer" *Curr Opin Cell Biol.*, 2006, 18(6), pp. 598-608.

Shyu et al., "Intramyocardial injection of naked DNA encoding HIF-1alpha/VP16 hybrid to enhance angiogenesis in an acute myocardial infarction model in the rat." *Cardiovasc Res.*, 2002, 54(3), pp. 576-583.

Siddiq et al. "Hypoxia-inducible Factor Prolyl 4-Hydroxylase Inhibition: A Target for Neuroprotection in the Central Nervous System", *J Biol Chem.*, 2005, 280(50), pp. 41732-41743.

Simon et al., "The role of oxygen availability in embryonic development and stem cell function" *Nature Reviews Molecular Cell Biology*, 2008, 9(4), pp. 285-296.

Singh et al., "Reaction of 2-hydrazinobenzimidazole with B-diketones: A Structural Reinvestigation" *Indian Journal of Chemistry, Section B: Organic Chemistry Including Medicinal Chemistry*, 1993, 32B(2):262-5.

Stahl & Wermuth Handbook of Pharmaceutical Salts, Properties, Selection and Use Stahl and Wermuth eds Wiley-VCH and VHCA Zurich 2002.

Steed, "Clinical Evaluation of Recombinant Human Platelet-Derived Growth Factor for the Treatment of Lower Extremity Ulcers" 2006, *Plast Reconstr Surg.*, 117(7 Suppl), pp. 143S-149S.

Tacchini et al. "Transferrin Receptor Induction by Hypoxia. HIF-1-Mediated Transcriptional Activation and Cell-Specific Post-Transcriptional Regulation", *J Biol Chem.*,1999, 274(34), pp. 24142-24146.

Thurston et al., "Angiopoietin-1 protects the adult vasculature against plasma leakage" *Nature Medicine*, 2000, 6(4), pp. 460-463.

Thurston et al., "Leakage-resistant blood vessels in mice transgenically overexpressing angiopoietin-1", *Science*,1999, 286, pp. 2511-2514.

Ulcerative Colitis Prevention, 2017, <http://www.healthcommunities.com/colitis/prevention.shtml>.

Ulcerative Colitis Cute, 2017 <http://uctclinic.com/can-ulcerative-colities-be-cured>.

Vincent et al., "Angiogenesis Is Induced in a Rabbit Model of Hindlimb Ischemia by Naked DNA Encoding an HIF-1[alpha]/VP16 Hybrid Transcription Factor", *Circulation*, 2000, 102 (18), pp. 2255-2261.

Wang et al. "Characterization of hypoxia-inducible factor 1 and regulation of DNA binding activity by hypoxia" *J Biol Chem.*, 1993, 268(29), pp. 21513-21518.

Wang et al. "General involvement of hypoxia-inducible factor 1 in transcriptional response to hypoxia" *Proceedings of the National Academy of Sciences of the United States of America*, 1993, 90, pp. 4304-4308.

Wang et al. "Purification and Characterization of Hypoxia-inducible Factor 1", *J Biol Chem.*,1995, 270(3), pp. 1230-1237.

Warshakoon et al., "A Novel Series of Imidazol[1,2-a]pyridine derivatives as HIF-1α prolyl hydroxylase inhibitors" *Bioorg Med Chem Lett.*, 2006, 16(21):5598-601.

Warshakoon et al., "Design and Synthesis of Substituted Pyridine Derivatives as HIF-1α Prolyl Hydroxylase Inhibitors", *Bioorg Med Chem Lett.*, 2006, 16(21):5616-20.

Wang et al "The Hypoxia Inducible Factor α Pathway Couples Angiogenesis to Osteogenesis During Skeletal Development" J Clin Invest 2007 17(6) pp. 1616-1626.

Zhu et al "Facile Preparation of Substituted Benzimidazole-2-Carboxylates" Heterocycles 2006 67(2) pp. 769-775.

Warshakoon et al., "Design and Synthesis of a Series of Novel Pyrazolopyridines as HIF 1-α prolyl hydroxylase inhibitors" *Bioorg Med Chem Lett.*, 2006, 16(21):5687-90.

Yoshida et al., "Hypoxia inducible factor 1-[alpha] regulates of platelet derived growth factor-B in human glioblastoma cells", J Neurooncol., 2006, 76(1), pp. 13-21.

Yun et al., "Inhibition of PPAR gamma 2 gene expression by the HIF-1-regulated gene DEC1/Stra13: a mechanism for regulation of adipogenesis by hypoxia." 2002, *Developmental Cell*, 2003, 2(3), pp. 331-341.

Zhang H et al. "Mitochondrial Autophagy Is an HIF-1-dependent Adaptive Metabolic Response to Hypoxia" *J Biol Chem.* 283, 2008, pp. 10892-10903.

Zou et al "Design Syhthesis and Antiviral Evaluation of 2-Chloro-5,6-dihalo-1-β-$_D$-ribofuranosylbenzimidazoles as Potential Agents for Human Cytomegalovirus Infections" J Med Chem 1997 40 pp. 811-818.

Terzioglu Et Al "Synthesis And Structure Activity Relationships Of Indole And Benzimidazole Piperazines As Histamine H4 Receptor Antagonist" Bioorg & Med Chem Letters 2004 vol. 14 pp. 5251-5256.

Dubey Et Al "Mass Spectral Studies Of 2,4-Disubstituted Benzimidazoles" Indian Journal Of Chemistry 1987 vol. 26b pp. 395-397.

CAS 1017666-50-0, CAS 101766-37-3, CAS 1017666-26-0, CAS 1006582-96-2.

Aquilina et al. "Polypeptidwe Modification and Cross Linking by Oxidized 3-Hydroxylynurenine" Biochemistry 2000 vol. 39 pp. 16176-16184.

Garcia-Sosa et al "Including Tightly-Bound Water Molecules in de Novo Drug Design. Exemplification through the Silico Generation of Poly(Adp-ribose)polymerase Ligands" J Chem Inf Model 2005 vol. 45 pp. 624-633.

Barrett et al ."Pharmacological Characterization of 1-(5-chloro-6-(trifluoromethoxy)-1Hbenzoimidazol-2-yl)-1H-pyrazole-4-carboxylic acid (JNJ-42041935), a Potent and SelectiveHypoxia-Inducible Factor Prolyl Hydroxylase Inhibitor" Mol. Pharmacol. 2011 vol. 79(6)pp. 910-920.

Rosen et al Benzimidazole-2-pyrazole HIP Prolyl 4-Hydroxylase Inhibitors as Oral Erythropoietin Secretagogues. ACS Medicinal Chemistry Letters, 2010, vol. 1 pp. 526-529.

(56) References Cited

OTHER PUBLICATIONS

Rabinowitz. et al. "Inhibitors of HIF Prolyl Hydroxylases" Annual Reports in Medicinal Chemistry. 2010 vol. 45 Chapter 8 pp. 123-139 Academic Press Elsevier Inc.,.
Kanelakis et al Characterization of a Robust Enzymatic Assay for Inhibitors of 2-Oxoglutarate-Dependent Hydroxylases. J. Biomol. Screen. 2009 vol. 14(6) pp. 627-635.
Rabinowitz et al "Structure Based Design and Biological Evaluation of Benzimidazole HIF Prolyl Hydroxylase Inhibitors for the Treatment of Anemia" Abstracts of Papers, 239th ACS National Meeting, San Francisco, CA, United States, Mar. 21-25, 2010.
Rabinowitz, M. "Inhibition of Hypoxia-Inducible Factor Prolyl Hydroxylase Domain Oxygen Sensors: Tricking the Body into Mounting Orchestrated Survival and Repair Responses" *J. Med. Chem.*, in press.
Purpero et al"The Diverse and Pervasive Chemistries of the a-keto Acid Dependent Enzymes" J. Biol. Inorg. Chem. 2007 vol. 12 pp. 587-601.
McDonough et al "Cellular Oxygen Sensing: Crystal Structure of Hypoxia-Inducible Factor Prolyl Hydroxylase (PHD2)" PNAS 2006 vol. 103(26) pp. 9814-9819.
Wang et al "Desferrioxamine Induces Erythropoietin Gene Expression and Hypoxia-Inducible Factor 1 DNA-Binding Activity: Implications for Models of Hypoxia Signal Transduction" Blood 1993 vol. 82 pp. 3610-3615.
Tan et al "Hypoxia-Inducible Factor-1 Improves the Actions of Positive Inotropic Agents in Stunned Cardiac Myocites" Clin. Exp. Pharmacol. Physiol., 2009 vol. 36 pp. 904-911.
Thangarajah et al "HIF-a Dysfunction in Diabetes" Cell Cycle 2010 vol. 9 pp. 75-79.
Thangarajah et al "The Molecular Basis for Impaired Hypoxia-Induced VEGF Expression in Diabetic Tissues" PNAS 2009 vol. 106(32) pp. 13505-13510.
Dongiovanni et al "Iron Depletion by Deferoxamine Up-Regultes Glucose Uptake and Insulin Signaling in Hepatoma Cells and Rat Liver" Am. J. Pathol., 2008, 172(3) pp. 738-747.
Lee et al "Inhibition of Prolyl Hydroxylase Protects against 1-Methyl-4phenyl-1,2,3,6-tetrahydropyridine-induced Neurotoxicity" J. Biol. Chem. 2009 vol. 284 (42) pp. 29065-29076.
Ttriantafyllou et a; "Flavonoids induce HIF-1a but Impair its Nuclear Accumulation and Activity" Free Radical Biol. Med. 2008 vol. 44 pp. 657-670.
Park et al "Flavonoids-Induced Accumulation of Hypoxia-Inducible Factor (HIF)-1a/2a is Mediated Through Chelation of Iron" J. Cell. Biochem., 2008 vol. 103 pp. 1989-1998.
Shui et al "HIF-1: An Age-Dependent Regulator of Lens Cell Proliferation" Invest. Opthal. Vis. Sci. 2008 vol. 49(11) pp. 4961-4970.
Xia et al "Identification of Chemical Compounds that Induce HIF-1a Activity" Toxicol. Sci. 2009 vol. 112(1) pp. 153-163.
Banerji et al "The Inhibition of Factor Inhibiting Hypoxia-Inducible Factor (FIH) by B-oxocarboxylic Acids" Chem. Commun. 2005 vol. 43 pp. 5438-5440.
Cunliffe et al "Novel Inhibitors of Prolyl 4-Hydroxylase. 3. Inhibition by the Substrate Analogue N-Oxalogycine and Its Derivatives" J. Med. Chem. 1992 vol. 35 pp. 2652-2658.
Franklin et al "Approaches to the Design of Anti-fibrotic Drugs" Biochem. Soc. Trans. 1991 vol. 19 pp. 812-815.
Frohn et al "Structure-Guided Design of Substituted Aza-Benzimidazoles as Potent Hypoxia Inducible Factor-1a Prolyl Hydroxylase-2 Inhibitors" Bioorg. Med. Chem. Lett. 2008 vol. 18 pp. 5023-5026.
Tegley et al "Discovery of Novel Hydroxy-Thiazoles as HIF-a Prolyl Hydroxylase Inhibitors: SAR, Synthesis, and Modeling Evaluation" Bioorg. Med. Chem. Lett., 2008 vol. 18 pp. 3925-3928.
Vidal Juan et al 2007 Caplus an 2007:409258.
Evdokimov et al "Crystal Structure of HIF Prolyl Hydroxylase EGLN-1 in Complex with a Biologically Active Inhibitor" 2006 RCSB Protein Data Bank ID 2HBT, http://www.rcsb.org/pdb/explore. do?structureId=2hbt Accessed Dec. 30, 2013.
Hamanaka et al caplus an 1999:566034 (examiner citation in parent case).
Smith et al Antioxidants & Reodx Signaling 210 vol. 12 pp. 431-433 (examiner citation in parent case).
ProlylHydroxylase 2012 http://en.wikipedia.org/wiki/HIF_prolyl-hydroxylase_inhibitor (examiner citation in parent case).
Anemia 2012 http://www.fibrogen.com/press/release/pr_1351722380 (examiner citation parent case).
Hipoxia 2012 http://lungcancer.about.com/od/Respiratory-Symptoms/a/Hypoxia.htm (examiner citation parent case).
Bone Fracture 2012 http://en.wikipedia.org/wiki/Bone_fracture (examiner citation parent case).
STN File Registry 1017666-26-0 Apr. 27, 2008.
FG4592, 2009, http://www.businesswire.com/news/home/20090130005581/en/Patient-Recruitment-Resumes.
Sickle-Cell-Disease, 2015, http://www.ncbi.nlm.nih.gov/pubmed/21429807.
CVT-510, 2014, http://www.evaluategroup.com/Universal/View.aspx?type=Story&id=39440.
CVT3619, 2014, http://diabposition.com/2008/09/cvtherapeutics-cvt3619-insulin.html.
Anemia, 2014, http://www.fibrogen.com/press/release/pr_1351722380.
CureAnemia, 2014, http://www.nhlbi.nih.gov/health-topics/topics/sca/treatment.html.
International search report dated Jul. 23, 2009, for corresponding international application PCT/US2009/041902 and international search report dated Jul. 3, 2009, for corresponding international application PCT/US2009/041908.
International search report dated Jul. 3, 2009, for corresponding international application PCT/US2009/041908.

* cited by examiner

BENZOIMIDAZOLES AS PROLYL HYDROXYLASE INHIBITORS

RELATED PRIORITY

This application is a continuation application of U.S. patent application Ser. No. 16/135,975 (pending), filed Sep. 19, 2018, which is a continuation of U.S. patent application Ser. No. 15/695,958 (abandoned), filed Sep. 5, 2017, which is a continuation of U.S. patent application Ser. No. 14/968,763 (abandoned), filed Dec. 14, 2015, which is a continuation of U.S. patent application Ser. No. 14/732,332 (abandoned), filed Jun. 5, 2015, which is a continuation of U.S. patent application Ser. No. 14/282,901, filed May 20, 2014, now U.S. Pat. No. 9,073,923, which is a continuation of U.S. patent application Ser. No. 12/990,104, filed Oct. 28, 2010, now U.S. Pat. No. 8,759,345, which is the § 371 U.S. National Stage of International Application No. PCT/US2009/041902, filed Apr. 28, 2009, which claims the benefit of U.S. Provisional Application No. 61/048,531, filed Apr. 28, 2008, the disclosures of which are incorporated by reference herein in their entireties.

FIELD OF THE INVENTION

The present invention relates to certain benzoimidazole compounds, pharmaceutical compositions containing them, and methods of using them for the treatment of disease states, disorders, and conditions mediated by prolyl hydroxylase activity.

BACKGROUND OF THE INVENTION

Cells respond to hypoxia by activating the transcription of genes involved in cell survival, oxygen delivery and utilization, angiogenesis, cellular metabolism, regulation of blood pressure, hematopoiesis, and tissue preservation. Hypoxia-inducible factors (HIFs) are key transcriptional regulators of these genes (Semenza et al., 1992, *Mol Cell Biol.*, 12(12):5447-54; Wang et al., 1993, *J Biol Chem.*, 268(29):21513-18; Wang et al., 1993, *Proc Natl Acad Sci.*, 90:4304-08; Wang et al., 1995, *J Biol Chem.*, 270(3):1230-37). Three forms of HIF-α have been described: HIF-1α, HIF-2α and HIF-3α (Scheuermann et al., 2007, *Methods Enzymol.*, 435:3-24). Pairing of a HIFα sub-unit with HIF-1β forms a functional heterodimeric protein that subsequently recruits other transcriptional factors such as p300 and CBP (Semenza, 2001, Trends Mol Med., 7(8):345-50).

A family of highly conserved oxygen, iron, and 2-oxo-glutarate-dependent prolyl hydroxylase (PHD) enzymes mediate the cells response to hypoxia via post-translational modification of HIF (Ivan et al., 2001, *Science*, 292:464-68; Jaakkola et al., 2001, *Science*, 292:468-72). Under normoxic conditions, PHD catalyzes the hydroxylation of two conserved proline residues within HIF. Von Hippel Lindau (VHL) protein binds selectively to hydroxylated HIF. The binding of VHL renders HIF a target for polyubiquitination by the E3 ubiquitin ligase complex and its subsequent degradation by the 26S proteasome (Ke et al., 2006, *Mol Pharmacol.* 70(5):1469-80; Semenza, *Sci STKE.*, 2007, 407 (cm8):1-3). As the affinity of PHD for oxygen is within the physiological range of oxygen and oxygen is a necessary co-factor for the reaction, PHD is inactivated when oxygen tension is reduced. In this way, HIF is rapidly degraded under normoxic conditions but accumulates in cells under hypoxic conditions or when PHD is inhibited.

Four isotypes of PHD have been described: PHD1, PHD2, PHD3, and PHD4 (Epstein et al., 2001, *Cell*, 107:43-54; Kaelin, 2005, *Annu Rev Biochem.*, 74:115-28; Schmid et al., 2004, *J Cell Mol Med.*, 8:423-31). The different isotypes are ubiquitously expressed but are differentially regulated and have distinct physiological roles in the cellular response to hypoxia. There is evidence that the various isotypes have different selectivity for the three different HIFα sub-types (Epstein et al., supra). In terms of cellular localization, PHD1 is primarily nuclear, PHD2 is primarily cytoplasmic, and PHD3 appears to be both cytoplasmic and nuclear (Metzen E, et al. 2003, *J Cell Sci.*, 116(7):1319-26). PHD2 appears to be the predominant HIFα prolyl hydroxylase under normoxic conditions (Ivan et al., 2002. *Proc Natl Acad Sci. USA*, 99(21):13459-64; Berra et al., 2003, *EMBO J.*, 22:4082-90). The three isotypes have a high degree of amino-acid homology and the active site of the enzyme is highly conserved.

The HIF target gene products are involved in a number of physiological and pathophysiological processes including but not limited to: erythropoiesis, angiogenesis, regulation of energy metabolism, vasomotor function, and cell apoptosis/proliferation. The first gene described as a HIF target was that encoding erythropoietin (EPO) (Wang et al., 1993, supra). It was recognized that a reduction in the oxygen carrying capacity of the blood is sensed in the kidney and that the kidney and liver respond by releasing more EPO, the hormone that stimulates red blood cell proliferation and maturation. EPO has a number of other important effects on non-hematopoietic cell types and has emerged as a key tissue-protective cytokine (Arcasoy, 2008, *Br J Haematol.*, 141:14-31). Thus EPO is now implicated in wound healing and angiogenesis as well as the response of tissues to ischemic insult. Most of the enzymes involved in anaerobic glycolysis are encoded by HIF target genes and as a result glycolysis is increased in hypoxic tissues (Shaw, 2006, *Curr Opin Cell Biol.*, 18(6):598-608). The known HIF target gene products in this pathway include but are not limited to: glucose transporters such as GLUT-1 (Ebert et al., 1995, *J Biol Chem.*, 270(49):29083-89), enzymes involved in the break down of glucose to pyruvate such as hexokinase and phosphoglycerate kinase 1 (Firth et al., 1994, *Proc Natl Acad Sci. USA*, 91:6496-6500) as well as lactate dehydrogenase (Firth et al., supra). HIF target gene products are also involved in the regulation of cellular metabolism. For example, pyruvate dehydrogenase kinase-1 is a target HIF gene product and regulates the entry of pyruvate into the Kreb's cycle by reducing the activity of pyruvate dehydrogenase by phosphorylation (Kim et al., 2006, *Cell Metab.*, 3:177-85; Papandreou et al., 2006, *Cell Metab.*, 3:187-197). HIF target gene products are also involved in angiogenesis. For example, vascular endothelial growth factor (VEGF) (Liu et al., 1995, *Circ Res.*, 77(3):638-43) is a known regulator of angiogenesis and vasculogenesis. HIF target gene products also function in the regulation of vascular tone and include heme oxygenase-1 (Lee et al., 1997, *J Biol Chem.*, 272(9):5375-81). A number of HIF regulated gene products such as platelet-derived growth factor (PDGF) (Yoshida et al., 2006, *J Neurooncol.*, 76(1):13-21), vascular endothelial growth factor (Breen, 2007, *J Cell Biochem.*, 102(6):1358-67) and EPO (Arcasoy, supra) also function in the coordinated response to wound healing.

Targeted disruption of the prolyl hydroxylase (PHD) enzyme activity by small molecules has potential utility in the treatment of disorders of oxygen sensing and distribution. Examples include but are not limited to: anemia; sickle cell anemia; peripheral vascular disease; coronary artery disease; heart failure; protection of tissue from ischemia in conditions such as myocardial ischemia, myocardial infarction and stroke; preservation of organs for transplant; treatment of tissue ischemia by regulating and/or restoring blood flow, oxygen delivery and/or energy utilization; acceleration of wound healing particularly in diabetic and aged patients; treatment of burns; treatment of infection; bone healing, and bone growth. In addition, targeted disruption of PHD is expected to have utility in treating metabolic disorders such as diabetes, obesity, ulcerative colitis, inflammatory bowel disease and related disorders such as Crohn's disease. (*Recent Patents on Inflammation & Allergy Drug Discovery*, 2009, 3, 1-16).

HIF has been shown to be the primary transcriptional factor that leads to increased erythropoietin production under conditions of hypoxia (Wang et al., 1993, supra). While treatment with recombinant human erythropoietin has been demonstrated to be an effective method of treating anemia, small molecule mediated PHD inhibition can be expected to offer advantages over treatment with erythropoietin. Specifically, the function of other HIF gene products are necessary for hematopoiesis and regulation of these factors increases the efficiency of hematopoiesis. Examples of HIF target gene products that are critical for hematopoiesis include: transferrin (Rolfs et al., 1997, *J Biol Chem.*, 272(32):20055-62), transferrin receptor (Lok et al., 1999, *J Biol Chem.*, 274(34):24147-52; Tacchini et al., 1999, *J Biol Chem.*, 274(34):24142-46) and ceruloplasmin (Mukhopadhyay et al., 2000, *J Biol Chem.*, 275(28):21048-54). Hepcidin expression is also suppressed by HIF (Peyssonnaux et al., 2007, *J Clin Invest.*, 117(7):1926-32) and small molecule inhibitors of PHD have been shown to reduce hepcidin production (Braliou et al., 2008, *J Hepatol.*, 48:801-10). Hepcidin is a negative regulator of the availability of the iron that is necessary for hematopoiesis, so a reduction in hepcidin production is expected to be beneficial to the treatment of anemia. PHD inhibition may also be useful when used in conjunction with other treatments for anemia including iron supplementation and/or exogenous erythropoietin. Studies of mutations in the PHD2 gene occurring naturally in the human population provide further evidence for the use of PHD inhibitors to treat anemia. Two recent reports have shown that patients with dysfunctional mutations in the PHD2 gene display increased erythrocytosis and elevated blood hemoglobin (Percy et al., 2007, *PNAS*, 103(3):654-59; Al-Sheikh et al., 2008, *Blood Cells Mol Dis.*, 40:160-65). In addition, a small molecule PHD inhibitor has been evaluated in healthy volunteers and patients with chronic kidney disease (U.S. pat. appl. US2006/0276477, Dec. 7, 2006). Plasma erythropoietin was increased in a dose-dependent fashion and blood hemoglobin concentrations were increased in the chronic kidney disease patients.

Metabolic adaptation and preservation of tissues are jeopardized by ischemia. PHD inhibitors increase the expression of genes that lead to changes in metabolism that are beneficial under ischemic conditions (Semenza, 2007, *Biochem J.*, 405:1-9). Many of the genes encoding enzymes involved in anaerobic glycolysis are regulated by HIF and glycolysis is increased by inhibiting PHD (Shaw, supra). Known HIF target genes in this pathway include but are not limited to: GLUT-1 (Ebert et al., supra), hexokinase, phosphoglycerate kinase 1, lactate dehydrogenase (Firth et al., supra), pyruvate dehydrogenase kinase-1 (Kim et al., supra; Papandreou et al., supra). Pyruvate dehydrogenase kinase-1 suppresses the entry of pyruvate into the Kreb's cycle. HIF mediates a switch in the expression of the cytochromes involved in electron transport in the mitochondria (Fukuda et al., 2007, *Cell*, 129(1):111-22). This change in the cytochrome composition optimizes the efficiency in ATP production under hypoxic conditions and reduces the production of injurious oxidative phosphorylation by-products such as hydrogen peroxide and superoxide. With prolonged exposure to hypoxia, HIF drives autophagy of the mitochondria resulting a reduction in their number (Zhang H et al., 2008, *J Biol Chem.* 283: 10892-10903). This adaptation to chronic hypoxia reduces the production of hydrogen peroxide and superoxide while the cell relies on glycolysis to produce energy. A further adaptive response produced by HIF elevation is up-regulation of cell survival factors. These factors include: Insulin-like growth factor (IGF) 2, IGF-binding protein 2 and 3 (Feldser et al., 1999, *Cancer Res.* 59:3915-18). Overall accumulation of HIF under hypoxic conditions governs an adaptive up-regulation of glycolysis, a reduction in oxidative phosphorylation resulting in a reduction in the production of hydrogen peroxide and superoxide, optimization of oxidative phosphorylation protecting cells against ischemic damage. Thus, PHD inhibitors are expected to be useful in organ and tissue transplant preservation (Bernhardt et al., 2007, *Methods Enzymol.*, 435:221-45). While benefit may be achieved by administering PHD inhibitors before harvesting organs for transplant, administration of an inhibitor to the organ/tissue after harvest, either in storage (e.g., cardioplegia solution) or post-transplant, may also be of therapeutic benefit.

PHD inhibitors are expected to be effective in preserving tissue from regional ischemia and/or hypoxia. This includes ischemia/hypoxia associated with inter alia: angina, myocardial ischemia, stroke, ischemia of skeletal muscle. There are a number of lines of experimental evidence that support the concept that PHD inhibition and subsequent elevation of HIF as a useful method for preserving ischemic tissue. Recently, ischemic pre-conditioning has been demonstrated to be a HIF-dependent phenomenon (Cai et al., 2008, *Cardiovasc Res.*, 77(3):463-70). Ischemic pre-conditioning is a well known phenomenon whereby short periods of hypoxia and/or ischemia protect tissue from subsequent longer periods of ischemia (Murry et al., 1986, *Circulation*, 1986 74(5):1124-36; Das et al., 2008, *IUBMB Life*, 60(4): 199-203). Ischemic pre-conditioning is known to occur in humans as well as experimental animals (Darling et al., 2007, *Basic Res Cardiol.*, 102(3):274-8; Kojima I et al., 2007, *J Am Soc Nephrol.*, 18:1218-26). While the concept of pre-conditioning is best known for its protective effects in the heart, it also applies to other tissues including but not limited to: liver, skeletal muscle, liver, lung, kidney, intestine and brain (Pasupathy et al., 2005, *Eur J Vasc Endovasc Surg.*, 29:106-15; Mallick et al., 2004, *Dig Dis Sci.*, 49(9): 1359-77). Experimental evidence for the tissue protective effects of PHD inhibition and elevation of HIF have been obtained in a number of animal models including: germ-line knock out of PHD1 which conferred protection of the skeletal muscle from ischemic insult (Aragonés et al., 2008, *Nat Genet.*, 40(2):170-80), silencing of PHD2 through the use of siRNA which protected the heart from ischemic insult (Natarajan et al., 2006, *Circ Res.*, 98(1):133-40), inhibition of PHD by administering carbon monoxide which protected the myocardium from ischemic injury (Chin et al., 2007, *Proc Natl Acad Sci. U.S.A.*, 104(12):5109-14), hypoxia in the brain which increased the tolerance to ischemia (Bernaudin et al., 2002, *J Cereb Blood Flow Metab.*, 22(4):393-403). In addition, small molecule inhibitors of PHD protect the brain in experimental stroke models (Siddiq et al., 2005, *J Biol Chem.*, 280(50):41732-43). Moreover, HIF up-regulation has also been shown to protect the heart of diabetic mice, where outcomes are generally worse (Natarajan et al., 2008, *J Cardiovasc Pharmacol.*, 51(2):178-187). The tissue protective effects may also be observed in Buerger's disease, Raynaud's disease, and acrocyanosis.

The reduced reliance on aerobic metabolism via the Kreb's cycle in the mitochondria and an increased reliance on anaerobic glycolysis produced by PHD inhibition may have beneficial effects in normoxic tissues. It is important to note that PHD inhibition has also been shown to elevate HIF under normoxic conditions. Thus, PHD inhibition produces a pseudohypoxia associated with the hypoxic response being initiated through HIF but with tissue oxygenation remaining normal. The alteration of metabolism produced by PHD inhibition can also be expected to provide a treatment paradigm for diabetes, obesity and related disorders, including co-morbidities.

Globally, the collection of gene expression changes produced by PHD inhibition reduce the amount of energy generated per unit of glucose and will stimulate the body to burn more fat to maintain energy balance. The mechanisms for the increase in glycolysis are discussed above. Other observations link the hypoxic response to effects that are expected to be beneficial for the treatment of diabetes and obesity. Thus, high altitude training is well known to reduce body fat (Armellini et al., 1997, *Horm Metab Res.*, 29(9): 458-61). Hypoxia and hypoxia mimetics such as desferrioxamine have been shown to prevent adipocyte differentiation (Lin et al., 2006, *J Biol Chem.*, 281(41):30678-83; Carriére et al., 2004, *J Biol Chem.*, 279(39):40462-69). The effect is reversible upon returning to normoxic conditions. Inhibition of PHD activity during the initial stages of adipogenesis inhibits the formation of new adipocytes (Floyd et al., 2007, *J Cell Biochem.*, 101:1545-57). Hypoxia, cobalt chloride and desferrioxamine elevated HIF and inhibited PPAR gamma 2 nuclear hormone receptor transcription (Yun et al., 2002, *Dev Cell.*, 2:331-41). As PPAR gamma 2 is an important signal for adipocyte differentiation, PHD inhibition can be expected to inhibit adipocyte differentiation. These effects were shown to be mediated by the HIF-regulated gene DEC1/Stra13 (Yun et al., supra).

Small molecular inhibitors of PHD have been demonstrated to have beneficial effects in animal models of diabetes and obesity (Intl. Pat. Appl. Publ. WO2004/052284, Jun. 24, 2004; WO2004/052285, Jun. 24, 2004). Among the effects demonstrated for PHD inhibitors in mouse diet-induced obesity, db/db mouse and Zucker fa/fa rat models were lowering of: blood glucose concentration, fat mass in both abdominal and visceral fat pads, hemoglobin A1c, plasma triglycerides, body weight as well as changes in established disease bio-markers such as increases in the levels of adrenomedullin and leptin. Leptin is a known HIF target gene product (Grosfeld et al., 2002, *J Biol Chem.*, 277(45):42953-57). Gene products involved in the metabolism in fat cells were demonstrated to be regulated by PHD inhibition in a HIF-dependent fashion (Intl. Pat. Appl. Publ. WO2004/052285, supra). These include apolipoprotein A-IV, acyl CoA thioesterase, carnitine acetyl transferase, and insulin-like growth factor binding protein (IGFBP)-1.

PHD inhibitors are expected to be therapeutically useful as stimulants of vasculogenesis, angiogenesis, and arteriogenesis. These processes establish or restore blood flow and oxygenation to the tissues under ischemia and/or hypoxia conditions (Semenza et al., 2007, *J Cell Biochem.*, 102:840-47; Semenza, 2007, *Exp Physiol.*, 92(6):988-91). It has been shown that physical exercise increases HIF-1 and vascular endothelial growth factor in experimental animal models and in humans (Gustafsson et al. 2001, *Front Biosci.*, 6: D75-89) and consequently the number of blood vessels in skeletal muscle. VEGF is a well-known HIF target gene product that is a key driver of angiogenesis (Liu et al., supra). While administration of various forms of VEGF receptor activators are potent stimuli for angiogenesis, the blood vessel resulting from this potential form of therapy are leaky. This is considered to limit the potentially utility of VEGF for the treatment of disorders of oxygen delivery. The increased expression of a single angiogenic factor may not be sufficient for functional vascularization (Semenza, 2007, supra). PHD inhibition offers a potential advantage over other such angiogenic therapies in that it stimulates a controlled expression of multiple angiogenic growth factors in a HIF-dependent fashion including but not limited to: placental growth factor (PLGF), angiopoietin-1 (ANGPT1), angiopoietin-2 (ANGPT2), platelet-derived growth factor beta (PDGFB) (Carmeliet, 2004, *J Intern Med.*, 255:538-61; Kelly et al., 2003, *Circ Res.*, 93:1074-81) and stromal cell derived factor 1 (SDF-1) (Ceradini et al., 2004, *Nat Med.*, 10(8):858-64). Expression of angiopoietin-1 during angiogenesis produces leakage-resistant blood vessels, in contrast to the vessels produced by administration of VEGF alone (Thurston et al., 1999, *Science*, 286:2511-14; Thurston et al., 2000, *Nat Med.*, 6(4):460-3; Elson et al., 2001, *Genes Dev.*, 15(19):2520-32). Stromal cell derived factor 1 (SDF-1) has been shown to be critical to the process of recruiting endothelial progenitor cells to the sites of tissue injury. SDF-1 expression increased the adhesion, migration and homing of circulating CXCR4-positive progenitor cells to ischemic tissue. Furthermore inhibition of SDF-1 in ischemic tissue or blockade of CXCR4 on circulating cells prevents progenitor cell recruitment to sites of injury (Ceradini et al., 2004, supra; Ceradini et al., 2005, *Trends Cardiovasc Med.*, 15(2):57-63). Importantly, the recruitment of endothelial progenitor cells to sites of injury is reduced in aged mice and this is corrected by interventions that increase HIF at the wound site (Chang et al., 2007, *Circulation*, 116(24):2818-29). PHD inhibition offers the advantage not only of increasing the expression of a number of angiogenic factions but also a co-ordination in their expression throughout the angiogenesis process and recruitment of endothelial progenitor cells to ischemic tissue.

Evidence for the utility of PHD inhibitors as pro-angiogenic therapies is provided by the following observations. Adenovirus-mediated over-expression of HIF has been demonstrated to induce angiogenesis in non-ischemic tissue of an adult animal (Kelly et al., 2003, *Circ Res.*, 93(11):1074-81) providing evidence that therapies that elevate HIF, such as PHD inhibition, will induce angiogenesis. Placental growth factor (PLGF), also a HIF target gene, has been show to play a critical role in angiogenesis in ischemic tissue (Carmeliet, 2004, *J Intern Med.*, 255(5):538-61; Luttun et al., 2002, *Ann N Y Acad Sci.*, 979:80-93). The potent pro-angiogenic effects of therapies that elevate HIF have been demonstrated, via HIF over-expression, in skeletal muscle (Pajusola et al., 2005, *FASEB J.*, 19(10):1365-7; Vincent et al., 2000, *Circulation*, 102:2255-61) and in the myocardium (Shyu et al., 2002, *Cardiovasc Res.*, 54:576-83). The recruitment of endothelial progenitor cells to the ischemic myocardium by the HIF target gene SDF-1 has also been demonstrated (Abbott et al., 2004, *Circulation*, 110 (21):3300-05). These findings support the general concept that PHD inhibitors will be effective in stimulating angiogenesis in the setting of tissue ischemia, particularly muscle ischemia. It is expected that therapeutic angiogenesis produced by PHD inhibitors will be useful in restoring blood flow to tissues and therefore the treatment of disease including but not restricted to angina pectoris, myocardial ischemia and infarction, peripheral ischemic disease, claudication, gastric and duodenal ulcers, ulcerative colitis, and inflammatory bowel disease.

PHD and HIF play a central role in tissue repair and regeneration including healing of wounds and ulcers. Recent studies have demonstrated that an increased expression of all three PHDs at wound sites in aged mice with a resulting reduction in HIF accumulation (Chang et al., supra). Thus, elevation of HIF in aged mice by administering desferrioxamine increased the degree of wound healing back to levels observed in young mice. Similarly, in a diabetic mouse model, HIF elevation was suppressed compared to non-diabetic litter mates (Mace et al., 2007, *Wound Repair Regen.*, 15(5):636-45). Topical administration of cobalt chloride, a hypoxia mimetic, or over-expression of a murine HIF that lacks the oxygen-dependent degradation domain and thus provides for a constitutively active form of HIF, resulted in increased HIF at the wound site, increased expression of HIF target genes such as VEGF, Nos2, and Hmox1 and accelerated wound healing. The beneficial effect of PHD inhibition is not restricted to the skin and small molecule inhibitors of PHD have recently been demonstrated to provide benefit in a mouse model of colitis (Robinson et al., 2008, *Gastroenterology*, 134(1):145-55).

PHD inhibition resulting in accumulation of HIF is expected to act by at least four mechanisms to contribute to accelerated and more complete healing of wounds and burns: 1) protection of tissue jeopardized by hypoxia and/or ischemia, 2) stimulation of angiogenesis to establish or restore appropriate blood flow to the site, 3) recruitment of endothelial progenitor cells to wound sites, 4) stimulation of the release of growth factors that specifically stimulate healing and regeneration.

Recombinant human platelet-derived growth factor (PDGF) is marketed as becaplermin (Regranex™) and has been approved by the Food and Drug Administration of the United States of America for "Treatment of lower extremity diabetic neuropathic ulcers that extend into the subcutaneous tissue or beyond, and have adequate blood supply". Becaplermin has been shown to be effective in accelerating wound healing in diabetic patients (Steed, 2006, *Plast Reconstr Surg.*, 117(7 Suppl):143S-149S; Nagai et al., 2002, *Expert Opin Biol Ther*, 2(2):211-8). As PDGF is a HIF gene target (Schultz et al., 2006, *Am J Physiol Heart Circ Physiol.*, 290(6):H2528-34; Yoshida et al., 2006, *J Neurooncol.*, 76(1):13-21), PHD inhibition is expected to increase the expression of endogenous PDGF and produce a similar or more beneficial effect to those produced with becaplermin alone. Studies in animals have shown that topical application of PDGF results in increased wound DNA, protein, and hydroxyproline amounts; formation of thicker granulation and epidermal tissue; and increased cellular repopulation of wound sites. PDGF exerts a local effect on enhancing the formation of new connective tissue. The effectiveness of PHD inhibition is expected to be greater than that produced by becaplermin due to the additional tissue protective and pro-angiogenic effects mediated by HIF.

The beneficial effects of inhibition of PHD are expected to extend not only to accelerated wound healing in the skin and colon but also to the healing of other tissue damage including but not limited to gastrointestinal ulcers, skin graft replacements, burns, chronic wounds and frost bite.

Stem cells and progenitor cells are found in hypoxic niches within the body and hypoxia regulates their differentiation and cell fate (Simon et al., 2008, *Nat Rev Mol Cell Biol.*, 9:285-96). Thus PHD inhibitors may be useful to maintain stem cells and progenitor cells in a pluripotent state and to drive differentiation to desired cell types. Stem cells may be useful in culturing and expanding stem cell populations and may hold cells in a pluripotent state while hormones and other factors are administered to the cells to influence the differentiation and cell fate.

A further use of PHD inhibitors in the area of stem cell and progenitor cell therapeutics relates to the use of PHD inhibitors to condition these cells to withstand the process of implantation into the body and to generate an appropriate response to the body to make the stem cell and progenitor cell implantation viable (Hu et al., 2008, *J Thorac Cardiovasc Surg.*, 135(4):799-808). More specifically PHD inhibitors may facilitate the integration of stem cells and draw in an appropriate blood supply to sustain the stem cells once they are integrated. This blood vessel formation will also function to carry hormones and other factors released from these cells to the rest of the body.

PHD inhibitors may also be useful in the treatment of infection (Peyssonnaux et al., 2005, *J Invest Dermatol.*, 115(7):1806-15; Peyssonnaux et al., 2008 *J Invest Dermatol.*, 2008 August; 128(8):1964-8). HIF elevation has been demonstrated to increase the innate immune response to infection in phagocytes and in keratinocytes. Phagocytes in which HIF is elevated show increased bacteriocidal activity, increased nitric oxide production and increased expressed of the anti-bacterial peptide cathelicidin. These effects may also be useful in treating infection from burns.

HIF has also been shown to be involved in bone growth and healing (Pfander D et al., 2003 *J Cell Sci.*, 116(Pt 9):1819-26, Wang et al., 2007 *J Clin Invest*, 17(6):1616-26) and may therefore be used to heal or prevent fractures. HIF stimulates of glycolysis to provide energy to allow the synthesis of extracellular matrix of the epiphyseal chondrocytes under a hypoxic environment. HIF also plays a role in driving the release of VEGF and angiogenesis in bone healing process. The growth of blood vessels into growing or healing bone can be the rate limiting step in the process.

Certain small molecules with Prolyl Hydroxylase antagonistic activities have been described in the literature. These include, but are not limited to, certain imidazo[1,2-a]pyridine derivatives (Warshakoon et al., 2006, *Bioorg Med Chem Lett.*, 16(21):5598-601), substituted pyridine derivatives (Warshakoon et al., 2006, *Bioorg Med Chem Lett.*, 16(21):5616-20), certain pyrazolopyridines (Warshakoon et al., 2006, *Bioorg Med Chem Lett.*, 16(21):5687-90), certain bicyclic heteroaromatic N-substituted glycine derivatives (Intl. Pat. Appl. Publ. WO2007/103905, Sep. 13, 2007), quinoline based compounds (Intl. Pat. Appl. Publ. WO2007/070359, Jun. 21, 2007), certain pyrimidinetrione N-substituted glycine derivatives (Intl. Pat. Appl. Publ. WO2007/150011, Dec. 27, 2007), and substituted aryl or heteroaryl amide compounds (U.S. Pat. Appl. Publ. No.: US 2007/0299086, Dec. 27, 2007).

Certain benzoimidazole derivatives have been disclosed in the literature. For example, LeCount et al., *Journal of the Chemical Society, Perkin Transactions 1: Organic and Bio-Organic Chemistry* (1972-1999) (1974), (2):297-301, Senga et al., *Journal of Heterocyclic Chemistry* (1975), 12(5):899-901, Kandeel et al., *Polish Journal of Chemistry* (1983), 57(1-3), 327-31, Povstyanoi et al., *Ukrainskii Khimicheskii Zhurnal* (Russian Edition) (1990), 56(10):1089-92, Singh et al., *Indian Journal of Chemistry, Section B: Organic Chemistry Including Medicinal Chemistry*, (1993) 32B(2):262-5, Lipunova et al., *Mendeleev Communications* (1996), (1):15-17, Lipunova et al., *Russian Journal of Organic Chemistry* (Translation of Zhurnal Organicheskoi, Khimii) (1997), 33(10):1476-86, benzoimidazole-pyrazoles intermediates for NHE-1 inhibitors (WO9943663), N-Heteroarylimidazoles as psychopharmaceuticals (DE3824658). Additionally, 1-(1H-Benzoimidazol-2-yl)-5-methyl-1H-pyrazole-4-carboxylic acid (CAS No. 1017666-26-0), 1-(1H-benzoimidazol-2-yl)-5-hydroxy-1H-pyrazole-4-carboxylic acid ethyl ester (CAS No. 1006582-96-2), 1-(1H-benzoimidazol-2-yl)-5-pyrrol-1-yl-1H-pyrazole-4-carboxylic acid (CAS No. 1017666-37-3), and 1-(1H-benzoimidazol-2-yl)-5-(2,5-dimethyl-pyrrol-1-yl)-1H-pyrazole-4-carboxylic acid (CAS No. 1017666-50-0) are commercially available.

However, there remains a need for potent prolyl hydroxylase modulators with desirable pharmaceutical properties. Notwithstanding the above, the present invention is directed to novel benzoimidazole derivatives which are useful for this purpose.

SUMMARY OF THE INVENTION

The present invention is generally directed to compounds that are PHD inhibitors and are of the formula (I),

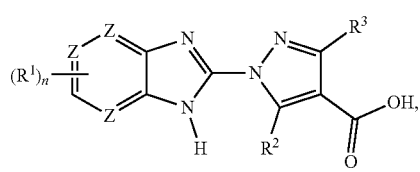

wherein:

n is 2-4;

$R^1$ is independently selected from H, halo, —$C_{1-4}$alkyl, —$C_{3-8}$cycloalkyl, —$C_{1-4}$perhaloalkyl, trifluoro$C_{1-4}$alkoxy, —OH, —$NO_2$, —CN, $CO_2$H, —O$C_{1-4}$alkyl, —S$C_{1-4}$alkyl, —S($C_{1-4}$alkyl)-$R^c$, —S$(O)_2$($C_{1-4}$alkyl)-$R^c$, —S(O)—$C_{1-4}$alkyl, —$SO_2$—$C_{1-4}$alkyl, —S—$R^c$, —S(O)—$R^c$, —$SO_2$—$R^c$, —$SO_2$—NH—$R^d$, —O—$R^c$, —$CH_2$—O—$R^c$, —C(O)NH—$R^c$, —$NR^aR^b$, benzyloxy optionally substituted with $R^d$, phenyl or monocyclic heteroaryl optionally substituted with one or more $R^d$, —$C_{3-8}$cycloalkyl optionally containing O, S or N wherein said —$C_{3-8}$cycloalkyl is optionally substituted with $R^d$, and two adjacent $R^1$ groups may be joined to form an optionally substituted 3-8 member ring optionally containing one or more O, S or N;

$R^a$ and $R^b$ are each independently H, $C_{1-4}$alkyl, —C(O)$C_{1-4}$alkyl, —C(O)—$R^c$, —C(O)$CH_2$—$R^e$, $C_{1-4}$alkyl-$R^e$, —$SO_2$—$R^c$, —$SO_2$—$C_{1-4}$alkyl, phenyl optionally substituted with $R^d$, benzyl optionally substituted with $R^d$ or monocyclic heteroaryl ring optionally substituted with $R^d$; or $R^a$ and $R^b$ can be taken together with the nitrogen to which they are attached to form an optionally substituted monocyclic heterocycloalkyl ring optionally containing one or more O, S or N;

$R^c$ is —$C_{3-8}$cycloalkyl, phenyl optionally substituted with $R^d$, benzyl optionally substituted with $R^d$, or a monocyclic heteroaryl ring optionally substituted with $R^d$;

$R^d$ is independently —H, halo, —OH, —$C_{1-4}$alkyl or —$C_{1-4}$perhaloalkyl, trifluoro$C_{1-4}$alkoxy, —O$C_{1-4}$alkyl, —O-phenyl, or —O-benzyl;

$R^e$ is —$C_{3-8}$heterocycloalkyl optionally containing one or more O, S or N;

$R^2$ and $R^3$ are both H, —$CF_3$, or —$CH_3$; and
each Z is C or N, provided that no more than two Zs can simultaneously be N; and
enantiomers, diastereomers, racemates thereof, or pharmaceutically acceptable salts thereof.

Isomeric forms of the compounds of formula (I), and of their pharmaceutically acceptable salts, are encompassed within the present invention, and reference herein to one of such isomeric forms is meant to refer to at least one of such isomeric forms. One of ordinary skill in the art will recognize that compounds according to this invention may exist, for example, in a single isomeric form whereas other compounds may exist in the form of a regioisomeric mixture.

The invention also relates to pharmaceutically acceptable salts, pharmaceutically acceptable prodrugs, and pharmaceutically active metabolites of compounds of Formula (I). In certain preferred embodiments, the compound of Formula (I) is a compound selected from those species described or exemplified in the detailed description below.

In a further general aspect, the invention relates to pharmaceutical compositions each comprising: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

In another general aspect, the invention is directed to a method of treating a subject suffering from or diagnosed with a disease, disorder, or medical condition mediated by a prolyl hydroxylase enzyme activity, comprising administering to the subject in need of such treatment an effective amount of a compound of Formula (I), or a pharmaceutically acceptable salt, pharmaceutically acceptable prodrug, or pharmaceutically active metabolite thereof.

In certain preferred embodiments of the inventive method, the disease, disorder, or medical condition is selected from: anemia, vascular disorders, metabolic disorders, and wound healing.

Additional embodiments, features, and advantages of the invention will be apparent from the following detailed description and through practice of the invention.

DETAILED DESCRIPTION

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "perhaloalkyl" refers to a straight- or branched-chain alkyl group having from 1 to 12 carbon atoms in the chain optionally substituting hydrogens with halogens. Examples of perhaloalkyl groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), trifluoroethyl ($CH_2CF_3$), and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

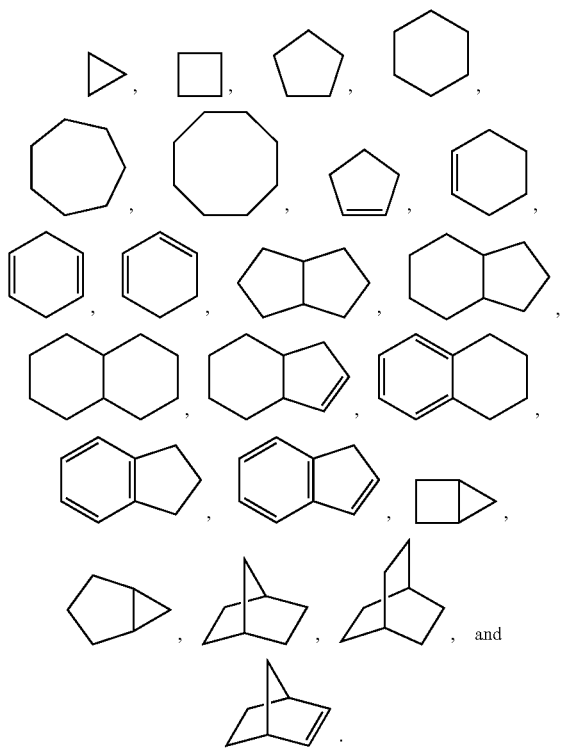

A "heterocycloalkyl" refers to a monocyclic ring structure that is saturated or partially saturated and has from 4 to 7 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

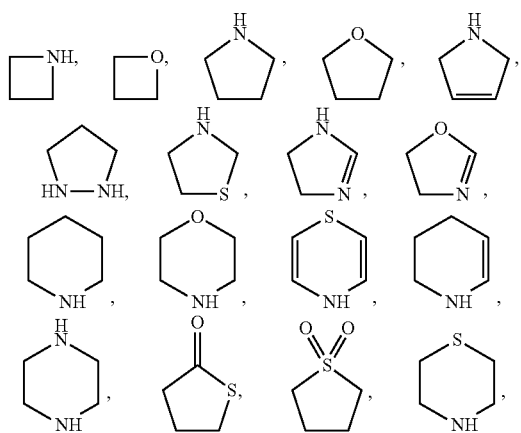

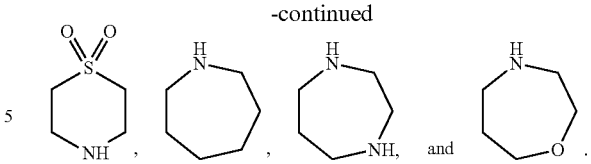

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

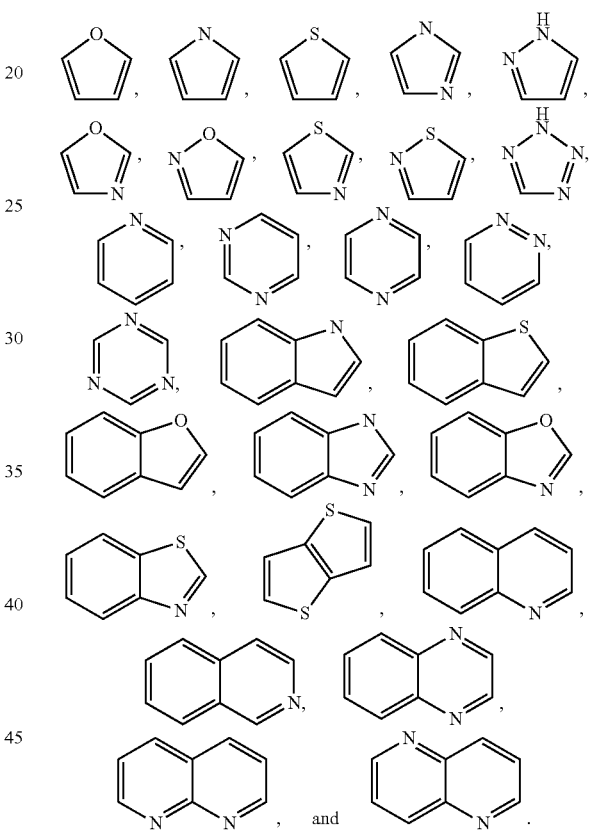

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Additionally, any formula given herein is intended to refer also to hydrates, solvates, and polymorphs of such compounds, and mixtures thereof, even if such forms are not listed explicitly. Certain compounds of Formula (I) or pharmaceutically acceptable salts of compounds of Formula (I) may be obtained as solvates. Solvates include those formed from the interaction or complexation of compounds of the invention with one or more solvents, either in solution or as a solid or crystalline form. In some embodiments, the solvent is water and then the solvates are hydrates. In addition, certain crystalline forms of compounds of Formula (I) or pharmaceutically acceptable salts of compounds of Formula (I) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^3$, A, $X^4$, $X^5$, $X^6$, $X^7$, $R^a$, $R^b$, $R^c$, $R^d$, and $R^e$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^3$, A, $X^4$, $X^5$, $X^6$, $X^7$, $R^a$, $R^b$, $R^c$, $R^d$, and $R^e$, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

Chemical depictions are intended to portray the compound portions containing the orientations as written.

The present invention is generally directed to compounds of formula (I),

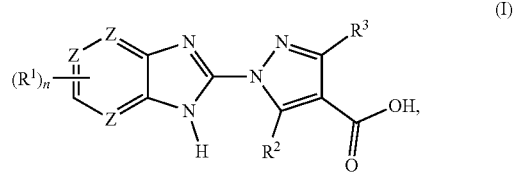

(I)

the use of compounds of Formula (I) and pharmaceutical compositions containing such compounds thereof to treat patients (humans or other mammals) with disorders related to the modulation of the prolyl hydroxylase enzyme. The instant invention also includes methods of making such a compound, pharmaceutical composition, pharmaceutically acceptable salt, pharmaceutically acceptable prodrug, and pharmaceutically active metabolites thereof.

In one preferred embodiment for Formula (I), each of $R^2$ and $R^3$ are H.

In another embodiment of Formula (I), Z is C.

In related embodiments for Formula (I), n is 4, and each $R^1$ is independently H, halo, hydroxyl, alkyl, alkoxy, thioalkyl, alkyl sulfoxide, alkyl sulfone, optionally substituted 3-8 membered aliphatic or aromatic or heterocyclic ring, amino, alkylamino, alkyl sulfonamide, aryl sulfonamide, nitro, cyano, substituted phenoxy, benzyloxy, substituted aryl sulfone, substituted aryl sulfoxide, substituted aryl sulfonyl, substituted benzyl sulfone, substituted benzyl sulfoxide, substituted benzyl sulfonyl or substituted phenylsulfamoyl.

$R^1$ can also independently be H, halo, straight- or branched-chain $C_{1-4}$alkyl, straight- or branched-chain $C_{1-4}$triflouroalkoxy, straight- or branched-chain $C_{1-4}$perhaloalkyl, or monocyclic $C_{3-8}$carbocycle saturated or partially saturated.

In another preferred embodiment, two adjacent $R^1$ groups may be joined to form an optionally substituted 3-8 member saturated or unsaturated carbocyclic or heterocyclic ring.

In other preferred embodiments for Formula (I), each $R^1$ is independently selected from the group consisting of hydrogen, —Cl, —F, —Br, —I, —$C_{1-4}$alkyl, —$CF_3$, —$C_{3-8}$ cycloalkyl, —$SC_{1-4}$alkyl, —$S(O)C_{1-4}$alkyl, —$S(O)_2C_{1-4}$ alkyl, —$OCF_3$, —$OC_{1-4}$alkyl, —CN, —$NO_2$, —$NH_2$, —NH—$C_{1-4}$alkyl, pyrrolidino, piperidino, morpholino, —$CO_2H$, —$NHS(O)_2C_{1-4}$alkyl, and —NH—$C(O)C_{1-4}$alkyl, phenyl, benzyl, phenoxy and benzyloxy.

In preferred embodiments of Formula (I), $R^1$ is H, 5,6-dichloro, 5-trifluoromethyl, 5-chloro-6-fluoro, 5,6-dimethyl, 5-bromo, 5-methoxy, 4-chloro-6-trifluoromethyl, 5,6-dimethoxy, 4,5-dimethyl, 5-trifluoromethoxy, 5-bromo, 5,6-dichloro, 5-bromo, 5,6-dichloro, 5-chloro, 5-bromo-6,7-dimethyl, 4-chloro, 5-chloro-7-trifluoromethyl, 7-bromo-5-trifluoromethoxy, 6-chloro-5-trifluoromethyl, 4,5,6-trifluoro, 4-bromo-5,6-difluoro, 6-chloro-4-methyl, 4,6-dichloro, 4-bromo-6-trifluoromethyl, 5,6-difluoro, 4-bromo-6-chloro, 6-methanesulfonyl, 5-chloro-6-cyano, 6-chloro-5-nitro, 5-amino-6-chloro, 5-fluoro, 6-chloro-5-pyrrolidin-1-yl, 6-chloro-5-piperidin-1-yl, 6-chloro-5-morpholin-4-yl, 6-chloro-5-methoxy, 4-carboxy, 5-bromo-7-fluoro, 5-bromo-7-methyl, 6-methylsulfanyl-5-trifluoromethyl, 6-propylsulfanyl-5-trifluoromethyl, 6-isopropylsulfanyl-5-trifluoromethyl, 5-fluoro-6-methylsulfanyl, 5-chloro-6-methylsulfanyl, 5-chloro-6-ethylsulfanyl, 5-chloro-6-isopropylsulfanyl, 5-chloro-6-propylsulfanyl, 6-methylsulfanyl-5-trifluoromethoxy, 6-isopropylsulfanyl-5-trifluoromethoxy, 6-propylsulfanyl-5-trifluoromethoxy, 5-chloro-6-ethanesulfinyl, 5-chloro-6-ethanesulfonyl, 6-methanesulfonyl-5-trifluoromethyl, 5-fluoro-6-methanesulfonyl, 5-chloro-6-methanesulfonyl, 6-methanesulfonyl-5-trifluoromethoxy, 5-chloro-6-(propane-2-sulfonyl), 5-chloro-6-(propane-1-sulfonyl), 6-(propane-2-sulfonyl)-5-trifluoromethyl, 6-(propane-1-sulfonyl)-5-trifluoromethyl, 6-[(1-methylethyl)sulfonyl]-5-(trifluoromethoxy), 6-(propane-2-sulfonyl)-5-trifluoromethoxy, 6-(methylsulfinyl)-5-(trifluoromethyl, 6-bromo-5-fluoro, 4-fluoro, 4,5-difluoro, 4,6-difluoro, 6-chloro-5-trifluoromethoxy, 5-fluoro-4-methyl, 5-piperidin-1-yl-6-(trifluoromethoxy, 5-fluoro-6-piperidin-1-yl, 6-ethoxy-5-fluoro, 4-bromo-6-fluoro, 5,6-bis-trifluoromethyl, 4,5,6-trichloro, 4-bromo-5,6-dichloro, 6-fluoro-5-trifluoromethyl, 6-chloro-5-ethylamino, 6-chloro-5-propylamino, 6-chloro-5-cyclopropanesulfonylamino, 6-chloro-5-methanesulfonylamino, 6-chloro-5-ethanesulfonylamino, 5-acetylamino-6-chloro, 6-chloro-5-propionylamino, 5-ethylsulfanyl-6-trifluoromethyl, 5-ethylsulfanyl-6-trifluoromethoxy, 5-ethylsulfanyl-6-fluoro, 6-fluoro-5-propylsulfanyl, 6-fluoro-5-isopropylsulfanyl, 5-ethylsulfonyl-6-trifluoromethyl, 5-ethylsulfonyl-6-trifluoromethoxy, 5-ethylsulfonyl-6-fluoro, 6-fluoro-5-propylsulfonyl, and 6-fluoro-5-isopropylsulfonyl.

In preferred embodiments of Formula (I), where each $R^1$ is independently selected from the group consisting of H, 3-(3-chloro-benzyloxy)-phenyl, 3-(2-chloro-benzyloxy)-phenyl, 3-(4-chloro-benzyloxy)-phenyl, 3-benzyloxy-phenyl, 4-benzyloxy-phenyl, 3-trifluoromethyl-phenyl, 3,4-dichlorophenyl, 4-hydroxyphenyl, 3-hydroxyphenyl, 3,4-dichloro-phenoxy)-6-trifluoromethyl, 6-chloro-5-(4-chlorophenoxy), (4-chloro-phenoxy)-6-trifluoromethoxy, 5-phenoxy-6-trifluoromethoxy, 4-fluoro-phenoxy)-6-trifluoromethyl, (4-chloro-phenoxy)-6-trifluoromethyl, 5-phenoxy-6-trifluoromethyl, 6-chloro-5-phenoxy, 5-benzyloxy-6-chloro, 6-chloro-5-m-tolylsulfanyl, 6-chloro-5-(4-chloro-phenylsulfanyl, 6-chloro-5-phenylsulfanyl, 6-chloro-5-(3,4-dichloro-phenylsulfanyl, 6-chloro-5-(3-methoxy-phenylsulfanyl, 6-chloro-5-(4-methoxy-phenylsulfanyl), 5-benzylsulfanyl-6-chloro, 4-tert-butyl-benzylsulfanyl)-6-chloro, 6-chloro-5-(4-fluoro-benzylsulfanyl, 6-chloro-5-(2-chloro-benzylsulfanyl, 6-chloro-5-phenethylsulfanyl, 6-chloro-5-(toluene-3-sulfonyl), 5-benzenesulfonyl-6-chloro, 6-chloro-5-(4-methoxy-benzenesulfonyl, 6-chloro-5-(4-chloro-benzenesulfonyl, 6-chloro-5-(4-trifluoromethoxy-benzenesulfonyl, 6-chloro-5-(3,4-dichloro-benzenesulfonyl, 6-chloro-5-(3-methoxy-benzenesulfonyl, 6-chloro-5-phenylmethanesulfonyl, 6-chloro-5-(2,4,6-trimethyl-phenylmethanesulfonyl, 6-chloro-5-(4-methoxy-phenylmethanesulfonyl, chloro-5-(4-fluoro-phenylmethanesulfonyl, 6-chloro-5-(2-chloro-phenylmethanesulfonyl, 6-chloro-5-(2-phenyl-ethanesulfonyl, 5-benzenesulfinyl-6-chloro, 5-phenylcarbamoyl, 5-benzylcarbamoyl, 5-(morpholin-4-ylcarbamoyl), 5-benzyloxymethyl, 5-benzylamino, 6-chloro-5-phenylamino, 6-chloro-5-(2-morpholin-4-yl-ethylamino), 5-benzenesulfonylamino-6-chloro, 5-benzoylamino-6-chloro, 6-chloro-5-(2-morpholin-4-yl-acetylamino), 6-chloro-5-(2-piperidin-1-yl-acetylamino), 6-chloro-5-[2-(4-methyl-piperazin-1-yl, 6-chloro-5-(4-methoxy-phenoxy), 6-chloro-5-(4-chloro-2-fluoro-phenoxy), 6-chloro-5-(4-trifluoromethoxy-phenoxy), 6-chloro-5-(3-chloro-4-fluoro-phenoxy), 5-phenylsulfanyl-6-trifluoromethyl, 5-(4-methoxy-phenylsulfanyl)-6-trifluoromethyl, 5-benzenesulfonyl-6-trifluoromethyl, 5-(4-methoxy-benzenesulfonyl)-6-trifluoromethyl, 6-chloro-5-(4-chloro-benzylsulfanyl, 6-chloro-5-(3-chloro-benzylsulfanyl), 6-chloro-5-cyclohexylmethylsulfanyl, 6-chloro-5-(2-morpholin-4-yl-ethylsulfanyl), -chloro-5-(3,4-dichloro-benzylsulfanyl, 6-chloro-5-(2,6-dichloro-benzylsulfanyl), 6-chloro-5-(4-methyl-benzylsulfanyl), 6-chloro-5-(4-trifluoromethyl-benzylsulfanyl), 5-(2,4-bis-trifluoromethyl-benzylsulfanyl)-6-chloro, 6-chloro-5-(2'-cyano-biphenyl-4-ylmethylsulfanyl), 6-chloro-5-(4-chloro-phenylmethanesulfonyl), 6-chloro-5-(3-chloro-phenylmethanesulfonyl), chloro-5-cyclohexylmethanesulfonyl, 6-chloro-5-(3,4-dichloro-phenylmethanesulfonyl), 6-chloro-5-(2,6-dichloro-phenylmethanesulfonyl), chloro-5-p-tolylmethanesulfonyl, 6-chloro-5-(4-trifluoromethyl-phenylmethanesulfonyl), 5-(2,4-bis-trifluoromethyl-benzylsulfanyl), chloro-5-(2'-cyano-biphenyl-4-ylmethanesulfonyl and 6-chloro-5-phenylsulfamoyl.

Exemplary compounds of the present invention are set forth in the Table below.

| Ex. | Chemical Name | Enzyme pIC50 | Cellular % EPO Stimulation |
|---|---|---|---|
| 1 | 1-(1H-Benzoimidazol-2-yl)-1H-pyrazole-4-carboxylic acid; | 6.1 | 7.1 |
| 2 | 1-(5,6-Dichloro-1H-benzoimidazol-2-yl)-1H-pyrazole-4-carboxylic acid; | 6.9 | 151.91 |
| 3 | 1-(5-Trifluoromethyl-1H-benzoimidazol-2-yl)-1H-pyrazole-4-carboxylic acid; | 6.6 | 109.74 |
| 4 | 1-(5-Chloro-6-fluoro-1H-benzoimidazol-2-yl)-1H-pyrazole-4-carboxylic acid; | 6.7 | 132.79 |
| 5 | 1-(5,6-Dimethyl-1H-benzoimidazol-2-yl)-1H-pyrazole-4-carboxylic acid; | 6.1 | 2.1 |
| 6 | 1-(5-Bromo-1H-benzoimidazol-2-yl)-1H-pyrazole-4-carboxylic acid; | 6.4 | 9.91 |
| 7 | 1-(5-Methoxy-1H-benzoimidazol-2-yl)-1H-pyrazole-4-carboxylic acid; | 6.4 | 16.8 |
| 8 | 1-(4-Chloro-6-trifluoromethyl-1H-benzoimidazol-2-yl)-1H-pyrazole-4-carboxylic acid; | 6.8 | 20.97 |
| 9 | 1-(5,6-Dimethoxy-1H-benzoimidazol-2-yl)-1H-pyrazole-4-carboxylic acid; | 6.4 | 4.26 |
| 10 | 1-(4,5-Dimethyl-1H-benzoimidazol-2-yl)-1H-pyrazole-4-carboxylic acid; | 5.1 | 10.7 |
| 11 | 1-(5-Trifluoromethoxy-1H-benzoimidazol-2-yl)-1H-pyrazole-4-carboxylic acid; | 6.5 | 123.68 |
| 12 | 1-{5-[3-(3-Chloro-benzyloxy)-phenyl]-1H-benzoimidazol-2-yl}-1H-pyrazole-4-carboxylic acid; | 7.5 | 8.76 |
| 13 | 1-{5-[3-(2-Chloro-benzyloxy)-phenyl]-1H-benzoimidazol-2-yl}-1H-pyrazole-4-carboxylic acid; | 7.6 | 18 |
| 14 | 1-{5-[3-(4-Chloro-benzyloxy)-phenyl]-1H-benzoimidazol-2-yl}-1H-pyrazole-4-carboxylic acid; | 7.4 | 20.15 |
| 15 | 1-[5-(3-Benzyloxy-phenyl)-1H-benzoimidazol-2-yl]-1H-pyrazole-4-carboxylic acid; | 7.3 | 10.77 |
| 16 | 1-[5-(4-Benzyloxy-phenyl)-1H-benzoimidazol-2-yl]-1H-pyrazole-4-carboxylic acid; | 6.7 | 6.97 |
| 17 | 1-[5-(3-Trifluoromethyl-phenyl)-1H-benzoimidazol-2-yl]-1H-pyrazole-4-carboxylic acid; | 7.1 | 5.8 |
| 18 | 1-[5-(3,4-Dichloro-phenyl)-1H-benzoimidazol-2-yl]-1H-pyrazole-4-carboxylic acid; | 7.1 | 15.3 |
| 19 | 1-(5-Bromo-1H-benzoimidazol-2-yl)-3-trifluoromethyl-1H-pyrazole-4-carboxylic acid; | <4 | 20.52 |
| 20 | 1-(5,6-dichloro-1H-benzoimidazol-2-yl)-3-trifluoromethyl-1H-pyrazole-4-carboxylic acid; | <4 | 18.81 |
| 21 | 1-(5-Bromo-1H-benzoimidazol-2-yl)-3,5-dimethyl-1H-pyrazole-4-carboxylic acid; | 4.2 | 7.24 |
| 22 | 1-(5,6-Dichloro-1H-benzoimidazol-2-yl)-3,5-dimethyl-1H-pyrazole-4-carboxylic acid; | <4 | 0.47 |
| 23 | 1-[5-(4-Hydroxy-phenyl)-1H-benzoimidazol-2-yl]-1H-pyrazole-4-carboxylic acid; | 6.6 | 6.49 |
| 24 | 1-[5-(3-Hydroxy-phenyl)-1H-benzoimidazol-2-yl]-1H-pyrazole-4-carboxylic acid; | 6.5 | 11.15 |
| 25 | 1-(5-Chloro-1H-benzoimidazol-2-yl)-1H-pyrazole-4-carboxylic acid; | 6.3 | 71.87 |
| 26 | 1-(5-Bromo-6,7-dimethyl-1H-benzoimidazol-2-yl)-1H-pyrazole-4-carboxylic acid; | 6.4 | 11.9 |
| 27 | 1-(4-Chloro-1H-benzoimidazol-2-yl)-1H-pyrazole-4-carboxylic acid; | 6.1 | 19.12 |
| 28 | 1-(5-Chloro-7-trifluoromethyl-1H-benzoimidazol-2-yl)-1H-pyrazole-4-carboxylic acid; | 6.4 | 16.6 |
| 29 | 1-(7-Bromo-5-trifluoromethoxy-1H-benzoimidazol-2-yl)-1H-pyrazole-4-carboxylic acid; | 6.8 | 57.55 |
| 30 | 1-(6-Chloro-5-trifluoromethyl-1H-benzoimidazol-2-yl)-1H-pyrazole-4-carboxylic acid; | 7.14 | 128.94 |
| 31 | 1-(4,5,6-Trifluoro-1H-benzoimidazol-2-yl)-1H-pyrazole-4-carboxylic acid; | 7 | 18.2 |
| 32 | 1-(4-Bromo-5,6-difluoro-1H-benzoimidazol-2-yl)-1H-pyrazole-4-carboxylic acid; | 6.7 | 33 |
| 33 | 1-(6-Chloro-4-methyl-1H-benzoimidazol-2-yl)-1H-pyrazole-4-carboxylic acid; | 6 | 13.4 |
| 34 | 1-(4,6-Dichloro-1H-benzoimidazol-2-yl)-1H-pyrazole-4-carboxylic acid; | 6.5 | 56.3 |
| 35 | 1-(4-Bromo-6-trifluoromethyl-1H-benzoimidazol-2-yl)-1H-pyrazole-4-carboxylic acid; | 6.8 | 29.7 |
| 36 | 1-(5,6-Difluoro-1H-benzoimidazol-2-yl)-1H-pyrazole-4-carboxylic acid; | 6.6 | 79.4 |
| 37 | 1-(4-Bromo-6-chloro-1H-benzoimidazol-2-yl)-1H-pyrazole-4-carboxylic acid; | 6.6 | 34.03 |
| 38 | 1-(6-Methanesulfonyl-1H-benzoimidazol-2-yl)-1H-pyrazole-4-carboxylic acid; | 7.1 | 40.93 |
| 39 | 1-(6-Chloro-5-cyano-1H-benzoimidazol-2-yl)-1H-pyrazole-4-carboxylic acid; | 7.4 | 29.93 |

-continued

| Ex. | Chemical Name | Enzyme pIC50 | Cellular % EPO Stimulation |
|---|---|---|---|
| 40 | 1-(6-Chloro-5-nitro-1H-benzoimidazol-2-yl)-1H-pyrazole-4-carboxylic acid; | 7.5 | 93.44 |
| 41 | 1-(5-Amino-6-chloro-1H-benzoimidazol-2-yl)-1H-pyrazole-4-carboxylic acid; | 6.4 | 30 |
| 42 | 1-(5-Fluoro-1H-benzoimidazol-2-yl)-1H-pyrazole-4-carboxylic acid; | 6.3 | 33.76 |
| 43 | 1-(6-Chloro-5-pyrrolidin-1-yl-1H-benzoimidazol-2-yl)-1H-pyrazole-4-carboxylic acid; | 6.7 | 177.5 |
| 44 | 1-(6-Chloro-5-piperidin-1-yl-1H-benzoimidazol-2-yl)-1H-pyrazole-4-carboxylic acid; | 6.7 | 138.8 |
| 45 | 1-(6-Chloro-5-morpholin-4-yl-1H-benzoimidazol-2-yl)-1H-pyrazole-4-carboxylic acid; | 6.6 | 30.85 |
| 46 | 1-(6-Chloro-5-methoxy-1H-benzoimidazol-2-yl)-1H-pyrazole-4-carboxylic acid; | 6.5 | 76 |
| 47 | 2-(4-Carboxy-pyrazol-1-yl)-1H-benzoimidazole-5-carboxylic acid; | 6.6 | 11 |
| 48 | 1-(5-Bromo-7-fluoro-1H-benzoimidazol-2-yl)-1H-pyrazole-4-carboxylic acid; | 6.3 | 44 |
| 49 | 1-(5-Bromo-7-methyl-1H-benzoimidazol-2-yl)-1H-pyrazole-4-carboxylic acid; | 6.1 | 24 |
| 50 | 1-[5-(3,4-Dichloro-phenoxy)-6-trifluoromethyl-1H-benzoimidazol-2-yl]-1H-pyrazole-4-carboxylic acid; | 7.4 | 17.98 |
| 51 | 1-[6-Chloro-5-(4-chloro-phenoxy)-1H-benzoimidazol-2-yl]-1H-pyrazole-4-carboxylic acid; | 7.4 | 150.4 |
| 52 | 1-[5-(4-Chloro-phenoxy)-6-trifluoromethoxy-1H-benzoimidazol-2-yl]-1H-pyrazole-4-carboxylic acid; | 7.4 | 21.55 |
| 53 | 1-(5-Phenoxy-6-trifluoromethoxy-1H-benzoimidazol-2-yl)-1H-pyrazole-4-carboxylic acid; | 7.2 | 137.71 |
| 54 | 1-[5-(4-Fluoro-phenoxy)-6-trifluoromethyl-1H-benzoimidazol-2-yl]-1H-pyrazole-4-carboxylic acid; | 7.3 | 75.52 |
| 55 | 1-[5-(4-Chloro-phenoxy)-6-trifluoromethyl-1H-benzoimidazol-2-yl]-1H-pyrazole-4-carboxylic acid; | 7.5 | 44.23 |
| 56 | 1-(5-Phenoxy-6-trifluoromethyl-1H-benzoimidazol-2-yl)-1H-pyrazole-4-carboxylic acid; | 7.2 | 142.55 |
| 57 | 1-(6-Chloro-5-phenoxy-1H-benzoimidazol-2-yl)-1H-pyrazole-4-carboxylic acid; | 6.9 | 55 |
| 58 | 1-(5-Bromo-7-methyl-1H-imidazo[4,5-f]quinolin-2-yl)-1H-pyrazole-4-carboxylic acid; | 7.2 | 50 |
| 59 | 1-(5-Benzyloxy-6-chloro-1H-benzoimidazol-2-yl)-1H-pyrazole-4-carboxylic acid; | 6.4 | 55.9 |
| 60 | 1-(6-Chloro-5-m-tolylsulfanyl-1H-benzoimidazol-2-yl)-1H-pyrazole-4-carboxylic acid; | 6.9 | 42.30 |
| 61 | 1-[6-Chloro-5-(4-chloro-phenylsulfanyl)-1H-benzoimidazol-2-yl]-1H-pyrazole-4-carboxylic acid; | 7.07 | 101.2 |
| 62 | 1-(6-Chloro-5-phenylsulfanyl-1H-benzoimidazol-2-yl)-1H-pyrazole-4-carboxylic acid; | 6.75 | 45.84 |
| 63 | 1-[6-Chloro-5-(3,4-dichloro-phenylsulfanyl)-1H-benzoimidazol-2-yl]-1H-pyrazole-4-carboxylic acid; | 6.18 | 26.54 |
| 64 | 1-[6-Chloro-5-(3-methoxy-phenylsulfanyl)-1H-benzoimidazol-2-yl]-1H-pyrazole-4-carboxylic acid; | 6.9 | 38.26 |
| 65 | 1-[6-Chloro-5-(4-methoxy-phenylsulfanyl)-1H-benzoimidazol-2-yl]-1H-pyrazole-4-carboxylic acid; | 6.6 | 56.3 |
| 66 | 1-(5-Benzylsulfanyl-6-chloro-1H-benzoimidazol-2-yl)-1H-pyrazole-4-carboxylic acid; | 6.7 | 41.64 |
| 67 | 1-[5-(4-tert-Butyl-benzylsulfanyl)-6-chloro-1H-benzoimidazol-2-yl]-1H-pyrazole-4-carboxylic acid; | 7.2 | 11.72 |
| 68 | 1-[6-Chloro-5-(4-fluoro-benzylsulfanyl)-1H-benzoimidazol-2-yl]-1H-pyrazole-4-carboxylic acid; | 6.8 | 58.37 |
| 69 | 1-[6-Chloro-5-(2-chloro-benzylsulfanyl)-1H-benzoimidazol-2-yl]-1H-pyrazole-4-carboxylic acid; | 6.8 | 85.3 |
| 70 | 1-(6-Chloro-5-phenethylsulfanyl-1H-benzoimidazol-2-yl)-1H-pyrazole-4-carboxylic acid; | 6.7 | 74.24 |
| 71 | 1-(6-Methylsulfanyl-5-trifluoromethyl-1H-benzoimidazol-2-yl)-1H-pyrazole-4-carboxylic acid; | 7.1 | 113.95 |
| 72 | 1-(6-Propylsulfanyl-5-trifluoromethyl-1H-benzoimidazol-2-yl)-1H-pyrazole-4-carboxylic acid; | 7.1 | NT |
| 73 | 1-(6-Isopropylsulfanyl-5-trifluoromethyl-1H-benzoimidazol-2-yl)-1H-pyrazole-4-carboxylic acid; | 7.2 | NT |
| 74 | 1-(5-Fluoro-6-methylsulfanyl-1H-benzoimidazol-2-yl)-1H-pyrazole-4-carboxylic acid; | 6.9 | 77.795 |
| 75 | 1-(5-Chloro-6-methylsulfanyl-1H-benzoimidazol-2-yl)-1H-pyrazole-4-carboxylic acid; | 7 | 106.17 |
| 76 | 1-(5-Chloro-6-ethylsulfanyl-1H-benzoimidazol-2-yl)-1H-pyrazole-4-carboxylic acid; | 6.9 | 211.75 |
| 77 | 1-(5-Chloro-6-isopropylsulfanyl-1H-benzoimidazol-2-yl)-1H-pyrazole-4-carboxylic acid; | 6.8 | 152.89 |

-continued

| Ex. | Chemical Name | Enzyme pIC50 | Cellular % EPO Stimulation |
|---|---|---|---|
| 78 | 1-(5-Chloro-6-propylsulfanyl-1H-benzoimidazol-2-yl)-1H-pyrazole-4-carboxylic acid; | 7 | 125.21 |
| 79 | 1-(6-Methylsulfanyl-5-trifluoromethoxy-1H-benzoimidazol-2-yl)-1H-pyrazole-4-carboxylic acid; | 7.1 | 83.83 |
| 80 | 1-(6-Isopropylsulfanyl-5-trifluoromethoxy-1H-benzoimidazol-2-yl)-1H-pyrazole-4-carboxylic acid; | 7 | NT |
| 81 | 1-(6-Propylsulfanyl-5-trifluoromethoxy-1H-benzoimidazol-2-yl)-1H-pyrazole-4-carboxylic acid; | 7 | NT |
| 82 | 1-[6-Chloro-5-(toluene-3-sulfonyl)-1H-benzoimidazol-2-yl]-1H-pyrazole-4-carboxylic acid; | 7.4 | 85.32 |
| 83 | 1-(5-Benzenesulfonyl-6-chloro-1H-benzoimidazol-2-yl)-1H-pyrazole-4-carboxylic acid; | 7.57 | 96.65 |
| 84 | 1-[6-Chloro-5-(4-methoxy-benzenesulfonyl)-1H-benzoimidazol-2-yl]-1H-pyrazole-4-carboxylic acid; | 7.3 | 42.71 |
| 85 | 1-[6-Chloro-5-(4-chloro-benzenesulfonyl)-1H-benzoimidazol-2-yl]-1H-pyrazole-4-carboxylic acid; | 7.3 | 51.64 |
| 86 | 1-[6-Chloro-5-(4-trifluoromethoxy-benzenesulfonyl)-1H-benzoimidazol-2-yl]-1H-pyrazole-4-carboxylic acid; | 7.3 | 48.9 |
| 87 | 1-[6-Chloro-5-(3,4-dichloro-benzenesulfonyl)-1H-benzoimidazol-2-yl]-1H-pyrazole-4-carboxylic acid; | 6.68 | 32.39 |
| 88 | 1-[6-Chloro-5-(3-methoxy-benzenesulfonyl)-1H-benzoimidazol-2-yl]-1H-pyrazole-4-carboxylic acid; | 7.4 | 69.43 |
| 89 | 1-(6-Chloro-5-phenylmethanesulfonyl-1H-benzoimidazol-2-yl)-1H-pyrazole-4-carboxylic acid; | 7.5 | 28.45 |
| 90 | 1-[6-Chloro-5-(2,4,6-trimethyl-phenylmethanesulfonyl)-1H-benzoimidazol-2-yl]-1H-pyrazole-4-carboxylic acid; | 7.3 | 8.25 |
| 91 | 1-[6-Chloro-5-(4-methoxy-phenylmethanesulfonyl)-1H-benzoimidazol-2-yl]-1H-pyrazole-4-carboxylic acid; | 7.7 | 22.01 |
| 92 | 1-[6-Chloro-5-(4-fluoro-phenylmethanesulfonyl)-1H-benzoimidazol-2-yl]-1H-pyrazole-4-carboxylic acid; | 7.5 | 61.2 |
| 93 | 1-[6-Chloro-5-(2-chloro-phenylmethanesulfonyl)-1H-benzoimidazol-2-yl]-1H-pyrazole-4-carboxylic acid; | 7.5 | 78.5 |
| 94 | 1-[6-Chloro-5-(2-phenyl-ethanesulfonyl)-1H-benzoimidazol-2-yl]-1H-pyrazole-4-carboxylic acid; | 7.4 | 65.1 |
| 95 | 1-(5-Chloro-6-ethanesulfinyl-1H-benzoimidazol-2-yl)-1H-pyrazole-4-carboxylic acid; | 7.2 | 46.3 |
| 96 | 1-(5-Chloro-6-ethanesulfonyl-1H-benzoimidazol-2-yl)-1H-pyrazole-4-carboxylic acid; | 7.4 | 67 |
| 97 | 1-(6-Methanesulfonyl-5-trifluoromethyl-1H-benzoimidazol-2-yl)-1H-pyrazole-4-carboxylic acid; | 7.6 | 75.88 |
| 98 | 1-(5-Fluoro-6-methanesulfonyl-1H-benzoimidazol-2-yl)-1H-pyrazole-4-carboxylic acid; | 7.3 | 41.37 |
| 99 | 1-(5-Chloro-6-methanesulfonyl-1H-benzoimidazol-2-yl)-1H-pyrazole-4-carboxylic acid; | 7.4 | 34.85 |
| 100 | 1-(6-Methanesulfonyl-5-trifluoromethoxy-1H-benzoimidazol-2-yl)-1H-pyrazole-4-carboxylic acid; | 7.5 | 50.16 |
| 101 | 1-[5-Chloro-6-(propane-2-sulfonyl)-1H-benzoimidazol-2-yl]-1H-pyrazole-4-carboxylic acid; | 7.3 | 62.2 |
| 102 | 1-[5-Chloro-6-(propane-1-sulfonyl)-1H-benzoimidazol-2-yl]-1H-pyrazole-4-carboxylic acid; | 7.5 | 54.94 |
| 103 | 1-[6-(Propane-2-sulfonyl)-5-trifluoromethyl-1H-benzoimidazol-2-yl]-1H-pyrazole-4-carboxylic acid; | 7.4 | NT |
| 104 | 1-[6-(Propane-1-sulfonyl)-5-trifluoromethyl-1H-benzoimidazol-2-yl]-1H-pyrazole-4-carboxylic acid; | 7.5 | NT |
| 105 | 1-[6-(Propane-2-sulfonyl)-5-trifluoromethoxy-1H-benzoimidazol-2-yl]-1H-pyrazole-4-carboxylic acid; | 7.4 | NT |
| 106 | 1-[6-(Propane-1-sulfonyl)-5-trifluoromethoxy-1H-benzoimidazol-2-yl]-1H-pyrazole-4-carboxylic acid; | 7.5 | 123.7 |
| 107 | 1-(5-Benzenesulfinyl-6-chloro-1H-benzoimidazol-2-yl)-1H-pyrazole-4-carboxylic acid; | 7.2 | 47.57 |
| 108 | 1-(6-Methanesulfinyl-5-trifluoromethyl-1H-benzoimidazol-2-yl)-1H-pyrazole-4-carboxylic acid; | 7.3 | 20.41 |
| 109 | 1-(6-Bromo-5-fluoro-1H-benzoimidazol-2-yl)-1H-pyrazole-4-carboxylic acid; | 6.7 | 99 |
| 110 | 1-(4-Fluoro-1H-benzoimidazol-2-yl)-1H-pyrazole-4-carboxylic acid; | 6.2 | 45.87 |
| 111 | 1-(4,5-Difluoro-1H-benzoimidazol-2-yl)-1H-pyrazole-4-carboxylic acid; | 6.6 | 32.58 |
| 112 | 1-(4,6-Difluoro-1H-benzoimidazol-2-yl)-1H-pyrazole-4-carboxylic acid; | 6.8 | 31.96 |
| 113 | 1-(6-Chloro-5-trifluoromethoxy-1H-benzoimidazol-2-yl)-1H-pyrazole-4-carboxylic acid; | 6.98 | 109.33 |
| 114 | 1-(1H-Naphtho[2,3-d]imidazol-2-yl)-1H-pyrazole-4-carboxylic acid; | 6.3 | 144.2 |
| 115 | 1-(3H-Naphtho[1,2-d]imidazol-2-yl)-1H-pyrazole-4-carboxylic acid; | 6.1 | 50 |

-continued

| Ex. | Chemical Name | Enzyme pIC50 | Cellular % EPO Stimulation |
|---|---|---|---|
| 116 | 1-(5-Fluoro-4-methyl-1H-benzoimidazol-2-yl)-1H-pyrazole-4-carboxylic acid; | 5.8 | 18.3 |
| 117 | 1-(5-Piperidin-1-yl-6-trifluoromethoxy-1H-benzoimidazol-2-yl)-1H-pyrazole-4-carboxylic acid | 6.5 | 80 |
| 118 | 1-(5-Fluoro-6-piperidin-1-yl-1H-benzoimidazol-2-yl)-1H-pyrazole-4-carboxylic acid; | 6.8 | 152 |
| 119 | 1-(6-Ethoxy-5-fluoro-1H-benzoimidazol-2-yl)-1H-pyrazole-4-carboxylic acid; | 6.5 | 69 |
| 120 | 1-(5-Phenylcarbamoyl-1H-benzoimidazol-2-yl)-1H-pyrazole-4-carboxylic acid; | 6.9 | 21.15 |
| 121 | 1-(5-Benzylcarbamoyl-1H-benzoimidazol-2-yl)-1H-pyrazole-4-carboxylic acid; | 7.1 | 18.5 |
| 122 | 1-[5-(Morpholin-4-ylcarbamoyl)-1H-benzoimidazol-2-yl]-1H-pyrazole-4-carboxylic acid; | 6.6 | 5.4 |
| 123 | 1-(5-Benzyloxymethyl-1H-benzoimidazol-2-yl)-1H-pyrazole-4-carboxylic acid; | 6.3 | 61.15 |
| 124 | 1-(4-Bromo-6-fluoro-1H-benzoimidazol-2-yl)-1H-pyrazole-4-carboxylic acid; | 6.3 | 2.4 |
| 125 | 1-(8H-Imidazo[4′,5′:3,4]benzo[2,1-d]thiazol-7-yl)-1H-pyrazole-4-carboxylic acid; | 6 | 46.75 |
| 126 | 1-(5,6-Bis-trifluoromethyl-1H-benzoimidazol-2-yl)-1H-pyrazole-4-carboxylic acid; | 7.4 | 82.65 |
| 127 | 1-(4,5,6-Trichloro-1H-benzoimidazol-2-yl)-1H-pyrazole-4-carboxylic acid; | 6.9 | 70.6 |
| 128 | 1-(4-Bromo-5,6-dichloro-1H-benzoimidazol-2-yl)-1H-pyrazole-4-carboxylic acid; | 7.1 | 24.1 |
| 129 | 1-(6-Fluoro-5-trifluoromethyl-1H-benzoimidazol-2-yl)-1H-pyrazole-4-carboxylic acid; | 7 | 70.8 |
| 130 | 1-(6-Chloro-5-ethylamino-1H-benzoimidazol-2-yl)-1H-pyrazole-4-carboxylic acid; | 6.2 | 48 |
| 131 | 1-(6-Chloro-5-propylamino-1H-benzoimidazol-2-yl)-1H-pyrazole-4-carboxylic acid; | 6.5 | 89 |
| 132 | 1-(5-Benzylamino-6-chloro-1H-benzoimidazol-2-yl)-1H-pyrazole-4-carboxylic acid; | 6.2 | 52.6 |
| 133 | 1-(6-Chloro-5-phenylamino-1H-benzoimidazol-2-yl)-1H-pyrazole-4-carboxylic acid; | 6.9 | 77 |
| 134 | 1-[6-Chloro-5-(2-morpholin-4-yl-ethylamino)-1H-benzoimidazol-2-yl]-1H-pyrazole-4-carboxylic acid; | 6.3 | 56.5 |
| 135 | 1-(6-Chloro-5-cyclopropanesulfonylamino-1H-benzoimidazol-2-yl)-1H-pyrazole-4-carboxylic acid; | 6.8 | 17 |
| 136 | 1-(6-Chloro-5-methanesulfonylamino-1H-benzoimidazol-2-yl)-1H-pyrazole-4-carboxylic acid; | 6.8 | 9 |
| 137 | 1-(6-Chloro-5-ethanesulfonylamino-1H-benzoimidazol-2-yl)-1H-pyrazole-4-carboxylic acid; | 6.6 | 11 |
| 138 | 1-(5-Benzenesulfonylamino-6-chloro-1H-benzoimidazol-2-yl)-1H-pyrazole-4-carboxylic acid; | 6.8 | 19 |
| 139 | 1-(5-Acetylamino-6-chloro-1H-benzoimidazol-2-yl)-1H-pyrazole-4-carboxylic acid; | 6.3 | 24 |
| 140 | 1-(6-Chloro-5-propionylamino-1H-benzoimidazol-2-yl)-1H-pyrazole-4-carboxylic acid; | 6.4 | 10 |
| 141 | 1-(5-Benzoylamino-6-chloro-1H-benzoimidazol-2-yl)-1H-pyrazole-4-carboxylic acid; | 6.6 | 33 |
| 142 | 1-[6-Chloro-5-(2-morpholin-4-yl-acetylamino)-1H-benzoimidazol-2-yl]-1H-pyrazole-4-carboxylic acid; | 6.4 | 17 |
| 143 | 1-[6-Chloro-5-(2-piperidin-1-yl-acetylamino)-1H-benzoimidazol-2-yl]-1H-pyrazole-4-carboxylic acid; | 6.2 | 20 |
| 144 | 1-{6-Chloro-5[2-(4-methyl-piperazin-1-yl)-acetylamino]-1H-benzoimidazol-2-yl}-1H-pyrazole-4-carboxylic acid; | 6.4 | 16 |
| 145 | 1-[6-Chloro-5-(4-methoxy-phenoxy)-1H-benzoimidazol-2-yl]-1H-pyrazole-4-carboxylic acid; | 7.1 | 13.92 |
| 146 | 1-[6-Chloro-5-(4-chloro-2-fluoro-phenoxy)-1H-benzoimidazol-2-yl]-1H-pyrazole-4-carboxylic acid; | 7.2 | 49.85 |
| 147 | 1-[6-Chloro-5-(4-trifluoromethoxy-phenoxy)-1H-benzoimidazol-2-yl]-1H-pyrazole-4-carboxylic acid; | 7.4 | 45.85 |
| 148 | 1-[6-Chloro-5-(3-chloro-4-fluoro-phenoxy)-1H-benzoimidazol-2-yl]-1H-pyrazole-4-carboxylic acid; | 7.1 | 38.12 |
| 149 | 1-(5-Ethylsulfanyl-6-trifluoromethyl-1H-benzoimidazol-2-yl)-1H-pyrazole-4-carboxylic acid; | 7.3 | 57.8 |
| 150 | 1-(5-Ethylsulfanyl-6-trifluoromethoxy-1H-benzoimidazol-2-yl)-1H-pyrazole-4-carboxylic acid; | 7.2 | 47.2 |
| 151 | 1-(5-Ethylsulfanyl-6-fluoro-1H-benzoimidazol-2-yl)-1H-pyrazole-4-carboxylic acid; | 6.9 | 106.61 |
| 152 | 1-(6-Fluoro-5-propylsulfanyl-1H-benzoimidazol-2-yl)-1H-pyrazole-4-carboxylic acid; | 6.9 | 91.38 |
| 153 | 1-(6-Fluoro-5-isopropylsulfanyl-1H-benzoimidazol-2-yl)-1H-pyrazole-4-carboxylic acid; | 6.9 | NT |

-continued

| Ex. Chemical Name | Enzyme pIC50 | Cellular % EPO Stimulation |
|---|---|---|
| 154 1-(5-Ethylsulfonyl-6-trifluoromethyl-1H-benzoimidazol-2-yl)-1H-pyrazole-4-carboxylic acid; | 7.6 | 53.82 |
| 155 1-(5-Ethylsulfonyl-6-trifluoromethoxy-1H-benzoimidazol-2-yl)-1H-pyrazole-4-carboxylic acid; | 7.6 | 47.21 |
| 156 1-(5-Ethylsulfonyl-6-fluoro-1H-benzoimidazol-2-yl)-1H-pyrazole-4-carboxylic acid; | 7.4 | 51.9 |
| 157 1-(6-Fluoro-5-propylsulfonyl-1H-benzoimidazol-2-yl)-1H-pyrazole-4-carboxylic acid; | 7.4 | NT |
| 158 1-(6-Fluoro-5-isopropylsulfonyl-1H-benzoimidazol-2-yl)-1H-pyrazole-4-carboxylic acid; | 7.3 | NT |
| 159 1-(5-Phenylsulfanyl-6-trifluoromethyl-1H-benzoimidazol-2-yl)-1H-pyrazole-4-carboxylic acid; | 7.4 | 11.01 |
| 160 1-[5-(4-Methoxy-phenylsulfanyl)-6-trifluoromethyl-1H-benzoimidazol-2-yl]-1H-pyrazole-4-carboxylic acid; | 7.5 | 36.1 |
| 161 1-(5-Benzenesulfonyl-6-trifluoromethyl-1H-benzoimidazol-2-yl)-1H-pyrazole-4-carboxylic acid; | 7.6 | 98.15 |
| 162 1-[5-(4-Methoxy-benzenesulfonyl)-6-trifluoromethyl-1H-benzoimidazol-2-yl]-1H-pyrazole-4-carboxylic acid; | 7.6 | 45.8 |
| 163 1-[6-Chloro-5-(4-chloro-benzylsulfanyl)-1H-benzoimidazol-2-yl]-1H-pyrazole-4-carboxylic acid; | 6.5 | 36.98 |
| 164 1-[6-Chloro-5-(3-chloro-benzylsulfanyl)-1H-benzoimidazol-2-yl]-1H-pyrazole-4-carboxylic acid; | 6.6 | 27.4 |
| 165 1-(6-Chloro-5-cyclohexylmethylsulfanyl-1H-benzoimidazol-2-yl)-1H-pyrazole-4-carboxylic acid; | 6.9 | 27.3 |
| 166 1-[6-Chloro-5-(2-morpholin-4-yl-ethylsulfanyl)-1H-benzoimidazol-2-yl]-1H-pyrazole-4-carboxylic acid; | 7 | 15.1 |
| 167 1-[6-Chloro-5-(3,4-dichloro-benzylsulfanyl)-1H-benzoimidazol-2-yl]-1H-pyrazole-4-carboxylic acid; | 6.4 | 25.8 |
| 168 1-[6-Chloro-5-(2,6-dichloro-benzylsulfanyl)-1H-benzoimidazol-2-yl]-1H-pyrazole-4-carboxylic acid; | 7.3 | 50.14 |
| 169 1-[6-Chloro-5-(4-methyl-benzylsulfanyl)-1H-benzoimidazol-2-yl]-1H-pyrazole-4-carboxylic acid; | 6.7 | NT |
| 170 1-[6-Chloro-5-(4-trifluoromethyl-benzylsulfanyl)-1H-benzoimidazol-2-yl]-1H-pyrazole-4-carboxylic acid; | 6.7 | NT |
| 171 1-[5-(2,4-Bis-trifluoromethyl-benzylsulfanyl)-6-chloro-1H-benzoimidazol-2-yl]-1H-pyrazole-4-carboxylic acid; | 6.7 | NT |
| 172 1-[6-Chloro-5-(2'-cyano-biphenyl-4-ylmethylsulfanyl)-1H-benzoimidazol-2-yl]-1H-pyrazole-4-carboxylic acid; | 7.5 | NT |
| 173 1-[6-Chloro-5-(4-chloro-phenylmethanesulfonyl)-1H-benzoimidazol-2-yl]-1H-pyrazole-4-carboxylic acid; | 7.8 | 60.41 |
| 174 1-[6-Chloro-5-(3-chloro-phenylmethanesulfonyl)-1H-benzoimidazol-2-yl]-1H-pyrazole-4-carboxylic acid; | 7.6 | 40.9 |
| 175 1-(6-Chloro-5-cyclohexylmethanesulfonyl-1H-benzoimidazol-2-yl)-1H-pyrazole-4-carboxylic acid; | 7.7 | 48.7 |
| 176 1-[6-Chloro-5-(3,4-dichloro-phenylmethanesulfonyl)-1H-benzoimidazol-2-yl]-1H-pyrazole-4-carboxylic acid; | 7.6 | 44.23 |
| 177 1-[6-Chloro-5-(2,6-dichloro-phenylmethanesulfonyl)-1H-benzoimidazol-2-yl]-1H-pyrazole-4-carboxylic acid; | 7.5 | 66.6 |
| 178 1-(6-Chloro-5-p-tolylmethanesulfonyl-1H-benzoimidazol-2-yl)-1H-pyrazole-4-carboxylic acid; | 7.7 | NT |
| 179 1-[6-Chloro-5-(4-trifluoromethyl-phenylmethanesulfonyl 1H-benzoimidazol-2-yl]-1H-pyrazole-4-carboxylic acid; | 7.7 | NT |
| 180 1-[5-(2,4-Bis-trifluoromethyl-phenylmethanesulfonyl)-6-chloro-1H-benzoimidazol-2-yl]-1H-pyrazole-4-carboxylic acid; | 7.6 | NT |
| 181 1-[6-Chloro-5-(2'-cyano-biphenyl-4-ylmethanesulfonyl)-1H-benzoimidazol-2-yl]-1H-pyrazole-4-carboxylic acid; | 7.7 | NT |
| 182 1-(1H-Imidazo[4,5-b]quinoxalin-2-yl)-1H-pyrazole-4-carboxylic acid; | 5.5 | 13.4 |
| 183 1-(6,7-Dichloro-1H-imidazo[4,5-b]quinoxalin-2-yl)-1H-pyrazole-4-carboxylic acid; | 6.4 | 3.3 |
| 184 1-(1H-Imidazo[4,5-b]pyrazin-2-yl)-1H-pyrazole-4-carboxylic acid; | 5.9 | 8.3 |
| 185 1-(6-Chloro-9H-purin-8-yl)-1H-pyrazole-4-carboxylic acid and | 5.3 | 11.7 |
| 186 1-(6-Chloro-5-phenylsulfamoyl-1H-benzoimidazol-2-yl)-1H-pyrazole-4-carboxylic acid. | 7.4 | 39.1 |

The invention also includes pharmaceutically acceptable salts of the compounds of Formula (I), preferably of those described above and of the specific compounds exemplified herein, and methods of treatment using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.,* 1977, 66:1-19, and *Handbook of Pharmaceutical Salts, Properties, Selection, and Use,* Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$ alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy) methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Greenwald, et al., *J Med Chem.* 1996, 39, 10, 1938-40. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I), which may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites of the present invention are useful as modulators of PHD in the methods of the invention. "Modulators" include both inhibitors and activators, where "inhibitors" refer to compounds that decrease, prevent, inactivate, desensitize or down-regulate PHD expression or activity, and "activators" are compounds that increase, activate, facilitate, sensitize, or up-regulate PHD expression or activity.

The term "treat" or "treating" as used herein is intended to refer to administration of an active agent or composition of the invention to a subject for the purpose of effecting a therapeutic or prophylactic benefit through modulation of prolyl hydroxylase activity. Treating includes reversing, ameliorating, alleviating, inhibiting the progress of, lessening the severity of, or preventing a disease, disorder, or condition, or one or more symptoms of such disease, disorder or condition mediated through modulation of PHD activity. The term "subject" refers to a mammalian patient in need of such treatment, such as a human.

Accordingly, the invention relates to methods of using the compounds described herein to treat subjects diagnosed with or suffering from a disease, disorder, or condition mediated by Prolyl Hydroxylase, such as: Anemia, vascular disorders, metabolic disorders, and wound healing. Symptoms or disease states are intended to be included within the scope of "medical conditions, disorders, or diseases."

As used herein the term "hypoxia" or "hypoxic disorder" refers to a condition where there is an insufficient level of oxygen provided in the blood or to tissues and organs. Hypoxic disorders can occur through a variety of mechanisms including where there is an insufficient capacity of the blood to carry oxygen (i.e. anemia), where there is an inadequate flow of blood to the tissue and/or organ caused by either heart failure or blockage of blood vessels and/or arteries (i.e. ischemia), where there is reduced barometric pressure (i.e. elevation sickness at high altitudes), or where dysfunctional cells are unable to properly make use of oxygen (i.e. hystotoxic conditions). Accordingly, one of skill in the art would readily appreciate the present invention to be useful in the treatment of a variety of hypoxic conditions including anemia, heart failure, coronary artery disease, thromboembolism, stroke, angina and the like.

In a preferred embodiment, molecules of the present invention are useful in the treatment or prevention of anemia comprising treatment of anemic conditions associated with chronic kidney disease, polycystic kidney disease, aplastic anemia, autoimmune hemolytic anemia, bone marrow transplantation anemia, Churg-Strauss syndrome, Diamond Blackfan anemia, Fanconi's anemia, Felty syndrome, graft versus host disease, hematopoietic stem cell transplantation, hemolytic uremic syndrome, myelodysplastic syndrome, nocturnal paroxysmal hemoglobinuria, osteomyelofibrosis, pancytopenia, pure red-cell aplasia, purpura Schoenlein-Henoch, refractory anemia with excess of blasts, rheumatoid arthritis, Shwachman syndrome, sickle cell disease, thalassemia major, thalassemia minor, thrombocytopenic purpura, anemic or non-anemic patients undergoing surgery, anemia associated with or secondary to trauma, sideroblastic anemia, anemic secondary to other treatment including: reverse transcriptase inhibitors to treat HIV, corticosteroid hormones, cyclic cisplatin or non-cisplatin-containing chemotherapeutics, vinca alkaloids, mitotic inhibitors, topoisomerase II inhibitors, anthracyclines, alkylating agents, particularly anemia secondary to inflammatory, aging and/or chronic diseases. PHD inhibition may also be used to treat symptoms of anemia including chronic fatigue, pallor and dizziness.

In another preferred embodiment, molecules of the present invention are useful for the treatment or prevention of diseases of metabolic disorders, including but not limited to diabetes and obesity. In another preferred embodiment, molecules of the present invention are useful for the treatment or prevention of vascular disorders. These include but are not limited to hypoxic or wound healing related diseases requiring pro-angiogenic mediators for vasculogenesis, angiogenesis, and arteriogenesis In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the agents of the invention may be used in combination with additional active ingredients in the treatment of the above conditions. The additional compounds may be co-administered separately with an agent of Formula (I) or included with such an agent as an additional active ingredient in a pharmaceutical composition according to the invention. In an exemplary embodiment, additional active ingredients are those that are known or discovered to be effective in the treatment of conditions, disorders, or diseases mediated by PHD enzyme or that are active against another targets associated with the particular condition, disorder, or disease, such as an alternate PHD modulator. The combination may serve to increase efficacy (e.g., by including in the combination a compound potentiating the potency or effectiveness of a compound according to the invention), decrease one or more side effects, or decrease the required dose of the compound according to the invention.

The compounds of the invention are used, alone or in combination with one or more other active ingredients, to formulate pharmaceutical compositions of the invention. A pharmaceutical composition of the invention comprises: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols. Suitable excipients may also include antioxidants. Such antioxidants may be used in a pharmaceutical composition or in a storage medium to prolong the shelf-life of the drug product.

Delivery forms of the pharmaceutical compositions containing one or more dosage units of the compounds of the invention may be prepared using suitable pharmaceutical excipients and compounding techniques now or later known or available to those skilled in the art. The compositions may be administered in the inventive methods by oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration. A preferred mode of use of the invention is local administration of PHD inhibitors particularly to sites where tissue has become or has been made ischemic. This may be achieved via a specialized catheter, angioplasty balloon or stent placement balloon.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl disteatate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Abbreviations and acronyms used herein including the following:

| Term | Acronym |
| --- | --- |
| Diisopropylethylamine | DIEA |
| Tetrahydrofuran | THF |
| Dichloromethane | DCM |
| Dimethyl Sulfoxide | DMSO |
| 2-Methoxyethoxymethyl chloride | MEMCl or MEMchloride |
| N,N-Dimethylformamide | DMF |
| Ethanol | EtOH |
| Acetonitrile | ACN |
| Ethyl Acetate | EtOAc |
| N-(3-Dimethylaminopropyl)-N-ethylcarbodiimide | EDCl |
| 1,8-Diazabicyclo[5.4.0]undec-7-ene | DBU |
| Dichloroethane | DCE |
| 1,2,3,4,5-Pentaphenyl-1'-(di-t-butylphosphino)ferrocene | Q-Phose ® |
| N-Chlorosuccinimide | NCS |
| N-Bromosuccinimide | NBS |

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may also be conducted in sealed pressure vessels above the normal reflux temperature of the solvent.

Within each scheme provided herein, numbers for each formula are presented for convenience only. Although generally specific to the respective scheme, these references however should not be considered limiting and each scheme, including all of its elements, are broadly applicable for various embodiments of the present invention.

Scheme A

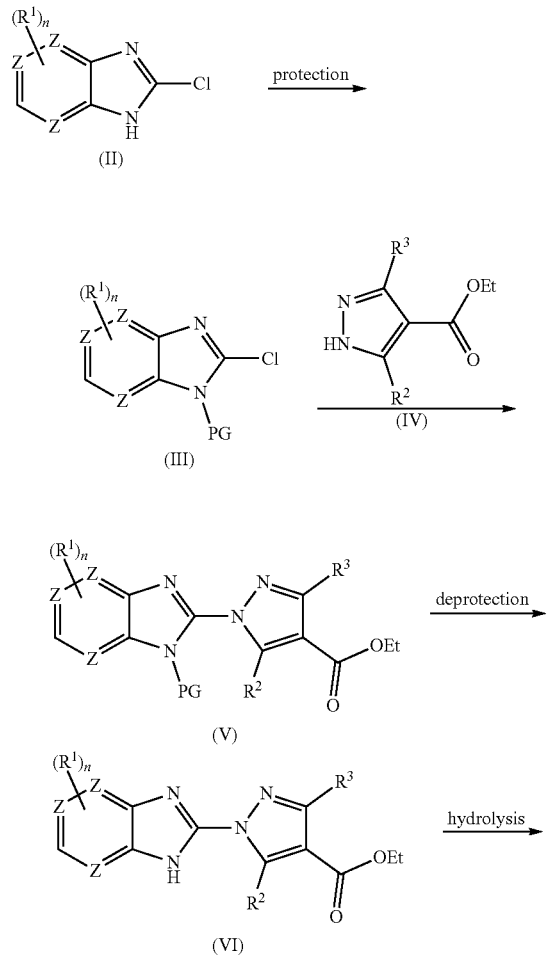

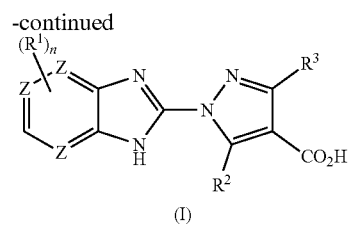

Referring to Scheme A, protection of 2-chloro-1H-benzoimidazoles (II), is achieved using a suitable protecting group reagent such as 2-methoxyethoxymethyl chloride (MEMCl) or 2-(trimethysilyl)-ethoxymethyl chloride (SEMCl) in the presence of a base such as NaH or DIPEA in a solvent such as THF to provide compounds of formula (III). Displacement of the 2-chloro substituent with commercially available pyrazole-4-carboxylates of formula (IV), where $R^2$ and $R^3$ are both H, $CF_3$ or $CH_3$, is accomplished in a polar aprotic solvent such as DMF, N,N-dimethylacetamide (DMA), or THF, or a mixture thereof, in the presence of a suitable base such as $Cs_2CO_3$, $K_2CO_3$, $Na_2CO_3$, NaH, or a mixture thereof at elevated temperatures generally ranging between 80° C. and 120° C. Subsequent deprotection of PG using an acid such as HCl in an appropriate solvent such as EtOH provides intermediates of formula (VIII). Saponification with a suitable base such as aq. NaOH, aq. LiOH or aq. KOH or a mixture thereof in a solvent such as THF provides compounds of Formula (I).

Scheme B

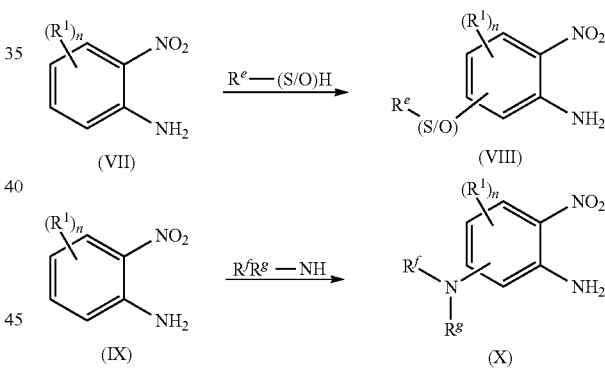

Aryl ether and aryl thioether intermediates of formula (VIII) are prepared according to Scheme B, where each $R^1$ can be H, —Cl, —F, —$CF_3$, or —$OCF_3$ provided that at least one $R^1$ is —Cl or —F. Commercially available substituted halo-nitro-phenylamines (VII) are reacted with substituted phenols, thiophenols, and substituted phenyl-alkylthiols in the presence of a base such as $K_2CO_3$, in a solvent such as DMF and the like, at temperatures between room temperature and the reflux temperature of the solvent, to provide nitro intermediates of formula (VIII), where $R^e$ is an aryl, —$C_{1-4}$alkyl-aryl, or heteroaryl ring. Alkyl ether and thioalkyl ether intermediates of formula (VIII), where $R^e$ is a $C_{1-6}$alkyl (branched or straight chain), are prepared by the reaction of optionally substituted halo-nitro-phenylamines with alcohols and alkylthiols in the presence of a base such as sodium methoxide, sodium-tert-butoxide, and the like, in a solvent such as MeOH, at temperatures ranging from room temperature to the reflux temperature of the solvent. Reactions may also be performed in a sealed tube at temperatures above the reflux temperature of the solvent. Thioalkyl intermediates of formula (VIII), are also synthesized by the reaction of optionally substituted halo-nitro phenylamines of formula (VII) with sodium thiomethoxide, sodium thioethoxide, sodium thioisopropoxide and the like, in a solvent such as DMF, at temperatures ranging from 80° C. to 100° C.

Amino intermediates of formula (X) are prepared according to Scheme B, where $R^1$ is H, —Cl, —F, —CF$_3$, or —OCF$_3$. Substituted halo-nitro-phenylamines (IX) and cycloalkyl and heterocycloalkyl amines are heated in a sealed tube at temperatures ranging from 80° C. to 100° C., to provide nitro intermediates of formula (X).

more $R^1$s are H, —Cl, —CN, —F and —CF$_3$, are reacted with acetic anhydride in a solvent such as toluene, in the presence of a base such as DMAP, at temperatures ranging from room temperature to the boiling point of the solvent, to afford acetylated intermediates of formula (XII). Subsequent nitration is achieved by reacting intermediates of formula (XII) with a nitrating reagent such as KNO$_3$ and an acid such as sulfuric acid, at 0° C., to afford nitrated intermediates of formula (XIII). Subsequent deprotection of the acetyl group with aqueous acid such as hydrochloric acid under heating affords nitro anilines of the formula (XIV).

Scheme C

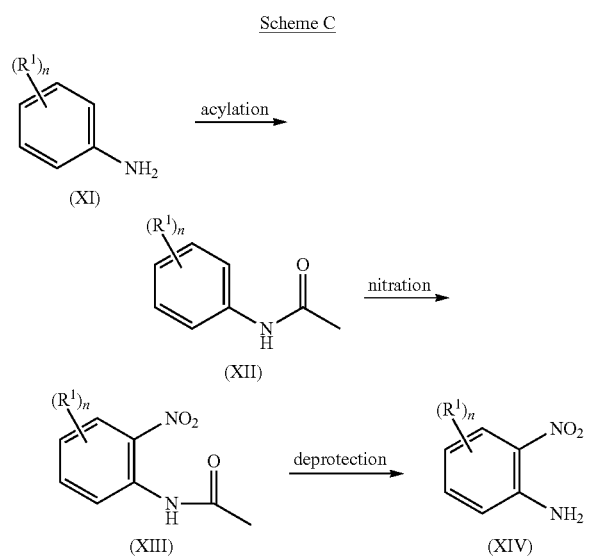

Scheme D

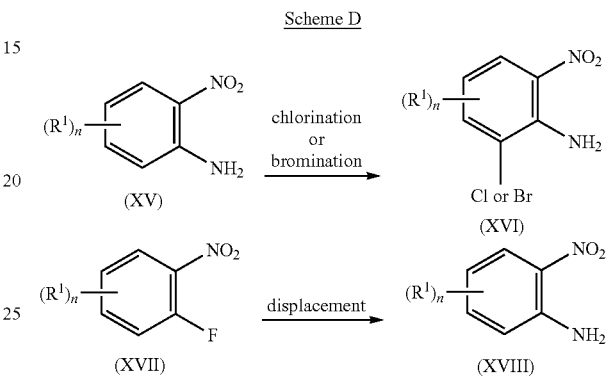

According to Scheme D, 2-halo-nitro anilines of formula (XVI) are prepared by the reaction of nitro anilines of formula (XV) with a chlorinating or brominating reagent such as NCS or NBS, at temperatures ranging from 80° C. to 120° C., in a solvent such as DMF. Additionally, halo-nitro benzene intermediates of formula (XVII), where $R^1$ is independently —F and —Br, are reacted with 7M ammonia in MeOH and heated conventionally or in a sealed tube at temperatures ranging from 50° C. to 70° C. to provide halo-nitro anilines of formula (XVIII).

2-Nitro-phenyl amines (XIV) are prepared according to Scheme C. Anilines of general formula (XI), where one or Scheme E

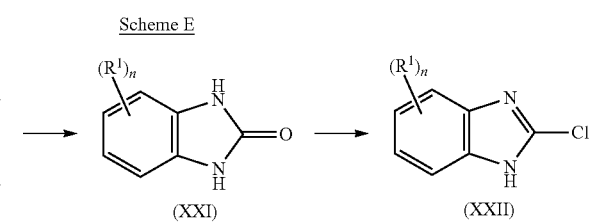

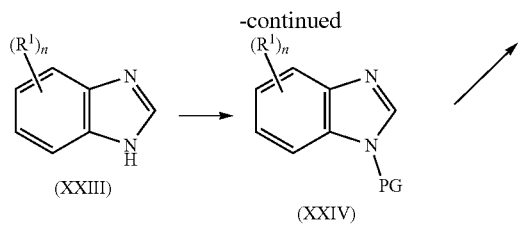

2-Chloro-1H-benzoimidazole intermediates of formula (XXV) are prepared by three methods as shown in Scheme E. Substituted nitro-phenylamines (either commercially available nitrophenylamines, known nitrophenylamines or nitrophenylamines prepared using the schemes as provided) are reduced by employing reduction methods known to one skilled in the art, such as zinc powder in the presence of a saturated aqueous solution of NH$_4$Cl in a solvent such as acetone, and the like, at temperatures ranging from 0° C. to room temperature, to provide diamine intermediates of formula (XX). Reaction of diamine intermediates of formula (XX), either commercially available or synthetically accessible diamines, with carbonyl diimidazole, in a solvent such as THF and the like, at temperatures between 0° C. and room temperature, provides 1,3-dihydro-benzoimidazol-2-one intermediates of formula (XXI). Subsequent chlorination of (XXI) using methods known to one skilled in the art, for example, employing neat phosphorus oxychloride (POCl$_3$), with heating, gives 2-chloro-1H-benzoimidazoles of formula (XXII). Subsequent protection of 1H-benzoimidazoles (XXII) is achieved using a suitable protecting group reagent heating, heating in a sealed tube or microwave heating at temperatures ranging from 80° C. to 130° C. In addition to the one pot reductive cyclization reaction described above, 1H-benzoimidazoles of formula (XXIII) are also synthesized by the reaction of diamines of formula (XX) in the presence of an aldehyde or aldehyde equivalent such as trimethyl orthoformate, and an acid such as HCl at temperatures ranging from 0° C. to room temperature. Subsequent protection of 1H-benzoimidazoles (XXIII) is achieved using a suitable protecting group reagent such as 2-methoxyethoxymethyl chloride (MEMCl) or 2-(trimethysilyl)-ethoxymethyl chloride (SEMCl) in the presence of a base such as NaH or DIPEA in a solvent such as THF to provide compounds of formula (XXIV). Deprotonation of the protected 1H-benzoimidazole intermediate (XXIV) with an organolithium base such as butyllithuim or lithium diisopropylamide, in a solvent such as THF, at temperatures ranging from −80° C. to −40° C., followed by the addition of N-chlorosuccinimide and the like, affords 2-chloro-1H-benzoimidazole intermediates of formula (XXV).

Scheme F

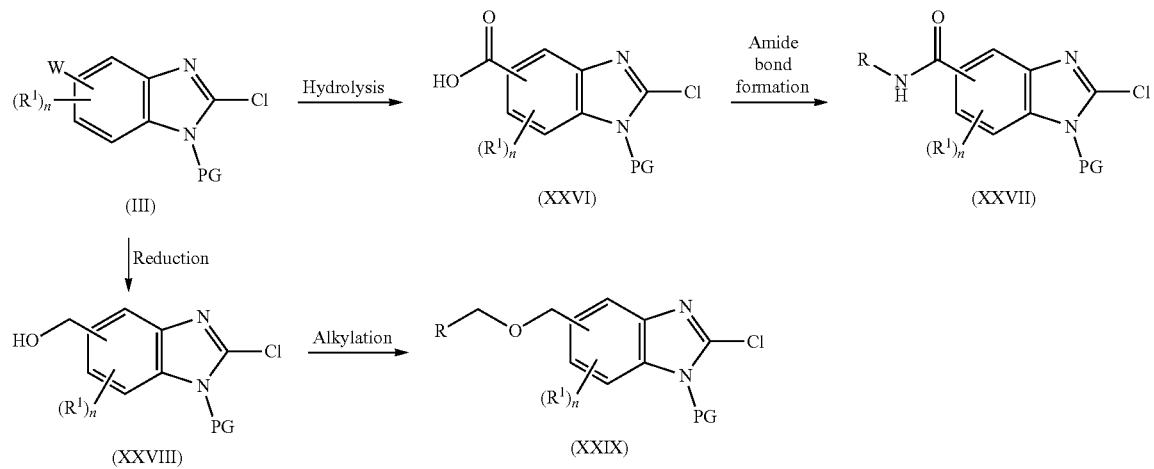

such as dimethylsulfamoyl chloride, 2-methoxyethoxymethyl chloride (MEMCl) or 2-(trimethysilyl)-ethoxymethyl chloride (SEMCl), in the presence of a suitable base in a solvent such as THF or DMF to provide compounds of formula (XXV).

Additionally, benzoimidazoles of formula (XXIII) are prepared in one-pot synthesis from o-nitroanilines via a reductive cyclization in the presence of a suitable reducing agent such as SnCl$_2$.H$_2$O, sodium dithionate, and the like, in the presence of an aldehyde or aldehyde equivalent such as trimethyl orthoformate, and the like, or an acid source such as acetic acid, formic acid, and the like, under conventional Referring to Scheme F, compounds of formula (III) where W is —CO$_2$C$_{1-4}$alkyl and R$^1$ is H, —F, —Cl, —CF$_3$ or —OCF$_3$, are saponified with a suitable base such as aq. NaOH, aq. LiOH or aq. KOH or a mixture thereof, at temperatures ranging from room temperature to the boiling point of the solvent, in a solvent such as THF, provides compounds of formula (XXVI). Subsequent amide bond formation employing methods known to one skilled in the art, provides benzoimidazole intermediates of formula (XXVII). Alternatively, benzoimidazole intermediates of formula (III), where W is —CO$_2$Me, are reduced with a suitable reducing agent such as lithium aluminum hydride, in a solvent such as THF, at 0° C., to afford the corresponding alcohol intermediate of formula (XXVIII). Alkylation of intermediate (XXVIII), employing a base such as NaH, alkylating agents such as alkyl halides and aryl halides, in a solvent such as DMF, provides benzoimidazole intermediates of formula (XXIX).

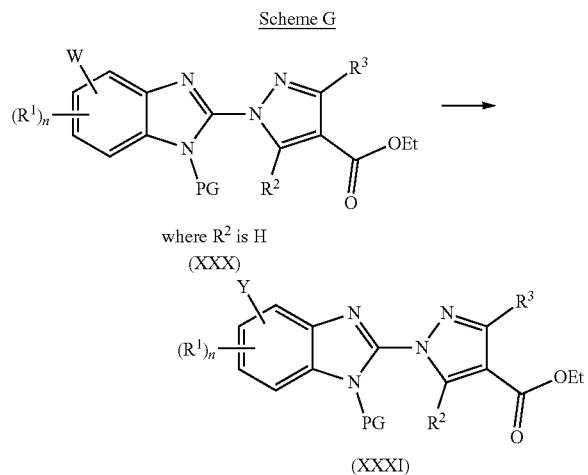

Scheme G where R² is H
(XXX)

(XXXI)

Referring to Scheme G, benzoimidazole intermediates of formula (XXX) under Suzuki conditions, where W is a suitable halogen or triflate and each R¹ is independently H, —Cl, —F, —CF₃ or —OCF₃, are reacted with aryl boronic acids or esters, in the presence of an organotransition metal catalyst such as PdCl₂(dppf) and a suitable base such as CsF to provide biaryl intermediates of formula (XXXI), where Y is a substituted or unsubstituted aryl or heteroaryl ring.

Referring to Scheme G, benzoimidazole intermediates of formula (XXX), where W is —S—C₁₋₄alkyl or —S—Ar (where Ar is a suitably substituted phenyl group), and each R¹ is independently H, —F, —Cl, —CF₃ or —OCF₃, are oxidized employing methods known to one skilled in the art, for example, employing an oxidizing agent such as potassium peroxomonosulfate, 3-chloroperoxybenzoic acid, and the like, to provide the corresponding sulfone and sulfoxide intermediates of formula (XXXI), where Y is —S(O)—C₁₋₄alkyl, —S(O)₂—C₁₋₄alkyl, —S(O)-aryl, or —S(O)₂-aryl.

Referring to Scheme G, benzoimidazole intermediates of formula (XXX), where W is —NO₂, and each R¹ is independently H, —Cl, —F, —CF₃ or —OCF₃, are reacted with a reducing agent, employing methods known to one skilled in the art, to provide benzoimidazole intermediates of formula (XXXI), where Y is —NH₂, and R¹ is —Cl, —CF₃ or —OCF₃.

Referring to Scheme G, benzoimidazole intermediates of formula (XXX), where W is —NH₂, and each R¹ is independently H, —Cl, —F, —CF₃ or —OCF₃, under reductive amination conditions employing methods known to one skilled in the art, are reacted with alkyl aldehydes and substituted aryl aldehydes, to provide alkyl and benzyl substituted amino intermediates of formula (XXXI), where Y is —NH—C₁₋₄alkyl or —NH—CH₂-aryl.

Referring to Scheme G, benzoimidazole intermediates of formula (XXX), where W is —NH₂, and each R¹ is independently H, —Cl, —F, —CF₃ or —OCF₃, are reacted with alkyl, aryl and cycloalkylsulfonyl chlorides, acyl and aryl chlorides, 2-bromoacetyl bromides and the like, to provide the corresponding substituted sulfonamide and amide intermediates.

Referring to Scheme G, benzoimidazole intermediates of formula (XXX), where W is —NH₂, and each R¹ is independently H, —Cl, —F, —CF₃ or —OCF₃, are reacted under amination conditions with an aryl bromide, an organotransition metal catalyst such as Pd(dba)₂, a ligand such as Q-Phos, a suitable base such as sodium tert-butoxide, in a solvent such as toluene, at temperatures ranging from room temperature to the boiling point of the solvent, to provide intermediates of formula (XXXI) where Y is —NHAr.

Referring to Scheme G, benzoimidazole intermediates of formula (XXX), where W is —NC(O)CH₂Br, and each R¹ is independently H, —Cl, —F, —CF₃ or —OCF₃, are reacted with heterocycloalkylamines, such as morpholine, N-methylpiperazine, piperidine, and the like, in a solvent such as dichloromethane, at temperatures ranging from 0° C. to room temperature, to provide substituted acetyl amino benzoimidazole intermediates.

Referring to Scheme G, benzoimidazole intermediates of formula (XXX), where W is —S-ᵗBu and each R¹ is independently H, —F, —Cl, —CF₃ or —OCF₃, are treated with 2-nitro benzene sulfenyl chloride in the presence of a base such as K₂CO₃ to provide the disulfide intermediate. Subsequent reduction of the disulfide with a reducing agent such as NaBH₄, in aqueous EtOH, at 0° C. affords the thiol intermediate (in certain circumstances, the thiol intermediate may dimerize upon itself to provide a disulfide by-product). Alkylation of the thiol with benzyl and alkyl bromides in the presence of base such as K₂CO₃, affords thioalkylated benzoimidazole intermediates of formula (XXXI), where Y is —S—C₁₋₄alkyl or —S—C₁₋₄alkyl-aryl. Additionally, the disulfide by-product as described above is reacted with NCS and aqueous HCl, in a solvent such as acetonitrile, at 0° C., to afford chlorosulfonyl intermediates (A. Nishiguchi, K. Maeda, S. Miki. *Synthesis*, 2006, 24, 4131-4134) which upon reaction with an appropriate aniline, in a solvent such as pyridine, provides aryl-sulfamoyl intermediates of formula (XXXI), where Y is —SO₂—NH-aryl.

Deprotection of intermediates-PG (XXXI) using an acid such as HCl in an appropriate solvent such as EtOH followed by saponification of the carboxy group on the pyrazole ring using a suitable base such as aq. NaOH, aq. LiOH or aq. KOH or a mixture thereof in a solvent such as THF, at temperatures between room temperature and the reflux temperature of the solvent provides compounds of Formula (I).

Additionally, conversion of intermediates of formula (XXXI) to compounds of Formula (I) is achieved in one step with acetic acid and aqueous hydrochloric acid at temperatures ranging from 80° C. to 100° C.

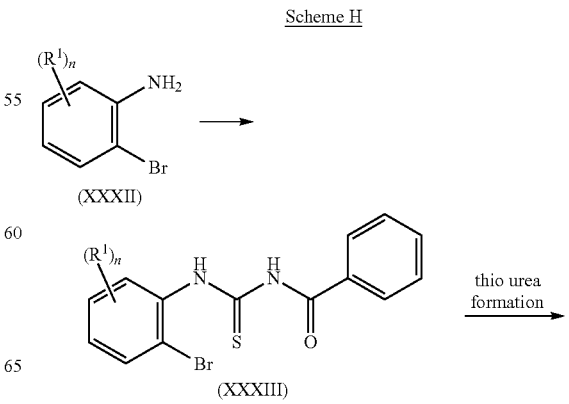

Scheme H (XXXII)

(XXXIII)

thio urea formation

Scheme I

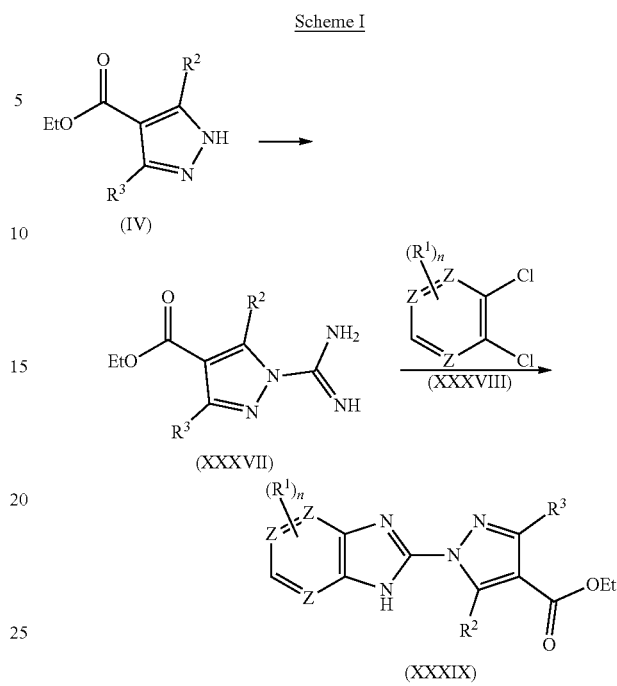

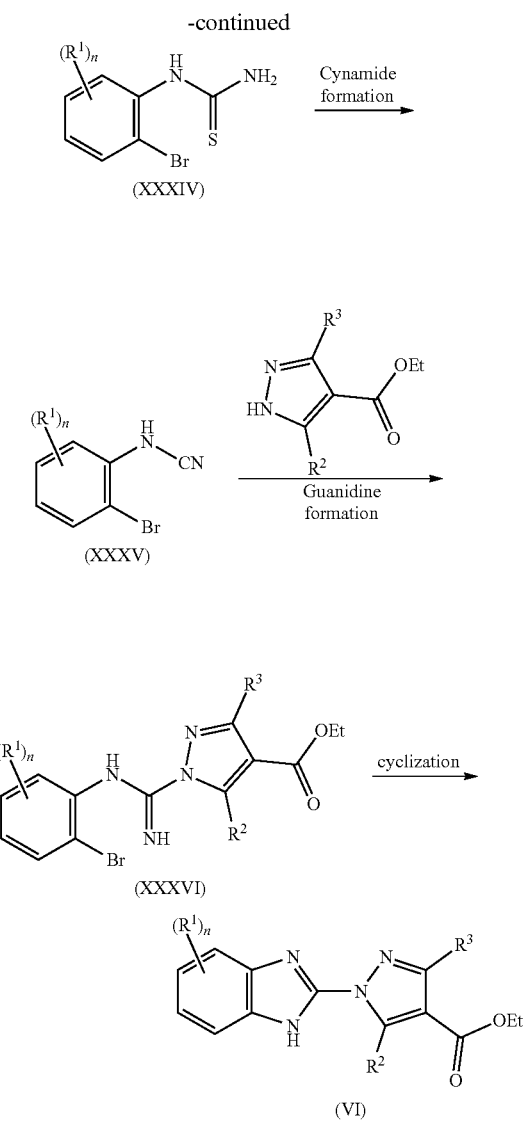

Benzoimidazoles of the formula (VI) can also be prepared according to Scheme H. Bromoanilines of general formula (XXXII) are treated with benzoyl isothiocyanate in a solvent such as toluene, in the presence of a base such as DMAP, at room temperature, to afford the corresponding thiourea derivative of formula (XXXIII). The benzoyl group is removed using a base such as sodium methoxide, in a solvent such as MeOH, at 0° C., to afford the thiourea derivative of formula (XXXIV). Reaction of thioureas of formula (XXXIV) with lead (II) acetate trihydrate in the presence of a base such as potassium hydroxide, in a solvent such as water, at temperatures ranging from 80° C. to 100° C., provides cyanamide intermediates of formula (XXXV). Subsequent reaction of the cyanamide intermediate with 1H-pyrazole-4-carboxylic acid ethyl ester, in the presence of an anhydrous acid such as HCl, in a solvent such as dioxane, at elevated temperatures such as 80° C. to 100° C., provides guanidine intermediates of formula (XXXVI). Further treatment of the guanidine intermediate with a coupling reagent such as CuI, and a base such as $Cs_2CO_3$, in a solvent such as DMF, at temperatures of 60° C. to 100° C., provides benzoimidazole intermediates of the formula (VI).

Benzoimidazole intermediates of formula (XXXIX) are synthesized according to Scheme I. Commercially available 1H-pyrazole-4-carboxylic acid ethyl ester (IV), is reacted with cyanamide, in a solvent such as dioxane, in the presence of an acid such as 4M HCl in dioxane, at temperatures ranging from 80° C. to 100° C., to provide carbamimidoyl-pyrazole-4-carboxylic acid ethyl esters of formula (XXXVII). Subsequent reaction of carbamimidoyl-pyrazole-4-carboxylic acid ethyl esters (XXXVII) with commercially available 2,3-dihalo-aromatic intermediates of formula (XXXVIII), where Z is one or two N (for example 2,3-dichloro-quinoxaline), and a base such as $Cs_2CO_3$ (catalysts such as CuI and the like, may optionally be employed) in a solvent such as DMF, DMA and the like, at temperatures ranging from room temperature to the boiling point of the solvent, provides benzoimidazole intermediates of formula (XXXIX).

Compounds of Formula (I) may be converted to their corresponding salts using methods known to those skilled in the art. For example, acids of Formula (I) may be treated with $K_2CO_3$ in water, in a solvent such as EtOH, at temperatures ranging from room temperature to the reflux temperature of the solvent, to provide the corresponding salt forms.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

For starting materials requiring stereospecific amino acid chemistry, these materials were purchased as preferred stereospecific enantiomers which retained their specificity throughout the synthesis reactions.

The following examples are provided to further illustrate the invention and various preferred embodiments.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

For starting materials requiring stereospecific amino acid chemistry, these materials were purchased as preferred stereospecific enantiomers which retained their specificity throughout the synthesis reactions.

The following examples are provided to further illustrate the invention and various preferred embodiments.

EXAMPLES

Chemistry:

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions were "dried," they were generally dried over a drying agent such as Na$_2$SO$_4$ or MgSO$_4$. Where mixtures, solutions, and extracts were "concentrated", they were typically concentrated on a rotary evaporator under reduced pressure.

Thin-layer chromatography (TLC) was performed using Merck silica gel 60 F$_{254}$ 2.5 cm×7.5 cm 250 μm or 5.0 cm×10.0 cm 250 μm pre-coated silica gel plates. Preparative thin-layer chromatography was performed using EM Science silica gel 60 F$_{254}$ 20 cm×20 cm 0.5 mm pre-coated plates with a 20 cm×4 cm concentrating zone.
Normal-phase flash column chromatography (FCC) was performed on silica gel (SiO$_2$) eluting with 2 M NH$_3$ in MeOH/DCM, unless otherwise noted. Reversed-phase HPLC was performed on a Hewlett Packard HPLC Series 1100, with a Phenomenex Luna C18 (5 μm, 4.6×150 mm) column. Detection was done at λ=230, 254 and 280 nm. The gradient was 10 to 99% acetonitrile/water (0.05% trifluoroacetic acid) over 5.0 min with a flow rate of 1 mL/min. Alternatively, HPLC was performed on a Dionex APS2000 LC/MS with a Phenomenex Gemini C18 (5 μm, 30×100 mm) column, and a gradient of 5 to 100% acetonitrile/water (20 mM NH$_4$OH) over 16.3 min, and a flow rate of 30 mL/min.

Mass spectra (MS) were obtained on an Agilent series 1100 MSD equipped with a ESI/APCI positive and negative multimode source unless otherwise indicated.

Nuclear magnetic resonance (NMR) spectra were obtained on Bruker model DRX spectrometers. The format of the $^1$H NMR data below is: chemical shift in ppm downfield of the tetramethylsilane reference (apparent multiplicity, coupling constant J in Hz, integration). Chemical names were generated using ChemDraw Version 6.0.2 (CambridgeSoft, Cambridge, Mass.) or ACD/Name Version 9 (Advanced Chemistry Development, Toronto, Ontario, Canada).

Example 1:
1-(1H-Benzoimidazol-2-yl)-1H-pyrazole-4-carboxylic Acid

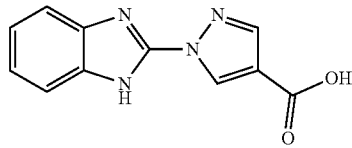 [SMILES: O=C(O)c1cnn(-c2nc3ccccc3[nH]2)c1]

Step A: Preparation of 2-chloro-1-(2-trimethylsilanyl-ethoxymethyl)-1H-benzoimidazole. According to Scheme A, a mixture of NaH (60% dispersion in oil, 0.40 g, 9.8 mmol) and THF (10 mL) was cooled to 0° C., then solid 2-chlorobenzoimidazole (1.0 g, 6.5 mmol) was added portion wise over 10 min. The resulting mixture was stirred at 0° C. for 1 h, then 2-(trimethylsilyl)-ethoxymethyl chloride (1.5 mL, 8.5 mmol) was added. The reaction mixture was allowed to warm to 23° C. and was stirred 16 h. The mixture was carefully poured over ice (200 g) and then was extracted with Et$_2$O (3×100 mL). The combined organic extracts were dried, filtered, and concentrated. The residue was purified (FCC) (1:99 to 15:85 EtOAc/hexanes) to yield the titled compound, which has been previously described (WO 2005/012296, Janssen Pharmaceutica N.V., Example 7).

Step B: 1-[1-(2-Trimethylsilanyl-ethoxymethyl)-1H-benzoimidazol-2-yl]-1H-pyrazole-4-carboxylic acid ethyl ester. A mixture of 2-chloro-1-(2-trimethylsilanyl-ethoxymethyl)-1H-benzoimidazole (0.34 g, 1.2 mmol), ethyl pyrazole-4-carboxylate (0.24 g, 1.7 mmol), cesium carbonate (0.78 g, 2.4 mmol), and anhydrous DMF (2.5 mL) was stirred at 100° C. for 5 h. The mixture was allowed to cool to 23° C. and was diluted with EtOAc, then filtered through a pad of silica gel. The resulting solution was concentrated. The residue was purified (FCC) (5:95 to 40:60 EtOAc/hexanes) to yield the titled compound (0.36 g, 77%). $^1$H NMR (500 MHz, CDCl$_3$): 8.88 (s, 1H), 8.18 (s, 1H), 7.77-7.69 (m, 1H), 7.60-7.50 (m, 1H), 7.40-7.30 (m, 2H), 6.03 (s, 2H), 4.34 (q, J=7.1 Hz, 2H), 3.57-3.50 (m, 2H), 1.37 (t, J=7.1, Hz, 3H), 0.87-0.80 (m, 2H), −0.11 (s, 9H).

Step C: 1-(1H-Benzoimidazol-2-yl)-1H-pyrazole-4-carboxylic acid ethyl ester hydrochloride. A solution of HCl and dioxane (4M, 2 mL, 8 mmol) was added to a mixture of 1-[1-(2-trimethylsilanyl-ethoxymethyl)-1H-benzoimidazol-2-yl]-1H-pyrrole-3-carboxylic acid ethyl ester (0.30 g, 0.78 mmol) and EtOH (4 mL). The reaction mixture was heated to reflux for 30 min, then cooled to 23° C. Et$_2$O was added (20 mL), and the mixture was cooled to 0° C. for 10 min. The resulting precipitate was collected by filtration and washed well with Et$_2$O to afford the titled compound (0.18 g, 91%). MS (ESI/CI): mass calcd. for C$_{13}$H$_{12}$N$_4$O$_2$, 256.3; m/z found, 257.1 [M+H]$^+$. $^1$H NMR (400 MHz, DMSO-d$_6$): 8.96 (s, 1H), 8.33 (s, 1H), 7.56 (s, 2H), 7.28-7.21 (m, 2H), 4.30 (q, J=7.1 Hz, 2H), 1.32 (t, J=7.1 Hz, 3H)

Step D: 1-(1H-Benzoimidazol-2-yl)-1H-pyrazole-4-carboxylic acid. A solution of LiOH and H$_2$O (1.0 M, 1.0 mL, 1.0 mmol) was added to a mixture of 1-(1H-benzoimidazol-2-yl)-1H-pyrrole-3-carboxylic acid ethyl ester hydrochloride (0.040 g, 0.16 mmol) and THF (2.0 mL), and the reaction mixture was stirred at 23° C. for 16 h. The THF was removed in vacuo and then aqueous HCl (1.0 M, 2 mL, 2 mmol) was added at 0° C. The resulting precipitate was collected and washed with water to give the titled compound (0.033 g, 90%). MS (ESI/CI): mass calcd. for C$_{11}$H$_8$N$_4$O$_2$, 228.2; m/z found, 229.0 [M+H]$^+$. $^1$H NMR (500 MHz, DMSO-d$_6$): 13.32 (s, 1H), 13.00-12.86 (br s, 1H), 8.90 (d, J=0.6 Hz, 1H), 8.28 (d, J=0.6 Hz, 1H), 7.64 (d, J=4.6 Hz, 1H), 7.49 (d, J=5.5 Hz, 1H), 7.28-7.20 (m, 2H).

Example 2: 1-(5,6-Dichloro-1H-benzoimidazol-2-yl)-1H-pyrazole-4-carboxylic Acid

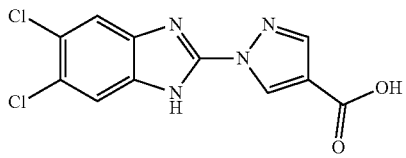 [SMILES: O=C(O)c1cnn(-c2nc3cc(Cl)c(Cl)cc3[nH]2)c1]

Method A:

The titled compound was prepared in a manner analogous to EXAMPLE 1, substituting 2,5,6-trichloro-1H-benzoimidazole for 2-chlorobenzoimidazole in Step A. MS (ESI/CI): mass calcd. for C$_{11}$H$_6$Cl$_2$N$_4$O$_2$, 297.1; m/z found, 296.0 [M−H]$^−$. $^1$H NMR (500 MHz, DMSO-d$_6$): 14.18-12.52 (br s, 2H), 8.89 (d, J=0.5 Hz, 1H), 8.31 (d, J=0.5 Hz, 1H), 7.80 (s, 2H).

Method B:

Step A: 5,6-Dichloro-1,3-dihydro-benzoimidazol-2-one: To the solution of 4,5-dichloro-benzene-1,2-diamine (25 g, 0.14 mol) in dry DMF (200 mL), was added CDI (23 g, 0.14 mol) as the solid. The reaction solution was stirred at room temperature for 1 hour, then water (500 mL) was added. The precipitated solid was collected by filtration, washed with water, dried thoroughly to afford the titled compound (26.0 g, 90%). The crude product was used in the following reaction without further purification.

Step B: 2,5,6-Trichloro-1H-benzoimidazole: Thoroughly dried 5,6-dichloro-1,3-dihydro-benzoimidazol-2-one (28.4 g, 0.14 mol) was suspended in POCl$_3$ (75 mL). The reaction solution was heated to reflux temperature for 3 hours and cooled to room temperature. The solution was poured into crushed ice/water (1.5 L) slowly with sufficient stirring. The solution was neutralized to pH=7.0 with NaOH. The precipitated solid was collected by filtration, washed with water, and dried to afford the title compound (27.9 g, 90%). The crude product was used in the following reaction without further purification.

Step C: 1-(5,6-Dichloro-1-dimethylsulfamoyl-1H-benzoimidazol-2-yl)-1H-pyrazole-4-carboxylic acid ethyl ester. 2,5,6-Trichloro-1H-benzoimidazole 2 (27.6 g, 0.125 mol) was dissolved in dry DMF (200 mL) and then K$_2$CO$_3$ (20.7 g, 0.15 mol) and dimethylsulfamoyl chloride (17.9 g, 0.125 mol) were added. The reaction mixture was stirred at room temperature for 16 hours. HPLC analysis showed the complete formation of 2,5,6-trichloro-benzoimidazole-1-sulfonic acid dimethylamide. In the same pot, without isolation of 2,5,6-trichloro-benzoimidazole-1-sulfonic acid dimethylamide, was added 1H-pyrazole-4-carboxylic acid ethyl ester (17.5 g, 0.125 mol) and K$_2$CO$_3$ (20.7 g, 0.15 mol). The reaction mixture was stirred at 70° C. for 4 hours and water (500 mL) was added while the reaction solution was still hot. The reaction solution was cooled to room temperature. The precipitated solid was collected via filtration, washed with water and dried. The crude product was used in the following reaction without further purification.

Step D: 1-(5,6-Dichloro-1H-benzoimidazol-2-yl)-1H-pyrazole-4-carboxylic acid. Crude 1-(5,6-Dichloro-1-dimethylsulfamoyl-1H-benzoimidazol-2-yl)-1H-pyrazole-4-carboxylic acid ethyl ester was dissolved in THF (125 mL) and LiOH.H$_2$O (21 g, 0.5 mol) in water (250 mL) was added. The reaction mixture was stirred at reflux temperature for 2 hours and cooled to room temperate. Concentrated HCl was added to adjust pH to 2.0. The solid precipitated was collected by filtration, washed with water and dried. The solid was triturated in hot EtOAc (1 L). After cooling to room temperature and filtration, the pure compound was obtained as a tan solid (18.5 g, 50%). MS [M+H]$^+$ found 297.0. $^1$H NMR (500 MHz, DMSO-d$_6$): 13.71 (s, 1H), 12.99 (s, 1H), 8.90 (s, 1H), 8.32 (s, 1H), 7.94 (s, 1H), 7.67 (s, 1H). The potassium salt of 1-(5,6-dichloro-1H-benzoimidazol-2-yl)-1H-pyrazole-4-carboxylic acid was prepared by suspending the free acid (55 g, 1.7 mol) in EtOH (1.5 L) at reflux temperature and then K$_2$CO$_3$ (12.79 g, 0.85 mol) in 20 mL water was added dropwise over 5 min. Strong mechanic stirring was required to ensure proper agitation. The suspension was stirred at reflux temperature for 8 hours and then cooled to room temperature over 5 hours. The precipitated solid was collected by filtration and washed with water (100 mL) quickly and then EtOH. The potassium salt was obtained as a white solid (38 g, 65%). The mother liquor was concentrated and the above process was repeated once to give the second crop of the potassium salt (13 g, 22%). MS [M+H]$^+$=297.0. $^1$H NMR (500 MHz, DMSO-d$_6$): 8.65 (s, 1H), 7.96 (s, 1H), 7.57 (s, 2H).

Example 3: 1-(5-Trifluoromethyl-1H-benzoimidazol-2-yl)-1H-pyrazole-4-carboxylic Acid

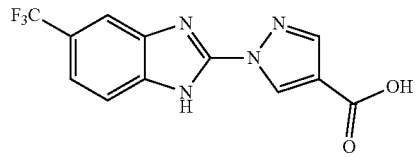 [SMILES: O=C(O)c1cnn(-c2nc3cc(C(F)(F)F)ccc3[nH]2)c1]

The titled compound was prepared in a manner analogous to EXAMPLE 1, substituting 2-chloro-5-trifluoromethyl-1H-benzoimidazole for 2-chlorobenzoimidazole in Step A. MS (ESI/CI): mass calcd. for C$_{12}$H$_7$F$_3$N$_4$O$_2$, 296.2; m/z found, 295.0 [M−H]$^−$. $^1$H NMR (500 MHz, DMSO-d$_6$): 14.44-12.32 (br s, 2H), 8.94 (d, J=0.5 Hz, 1H), 8.33 (d, J=0.5 Hz, 1H), 7.96-7.83 (br. s, 1H), 7.75 (br d, 1H), 7.58 (dd, J=8.49, 1.41 Hz, 1H).

Example 4: 1-(5-Chloro-6-fluoro-1H-benzoimidazol-2-yl)-1H-pyrazole-4-carboxylic Acid

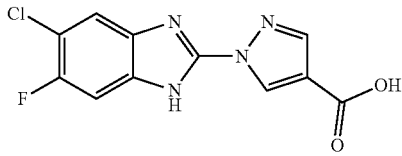

The titled compound was prepared in a manner analogous to EXAMPLE 1, substituting 2,5-dichloro-6-fluoro-1H-benzoimidazole for 2-chlorobenzoimidazole in Step A. MS (ESI/CI): mass calcd. for $C_{11}H_6ClFN_4O_2$, 280.7; m/z found, 279.0 [M–H]−. $^1$H NMR (500 MHz, DMSO-$d_6$): 14.21-12.25 (br s, 2H), 8.88 (d, J=0.6 Hz, 1H), 8.30 (d, J=0.6 Hz, 1H), 7.81-7.67 (br s, 1H), 7.65-7.52 (br s, 1H).

Example 5: 1-(5,6-Dimethyl-1H-benzoimidazol-2-yl)-1H-pyrazole-4-carboxylic Acid

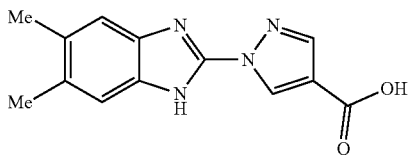 [SMILES: Cc1cc2nc(-n3cc(C(=O)O)cn3)[nH]c2cc1C]

The titled compound was prepared in a manner analogous to EXAMPLE 1, substituting 2-chloro-5,6-dimethyl-1H-benzoimidazole for 2-chlorobenzoimidazole in Step A. MS (ESI/CI): mass calcd. for $C_{13}H_{12}N_4O_2$, 256.3; m/z found, 257.1 [M+H]+. $^1$H NMR (500 MHz, DMSO-$d_6$): 13.16-12.81 (m, 2H), 8.85 (d, J=0.6 Hz, 1H), 8.25 (d, J=0.6 Hz, 1H), 7.43-7.21 (br s, 2H), 2.31 (s, 6H).

Example 6: 1-(5-Bromo-1H-benzoimidazol-2-yl)-1H-pyrazole-4-carboxylic Acid

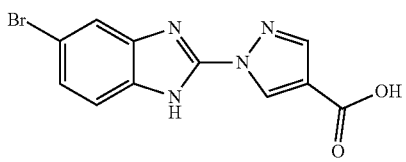 [SMILES: O=C(O)c1cnn(-c2nc3cc(Br)ccc3[nH]2)c1]

The titled compound was prepared in a manner analogous to EXAMPLE 1, substituting 5-bromo-2-chloro-1H-benzoimidazole for 2-chlorobenzoimidazole in Step A. MS (ESI/CI): mass calcd. for $C_{11}H_7BrN_4O_2$, 306.0; m/z found, 307.0 [M+H]+. $^1$H NMR (400 MHz, DMSO-$d_6$): 8.82 (d, J=0.5 Hz, 1H), 8.22 (s, 1H), 7.67 (d, J=1.2 Hz, 1H), 7.45 (d, J=8.5 Hz, 1H), 7.32 (dd, J=8.5, 1.9 Hz, 1H).

Example 7: 1-(5-Methoxy-1H-benzoimidazol-2-yl)-1H-pyrazole-4-carboxylic Acid

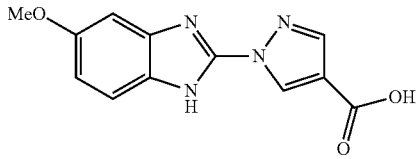 [SMILES: COc1ccc2[nH]c(-n3cc(C(=O)O)cn3)nc2c1]

The titled compound was prepared in a manner analogous to EXAMPLE 1, substituting 2-chloro-5-methoxy-1H-benzoimidazole for 2-chlorobenzoimidazole in Step A. MS (ESI/CI): mass calcd. for $C_{12}H_{10}N_4O_3$, 258.2; m/z found, 259.1[M+H]+. $^1$H NMR (500 MHz, DMSO-$d_6$, tautomeric mixture): 13.16 (s, 1H), 12.91 (s, 1H), 8.84 (s, 1H), 8.26 (s, 1H), 6.83-7.54 (m, 3H), 3.80 (s, 3H).

Example 8: 1-(4-Chloro-6-trifluoromethyl-1H-benzoimidazol-2-yl)-1H-pyrazole-4-carboxylic Acid

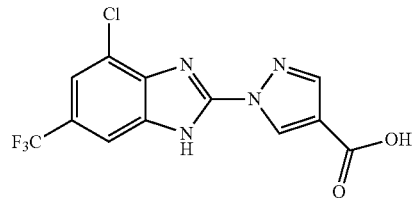 [SMILES: O=C(O)c1cnn(-c2nc3c(Cl)cc(C(F)(F)F)cc3[nH]2)c1]

The titled compound was prepared in a manner analogous to EXAMPLE 1, substituting 2,4-dichloro-6-trifluoromethyl-1H-benzoimidazole for 2-chlorobenzoimidazole in Step A. MS (ESI/CI): mass calcd. for $C_{12}H_6ClF_3N_4O_2$, 330.7; m/z found, 329.0 [M–H]−. $^1$H NMR (500 MHz, DMSO-$d_6$): 13.90-14.50 (br s, 1H), 12.75-13.45 (br s, 1H), 8.95 (s, 1H), 8.36 (s, 1H), 7.72 (s, 1H), 7.70 (s, 1H).

Example 9: 1-(5,6-Dimethoxy-1H-benzoimidazol-2-yl)-1H-pyrazole-4-carboxylic Acid

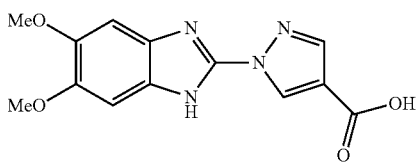 [SMILES: COc1cc2nc(-n3cc(C(=O)O)cn3)[nH]c2cc1OC]

The titled compound was prepared in a manner analogous to EXAMPLE 1, substituting 2-chloro-5,6-dimethoxy-1H-benzoimidazole for 2-chlorobenzoimidazole in Step A. MS (ESI/CI): mass calcd. for $C_{13}H_{12}N_4O_4$, 288.3; m/z found, 289.1 [M+H]+. $^1$H NMR (500 MHz, DMSO-$d_6$): 8.81 (s, 1H), 8.25 (s, 1H), 7.09 (s, 2H), 3.80 (s, 6H).

Example 10: 1-(4,5-Dimethyl-1H-benzoimidazol-2-yl)-1H-pyrazole-4-carboxylic Acid

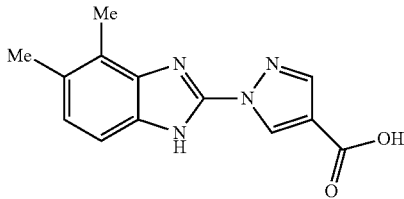 [SMILES: Cc1ccc2[nH]c(-n3cc(C(=O)O)cn3)nc2c1C]

The titled compound was prepared in a manner analogous to EXAMPLE 1, substituting 2-chloro-4,5-dimethyl-1H-benzoimidazole for 2-chlorobenzoimidazole in Step A. MS (ESI/CI): mass calcd. for $C_{13}H_{12}N_4O_2$, 256.3; m/z found, 257.2 [M+H]$^+$. $^1$H NMR (500 MHz, DMSO-d$_6$, tautomeric mixture): 12.60-13.30 (br. m, 2H), 8.83-8.90 (m, 1H), 8.23-8.29 (m, 1H), 7.0-7.35 (m, 2H), 2.47 (s, 3H), 2.33 (s, 3H).

Example 11: 1-(5-Trifluoromethoxy-1H-benzoimidazol-2-yl)-1H-pyrazole-4-carboxylic Acid

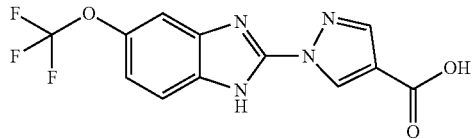 [SMILES: O=C(O)c1cnn(-c2nc3cc(OC(F)(F)F)ccc3[nH]2)c1]

The titled compound was prepared in a manner analogous to EXAMPLE 1, substituting 2-chloro-5-trifluoromethoxy-1H-benzoimidazole for 2-chlorobenzoimidazole in Step A. MS (ESI/CI): Mass calcd. for $C_{12}H_7F_3N_4O_3$ 312.0. m/z found: 313.1 [M+H]$^+$. $^1$H NMR (400 MHz, DMSO-d$_6$): 8.91 (s, 1H), 8.31 (s, 1H), 7.83-7.41 (m, 2H), 7.30-7.21 (m, 1H).

Example 12: 1-{5-[3-(3-Chloro-benzyloxy)-phenyl]-1H-benzoimidazol-2-yl}-1H-pyrazole-4-carboxylic Acid

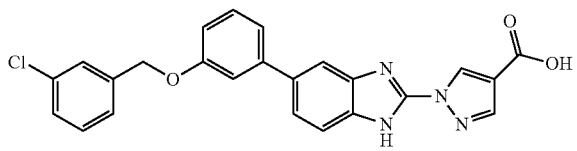 [SMILES: O=C(O)c1cnn(-c2nc3cc(-c4cccc(OCc5cccc(Cl)c5)c4)ccc3[nH]2)c1]

Step A: 1-{5-[3-(3-Chloro-benzyloxy)-phenyl]-1-(2-trimethylsilanyl-ethoxymethyl)-1H-benzoimidazol-2-yl}-1H-pyrazole-4-carboxylic acid ethyl ester and 1-{6-[3-(3-Chloro-benzyloxy)-phenyl]-1-(2-trimethylsilanyl-ethoxymethyl)-1H-benzoimidazol-2-yl}-1H-pyrazole-4-carboxylic acid ethyl ester. According to Scheme B, [1,1'-bis(diphenylphosphino)ferrocene]dichloro palladium (0.12 g, 0.16 mmol) was added to a mixture of cesium fluoride (0.33 g 2.2 mmol), 3-(3'chlorobenzyloxy)phenylboronic acid (0.37 g, 1.3 mmol), 1-[5-bromo-1-(2-trimethylsilanyl-ethoxymethyl)-1H-benzoimidazol-2-yl]-1H-pyrazole-4-carboxylic acid ethyl ester and 1-[6-bromo-1-(2-trimethylsilanyl-ethoxymethyl)-1H-benzoimidazol-2-yl]-1H-pyrazole-4-carboxylic acid ethyl ester (Intermediate from Example 6). MS (ESI/CI): Mass calcd. for $C_{19}H_{25}BrN_4O_3Si$, 464.1; m/z found, 465.1), (0.5 g, 1.1 mmol), and DME (5 ml) in a sealable tube. The reaction was stirred at 80° C. After 3 h, the mixture was cooled to rt, then was diluted with EtOAc (50 ml) and filtered. The filtrate was concentrated. The residue was purified (FCC) (15:85 EtOAc/hexanes) to yield the titled compounds as a regioisomeric mixture (0.47 g, 72%). MS (ESI/CI): mass calcd. for $C_{32}H_{35}ClN_4O_4Si$, 602.2; m/z found, 603.2 [M+H]$^+$.

Step B: 1-{5-[3-(3-Chloro-benzyloxy)-phenyl]-1H-benzoimidazol-2-yl}-1H-pyrazole-4-carboxylic acid. The titled compound was prepared in a manner analogous to Example 1, Steps C-D. MS (ESI/CI): mass calcd. for $C_{24}H_{17}ClN_4O_3$ 444.1; m/z found, 445.1 [M+H]$^+$. $^1$H NMR (400 MHz, DMSO-d$_6$): 8.93 (d, J=0.5 Hz, 1H), 8.32 (s, 1H), 7.84-7.79 (m, 1H), 7.68-7.63 (m, 1H), 7.60-7.55 (m, 2H), 7.52-7.37 (m, 4H), 7.36-7.27 (m, 2H), 7.03 (dd, J=7.8, 2.1 Hz, 1H), 5.26 (s, 2H).

Example 13: 1-{5-[3-(2-Chloro-benzyloxy)-phenyl]-1H-benzoimidazol-2-yl}-1H-pyrazole-4-carboxylic Acid

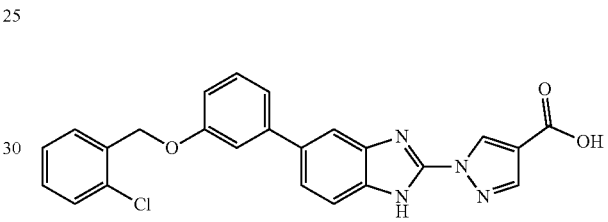

The titled compound was prepared in a manner analogous to EXAMPLE 12, substituting 3-(2'-chlorobenzyloxy)phenylboronic acid for 3-(3'-chlorobenzyloxy)phenylboronic acid in Step A. MS (ESI/CI): mass calcd. for $C_{24}H_{17}ClN_4O_3$, 444.1; m/z found, 445.1 [M+H]$^+$. $^1$H NMR (400 MHz, DMSO-d$_6$): 8.91 (s, 1H), 8.30 (s, 1H), 7.80 (s, 1H), 7.72-7.60 (m, 2H), 7.59-7.48 (m, 2H), 7.48-7.36 (m, 3H), 7.36-7.25 (m, 2H), 7.02 (dd, J=8.1, 1.9 Hz, 1H), 5.27 (s, 2H).

Example 14: 1-{5-[3-(4-Chloro-benzyloxy)-phenyl]-1H-benzoimidazol-2-yl}-1H-pyrazole-4-carboxylic Acid

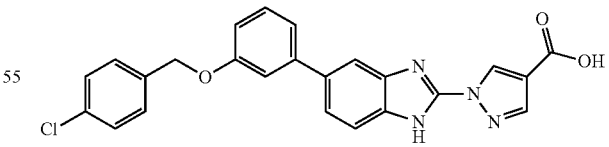

The titled compound was prepared in a manner analogous to EXAMPLE 12, substituting 3-(4'-chlorobenzyloxy)phenylboronic acid for 3-(3'-chlorobenzyloxy)phenylboronic acid in Step A. MS (ESI/CI): mass calcd. for $C_{24}H_{17}ClN_4O_3$, 444.1; m/z found, 445.1 [M+H]$^+$. $^1$H NMR (600 MHz, DMSO-d$_6$): 8.91 (s, 1H), 8.30 (s, 1H), 7.98-7.50 (m, 5H), 7.50-7.44 (m, 2H), 7.43-7.35 (m, 1H), 7.35-7.22 (m, 2H), 7.00 (s, 1H), 5.22 (s, 2H).

Example 15: 1-[5-(3-Benzyloxy-phenyl)-1H-benzo-imidazol-2-yl]-1H-pyrazole-4-carboxylic Acid

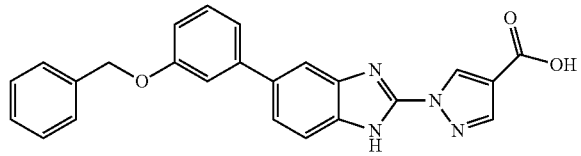 [SMILES: O=C(O)c1cnn(-c2nc3cc(-c4cccc(OCc5ccccc5)c4)ccc3[nH]2)c1]

The titled compound was prepared in a manner analogous to EXAMPLE 12, substituting 3-(benzyloxy)phenylboronic acid for 3-(3'-chlorobenzyloxy)phenylboronic acid in Step A. MS (ESI/CI): mass calcd. for $C_{24}H_{18}N_4O_3$, 410.1; m/z found, 411.2 [M+H]$^+$. $^1$H NMR (400 MHz, DMSO-d$_6$): 8.99 (s, 1H), 8.38 (s, 1H), 8.02-7.28 (m, 11H), 7.09 (dd, J=8.1, 1.9 Hz, 1H), 5.31 (s, 2H).

Example 16: 1-[5-(4-Benzyloxy-phenyl)-1H-benzo-imidazol-2-yl]-1H-pyrazole-4-carboxylic Acid

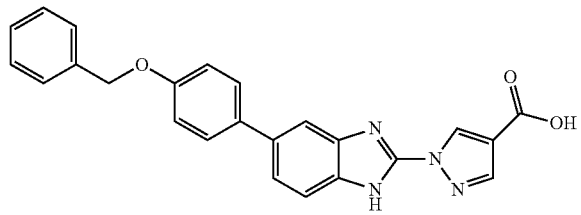 [SMILES: O=C(O)c1cnn(-c2nc3cc(-c4ccc(OCc5ccccc5)cc4)ccc3[nH]2)c1]

The titled compound was prepared in a manner analogous to EXAMPLE 12, substituting 4-(benzyloxy)phenylboronic acid for 3-(3'-chlorobenzyloxy)phenylboronic acid in Step A. MS (ESI/CI): mass calcd. for $C_{24}H_{18}N_4O_3$, 410.1; m/z found; 411.2 [M+H]$^+$. $^1$H NMR (400 MHz, DMSO-d$_6$): 9.00 (s, 1H), 8.39 (s, 1H), 7.81-7.39 (m, 10H), 7.20 (d, J=8.8 Hz, 2H), 5.26 (s, 2H).

Example 17: 1-[5-(3-Trifluoromethyl-phenyl)-1H-benzoimidazol-2-yl]-1H-pyrazole-4-carboxylic Acid

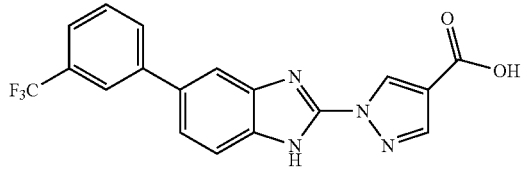 [SMILES: O=C(O)c1cnn(-c2nc3cc(-c4cccc(C(F)(F)F)c4)ccc3[nH]2)c1]

The titled compound was prepared in a manner analogous to EXAMPLE 12, substituting 3-trifluoromethylphenyl boronic acid for 3-(3'-chlorobenzyloxy)phenylboronic acid in Step A. MS (ESI/CI): mass calcd. for $C_{18}H_{11}F_3N_4O_2$, 372.1; m/z found, 373.1 [M+H]$^+$. $^1$H NMR (400 MHz, DMSO-d$_6$): 8.91 (s, 1H), 8.31 (s, 1H), 8.11-7.79 (m, 3H), 7.78-7.52 (m, 4H).

Example 18: 1-[5-(3,4-Dichloro-phenyl)-1H-benzo-imidazol-2-yl]-1H-pyrazole-4-carboxylic Acid

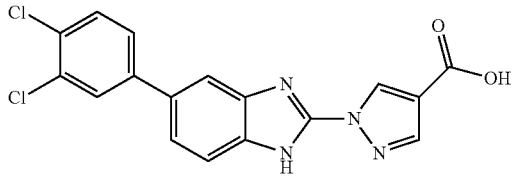 [SMILES: O=C(O)c1cnn(-c2nc3cc(-c4ccc(Cl)c(Cl)c4)ccc3[nH]2)c1]

The titled compound was prepared in a manner analogous to EXAMPLE 12, substituting 3,4-dichlorophenylboronic acid for 3-(3'-chlorobenzyloxy)phenylboronic acid in Step A. MS (ESI/CI): Mass calcd. for $C_{17}H_{10}Cl_2N_4O_2$ 372.0. m/z found: 373.0 [M+H]$^+$. $^1$H NMR (400 MHz, DMSO-d$_6$): 9.01 (s, 1H), 8.41 (s, 1H), 8.06 (s, 1H), 7.95 (s, 1H), 7.81 (d, J=1.2 Hz, 2H), 7.74 (d, J=8.4 Hz, 1H), 7.69 (dd, J=8.5, 1.7 Hz, 1H).

Example 19: 1-(5-Bromo-1H-benzoimidazol-2-yl)-3-trifluoromethyl-1H-pyrazole-4-carboxylic Acid

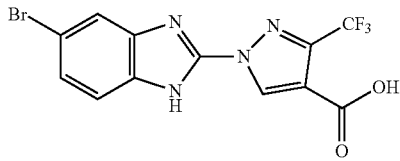 [SMILES: O=C(O)c1cn(-c2nc3cc(Br)ccc3[nH]2)nc1C(F)(F)F]

The titled compound was prepared in a manner analogous to EXAMPLE 1, substituting 5-bromo-2-chloro-1H-benzoimidazole for 2-chlorobenzoimidazole in Step A and 3-trifluoromethyl-1H-pyrazole-4-carboxylic acid ethyl ester ethyl pyrazole-4-carboxylate in step B. MS (ESI/CI): mass calcd. for $C_{12}H_6BrF_3N_4O_2$, 374.0; m/z found, 375.0 [M+H]$^+$. $^1$H NMR (400 MHz, DMSO-d$_6$): 13.69 (br s, 1H), 9.09 (s, 1H), 7.79 (br s, 1H), 7.55 (br s, 1H), 7.43 (dd, J=8.4, 1.6 Hz, 1H).

Example 20: 1-(5,6-dichloro-1H-benzoimidazol-2-yl)-3-trifluoromethyl-1H-pyrazole-4-carboxylic Acid

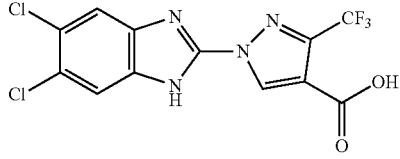 [SMILES: O=C(O)c1cn(-c2nc3cc(Cl)c(Cl)cc3[nH]2)nc1C(F)(F)F]

The titled compound was prepared in a manner analogous to EXAMPLE 1, substituting 2,5,6-trichloro-1H-benzoimidazole for 2-chlorobenzoimidazole in Step A and 3-trifluoromethyl-1H-pyrazole-4-carboxylic acid ethyl ester ethyl pyrazole-4-carboxylate in step B. MS (ESI/CI): mass calcd. for $C_{12}H_5Cl_2F_3N_4O_2$, 365.1; m/z found, 363.0 [M+H]$^+$. $^1$H NMR (500 MHz, DMSO-d$_6$): 13.25-14.30 (br s, 2H), 9.10 (s, 1H), 7.87 (br s, 2H).

Example 21: 1-(5-Bromo-1H-benzoimidazol-2-yl)-3,5-dimethyl-1H-pyrazole-4-carboxylic Acid

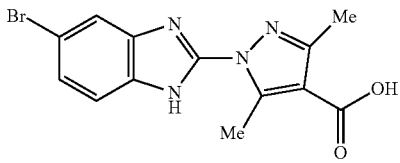 [SMILES: Cc1nn(-c2nc3cc(Br)ccc3[nH]2)c(C)c1C(=O)O]

The titled compound was prepared in a manner analogous to EXAMPLE 1, substituting 5-bromo-2-chloro-1H-benzoimidazole for 2-chlorobenzoimidazole in Step A and 3,5-dimethyl-1H-4-pyrazole-4-carboxylate for ethyl pyrazole-4-carboxylate in step B. MS (ESI/CI): mass calcd. for $C_{13}H_{11}BrN_4O_2$, 334.0; m/z found, 335.0 [M+H]$^+$. $^1$H NMR (400 MHz, DMSO-d$_6$): 13.21 (br s, 1H), 12.77 (br s, 1H), 7.73 (br s, 1H), 7.51 (br s, 1H), 7.36 (dd, J=8.4, 1.6 Hz, 1H), 2.98 (s, 3H), 2.46 (s, 3H).

Example 22: 1-(5,6-Dichloro-1H-benzoimidazol-2-yl)-3,5-dimethyl-1H-pyrazole-4-carboxylic Acid

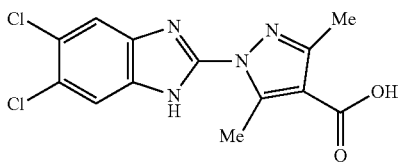 [SMILES: Cc1nn(-c2nc3cc(Cl)c(Cl)cc3[nH]2)c(C)c1C(=O)O]

The titled compound was prepared in a manner analogous to EXAMPLE 1, substituting 2,5,6-trichloro-1H-benzoimidazole for 2-chlorobenzoimidazole in Step A and 3,5-dimethyl-1H-4-pyrazole-4-carboxylate for ethyl pyrazole-4-carboxylate in step B. and purified by preparatory HPLC. MS (ESI/CI): mass calcd. for $C_{13}H_{11}Cl_2N_4O_2$, 325.2; m/z found, 327.1 [M+H]$^+$. $^1$H NMR (500 MHz, DMSO-d$_6$): 7.79 (s, 2H), 2.98 (s, 3H), 2.46 (s, 3H).

Example 23: 1-[5-(4-Hydroxy-phenyl)-1H-benzoimidazol-2-yl]-1H-pyrazole-4-carboxylic Acid

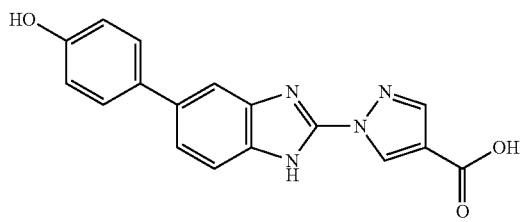 [SMILES: O=C(O)c1cnn(-c2nc3cc(-c4ccc(O)cc4)ccc3[nH]2)c1]

The titled compound was prepared in a manner analogous to EXAMPLE 12, substituting 4-hydroxy-phenyl boronic acid for 3-(3'-chlorobenzyloxy)phenylboronic acid in Step A. MS (ESI/CI): mass calcd. for $C_{17}H_{12}N_4O_3$, 320.3; m/z found, 321.1 [M+H]$^+$. $^1$H NMR (600 MHz, DMSO-d$_6$): 12.52-13.80 (br s, 1H), 9.25-10.05 (br s, 1H), 8.84 (s, 1H), 8.25 (s, 1H), 7.43-7.80 (m, 5H), 6.86 (d, J=8.6, 2H).

Example 24: 1-[5-(3-Hydroxy-phenyl)-1H-benzoimidazol-2-yl]-1H-pyrazole-4-carboxylic Acid

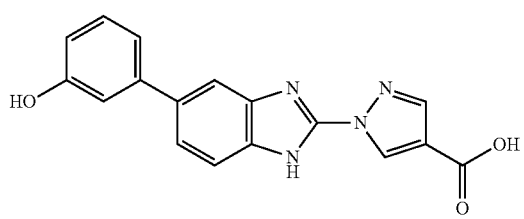 [SMILES: O=C(O)c1cnn(-c2nc3cc(-c4cccc(O)c4)ccc3[nH]2)c1]

The titled compound was prepared in a manner analogous to EXAMPLE 12, substituting 3-hydroxy-phenyl boronic acid for 3-(3'-chlorobenzyloxy)phenylboronic acid in Step A. MS (ESI/CI): mass calcd. for $C_{17}H_{12}N_4O_3$, 320.3; m/z found, 321.1 [M+H]$^+$. $^1$H NMR (600 MHz, DMSO-d$_6$): 12.50-13.56 (br m, 2H), 9.54 (br s, 1H), 8.91 (s, 1H), 8.30 (s, 1H), 7.45-7.88 (br m, 3H), 7.26 (t, J=7.8 Hz, 1H), 7.04-7.14 (m, 2H), 6.75 (dd, J=8.0, 1.7 Hz, 1H).

Example 25: 1-(5-Chloro-1H-benzoimidazol-2-yl)-1H-pyrazole-4-carboxylic Acid

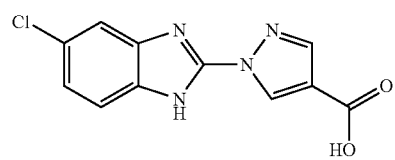 [SMILES: O=C(O)c1cnn(-c2nc3cc(Cl)ccc3[nH]2)c1]

The titled compound was prepared in a manner analogous to EXAMPLE 1, substituting 2,5-dichloro-1H-benzoimidazole for 2-chlorobenzoimidazole in Step A. MS (ESI/CI): mass calcd. for $C_{11}H_7ClN_4O_2$, 262.0; m/z found, 263.0 [M+H]$^+$. $^1$H NMR (400 MHz, CD$_3$OD, tautomeric broadening): 8.89 (s, 1H), 8.17 (s, 1H), 7.67-7.44 (m, 2H), 7.26 (dd, J=8.6, 1.9 Hz, 1H).

Example 26: 1-(5-Bromo-6,7-dimethyl-1H-benzoimidazol-2-yl)-1H-pyrazole-4-carboxylic Acid

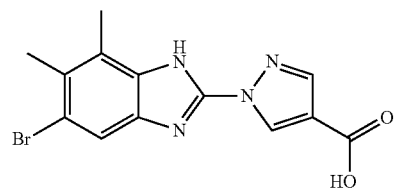 [SMILES: Cc1c(Br)cc2nc(-n3cc(C(=O)O)cn3)[nH]c2c1C]

The titled compound was prepared in a manner analogous to EXAMPLE 1, substituting 5-bromo-2-chloro-6,7-dimethyl-1H-benzoimidazole for 2-chlorobenzoimidazole in Step A. MS (ESI/CI): mass calcd. for $C_{11}H_7ClN_4O_2$, 334.0; m/z found, 335.0 [M+H]$^+$. $^1$H NMR (400 MHz, DMSO-d$_6$, tautomeric broadening): 13.51-12.68 (m, 2H), 8.88 (s, 1H), 8.29 (s, 1H), 7.80-7.40 (m, 1H), 2.56 (s, 3H), 2.40 (s, 3H).

Example 27: 1-(4-Chloro-1H-benzoimidazol-2-yl)-1H-pyrazole-4-carboxylic Acid

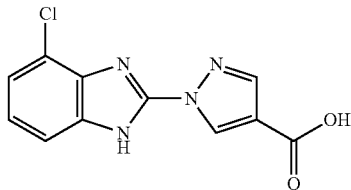 [SMILES: O=C(O)c1cnn(-c2nc3c(Cl)cccc3[nH]2)c1]

Step A: 3-Chloro-benzene-1,2-diamine. To a solution of 3-chloro-2-nitro-phenylamine (1.73 g, 10.0 mmol), NH$_4$Cl (2.68 g, 50.0 mmol), acetone (40 mL) and water (10 mL), was added zinc powder portion-wise (three equal portions over 5 minutes) (3.26 g, 50.0 mmol) at 0° C. The mixture was stirred for 2 h then warmed to 23° C. The mixture was filtered through Celite® and the solvents were concentrated under reduced pressure. The mixture was re-dissolved in EtOAc/DCM and filtered a second time through Celite® and the solvents were evaporated. The crude mixture was diluted with EtOAc (100 mL), washed with brine (40 mL), dried, filtered, and concentrated under reduced pressure. The residue was purified (FCC) (10-50% EtOAc/hexanes) to yield the titled compound (1.00 g, 70%). MS (ESI/CI): mass calcd. for C$_6$H$_7$ClN$_2$, 142.0; m/z found, 143.1 [M+H]$^+$. $^1$H NMR (500 MHz, CDCl$_3$): 6.86-6.78 (m, 1H), 6.65-6.58 (m, 2H), 3.74 (br s, 2H), 3.46 (br s, 2H).

Step B: 4-Chloro-1,3-dihydro-benzoimidazol-2-one. To a solution of 3-chloro-benzene-1,2-diamine (0.820 g, 5.75 mmol) and THF (25 mL), was added carbonyl diimidazole (1.12 g, 6.90 mmol) at 0° C. The mixture was stirred for 16 h and allowed to warm to 23° C. A solution of 1M aqueous HCl (25 mL) was added to the reaction mixture at 0° C., followed by water (100 mL) and the mixture was stirred for 1 h. The precipitated solid was filtered and dried under high vacuum for 18 h to yield the titled compound, which was used in the next step without further purification (0.800 g, 83%). MS (ESI/CI): mass calcd. for C$_7$H$_5$ClN$_2$O, 168.0; m/z found, 169.1 [M+H]$^+$. $^1$H NMR (500 MHz, DMSO-d$_6$): 11.13 (s, 1H), 10.88 (s, 1H), 7.00-6.86 (m, 3H).

Step C: 2,4-Dichloro-1H-benzoimidazole. Phosphorus oxychloride (10 mL) was added to 4-chloro-1,3-dihydro-benzoimidazol-2-one (0.750 g, 4.45 mmol), and the mixture heated to 80° C. for 48 h. The mixture was cooled to 23° C. and POCl$_3$ removed under reduced pressure. The residue was cooled to 0° C., and cold saturated aqueous NaHCO$_3$ (20 mL) was added cautiously. After stirring at 23° C. for 15 min, the mixture was sonicated and the resulting residue was filtered to yield the titled compound (0.760 g, 92%), which was used in the next step without further purification. MS (ESI/CI): mass calcd. for C$_7$H$_5$Cl$_2$N$_2$, 186.0; m/z found, 187.0 [M+H]$^+$. $^1$H NMR (500 MHz, DMSO-d$_6$): 13.68 (s, 1H), 7.51-7.42 (m, 1H), 7.32-7.25 (m, 1H), 7.22 (m, 1H).

Step D: 2,4-Dichloro-1-(2-methoxy-ethoxymethyl)-1H-benzoimidazole. To a mixture of 2,4-dichloro-1H-benzoimidazole (0.550 g, 2.94 mmol) and THF (15 mL) was added DIPEA (1.54 mL, 8.82 mmol) followed by 1-chloromethoxy-2-methoxy-ethane (0.550 g, 4.41 mmol) at 23° C. After stirring for 18 h, EtOAc (100 mL) was added. The organic layer was washed with saturated aqueous NaHCO$_3$ (30 mL) and brine (30 mL). The organic layers were combined, dried, filtered, and concentrated under reduced pressure. The residue was purified (FCC) (10-50% EtOAc/hexanes to yield the titled compound as a mixture of regioisomers (0.660 g, 82%). MS (ESI/CI): mass calcd. for C$_{11}$H$_{12}$Cl$_2$N$_2$O$_2$, 274.0; m/z found, 275.1 [M+H]$^+$. $^1$H NMR (500 MHz, CDCl$_3$): 7.61 (dd, J=8.0, 1.0 Hz, 1H), 7.41 (dd, J=8.1, 0.9 Hz, 1H), 7.33 (dd, J=7.9, 1.0 Hz, 1H), 7.31-7.20 (m, 3H), 5.98 (s, 2H), 5.66 (s, 2H), 3.76-3.69 (m, 2H), 3.67-3.60 (m, 2H), 3.55-3.46 (m, 4H), 3.37 (s, 3H), 3.36 (s, 3H).

Step E: 1-[4-Chloro-1-(2-methoxy-ethoxymethyl)-1H-benzoimidazol-2-yl]-1H-pyrazole-4-carboxylic acid ethyl ester. To a mixture of 2,4-dichloro-1-(2-methoxy-ethoxymethyl)-1H-benzoimidazole (0.660 g, 2.40 mmol) and DMF (10 mL), was added Cs$_2$CO$_3$ (1.88 g, 5.76 mmol) and 1H-pyrazole-4-carboxylic acid ethyl ester (0.400 g, 2.88 mmol). The resulting mixture was then heated to 80° C. for 2 h. The mixture was cooled to 23° C., poured into brine (40 mL), and extracted with EtOAc (3×40 mL). The combined organic layers were washed with brine (40 mL), dried, filtered, and concentrated under reduced pressure. The residue was purified (FCC) (10-50% EtOAc/hexanes) to yield the titled compound as a mixture of regioisomers (0.880 g, 97%). MS (ESI/CI): mass calcd. for C$_{17}$H$_{19}$ClN$_4$O$_4$, 378.1; m/z found, 379.1 [M+H]$^+$. $^1$H NMR (500 MHz, CDCl$_3$): 8.97 (s, 1H), 8.80 (s, 1H), 8.22 (s, 1H), 8.20 (s, 1H), 7.65 (s, 1H), 7.53 (s, 1H), 7.40-7.23 (m, 4H), 6.38 (s, 2H), 6.16 (s, 2H), 4.41-4.31 (m, 4H), 3.68-3.59 (m, 2H), 3.57-3.49 (m, 2H), 3.48-3.41 (m, 2H), 3.41-3.35 (m, 2H), 3.31 (s, 3H), 3.25 (s, 3H), 1.38 (td, J=7.1, 1.2 Hz, 6H).

Step F: 1-(4-Chloro-1H-benzoimidazol-2-yl)-1H-pyrazole-4-carboxylic acid ethyl ester. To a mixture of 1-[4-chloro-1-(2-methoxy-ethoxymethyl)-1H-benzoimidazol-2-yl]-1H-pyrazole-4-carboxylic acid ethyl ester (0.370 g, 0.980 mmol) and EtOH (2.5 mL), was added 4M HCl in dioxane (2.5 mL, 10 mmol). The mixture was stirred for 18 h at 23° C. The resulting white precipitate was filtered and washed with EtOH to yield the titled compound (0.260 g, 93%). MS (ESI/CI): mass calcd. for C$_{13}$H$_{11}$ClN$_4$O$_2$, 290.1; m/z found, 291.1 [M+H]$^+$. $^1$H NMR (500 MHz, DMSO-d$_6$): 13.83 (s, 1H), 8.98 (s, 1H), 8.45-8.29 (m, 1H), 7.46 (s, 1H), 7.38-7.16 (m, 2H), 4.59-4.01 (m, 2H), 1.60-1.01 (m, 3H).

Step G: Preparation of 1-(4-Chloro-1H-benzoimidazol-2-yl)-1H-pyrazole-4-carboxylic acid. To a mixture of 1-(4-chloro-1H-benzoimidazol-2-yl)-1H-pyrazole-4-carboxylic acid ethyl ester (0.180 g, 0.550 mmol), THF (3 mL), and water (1 mL), was added LiOH.H$_2$O (95.0 mg, 2.20 mmol). The mixture was stirred 18 h at 23° C. The solvent was evaporated, water (3 mL) was added and the mixture acidified with aq. 1 M HCl. The resulting white precipitate was filtered and dried to yield the titled compound (0.130 g, 90%). MS (ESI/CI): mass calcd. for C$_{11}$H$_7$ClN$_4$O$_2$, 262.0; m/z found, 263.0 [M+H]$^+$. $^1$H NMR (400 MHz, DMSO-d$_6$): 13.64 (s, 1H), 12.97 (s, 1H), 8.90 (s, 1H), 8.30 (s, 1H), 7.48 (d, J=7.4 Hz, 1H), 7.32 (dd, J=7.8, 1.0 Hz, 1H), 7.25 (t, J=7.9 Hz, 1H).

Example 28: 1-(5-Chloro-7-trifluoromethyl-1H-benzoimidazol-2-yl)-1H-pyrazole-4-carboxylic Acid

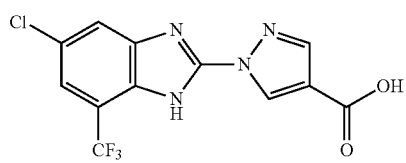 [SMILES: O=C(O)c1cnn(-c2nc3cc(Cl)cc(C(F)(F)F)c3[nH]2)c1]

The titled compound was prepared in a manner analogous to EXAMPLE 27, substituting 4-chloro-2-nitro-6-trifluoromethyl-phenylamine for 3-chloro-2-nitro-phenylamine in Step A. MS (ESI/CI): mass calcd. for $C_{12}H_6ClF_3N_4O_2$, 330.0; m/z found, 331.0 [M+H]$^+$. $^1$H NMR (600 MHz, DMSO-d$_6$): 14.08 (s, 1H), 12.97 (s, 1H), 8.87 (s, 1H), 8.34 (s, 1H), 7.80 (s, 1H), 7.64-7.58 (m, 1H).

Example 29: 1-(7-Bromo-5-trifluoromethoxy-1H-benzoimidazol-2-yl)-1H-pyrazole-4-carboxylic Acid

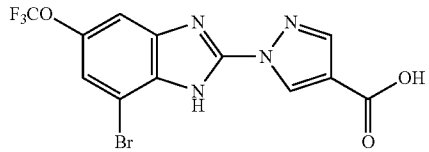 [SMILES: O=C(O)c1cnn(-c2nc3cc(OC(F)(F)F)cc(Br)c3[nH]2)c1]

The titled compound was prepared in a manner analogous to EXAMPLE 27, substituting 2-bromo-6-nitro-4-trifluoromethoxy-phenylamine for 3-chloro-2-nitro-phenylamine in Step A. MS (ESI/CI): mass calcd. for $C_{12}H_6BrF_3N_4O_3$, 390.0; m/z found, 391.0 [M+H]$^+$. $^1$H NMR (400 MHz, DMSO-d$_6$): 13.98 (s, 1H), 12.94 (s, 1H), 8.90 (s, 1H), 8.32 (d, J=0.4 Hz, 1H), 7.57-7.52 (m, 1H), 7.48 (s, 1H).

Example 30: 1-(6-Chloro-5-trifluoromethyl-1H-benzoimidazol-2-yl)-1H-pyrazole-4-carboxylic Acid

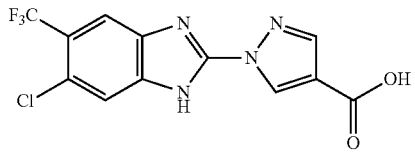

The titled compound was prepared in a manner analogous to EXAMPLE 27, substituting 4-chloro-2-nitro-5-trifluoromethyl-phenylamine for 3-chloro-2-nitro-phenylamine in Step A. MS (ESI/CI): mass calcd. for $C_{12}H_6ClF_3N_4O_2$, 330.0; m/z found, 331.0 [M+H]$^+$. $^1$H NMR (500 MHz, DMSO-d$_6$): 8.93 (s, 1H), 8.34 (s, 1H), 7.99 (s, 1H), 7.85 (s, 1H).

Example 31: 1-(4,5,6-Trifluoro-1H-benzoimidazol-2-yl)-1H-pyrazole-4-carboxylic Acid

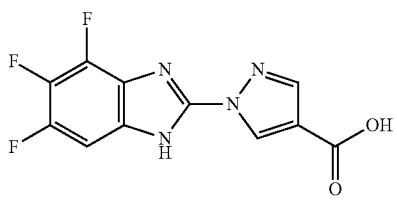 [SMILES: O=C(O)c1cnn(-c2nc3c(F)c(F)c(F)cc3[nH]2)c1]

The titled compound was prepared in a manner analogous to EXAMPLE 27, substituting 2,3,4-trifluoro-6-nitro-phenylamine for 3-chloro-2-nitro-phenylamine in Step A. MS (ESI/CI): mass calcd. for $C_{11}H_5F_3N_4O_2$, 282.0; m/z found, 283.0 [M+H]$^+$. $^1$H NMR (400 MHz, DMSO-d$_6$): 13.95 (s, 1H), 12.96 (s, 1H), 8.92 (s, 1H), 8.31 (s, 1H), 7.42 (s, 1H).

Example 32: 1-(4-Bromo-5,6-difluoro-1H-benzoimidazol-2-yl)-1H-pyrazole-4-carboxylic Acid

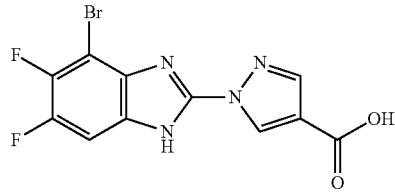 [SMILES: O=C(O)c1cnn(-c2nc3c(Br)c(F)c(F)cc3[nH]2)c1]

The titled compound was prepared in a manner analogous to EXAMPLE 27, Steps B-G, substituting 3-bromo-4,5-difluoro-benzene-1,2-diamine for 3-chloro-benzene-1,2-diamine in Step B. MS (ESI/CI): mass calcd. for $C_{11}H_5BrF_2N_4O_2$, 342.0; m/z found, 343.0 [M+H]$^+$. $^1$H NMR (400 MHz, DMSO-d$_6$): 13.93 (s, 1H), 12.93 (s, 1H), 8.88 (s, 1H), 8.30 (s, 1H), 7.55 (s, 1H).

Example 33: 1-(6-Chloro-4-methyl-1H-benzoimidazol-2-yl)-1H-pyrazole-4-carboxylic Acid

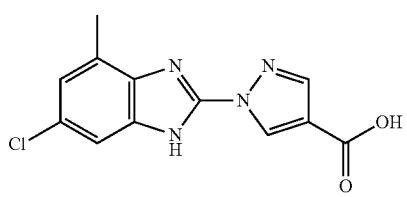 [SMILES: Cc1cc(Cl)cc2[nH]c(-n3cc(C(=O)O)cn3)nc12]

The titled compound was prepared in a manner analogous to EXAMPLE 27, substituting 4-chloro-2-methyl-6-nitro-phenylamine for 3-chloro-2-nitro-phenylamine in Step A. MS (ESI/CI): mass calcd. for $C_{12}H_9ClN_4O_2$, 276.0; m/z found, 277.1 [M+H]$^+$. $^1$H NMR (400 MHz, DMSO-d$_6$): 13.77-13.17 (m, 1H), 8.87 (s, 1H), 8.29 (s, 1H), 7.39 (s, 1H), 7.11 (dd, J=1.9, 0.8 Hz, 1H), 2.53 (s, 3H).

Example 34: 1-(4,6-Dichloro-1H-benzoimidazol-2-yl)-1H-pyrazole-4-carboxylic Acid

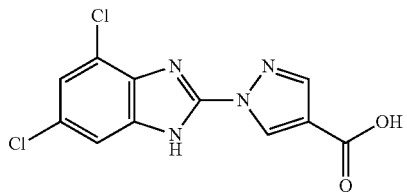 [SMILES: O=C(O)c1cnn(-c2nc3c(Cl)cc(Cl)cc3[nH]2)c1]

The titled compound was prepared in a manner analogous to EXAMPLE 27, substituting 2,4-dichloro-6-nitro-phenylamine for 3-chloro-2-nitro-phenylamine in Step A. MS (ESI/CI): mass calcd. for $C_{11}H_6Cl_2N_4O_2$, 296.0; m/z found, 297.0 [M+H]$^+$. $^1$H NMR (500 MHz, DMSO-d$_6$): 13.76-13.08 (m, 1H), 8.89 (s, 1H), 8.29 (s, 1H), 7.49 (s, 1H), 7.40 (d, J=1.7 Hz, 1H).

Example 35: 1-(4-Bromo-6-trifluoromethyl-1H-benzoimidazol-2-yl)-1H-pyrazole-4-carboxylic Acid

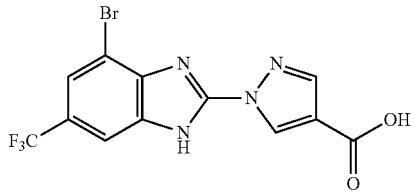 [SMILES: O=C(O)c1cnn(-c2nc3c(Br)cc(C(F)(F)F)cc3[nH]2)c1]

The titled compound was prepared in a manner analogous to EXAMPLE 27, substituting 2-bromo-6-nitro-4-trifluoromethyl-phenylamine for 3-chloro-2-nitro-phenylamine in Step A. MS (ESI/CI): mass calcd. for $C_{12}H_6BrF_3N_4O_2$, 375.0; m/z found, 376.0 [M+H]$^+$. $^1$H NMR (500 MHz, DMSO-d$_6$): 14.21 (s, 1H), 13.02 (s, 1H), 8.94 (s, 1H), 8.36 (s, 1H), 7.81 (s, 1H), 7.78 (s, 1H).

Example 36: 1-(5,6-Difluoro-1H-benzoimidazol-2-yl)-1H-pyrazole-4-carboxylic Acid

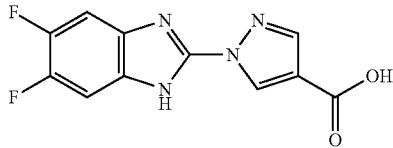 [SMILES: O=C(O)c1cnn(-c2nc3cc(F)c(F)cc3[nH]2)c1]

The titled compound was prepared in a manner analogous to EXAMPLE 27, Steps D-G, substituting 2-chloro-5,6-difluoro-1H-benzoimidazole (*J. Med. Chem.* 1997, 40(5), 811-818) for 2,4-dichloro-1H-benzoimidazole in Step D. MS (CI): mass calcd. for $C_{11}H_6F_2N_4O_2$, 264.1; m/z found, 263.0 [M–H]$^-$. $^1$H NMR (500 MHz, DMSO-d$_6$): 12.50-14.10 (br m, 2H), 8.86 (s, 1H), 8.28 (s, 1H), 7.55-7.66 (br s, 2H).

Example 37: 1-(4-Bromo-6-chloro-1H-benzoimidazol-2-yl)-1H-pyrazole-4-carboxylic Acid

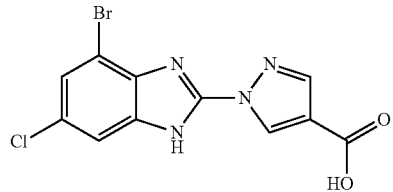 [SMILES: O=C(O)c1cnn(-c2nc3c(Br)cc(Cl)cc3[nH]2)c1]

The titled compound was prepared in a manner analogous to EXAMPLE 27, substituting 2-bromo-4-chloro-6-nitro-phenylamine for 3-chloro-2-nitro-phenylamine in Step A. MS (ESI/CI): mass calcd. for $C_{11}H_6BrClN_4O_2$, 339.9; m/z found, 340.9 [M+H]$^+$. $^1$H NMR (600 MHz, DMSO-d$_6$): 8.72 (s, 1H), 8.00 (s, 1H), 7.36 (d, J=1.8 Hz, 1H), 7.11 (d, J=1.7 Hz, 1H).

Example 38: 1-(6-Methanesulfonyl-1H-benzoimidazol-2-yl)-1H-pyrazole-4-carboxylic Acid

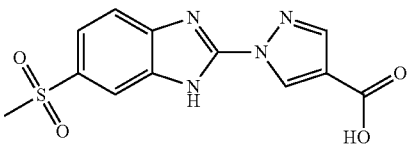 [SMILES: CS(=O)(=O)c1ccc2nc(-n3cc(C(=O)O)cn3)[nH]c2c1]

The titled compound was prepared in a manner analogous to EXAMPLE 27, substituting 4-methanesulfonyl-2-nitro-phenylamine for 3-chloro-2-nitro-phenylamine in Step A. MS (ESI/CI): mass calcd. for $C_{12}H_{10}N_4O_4S$, 306.0; m/z found, 307.1 [M+H]$^+$. $^1$H NMR (400 MHz, DMSO-d$_6$, tautomeric broadening): 13.94 (br s, 1H), 13.02 (br s, 1H), 8.96 (d, J=0.4 Hz, 1H), 8.35 (s, 1H), 8.29-7.60 (m, 3H), 3.24 (s, 3H).

Example 39: 1-(6-Chloro-5-cyano-1H-benzoimidazol-2-yl)-1H-pyrazole-4-carboxylic Acid

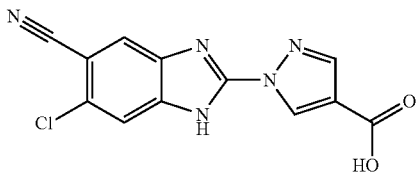 [SMILES: N#Cc1cc2nc(-n3cc(C(=O)O)cn3)[nH]c2cc1Cl]

Step A: N-(4-Chloro-3-cyano-phenyl)-acetamide. Acetic anhydride (2.79 mL, 29.5 mmol), 5-amino-2-chloro-benzonitrile (3.00 g, 19.7 mmol), N,N-dimethylaminopyridine (0.241 g, 1.97 mmol), and toluene (50 mL) were combined and heated to reflux for 1.5 h. The reaction mixture was cooled, and water and EtOAc (150 mL) were added. The solid remaining in the mixture was collected and set aside. The aqueous layer was extracted once more with EtOAc, and the combined layers were washed with brine. The reserved precipitate was then dissolved in EtOAc, which was washed with brine. All organic layers were combined, dried, filtered, and concentrated. The residue was triturated with DCM/hexanes to yield the titled compound (3.52 g, 92% yield). This compound did not yield MS data. $^1$H NMR (400 MHz, CDCl$_3$): 7.92 (d, J=1.0 Hz, 1H), 7.57 (dd, J=2.1, 1.2 Hz, 2H), 2.17 (s, 3H).

Step B: N-(4-Chloro-5-cyano-2-nitro-phenyl)-acetamide. N-(4-Chloro-3-cyano-phenyl)-acetamide (3.00 g, 15.4 mmol) was dissolved in conc. sulfuric acid (15 mL) and cooled to 0° C. A solution of potassium nitrate (3.12 g, 30.8 mmol) in conc. sulfuric acid (15 mL) was added drop-wise with stirring. The reaction mixture was kept at 0° C. for 3.5 h, then slowly added to stirred ice/water. The resulting precipitate was collected, dissolved in EtOAc, dried, filtered, and concentrated. The residue was purified (FCC) (10-80% EtOAc/hexanes) to yield the titled compound (1.06 g, 29% yield). This compound did not yield MS data. $^1$H NMR (400 MHz, CDCl$_3$): 10.60 (s, 1H), 9.18 (s, 1H), 8.58 (s, 1H), 2.36 (s, 3H).

Step C: 4-amino-2-chloro-5-nitro-benzonitrile. N-(4-Chloro-5-cyano-2-nitro-phenyl)-acetamide (1.06 g, 4.415 mmol) was added to 2 M HCl (45 mL) and heated to reflux for 2 h, then kept at 60° C. for 16 h. The reaction mixture was cooled and brought to pH 9 with saturated aqueous sodium bicarbonate. This was extracted with EtOAc (3×50 mL), washed with brine (1×15 mL), dried, filtered, and concentrated to yield the titled compound (0.868 g, 99%). This compound did not yield MS data. $^1$H NMR (400 MHz, CDCl$_3$): 8.49 (s, 1H), 7.23 (br s, 2H), 7.02 (s, 1H), 2.40 (s, 3H).

Step D: 1-(6-Chloro-5-cyano-1H-benzoimidazol-2-yl)-1H-pyrazole-4-carboxylic acid. The titled compound was prepared in a manner analogous to EXAMPLE 27, substituting 4-amino-2-chloro-5-nitro-benzonitrile for 3-chloro-2-nitro-phenylamine in Step A. MS (ESI/CI): mass calcd. for C$_{12}$H$_6$ClN$_5$O$_2$, 287.0; m/z found, 288.0 [M+H]$^+$. $^1$H NMR (400 MHz, DMSO-d$_6$): 13.51 (br s, 1H), 8.93 (d, J=0.5 Hz, 1H), 8.33 (d, J=0.4 Hz, 1H), 8.19 (s, 1H), 7.84 (s, 1H).

Example 40: 1-(6-Chloro-5-nitro-1H-benzoimidazol-2-yl)-1H-pyrazole-4-carboxylic Acid

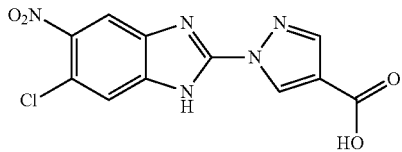 [SMILES: O=C(O)c1cnn(-c2nc3cc([N+](=O)[O-])c(Cl)cc3[nH]2)c1]

Step A: 5-Chloro-6-nitro-1,3-dihydro-benzoimidazol-2-one. To a solution of 4-chloro-5-nitro-benzene-1,2-diamine (8.34 g, 44.4 mmol) and THF (625 mL) was added carbonyl diimidazole (8.65 g, 53.3 mmol) at 0° C. The reaction mixture was allowed to warm to 23° C. and was stirred for 20 h at this temperature. The reaction mixture was concentrated to a volume of 300 mL and 500 mL aqueous 1M HCl was added, followed by water (total volume 2 L). The resulting suspension was cooled at 0° C. for 2 h, and the precipitate was collected and dried on the filter. It was then triturated with cold EtOAc (20 mL) and rinsed EtOAc (2×5 mL) to yield the titled compound (7.26 g, 76% yield). MS (ESI/CI): mass calcd. for C$_7$H$_4$ClN$_3$O$_3$, 213.0; m/z found, 214.0 [M+H]$^+$.

Step B: 2,6-Dichloro-5-nitro-1H-benzoimidazole. To 5-chloro-6-nitro-1,3-dihydro-benzoimidazol-2-one (5.63 g, 26.35 mmol) was added phosphorus oxychloride (35 mL) and the reaction mixture was heated to 85° C. for 36 h. The reaction mixture was concentrated and the residue triturated with cold saturated aqueous sodium bicarbonate (to pH 8, 0.8 L). The resulting precipitate was collected and dried to yield the titled compound (5.43 g, 89% yield). MS (ESI/CI): mass calcd. for C$_7$H$_3$Cl$_2$N$_3$O$_2$, 231.0; m/z found, 232.0 [M+H]$^+$.

Step C: 2,6-Dichloro-1-(2-methoxy-ethoxymethyl)-5-nitro-1H-benzoimidazole. To a stirred solution of 2,6-dichloro-5-nitro-1H-benzoimidazole (5.43 g, 23.4 mmol), diisopropylethylamine (12.2 mL, 70.2 mmol), and THF (120 mL) was added portionwise 1-chloromethoxy-2-methoxyethane (3.30 mL, 28.1 mmol). The reaction mixture was stirred for 2.5 h and concentrated. Water (50 mL) was added to the residue, the mixture was extracted with EtOAc (3×125 mL). The combined organic layers were washed with brine (100 mL), dried, filtered, and concentrated under reduced pressure. The residue was purified (FCC) (20-55% EtOAc/hexanes) to yield the titled compound (6.23 g, 83% yield) as a 1:1 mixture of regioisomers. MS (ESI/CI): mass calcd. for C$_{11}$H$_{11}$Cl$_2$N$_3$O$_4$, 319.0; m/z found, 320.0 [M+H]$^+$. $^1$H NMR (400 MHz, CDCl$_3$): 8.24 (s, 1H), 8.16 (s, 1H), 7.83 (s, 1H), 7.69 (s, 1H), 5.71 (s, 2H), 5.68 (s, 2H), 3.72-3.64 (m, 4H), 3.57-3.50 (m, 4H), 3.35 (s, 3H), 3.35 (s, 3H).

Step D: 1-[6-Chloro-1-(2-methoxy-ethoxymethyl)-5-nitro-1H-benzoimidazol-2-yl]-1H-pyrazole-4-carboxylic acid ethyl ester. To a solution of 2,6-dichloro-1-(2-methoxy-ethoxymethyl)-5-nitro-1H-benzoimidazole (6.15 g, 19.2 mmol), 1H-pyrazole-4-carboxylic acid ethyl ester (2.96 g, 21.1 mmol) and DMF (40 mL) was added cesium carbonate (12.5 g, 38.4 mmol) in a sealable pressure vessel. The vessel was purged with nitrogen, sealed, and heated at 60° C. for 2 h. The reaction mixture was poured into a 1:1 mixture of brine/water (80 mL), and was extracted with EtOAc (3×125 mL). The combined organic layers were washed with brine (3×125 mL), dried, filtered, and concentrated under reduced pressure. The residue was purified (FCC) (5-45% EtOAc/hexanes) to yield the titled compound (8.09 g, 98%) as a mixture of regioisomers. MS (ESI/CI): mass calcd. for C$_{17}$H$_{18}$ClN$_5$O$_6$, 423.1; m/z found, 424.1 [M+H]$^+$. $^1$H NMR (400 MHz, CDCl$_3$): 8.93 (d, J=0.6 Hz, 1H), 8.28 (s, 1H), 8.22 (d, J=0.6 Hz, 1H), 7.83 (s, 1H), 6.26 (s, 2H), 4.37 (q, J=7.1 Hz, 2H), 3.73-3.67 (m, 2H), 3.49-3.44 (m, 2H), 3.29 (s, 3H), 1.39 (t, J=7.1 Hz, 3H).

Step E: 1-(6-Chloro-5-nitro-1H-benzoimidazol-2-yl)-1H-pyrazole-4-carboxylic acid. The titled compound was prepared in a manner analogous to EXAMPLE 27, Steps F-G. MS (ESI/CI): mass calcd. for C$_{11}$H$_6$ClN$_5$O$_4$, 307.0; m/z found, 308.0 [M+H]$^+$. $^1$H NMR (600 MHz, DMSO-d$_6$, tautomeric broadening): 14.14 (br s, 1H), 13.03 (br s, 1H), 8.94 (s, 1H), 8.57-7.52 (m, 3H).

Example 41: 1-(5-Amino-6-chloro-1H-benzoimidazol-2-yl)-1H-pyrazole-4-carboxylic Acid

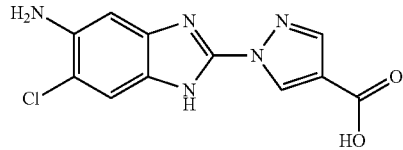

Step A. 1-[5-Amino-6-chloro-1-(2-methoxy-ethoxymethyl)-1H-benzoimidazol-2-yl]-1H-pyrazole-4-carboxylic acid ethyl ester. To a solution of 1-[6-chloro-1-(2-methoxy-ethoxymethyl)-5-nitro-1H-benzoimidazol-2-yl]-1H-pyrazole-4-carboxylic acid ethyl ester (Intermediate D from Example 40) (7.88 g, 18.6 mmol), ammonium chloride (14.9 g, 0.279 mol), acetone (75 mL), and water (15 mL) at 0° C. was added portion-wise zinc dust (12.2 g, 0.186 mol). The reaction mixture was removed from the ice bath and after 15 min, the reaction mixture was filtered through Celite®/diatomaceous earth and rinsed with EtOAc. The filtrate was concentrated and the remainder was partitioned between EtOAc (300 mL) and saturated aqueous sodium bicarbonate (55 mL). The aqueous layer was further extracted with EtOAc (2×125 mL). The combined organic layers were washed with brine (2×40 mL), dried, filtered, and concentrated under reduced pressure. The residue was purified (FCC) (5-65% EtOAc/hexanes) to yield the titled compound (6.29 g, 86% yield) as a 1:1 mixture of regioisomers. MS (ESI/CI): mass calcd. for C$_{17}$H$_{20}$ClN$_5$O$_4$, 393.1; m/z found, 394.1 [M+H]$^+$. $^1$H NMR (400 MHz, CDCl$_3$): 8.83 (d, J=0.6 Hz, 1H), 8.78 (d, J=0.6 Hz, 1H), 8.16 (dd, J=1.9, 0.6 Hz, 2H), 7.63 (s, 1H), 7.54 (s, 1H), 7.09 (s, 1H), 6.96 (s, 1H), 6.03 (s, 2H), 6.00 (s, 2H), 4.35 (q, J=7.1 Hz, 4H), 4.18 (s, 2H), 4.07 (s, 2H), 3.66-3.60 (m, 4H), 3.49-3.42 (m, 4H), 3.32 (s, 3H), 3.31 (s, 3H), 1.37 (t, J=7.1 Hz, 6H).

Step B: 1-(5-Amino-6-chloro-1H-benzoimidazol-2-yl)-1H-pyrazole-4-carboxylic acid. The titled compound was prepared in a manner analogous to EXAMPLE 27, Steps F-G. MS (ESI/CI): mass calcd. for $C_{11}H_8ClN_5O_2$, 277.0; m/z found, 278.1 $[M+H]^+$. $^1$H NMR (400 MHz, DMSO-$d_6$): 12.90 (br s, 1H), 8.81 (s, 1H), 8.25 (s, 1H), 7.47 (s, 1H), 6.98 (s, 1H).

Example 42: 1-(5-Fluoro-1H-benzoimidazol-2-yl)-1H-pyrazole-4-carboxylic Acid

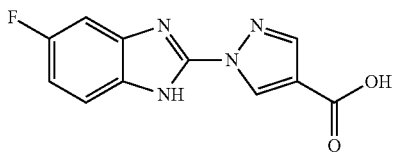 [SMILES: O=C(O)c1cnn(-c2nc3cc(F)ccc3[nH]2)c1]

The titled compound was prepared in a manner analogous to EXAMPLE 27, Steps B-G, substituting 4-fluoro-benzene-1,2-diamine for 3-chloro-benzene-1,2-diamine in Step B. MS (ESI/CI): mass calcd. for $C_{11}H_7FN_4O_2$, 246.1; m/z found, 247.1 $[M+H]^+$. $^1$H NMR (500 MHz, DMSO-$d_6$): 13.47 (s, 1H), 12.94 (s, 1H), 8.88 (s, 1H), 8.29 (s, 1H), 7.54 (br s, 1H), 7.39 (br s, 1H), 7.13-7.07 (m, 1H).

Example 43: 1-(6-Chloro-5-pyrrolidin-1-yl-1H-benzoimidazol-2-yl)-1H-pyrazole-4-carboxylic Acid

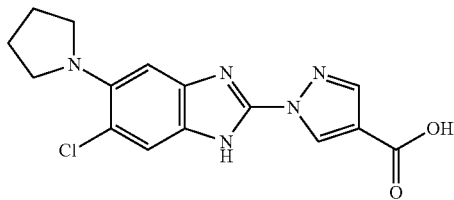 [SMILES: O=C(O)c1cnn(-c2nc3cc(N4CCCC4)c(Cl)cc3[nH]2)c1]

Step A: 4-chloro-2-nitro-5-pyrrolidin-1-yl-phenylamine. Pyrrolidine (6 mL) was added to 4,5-dichloro-2-nitro-phenylamine (2.58 g, 12.5 mmol) in a sealed tube and the mixture heated to 100° C. for 6 h. The mixture was cooled to 23° C., poured into water (100 mL) and extracted with EtOAc (3×100 mL). The combined organic layers were washed with brine (50 mL), dried, filtered, and concentrated under reduced pressure to afford the titled compound (3.00 g, 99%). MS (ESI/CI): mass calcd. for $C_{10}H_{12}ClN_3O_2$, 241.1; m/z found, 242.1 $[M+H]^+$. $^1$H NMR (400 MHz, CDCl$_3$): 8.08 (s, 1H), 6.06 (s, 2H), 5.82 (s, 1H), 3.58 (ddd, J=6.6, 4.2, 2.7 Hz, 4H), 2.02-1.90 (m, 4H).

Step B: 6-chloro-5-pyrrolidin-1-yl-1H-benzoimidazole. Formic acid (2.9 mL) was added to a mixture of 4-chloro-2-nitro-5-pyrrolidin-1-yl-phenylamine (0.240 g, 1.00 mmol) and SnCl$_2$.H$_2$O (0.680 g, 3.00 mmol), and the mixture was heated to 130° C. in a microwave reactor for 5 min. Six reactions were performed on the same scale. The combined crude mixture was filtered and washed with EtOAc (100 mL). The organic layer was treated with water (25 mL) and neutralized with aqueous 6M NaOH. The aqueous layer was extracted with EtOAc (3×30 mL). The combined organic layers were washed with brine (50 mL), dried, filtered, and concentrated under reduced pressure. The residue was triturated with EtOAc and the solid was collected to yield the titled compound (1.08 g, 70%) as the formate salt. MS (ESI/CI): mass calcd. for $C_{11}H_{12}ClN_3$, 221.1; m/z found, 222.1 $[M+H]^+$. $^1$H NMR (400 MHz, DMSO-$d_6$): 12.84-12.16 (br s, 1H), 8.13 (s, 1H), 8.11 (s, 1H), 7.59 (s, 1H), 7.20 (s, 1H), 3.20 (t, J=6.3 Hz, 4H), 2.06-1.66 (m, 4H).

Step C: 5-chloro-1-(2-methoxy-ethoxymethyl)-6-pyrrolidin-1-yl-1H-benzoimidazole. To a mixture of 6-chloro-5-pyrrolidin-1-yl-1H-benzoimidazole (0.443 g, 2.00 mmol) and THF (5 mL) was added NaH (96.0 mg, 60% dispersion in mineral oil, 2.40 mmol) at 0° C. After stirring the reaction mixture for 30 min at 0° C., 1-chloromethoxy-2-methoxy-ethane (0.299 g, 2.40 mmol) was added and the mixture was stirred for 18 h. The reaction mixture was quenched with water and the aqueous layer was extracted with EtOAc (3×50 mL). The combined organic layers were washed with brine (2×20 mL), dried, filtered, and concentrated under reduced pressure. The residue was purified (FCC) (0-10% MeOH/DCM) to yield the titled compound as a mixture of regioisomers (0.240 g, 39%) with a purity of 90%. MS (ESI/CI): mass calcd. for $C_{15}H_{20}ClN_3O_2$, 309.1; m/z found, 310.1 $[M+H]^+$.

Step D: 2,5-Dichloro-1-(2-methoxy-ethoxymethyl)-6-pyrrolidin-1-yl-1H-benzoimidazole. A solution of 5-chloro-1-(2-methoxy-ethoxymethyl)-6-pyrrolidin-1-yl-1H-benzoimidazole (0.221 g, 0.714 mmol) and THF (2.5 mL) was cooled to −78° C. in an acetone/dry ice bath. Lithium diisopropylamide (2.0M solution in THF/heptane/ethylbenzene, 0.90 mL, 1.8 mmol) was added dropwise and the reaction mixture was stirred at −78° C. for 30 min. N-chlorosuccinimide (267 mg, 2.00 mmol) was added at −78° C. and the reaction mixture was warmed to 23° C. and stirred for 2 h. Saturated aqueous NH$_4$Cl (20 mL) was added and the crude product was extracted into EtOAc (3×50 mL). The combined organic layers were washed with brine (50 mL), dried, filtered, and concentrated under reduced pressure. The residue was purified (FCC) (0-100% EtOAc/hexanes) to yield the titled compound (0.240 g, 71%) as a mixture of regioisomers with purity of 70%. MS (ESI/CI): mass calcd. for $C_{15}H_{19}Cl_2N_3O_2$, 343.1; m/z found, 344.1 $[M+H]^+$.

Step E: 1-(6-Chloro-5-pyrrolidin-1-yl-1H-benzoimidazol-2-yl)-1H-pyrazole-4-carboxylic acid. The titled compound was prepared in a manner analogous to EXAMPLE 27, Steps E-G. MS (ESI/CI): mass calcd. for $C_{15}H_{14}ClN_5O_2$, 331.1; m/z found, 332.1 $[M+H]^+$. $^1$H NMR (DMSO-$d_6$): 13.35 (s, 1H), 12.88 (s, 1H), 8.85 (s, 1H), 8.28 (d, J=0.6 Hz, 1H), 7.71 (s, 0.6H), 7.50 (s, 0.4H), 7.44 (s, 0.4H), 7.20 (s, 0.6H), 3.83-3.72 (m, 4H), 3.03-2.89 (m, 4H).

Example 44: 1-(6-Chloro-5-piperidin-1-yl-1H-benzoimidazol-2-yl)-1H-pyrazole-4-carboxylic Acid

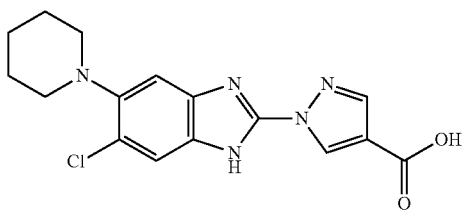 [SMILES: O=C(O)c1cnn(-c2nc3cc(N4CCCCC4)c(Cl)cc3[nH]2)c1]

Step A: 4-Chloro-2-nitro-5-piperidin-1-yl-phenylamine: The titled compound was prepared in a manner analogous to Example 43, substituting piperidine for pyrrolidine in Step A. MS (ESI/CI): mass calcd. for $C_{11}H_{14}ClN_3O_2$, 255.1; m/z found, 256.1 [M+H]$^+$.

Step B: 1-(6-Chloro-5-piperidin-1-yl-1H-benzoimidazol-2-yl)-1H-pyrazole-4-carboxylic acid: The titled compound was prepared in a manner analogous to EXAMPLE 27. MS (ESI/CI): mass calcd. for $C_{16}H_{16}ClN_5O_2$, 345.1; m/z found, 346.1 [M+H]$^+$. $^1$H NMR (500 MHz, DMSO-$d_6$): 8.86 (s, 1H), 8.29 (s, 1H), 7.63 (s, 1H), 7.35 (s, 1H), 2.99 (s, 4H), 1.72 (s, 4H), 1.56 (s, 2H).

Example 45: 1-(6-Chloro-5-morpholin-4-yl-1H-benzoimidazol-2-yl)-1H-pyrazole-4-carboxylic Acid

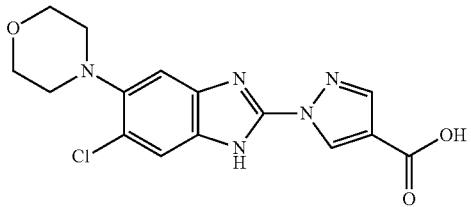 [SMILES: O=C(O)c1cnn(-c2nc3cc(N4CCOCC4)c(Cl)cc3[nH]2)c1]

Step A: 4-Chloro-5-morpholin-4-yl-2-nitro-phenylamine: The titled compound was prepared in a manner analogous to Example 43, substituting morpholine for pyrrolidine in Step A. MS (ESI/CI): mass calcd. for $C_{10}H_{12}ClN_3O_3$, 257.1; m/z found, 258.1 [M+H]$^+$.

Step B: 1-(6-Chloro-5-morpholin-4-yl-1H-benzoimidazol-2-yl)-1H-pyrazole-4-carboxylic acid. The titled compound was prepared in a manner analogous to EXAMPLE 27. MS (ESI/CI): mass calcd. for $C_{15}H_{14}ClN_5O_3$, 347.1; m/z found, 348.1 [M+H]$^+$. $^1$H NMR (DMSO-$d_6$): 13.17 (s, 1H), 12.86 (s, 1H), 8.83 (d, J=0.4 Hz, 1H), 8.26 (s, 1H), 7.62 (s, 0.7H), 7.43 (s, 0.3H), 7.31 (s, 0.3H), 7.08 (s, 0.7H), 3.23 (s, 5H), 1.90 (s, 4H).

Example 46: 1-(6-Chloro-5-methoxy-1H-benzoimidazol-2-yl)-1H-pyrazole-4-carboxylic Acid

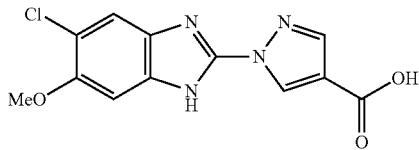 [SMILES: COc1cc2[nH]c(-n3cc(C(=O)O)cn3)nc2cc1Cl]

Step A: 4-Chloro-5-methoxy-2-nitro-phenylamine. To a mixture of 4,5-dichloro-2-nitro-phenylamine (1.29 g, 6.23 mmol) and dry MeOH (2 mL), a 25 wt % solution of sodium methoxide in MeOH (10 mL) was added and the mixture stirred for 6 h at 100° C. in a sealed tube. The mixture was cooled to 23° C., poured into water (50 mL), and extracted with EtOAc (3×50 mL). The combined organic layers were washed with brine (25 mL), dried, filtered, and concentrated under reduced pressure to afford the titled compound (0.700 g, 56%). The crude material was used without further purification in the next reaction.

Step B: 5-Chloro-6-methoxy-1H-benzoimidazole. The titled compound was prepared in a manner analogous to Example 45, Step B substituting 4-chloro-5-methoxy-2-nitro-phenylamine for 4-chloro-2-nitro-5-pyrrolidin-1-yl-phenylamine. MS (ESI/CI): mass calcd. for $C_8H_7ClN_2O$, 182.1; m/z found, 183.1 [M+H]$^+$.

Step C: 5-Chloro-6-methoxy-1-(2-methoxy-ethoxymethyl)-1H-benzoimidazole. To a mixture of 5-chloro-6-methoxy-1H-benzoimidazole (0.320 g, 1.75 mmol) and THF (10 mL), was added DIPEA (0.850 mL, 4.9 mmol) followed by 1-chloromethoxy-2-methoxy-ethane (0.310 g, 2.45 mmol) at 23° C. After stirring for 18 h, EtOAc (50 mL) was added. The organic layer was washed with brine (20 mL), dried, filtered, and concentrated under reduced pressure to afford (0.31 g) of crude material which was used without further purification in the next reaction.

Step D: 1-(6-Chloro-5-methoxy-1H-benzoimidazol-2-yl)-1H-pyrazole-4-carboxylic acid. The titled compound was prepared in a manner analogous to Example 43, Step D-E. MS (ESI/CI): mass calcd. for $C_{12}H_9ClN_4O_3$, 292.0; m/z found, 293.0 [M+H]$^+$. $^1$H NMR (400 MHz, DMSO-$d_6$): 8.85 (d, J=0.6 Hz, 1H), 8.29 (d, J=0.6 Hz, 1H), 7.63 (s, 1H), 7.23 (s, 1H), 3.90 (s, 3H). Note Steps D-E refers to another example Example 47: 2-(4-Carboxy-pyrazol-1-yl)-1H-benzoimidazole-5-carboxylic Acid

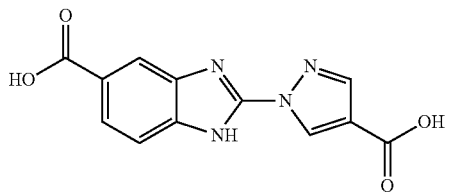 [SMILES: O=C(O)c1ccc2[nH]c(-n3cc(C(=O)O)cn3)nc2c1]

Step A: 2-(4-ethoxycarbonyl-pyrazol-1-yl)-1-(2-methoxy ethoxymethyl)-1H-benzoimidazole-5-carboxylic acid methyl ester. The titled compound was prepared in a manner analogous to EXAMPLE 27, Steps B-E substituting 3,4-diamino-benzoic acid methyl ester for 3-chloro-benzene-1,2-diamine in Step B, to give a mixture of regioisomers. MS (ESI/CI): mass calcd. for $C_{19}H_{22}N_4O_6$, 402.2; m/z found, 403.2 [M+H]$^+$. $^1$H NMR (600 MHz, DMSO-$d_6$): 9.02 (s, 1H), 9.01 (s, 1H), 8.40 (s, 2H), 8.39 (s, 1H), 8.29 (s, 1H), 8.03 (dd, J=8.6, 1.4 Hz, 1H), 7.98 (dd, J=8.5, 1.4 Hz, 1H), 7.91 (d, J=8.6 Hz, 1H), 7.83 (d, J=8.5 Hz, 1H), 6.08 (s, 2H), 6.01 (s, 2H), 4.31 (q, J=7.1 Hz, 4H), 3.91 (s, 3H), 3.90 (s, 3H), 3.55-3.52 (m, 4H), 3.33-3.30 (m, 4H), 3.11 (s, 3H), 3.11 (s, 3H), 1.32 (t, J=7.1 Hz, 6H).

Step B: 2-(4-carboxy-pyrazol-1-yl)-1H-benzoimidazole-5-carboxylic acid. To a stirred solution of 2-(4-ethoxycarbonyl-pyrazol-1-yl)-1-(2-methoxy ethoxymethyl)-1H-benzoimidazole-5-carboxylic acid methyl ester (0.150 g, 0.373 mmol) and acetic acid (4.5 mL) was added aqueous hydrochloric acid (6M, 4.5 mL). The reaction mixture was heated to 100° C. for 18 h and then cooled to 23° C. The resulting precipitate was collected to yield the titled compound (0.30 mg, 30% yield). MS (ESI/CI): mass calcd. for $C_{12}H_8N_4O_4$, 272.1; m/z found, 273.1 [M+H]$^+$. $^1$H NMR (600 MHz, DMSO-$d_6$): 8.94 (s, 1H), 8.32 (s, 1H), 8.14 (s, 1H), 7.87 (dd, J=8.4, 1.5 Hz, 1H), 7.63 (d, J=8.4 Hz, 1H).

Example 48: 1-(5-Bromo-7-fluoro-1H-benzoimidazol-2-yl)-1H-pyrazole-4-carboxylic Acid

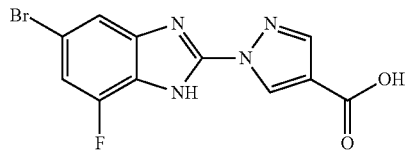

Step A: 5-Bromo-3-fluoro-benzene-1,2-diamine. To a solution of 5-bromo-3-fluoro-2-nitro-phenylamine (2 g, 8.5 mmol), NH$_4$Cl (6.81 g, 127.6 mmol), acetone (100 mL) and water (20 mL), was added zinc powder portion-wise (three equal portions over 5 minutes) (8.34 g, 127.6 mmol) at 0° C. The mixture was stirred for 2 h then warmed to 23° C. The mixture was filtered through Celite® and the solvents were concentrated under reduced pressure. The mixture was re-dissolved in EtOAc/DCM and filtered a second time through Celite® and the solvents were evaporated. The crude mixture was diluted with EtOAc (200 mL), washed with brine (40 mL), dried, filtered, and concentrated under reduced pressure. The resultant residue was used in the next reaction without further purification.

Step B: 1-(5-Bromo-7-fluoro-1H-benzoimidazol-2-yl)-1H-pyrazole-4-carboxylic acid. The titled compound was prepared in a manner analogous to EXAMPLE 47, substituting 5-bromo-3-fluoro-benzene-1,2-diamine for 3-chloro-benzene-1,2-diamine in Step A. MS (ESI/CI): mass calcd. for C$_{11}$H$_6$BrFN$_4$O$_2$, 324.0; m/z found, 325.0 [M+H]$^+$. $^1$H NMR (600 MHz, DMSO-d$_6$): 8.88 (s, 1H), 8.30 (s, 1H), 7.45 (dd, J=9.5, 2.3 Hz, 1H), 7.34 (d, J=7.6 Hz, 1H).

Example 49: 1-(5-Bromo-7-methyl-1H-benzoimidazol-2-yl)-1H-pyrazole-4-carboxylic Acid

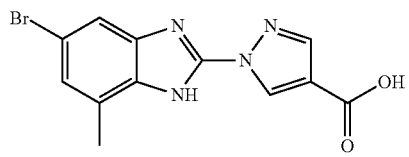 [SMILES: Cc1cc(Br)cc2nc(-n3cc(C(=O)O)cn3)[nH]c12]

The titled compound was prepared in a manner analogous to EXAMPLE 47 substituting 5-bromo-3-methyl-benzene-1,2-diamine for 3-chloro-benzene-1,2-diamine in Step A. MS (ESI/CI): mass calcd. for C$_{12}$H$_9$BrN$_4$O$_2$, 320.0; m/z found, 321.0 [M+H]$^+$. $^1$H NMR (600 MHz, DMSO-d$_6$): 8.88 (s, 1H), 8.29 (s, 1H), 7.53 (s, 1H), 7.23 (s, 1H), 2.53 (s, 3H).

Example 50: 1-[5-(3,4-Dichloro-phenoxy)-6-trifluoromethyl-1H-benzoimidazol-2-yl]-1H-pyrazole-4-carboxylic Acid

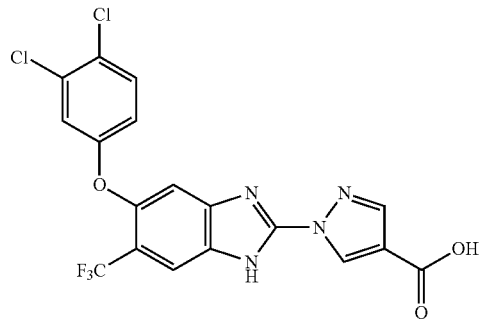

Step A: 5-(3,4-Dichloro-phenoxy)-2-nitro-4-trifluoromethyl-phenylamine. To a mixture of 5-chloro-2-nitro-4-trifluoromethyl-phenylamine (1.00 g, 4.16 mmol) and DMA (21 mL) was added K$_2$CO$_3$ (1.15 g, 8.32 mmol) and 3,4-dichloro-phenol (1.36 g, 8.32 mmol). The mixture was heated to 85° C. for 18 h. The mixture was cooled to 23° C. and poured into ice water. The precipitate was collected, dissolved in EtOAc (150 mL) and washed with brine (2×30 mL). The organic layers were combined, dried, filtered, and concentrated under reduced pressure to yield the titled compound (1.51 g, 99%). $^1$H NMR (500 MHz, CDCl$_3$): 8.52 (s, 1H), 7.53 (d, J=8.7 Hz, 1H), 7.26 (d, J=3.2 Hz, 1H), 7.00 (dd, J=8.7, 2.7 Hz, 1H), 6.37 (s, 2H), 6.06 (s, 1H).

Step B: 1-[5-(3,4-Dichloro-phenoxy)-6-trifluoromethyl-1H-benzoimidazol-2-yl]-1H-pyrazole-4-carboxylic acid. The titled compound was prepared in a manner analogous to EXAMPLE 27. MS (ESI/CI): mass calcd. for C$_{18}$H$_9$Cl$_2$F$_3$N$_4$O$_3$, 456.0; m/z found, 457.0 [M+H]$^+$. $^1$H NMR (400 MHz, DMSO-d$_6$): 13.29 (s, 2H), 8.90 (d, J=0.4 Hz, 1H), 8.32 (s, 1H), 7.96 (s, 1H), 7.63 (d, J=8.9 Hz, 1H), 7.38 (s, 1H), 7.33 (d, J=2.8 Hz, 1H), 7.01 (dd, J=8.9, 2.9 Hz, 1H).

Example 51: 1-[6-Chloro-5-(4-chloro-phenoxy)-1H-benzoimidazol-2-yl]-1H-pyrazole-4-carboxylic Acid

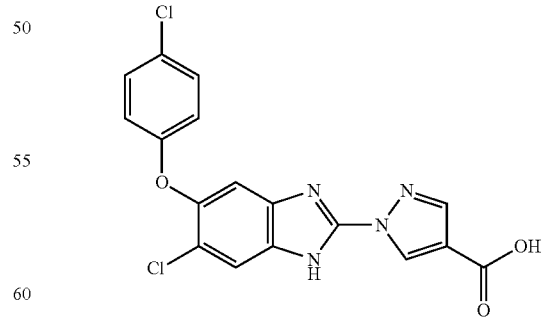

The titled compound was prepared in a manner analogous to EXAMPLE 50, substituting 4-chloro-phenol for 3,4-dichloro-phenol and 4,5-dichloro-2-nitro-phenylamine for 5-chloro-2-nitro-4-trifluoromethyl-phenylamine in Step A. MS (ESI/CI): mass calcd. for C$_{17}$H$_{10}$Cl$_2$N$_4$O$_3$, 388.0; m/z found, 389.0 [M+H]+. 1H NMR (DMSO-d6): 13.25 (br s, 2H), 8.88 (s, 1H), 8.29 (s, 1H), 7.78 (s, 1H), 7.50-7.22 (m, 3H), 7.04-6.80 (m, 2H).

Example 52: 1-[5-(4-Chloro-phenoxy)-6-trifluoromethoxy-1H-benzoimidazol-2-yl]-1H-pyrazole-4-carboxylic Acid

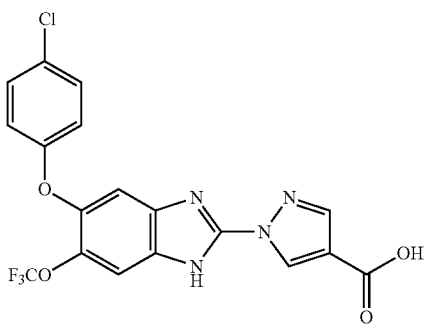 [SMILES: O=C(O)c1cnn(-c2nc3cc(Oc4ccc(Cl)cc4)c(OC(F)(F)F)cc3[nH]2)c1]

The titled compound was prepared in a manner analogous to EXAMPLE 50, substituting 4-chloro-phenol for 3,4-dichloro-phenol and 5-chloro-2-nitro-4-trifluoromethoxy-phenylamine for 5-chloro-2-nitro-4-trifluoromethyl-phenylamine in Step A. MS (ESI/CI): mass calcd. for $C_{16}H_{10}ClF_3N_4O_4$, 438.0; m/z found, 439.0 [M+H]+. 1H NMR (DMSO-d6): 8.82 (s, 1H), 8.22 (s, 1H), 7.67 (s, 1H), 7.41 (d, J=9.0 Hz, 2H), 7.33 (s, 1H), 6.99 (d, J=9.0 Hz, 2H).

Example 53: 1-(5-Phenoxy-6-trifluoromethoxy-1H-benzoimidazol-2-yl)-1H-pyrazole-4-carboxylic Acid

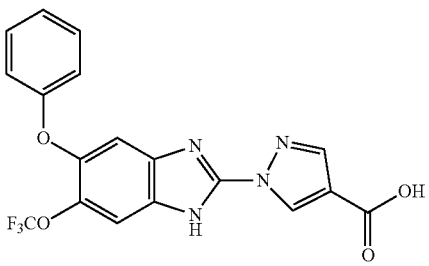 [SMILES: O=C(O)c1cnn(-c2nc3cc(Oc4ccccc4)c(OC(F)(F)F)cc3[nH]2)c1]

The titled compound was prepared in a manner analogous to EXAMPLE 50, substituting phenol for 3,4-dichloro-phenol and 5-chloro-2-nitro-4-trifluoromethoxy-phenylamine for 5-chloro-2-nitro-4-trifluoromethyl-phenylamine in Step A. MS (ESI/CI): mass calcd. for $C_{18}H_{11}F_3N_4O_4$, 404.1; m/z found, 405.1 [M+H]+. 1H NMR (DMSO-d6): 13.30 (s, 1H), 8.88 (s, 1H), 8.30 (s, 1H), 7.72 (s, 1H), 7.48-7.34 (m, 2H), 7.27 (s, 1H), 7.14 (t, J=7.4 Hz, 1H), 7.00 (d, J=7.9 Hz, 2H).

Example 54: 1-[5-(4-Fluoro-phenoxy)-6-trifluoromethyl-1H-benzoimidazol-2-yl]-1H-pyrazole-4-carboxylic Acid

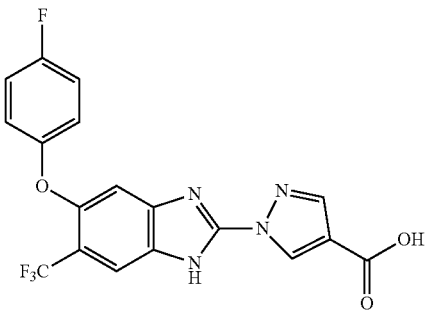 [SMILES: O=C(O)c1cnn(-c2nc3cc(Oc4ccc(F)cc4)c(C(F)(F)F)cc3[nH]2)c1]

The titled compound was prepared in a manner analogous to EXAMPLE 50, substituting 4-fluoro-phenol for 3,4-dichloro-phenol in Step A. MS (ESI/CI): mass calcd. for $C_{18}H_{10}F_4N_4O_3$, 406.1; m/z found, 407.1 [M+H]+. 1H NMR (DMSO-d6): 13.30 (s, 2H), 8.87 (s, 1H), 8.29 (s, 1H), 7.93 (s, 1H), 7.31-7.18 (m, 2H), 7.10 (ddd, J=6.7, 5.4, 3.1 Hz, 3H).

Example 55: 1-[5-(4-Chloro-phenoxy)-6-trifluoromethyl-1H-benzoimidazol-2-yl]-1H-pyrazole-4-carboxylic Acid

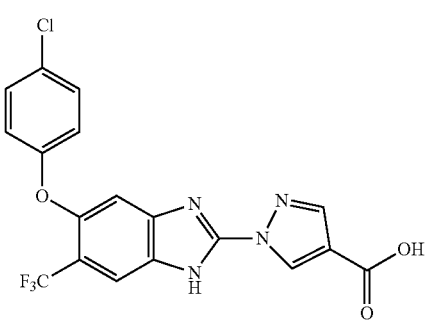 [SMILES: O=C(O)c1cnn(-c2nc3cc(Oc4ccc(Cl)cc4)c(C(F)(F)F)cc3[nH]2)c1]

The titled compound was prepared in a manner analogous to EXAMPLE 50, substituting 4-chloro-phenol for 3,4-dichloro-phenol in Step A. MS (ESI/CI): mass calcd. for $C_{18}H_{10}ClF_3N_4O_3$, 422.0; m/z found, 423.0 [M+H]+. 1H NMR (DMSO-d6): 8.81 (s, 1H), 8.18 (s, 1H), 7.87 (s, 1H), 7.50-7.32 (m, 2H), 7.18 (s, 1H), 7.07-6.91 (m, 2H).

Example 56: 1-(5-Phenoxy-6-trifluoromethyl-1H-benzoimidazol-2-yl)-1H-pyrazole-4-carboxylic Acid

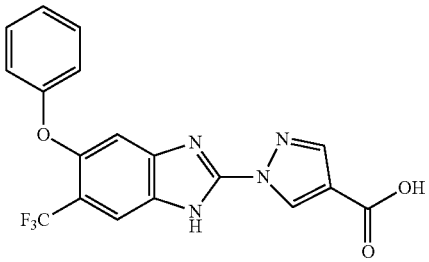 [SMILES: O=C(O)c1cnn(-c2nc3cc(Oc4ccccc4)c(C(F)(F)F)cc3[nH]2)c1]

The titled compound was prepared in a manner analogous to EXAMPLE 50, substituting phenol for 3,4-dichlorophenol in Step A. MS (ESI/CI): mass calcd. for $C_{18}H_{11}F_3N_4O_3$, 388.1; m/z found, 389.1 [M+H]$^+$. $^1$H NMR (DMSO-d$_6$): 13.32 (s, 2H), 8.87 (s, 1H), 8.28 (s, 1H), 7.93 (s, 1H), 7.41 (t, J=7.9 Hz, 2H), 7.16 (dd, J=16.1, 8.7 Hz, 2H), 7.04 (d, J=8.0 Hz, 2H).

Example 57: 1-(6-Chloro-5-phenoxy-1H-benzoimidazol-2-yl)-1H-pyrazole-4-carboxylic Acid

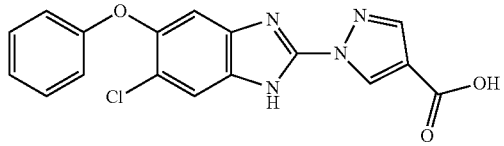 [SMILES: O=C(O)c1cnn(-c2nc3cc(Oc4ccccc4)c(Cl)cc3[nH]2)c1]

Step A: 5-Chloro-2-nitro-4-phenoxyphenylamine. To a solution of phenol (0.500 g, 5.31 mmol) in dry DMF (20 mL) was added solid sodium t-butoxide (0.510 g, 5.31 mmol). The mixture was heated to 100° C. for 60 min, then 4,5-dichloro-2-nitro-phenylamine (1.00 g, 4.83 mmol) was added and the reaction mixture was heated at 100° C. for 19 h. The reaction mixture was allowed to cool to ambient temperature. The reaction mixture was added to water and extracted with EtOAc. The combined organic layers were washed with 1M Na$_2$CO$_3$, dried, filtered, and concentrated under reduced pressure. The residue was purified (FCC) (hexanes:EtOAc, 5% to 30% over 20 minutes) to yield the titled compound as an orange solid (0.821 g, 64%). $^1$H NMR (400 MHz, CDCl$_3$): 8.27 (s, 1H), 7.50-7.34 (m, 2H), 7.27 (d, J=8.9 Hz, 2H), 7.10 (dd, J=8.6, 1.1 Hz, 2H), 6.02 (s, 3H).

Step B: 6-Chloro-5-phenoxy-1H-benzoimidazole. To a solution of 5-chloro-2-nitro-4-phenoxyphenylamine (0.810 g, 3.06 mmol) in DMF (12 mL) was added trimethylorthoformate (12 mL) followed by sodium dithionite (2.66 g, 15.3 mmol), and glacial acetic acid (1.5 mL). The reaction mixture was heated in a sealed tube at 100° C. for 14 h. Additional sodium dithionite (0.5 g) and acetic acid (1 mL) were added and heating was continued at 120° C. for an additional 3 h. The reaction flask was cooled in ice, added cautiously to half-saturated sodium bicarbonate solution (300 mL) and extracted with EtOAc. Combined organic layers were washed with 5% NaHCO$_3$, brine, dried, filtered, and concentrated under reduced pressure. The residue was purified (FCC) (hexanes:EtOAc, 0% to 5% over 20 minutes) to yield the titled compound as a yellow amorphous solid (0.57 g, 76%) as a mixture of tautomers. MS (ESI/CI): mass calcd. for $C_{13}H_9ClN_2O$, 244; m/z found, 245 [M+H]$^+$. $^1$H NMR (500 MHz, CDCl$_3$): 9.55 (s, 1H), 8.06 (s, 1H), 8.0-7.2 (m, 2H), 7.32 (t, J=7.9 Hz, 2H), 7.09 (t, J=7.3 Hz, 1H), 6.96 (d, J=8.3 Hz, 2H).

Step C: 6-Chloro-1-(2-methoxy-ethoxymethyl)-5-phenoxy-1H-benzoimidazole. To a solution of 6-chloro-5-phenoxy-1H-benzoimidazole (0.565 g, 2.31 mmol) and diisopropylethylamine (0.890 mL, 5.08 mmol) in dry DMF (10 mL) was added MEM chloride (0.29 mL, 2.54 mmol) at 0° C. After 3 d at ambient temperature, the reaction mixture was added to saturated NH$_4$Cl (100 mL) and extracted with EtOAc. Combined organic layers were washed with 0.5 M citric acid, 5% NaHCO$_3$, brine, and dried, filtered, and concentrated under reduced pressure. The residue was purified (FCC) (DCM:MeOH, 0% to 5% over 10 min) to yield the title compound as a red oil that was a 1:1 mixture of regioisomers (0.563 g, 73%). This material was used directly in the next step.

Step D: 2,6-Dichloro-1-(2-methoxy-ethoxymethyl)-5-phenoxy-1H-benzoimidazole. To a solution of diisopropylamine (260 μL, 1.85 mmol) in dry THF (2 mL) cooled in −78° C. bath was added n-butyllithium in hexanes (1.16 mL of a 1.6 M solution). After 45 min, the contents of the flask were added via syringe to a −78° C. solution of 6-chloro-1-(2-methoxy-ethoxymethyl)-5-phenoxy-1H-benzoimidazole (0.560 g, 1.68 mmol) in dry THF (2 mL). After 60 min, N-chlorosuccinimide (0.247 g, 1.85 mmol) in THF (3 mL) was added via syringe to the dark solution at which time the color changed to light brown. The reaction mixture was allowed to warm to ambient temperature then was added to saturated aq. NH$_4$Cl and extracted with EtOAc. The combined organic layers were washed with 0.5 M citric acid, 5% aq. NaHCO$_3$, brine, dried, filtered, and concentrated under reduced pressure. The residue was purified (FCC) to yield the titled compound as a mixture of regioisomers (0.251 g, 41%; orange oil). MS (ESI/CI): mass calcd. for $C_{17}H_{16}Cl_2N_2O_3$, 366; m/z found, 367 [M+H]$^+$. $^1$H NMR (400 MHz, CDCl$_3$) δ 7.80 (s, 1H), 7.62 (s, 1H), 7.37 (s, 1H), 7.36-7.29 (m, 4H), 7.18 (s, 1H), 7.14-7.04 (m, 2H), 6.98-6.90 (m, 4H), 5.63 (s, 2H), 5.54 (s, 2H), 3.72-3.63 (m, 2H), 3.63-3.57 (m, 2H), 3.57-3.50 (m, 2H), 3.49-3.42 (m, 2H), 3.38 (s, 3H), 3.28 (s, 3H).

Step E: 1-(6-Chloro-5-phenoxy-1H-benzoimidazol-2-yl)-1H-pyrazole-4-carboxylic acid ethyl ester. To a stirred solution of 2,6-dichloro-1-(2-methoxy-ethoxymethyl)-5-phenoxy-1H-benzoimidazole (0.251 g, 0.684 mmol) and ethyl pyrazole-4-carboxylate (0.115 g, 0.820 mmol) in dry DMF (4 mL) was added anhydrous cesium carbonate (0.535 g, 1.64 mmol). The stirred suspension was heated in 80° C. bath in a sealed tube for 2 h. After coming to ambient temperature, the reaction mixture was added to ice water (100 mL), acidified with 1N HCl (3 mL) and extracted with dichloromethane. The combined organic layers were washed with water, brine, dried, filtered, and concentrated under reduced pressure to afford the titled product as a crude orange paste (0.361 g). MS (ESI/CI): mass calcd. for $C_{23}H_{23}ClN_4O_5$, 470; m/z found, 471 [M+H]$^+$.

Step F: 1-(6-Chloro-5-phenoxy-1H-benzoimidazol-2-yl)-1H-pyrazole-4-carboxylic acid. 1-(6-Chloro-5-phenoxy-1H-benzoimidazol-2-yl)-1H-pyrazole-4-carboxylic acid ethyl ester (0.361 g) was dissolved in glacial acetic acid (9 mL) and 6N HCl (9 mL) and heated in a sealed tube at 100° C. for 6 h. After cooling in ice, water (5 mL) was added and the solids were collected via filtration, washed with water, and dried under vacuum (60° C., 10 mmHg). The resulting tan powder was recrystallized from MeOH:water (10 mL, 10:1), collected via filtration and dried under reduced pressure to afford the title compound as a tan solid (115 mg, 90%). Mp=134-138° C. (dec.). MS (ESI/CI): mass calcd. for $C_{17}H_{11}ClN_4O_3$, 354; m/z found, 355 [M+H]$^+$, 396 [MH+MeCN]$^+$. $^1$H NMR (mixture of tautomers) (500 MHz, DMSO-d6): 13.60 (s, 0.5H), 13.50 (s, 0.5H), 12.93 (s, 1H), 8.89 (s, 1H), 8.30 (s, 1H), 7.90 (s, 0.5H), 7.65 (s, 0.5H), 7.42 (m, 2.5H), 7.15 (m, 1.5H), 7.02-6.75 (m, 2H).

Example 58: 1-(5-Bromo-7-methyl-1H-imidazo[4,5-f]quinolin-2-yl)-1H-pyrazole-4-carboxylic Acid

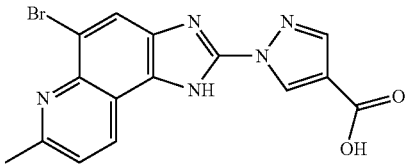 [SMILES: Cc1ccc2c(n1)c(Br)cc1nc(-n3cc(C(=O)O)cn3)[nH]c12]

The titled compound was prepared in a manner analogous to Example 57 steps B-F substituting 8-bromo-2-methyl-6-nitro-quinolin-5-ylamine for 5-chloro-2-nitro-4-phenoxy-phenylamine in Step B. MS (ESI/CI): mass calcd. for $C_{15}H_{10}BrN_5O_2$, 371.0; m/z found, 372.0 [M+H]$^+$. $^1$H NMR (600 MHz, DMSO-d$_6$): 8.94 (s, 1H), 8.83 (d, J=8.3 Hz, 1H), 8.33 (s, 1H), 8.28 (s, 1H), 7.62 (d, J=8.4 Hz, 1H), 2.74 (s, 3H).

Example 59: 1-(5-Benzyloxy-6-chloro-1H-benzoimidazol-2-yl)-1H-pyrazole-4-carboxylic Acid

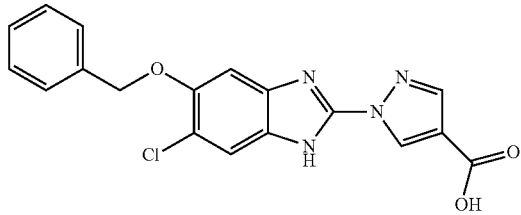 [SMILES: O=C(O)c1cnn(-c2nc3cc(OCc4ccccc4)c(Cl)cc3[nH]2)c1]

Step A: Preparation of 5-benzyloxy-4-chloro-2-nitro-phenylamine. Benzyl alcohol (12.5 mL, 0.121 mol), 4,5-dichloro-2-nitro-phenylamine (5.00 g, 24.2 mmol), cesium carbonate (15.7 g, 48.3 mmol), and DMA (110 mL) were combined in a sealable pressure vessel. The vessel was purged with dry nitrogen, sealed, and heated at 80° C. for 17 h. The reaction mixture was poured into brine (400 mL) and cooled to 0° C. The resulting precipitate was collected and dissolved in EtOAc (400 mL). The organic layer was washed with water (50 mL) and brine (50 mL). The organic layers were combined, dried, filtered, and concentrated under reduced pressure. The residue was purified (FCC) (1-50% EtOAc/hexanes, dryloaded) to yield the titled compound (2.47 g, 37% yield). MS (ESI/CI): mass calcd. for $C_{13}H_{11}ClN_2O_3$, 278.1; m/z found, 279.2 [M+H]$^+$. $^1$H NMR (400 MHz, CDCl$_3$): 8.20 (s, 1H), 7.50-7.30 (m, 5H), 6.23 (s, 1H), 6.19 (br s, 2H), 5.16 (s, 2H).

Step B: 1-(5-Benzyloxy-6-chloro-1H-benzoimidazol-2-yl)-1H-pyrazole-4-carboxylic acid. The titled compound was prepared in a manner analogous to EXAMPLE 27. MS (ESI/CI): mass calcd. for $C_{18}H_{13}ClN_4O_3$, 368.1; m/z found, 369.1 [M+H]$^+$. $^1$H NMR (400 MHz, DMSO-d$_6$, tautomeric broadening): 13.45-13.28 (m, 1H), 12.93 (br s, 1H), 8.84 (s, 1H), 8.27 (s, 1H), 7.81-7.13 (m, 7H), 5.25 (s, 2H).

Example 60: 1-(6-Chloro-5-m-tolylsulfanyl-1H-benzoimidazol-2-yl)-1H-pyrazole-4-carboxylic Acid

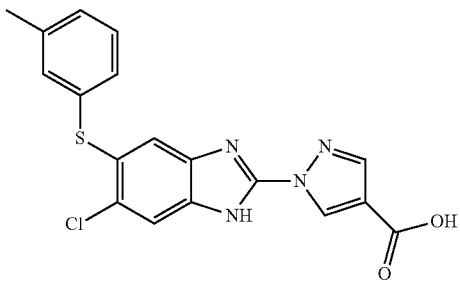 [SMILES: Cc1cccc(Sc2cc3nc(-n4cc(C(=O)O)cn4)[nH]c3cc2Cl)c1]

Step A: 4-chloro-2-nitro-5-m-tolylsulfanyl-phenylamine. A mixture of 3-methyl-benzenethiol (2.30 mL, 19.3 mmol), 4,5-dichloro-2-nitro-phenylamine (2.00 g, 9.66 mmol), potassium carbonate (2.67 g, 19.3 mmol), and DMF (48 mL) was heated at 90° C. for 16 h. The reaction mixture was cooled to 23° C. EtOAc was added and the organic layer was washed with saturated aqueous NaHCO$_3$ (2×80 mL) and brine (1×80 mL). The aqueous layers were extracted with EtOAc (3×80 mL). The organic layers were combined, dried, filtered, and concentrated under reduced pressure. The residue was purified (FCC) (0-100% EtOAc/hexanes) to yield the titled compound (2.30 g, 81%). $^1$H NMR (400 MHz, CDCl$_3$): 8.12 (s, 1H), 7.41-7.36 (m, 3H), 7.34-7.30 (m, 1H), 5.95 (s, 1H), 5.88 (br s, 2H), 2.41 (s, 3H).

Step B: Preparation of 4-chloro-5-m-tolylsulfanyl-benzene-1,2-diamine. To an ice bath cooled solution (0° C.) of 4-chloro-2-nitro-5-m-tolylsulfanyl-phenylamine (2.30 g, 7.80 mmol), ammonium chloride (6.26 g, 117 mmol), acetone (32.5 mL), and water (6.5 mL) was added portion-wise zinc powder (5.10 g, 78.0 mmol). The reaction mixture was removed from the ice bath and after 30 min, the reaction mixture was filtered through a pad of Celite® and washed with EtOAc. The filtrate was placed in a step funnel and the organic layer was collected. The organic layers dried, filtered, and concentrated under reduced pressure. The crude material was used without further purification in the next reaction.

Step C: Preparation of 6-chloro-5-m-tolylsulfanyl-1H-benzoimidazole. To a cooled (0° C.) solution of 4-chloro-5-m-tolylsulfanyl-benzene-1,2-diamine (2.07 g, 7.80 mmol) and trimethyl orthoformate (5.81 mL, 53.0 mmol) was added concentrated HCl (0.722 mL, 11.5 mmol). The reaction mixture was warmed to 23° C. over 16 h, then concentrated under reduced pressure. EtOAc (100 mL) was added to the crude product and the organic layer was washed with saturated aqueous NaHCO$_3$ (2×75 mL). The aqueous layer was extracted with EtOAc (2×50 mL). The organic layers were combined, dried, filtered, and concentrated under reduced pressure. The crude material was used in the next step without further purification. MS (ESI/CI): mass calcd. for $C_{14}H_{11}ClN_2S$, 274.0; m/z found, 275.1 [M+H]$^+$.

Step D: 6-chloro-1-(2-methoxy-ethoxymethyl)-5-m-tolylsulfanyl-1H-benzoimidazole. To a cooled solution (0° C.) of 6-chloro-5-m-tolylsulfanyl-1H-benzoimidazole (2.14 g, 7.78 mmol) and THF (39 mL) was added DIPEA (2.71 mL, 15.6 mmol). 1-Chloromethoxy-2-methoxy-ethane (0.977 mL, 8.56 mmol) was added dropwise, and the reaction mixture was allowed to warm to 23° C. over 16 h. The reaction mixture was concentrated. The residue was purified (FCC) (0-100% EtOAc/hexanes) to yield the titled compound (1.89 g, 67%) as a 1:1 mixture of regioisomers. MS (ESI/CI): mass calcd. for $C_{18}H_{19}ClN_2O_2S$, 362.1; m/z found, 363.1 [M+H]$^+$. $^1$H NMR (500 MHz, CDCl$_3$): 7.95 (s, 1H), 7.92 (s, 1H), 7.88 (s, 1H), 7.64 (s, 1H), 7.59 (s, 1H), 7.41 (s, 1H), 7.22-7.18 (m, 3H), 7.16-7.13 (m, 2H), 7.11-7.05 (m, 3H), 5.56 (s, 2H), 5.47 (s, 2H), 3.57-3.54 (m, 2H), 3.52-3.49 (m, 2H), 3.48-3.45 (m, 2H), 3.44-3.42 (m, 2H), 3.35 (s, 3H), 3.30 (s, 3H), 2.30 (s, 6H).

Step E: 2,6-dichloro-1-(2-methoxy-ethoxymethyl)-5-m-tolylsulfanyl-1H-benzoimidazole. A solution of 6-chloro-1-(2-methoxy-ethoxymethyl)-5-m-tolylsulfanyl-1H-benzo-imidazole (1.89 g, 5.21 mmol) and THF (13 mL) was cooled to −78° C. in an acetone/dry ice bath. Buthyllithium (2.2M solution in hexanes, 2.60 mL, 5.73 mmol) was added dropwise and the reaction mixture was stirred at −78° C. for 1 h. (Lithium diisopropylamide as a 2.0M solution in THF/heptane/ethylbenzene can also be used as a base.) A solution of N-chlorosuccinimide (765 mg, 5.73 mmol) and THF (11.5 mL) was added. The reaction mixture was warmed to 23° C. and stirred for 2 h. Saturated aqueous NH$_4$Cl (20 mL) was added and the crude product was extracted into CH$_2$Cl$_2$ (3×75 mL). The organic layers were dried, filtered, and concentrated under reduced pressure. The residue was purified (FCC) (0-100% EtOAc/hexanes) to provide the titled compound (1.46 g, 71%) as a 1:1 mixture of regioisomers. MS (ESI/CI): mass calcd. for $C_{18}H_{18}Cl_2N_2O_2S$, 396.0; m/z found, 397.0 [M+H]$^+$. $^1$H NMR (500 MHz, CDCl$_3$): 7.74 (s, 1H), 7.57 (s, 1H), 7.40 (s, 1H), 7.29 (s, 1H), 7.23-7.18 (m, 3H), 7.18-7.14 (m, 2H), 7.12-7.07 (m, 3H), 5.58 (s, 2H), 5.48 (s, 2H), 3.64-3.60 (m, 2H), 3.54-3.48 (m, 4H), 3.43-3.40 (m, 2H), 3.34 (s, 3H), 3.29 (s, 3H), 2.30 (s, 6H).

Step F: 1-[6-chloro-1-(2-methoxy-ethoxymethyl)-5-m-tolylsulfanyl-1H-benzoimidazol-2-yl]-1H-pyrazole-4-carboxylic acid ethyl ester. To a mixture of 2,6-dichloro-1-(2-methoxy-ethoxymethyl)-5-m-tolylsulfanyl-1H-benzoimidazole (0.500 g, 1.26 mmol) and DMF (2.52 mL) was added cesium carbonate (0.820 g, 2.52 mmol) and 1H-pyrazole-4-carboxylic acid ethyl ester (0.194 g, 1.38 mmol). The mixture was heated at 80° C. for 2 h in a sealed tube. The mixture was cooled to 23° C. and poured into brine (40 mL), and extracted with EtOAc (3×50 mL). The organic layers were washed with brine (40 mL), dried, filtered, and concentrated under reduced pressure. The residue was purified (FCC) (0-50% EtOAc/hexanes) to yield the titled compound as a 1:1 mixture of regioisomers (0.387 g, 61%). $^1$H NMR (500 MHz, CDCl$_3$): 8.84 (s, 1H), 8.79 (s, 1H), 8.14 (s, 2H), 7.77 (s, 1H), 7.68 (s, 1H), 7.44 (s, 1H), 7.41 (s, 1H), 7.23-7.18 (m, 4H), 7.18-7.16 (m, 1H), 7.12 (d, J=7.6 Hz, 2H), 7.09 (d, J=7.5 Hz, 1H), 6.09 (s, 2H), 5.98 (s, 2H), 4.36-4.27 (m, 4H), 3.66-3.60 (m, 2H), 3.55-3.50 (m, 2H), 3.48-3.42 (m, 2H), 3.38-3.34 (m, 2H), 3.28 (s, 3H), 3.24 (s, 3H), 2.32 (s, 3H), 2.31 (s, 3H), 1.38-1.30 (m, 6H).

Step G: 1-(6-chloro-5-m-tolylsulfanyl-1H-benzoimidazol-2-yl)-1H-pyrazole-4-carboxylic acid ethyl ester. To a mixture of 1-[6-chloro-1-(2-methoxy-ethoxymethyl)-5-m-tolylsulfanyl-1H-benzoimidazol-2-yl]-1H-pyrazole-4-carboxylic acid ethyl ester (0.190 g, 0.379 mmol) and EtOH (1 mL) was added 4M HCl in dioxane (1 mL). The mixture was stirred for 3 h at 23° C. The reaction mixture was concentrated and Et$_2$O (10 mL) was added. The solids were filtered and washed with Et$_2$O to yield the titled compound (0.143 g, 91%). MS (ESI/CI): mass calcd. for $C_{20}H_{17}ClN_4O_2S$, 412.1; m/z found, 413.1 [M+H]$^+$. $^1$H NMR (400 MHz, DMSO-d$_6$): 8.95 (s, 1H), 8.35 (s, 1H), 7.77 (s, 1H), 7.41 (s, 1H), 7.29 (t, J=7.7 Hz, 1H), 7.19-7.14 (m, 2H), 7.12-7.06 (m, 1H), 4.30 (q, J=7.1 Hz, 2H), 2.29 (s, 3H), 1.31 (t, J=7.0 Hz, 3H).

Step H: 1-(6-chloro-5-m-tolylsulfanyl-1H-benzoimidazol-2-yl)-1H-pyrazole-4-carboxylic acid. To a mixture of 1-(6-chloro-5-m-tolylsulfanyl-1H-benzoimidazol-2-yl)-1H-pyrazole-4-carboxylic acid ethyl ester (0.100 g, 0.242 mmol), THF (1 mL), and water (0.3 mL) was added LiOH.H$_2$O (40.7 mg, 0.969 mmol). The mixture was stirred for 18 h at 23° C. The solvent was evaporated, water (3 mL) was added and the mixture acidified with 1M HCl. The resulting white precipitate was filtered and dried to yield the titled compound (85.0 mg, 89%). MS (ESI/CI): mass calcd. for $C_{18}H_{13}ClN_4O_2S$, 384.0; m/z found, 385.0 [M+H]$^+$. $^1$H NMR (500 MHz, DMSO-d$_6$): 8.82 (s, 1H), 8.22 (s, 1H), 7.73 (s, 1H), 7.43 (s, 1H), 7.27 (t, J=7.9 Hz, 1H), 7.15-7.10 (m, 2H), 7.04 (d, J=7.9 Hz, 1H), 2.27 (s, 3H).

Example 61: 1-[6-Chloro-5-(4-chloro-phenylsulfanyl)-1H-benzoimidazol-2-yl]-1H-pyrazole-4-carboxylic Acid

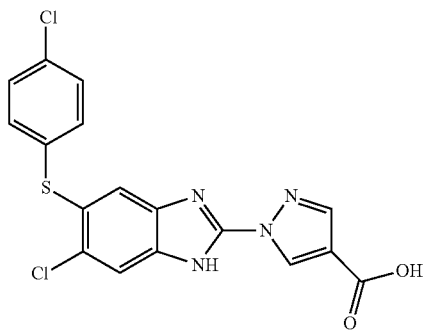 [SMILES: O=C(O)c1cnn(-c2nc3cc(Sc4ccc(Cl)cc4)c(Cl)cc3[nH]2)c1]

The titled compound was prepared in a manner analogous to EXAMPLE 60, substituting 4-chloro-benzenethiol for 3-methyl-benzenethiol in Step A, and substituting lithium diisopropylamide for butyllithium in Step E. MS (ESI/CI): mass calcd. for $C_{17}H_{10}Cl_2N_4O_2S$, 404.0; m/z found, 405.0 [M+H]$^+$. $^1$H NMR (500 MHz, DMSO-d$_6$): 8.84 (s, 1H), 8.23 (s, 1H), 7.76 (s, 1H), 7.57 (s, 1H), 7.44-7.40 (m, 2H), 7.23-7.18 (m, 2H).

Example 62: 1-(6-Chloro-5-phenylsulfanyl-1H-benzoimidazol-2-yl)-1H-pyrazole-4-carboxylic Acid

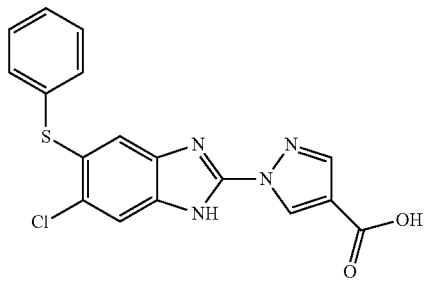 [SMILES: O=C(O)c1cnn(-c2nc3cc(Sc4ccccc4)c(Cl)cc3[nH]2)c1]

The titled compound was prepared in a manner analogous to EXAMPLE 60, substituting benzenethiol for 3-methylbenzenethiol in Step A, and substituting lithium diisopropylamide for butyllithium in Step E. MS (ESI/CI): mass calcd. for $C_{17}H_{11}ClN_4O_2S$, 370.0; m/z found, 371.0 [M+H]$^+$. $^1$H NMR (400 MHz, DMSO-d$_6$): 12.93 (s, 1H), 8.87 (s, 1H), 8.29 (s, 1H), 7.78 (br s, 1H), 7.49-7.37 (m, 3H), 7.37-7.27 (m, 3H).

Example 63: 1-[6-Chloro-5-(3,4-dichloro-phenylsulfanyl)-1H-benzoimidazol-2-yl]-1H-pyrazole-4-carboxylic Acid

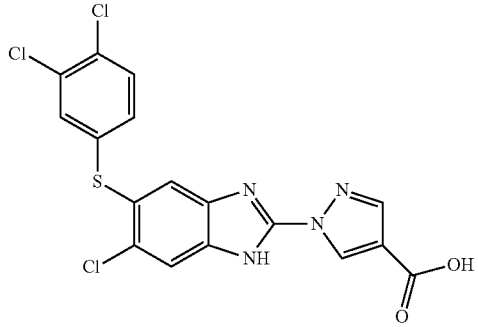 [SMILES: O=C(O)c1cnn(-c2nc3cc(Sc4ccc(Cl)c(Cl)c4)c(Cl)cc3[nH]2)c1]

The titled compound was prepared in a manner analogous to EXAMPLE 60, substituting 3,4-dichloro-benzenethiol for 3-methyl-benzenethiol in Step A. MS (ESI/CI): mass calcd. for $C_{17}H_9Cl_3N_4O_2S$, 437.9; m/z found, 438.9 [M+H]$^+$. $^1$H NMR (600 MHz, DMSO-d$_6$): 8.82 (s, 1H), 8.17 (s, 1H), 7.78 (s, 1H), 7.75 (s, 1H), 7.56 (d, J=8.5 Hz, 1H), 7.33 (d, J=1.8 Hz, 1H), 7.06 (dd, J=8.5, 2.2 Hz, 1H).

Example 64: 1-[6-Chloro-5-(3-methoxy-phenylsulfanyl)-1H-benzoimidazol-2-yl]-1H-pyrazole-4-carboxylic Acid

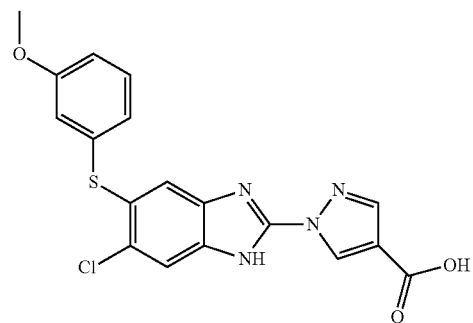 [SMILES: COc1cccc(Sc2cc3nc(-n4cc(C(=O)O)cn4)[nH]c3cc2Cl)c1]

The titled compound was prepared in a manner analogous to EXAMPLE 60, substituting 3-methoxy-benzenethiol for 3-methyl-benzenethiol in Step A. MS (ESI/CI): mass calcd. for $C_{18}H_{13}ClN_4O_3S$, 400.0; m/z found, 401.0 [M+H]$^+$. $^1$H NMR (600 MHz, DMSO-d$_6$): 8.87 (d, J=0.5 Hz, 1H), 8.28 (d, J=0.5 Hz, 1H), 7.78 (br s, 1H), 7.50 (br s, 1H), 7.32-7.29 (m, 1H), 6.89 (ddd, J=8.3, 2.4, 0.9 Hz, 1H), 6.82-6.79 (m, 2H), 3.72 (s, 3H).

Example 65: 1-[6-Chloro-5-(4-methoxy-phenylsulfanyl)-1H-benzoimidazol-2-yl]-1H-pyrazole-4-carboxylic Acid

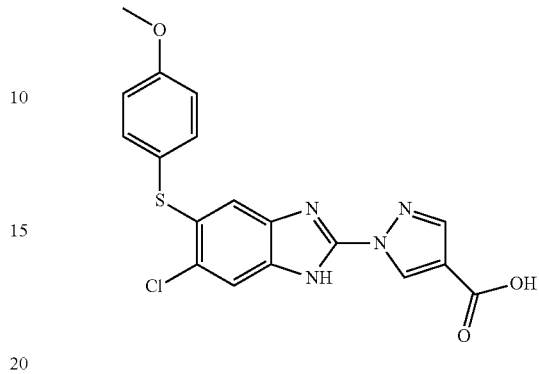

The titled compound was prepared in a manner analogous to EXAMPLE 60, substituting 4-methoxy-benzenethiol for 3-methyl-benzenethiol in Step A, and substituting lithium diisopropylamide for butyllithium in Step E. MS (ESI/CI): mass calcd. for $C_{18}H_{13}ClN_4O_3S$, 400.0; m/z found, 401.0 [M+H]$^+$. $^1$H NMR (600 MHz, DMSO-d$_6$): 8.72 (s, 1H), 8.14 (s, 1H), 7.64 (s, 1H), 7.39 (d, J=8.6 Hz, 2H), 7.08 (s, 1H), 7.04 (d, J=8.8 Hz, 2H), 3.80 (s, 3H).

Example 66: 1-(5-Benzylsulfanyl-6-chloro-1H-benzoimidazol-2-yl)-1H-pyrazole-4-carboxylic Acid

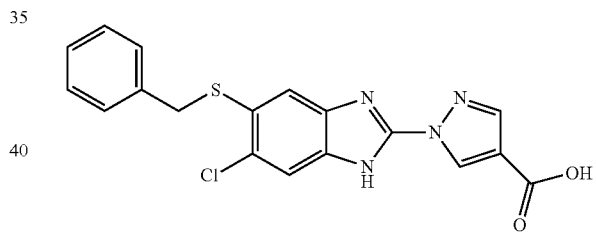

Method A:

Step A: 5-benzylsulfanyl-4-chloro-2-nitro-phenylamine. To a mixture of 4,5-dichloro-2-nitro-phenylamine (3.00 g, 14.5 mmol) and DMF (72 mL) was added K$_2$CO$_3$ (5.31 g, 29.0 mmol) and phenyl-methanethiol (3.94 g, 31.7 mmol). The mixture was heated to 70° C. for 18 h and then cooled to 23° C. The reaction mixture was dissolved in EtOAc (200 mL), washed with saturated sodium bicarbonate solution (100 mL), washed with brine (3×100 mL). The organic layers were combined, dried, filtered, and concentrated under reduced pressure. The residue was purified (FCC) (5-45% EtOAc/hexanes) to yield the titled compound (2.39 g, 56%). MS (ESI/CI): mass calcd. for $C_{13}H_{11}ClN_2O_2S$, 294.0; m/z found, 295.0 [M+H]$^+$. $^1$H NMR (600 MHz, DMSO-d$_6$): 7.96 (s, 1H), 7.56 (s, 2H), 7.50 (d, J=7.2 Hz, 2H), 7.37 (t, J=7.5 Hz, 2H), 7.31 (t, J=7.4 Hz, 1H), 7.05 (s, 1H), 4.27 (s, 2H).

Step B: 1-[5-benzylsulfanyl-6-chloro-1-(2-methoxyethoxymethyl)-1H-benzoimidazol-2-yl]-1H-pyrazole-4-carboxylic acid ethyl ester. The titled compound was prepared in a manner analogous to EXAMPLE 27, Steps A-E substituting 5-benzylsulfanyl-4-chloro-2-nitro-phenylamine for 3-chloro-2-nitro-phenylamine in Step A. MS (ESI/CI): mass calcd. for $C_{24}H_{25}ClN_4O_4S$, 500.1; m/z found, 501.1 [M+H]$^+$.

Step C: 1-(5-benzylsulfanyl-6-chloro-1H-benzoimidazol-2-yl)-1H-pyrazole-4-carboxylic acid ethyl ester. To a mixture of 1-[5-benzylsulfanyl-6-chloro-1-(2-methoxy-ethoxymethyl)-1H-benzoimidazol-2-yl]-1H-pyrazole-4-carboxylic acid ethyl ester (96.0 mg, 0.192 mmol) and EtOH (5 mL) was added 4M HCl in dioxane (5 mL, 20 mmol). The mixture was stirred for 18 h at 23° C. The reaction mixture was concentrated under reduced pressure and the resulting residue was triturated in Et$_2$O. The resultant suspension was filtered and washed with Et$_2$O to yield the titled compound (69.0 mg, 87%). MS (ESI/CI): mass calcd. for $C_{20}H_{17}ClN_4O_2S$, 412.1; m/z found, 413.1 [M+H]$^+$. $^1$H NMR (600 MHz, DMSO-d$_6$): 13.53 (d, J=12.3 Hz, 1H), 8.95 (s, 1H), 8.35 (s, 1H), 7.78 (s, 0.5H), 7.65 (s, 0.5H), 7.55 (s, 0.5H), 7.44 (s, 0.5H), 7.38 (d, J=7.2 Hz, 2H), 7.31 (t, J=7.4 Hz, 2H), 7.25 (s, 1H), 4.32-4.26 (m, 4H), 1.32 (t, J=7.1 Hz, 3H).

Step D: 1-(5-benzylsulfanyl-6-chloro-1H-benzoimidazol-2-yl)-1H-pyrazole-4-carboxylic acid. To a mixture of 1-(5-benzylsulfanyl-6-chloro-1H-benzoimidazol-2-yl)-1H-pyrazole-4-carboxylic acid ethyl ester (57.0 mg, 0.127 mmol), THF (2 mL), and water (0.67 mL) was added LiOH.H$_2$O (27.0 mg, 0.654 mmol). The mixture was stirred for 18 h at 23° C. The reaction mixture was concentrated under reduced pressure, water (3 mL) was added and the mixture acidified to pH=3 with 1M HCl. The resulting white precipitate was filtered and dried to yield the titled compound (39.0 mg, 80%). MS (ESI/CI): mass calcd. for $C_{18}H_{13}ClN_4O_2S$, 384.0; m/z found, 385.0 [M+H]$^+$. $^1$H NMR (600 MHz, DMSO-d$_6$): 8.86 (s, 1H), 8.29 (s, 1H), 7.67 (s, 1H), 7.53 (s, 1H), 7.39 (d, J=7.4 Hz, 2H), 7.31 (t, J=7.4 Hz, 2H), 7.25 (t, J=7.1 Hz, 1H), 4.29 (s, 2H).

Method B:

Step A: 1-[5-tert-butylsulfanyl-6-chloro-1-(2-methoxy-ethoxymethyl)-1H-benzoimidazol-2-yl]-1H-pyrazole-4-carboxylic acid ethyl ester. The titled compound was prepared in a manner analogous to EXAMPLE 66, Method A, Steps A-B, substituting 2-methyl-propane-2-thiol for phenyl-methanethiol in Step A to give a 1:1 mixture of regioisomers. MS (ESI/CI): mass calcd. for $C_{21}H_{27}ClN_4O_4S$, 466.1; m/z found, 467.1 [M+H]$^+$. $^1$H NMR (400 MHz, CDCl$_3$): 8.89-8.88 (m, 2H), 8.19 (s, 2H), 8.03 (s, 1H), 7.93 (s, 1H), 7.85 (s, 1H), 7.78 (s, 1H), 6.17 (s, 2H), 6.13 (s, 2H), 4.39-4.33 (m, 4H), 3.71-3.64 (m, 4H), 3.50-3.42 (m, 4H), 3.31 (s, J=5.1 Hz, 3H), 3.30 (s, 3H), 1.43-1.29 (m, 24H).

Step B: 1-[6-chloro-1-(2-methoxy-ethoxymethyl)-5-(2-nitro-phenyldisulfanyl)-1H-benzoimidazol-2-yl]-1H-pyrazole-4-carboxylic acid ethyl ester. To a stirred solution of 1-[5-tert-butylsulfanyl-6-chloro-1-(2-methoxy-ethoxymethyl)-1H-benzoimidazol-2-yl]-1H-pyrazole-4-carboxylic acid ethyl ester (3.00 g, 6.42 mmol) and DCM (32 mL) was added potassium carbonate (1.78 g, 12.9 mmol). The reaction mixture was treated with 2-nitrobenzenesulfenyl chloride (3.05 g, 16.1 mmol) and stirred at 23° C. for 16 h. The resulting residue was concentrated and purified by FCC (5-30% EtOAc/hexanes) to provide the titled compound (2.99 g, 82% crude yield) as a 2:1 ratio of regioisomers. This compound was used without further purification in subsequent reactions. MS (ESI/CI): mass calcd. for $C_{23}H_{22}ClN_5O_6S_2$, 563.1; m/z found, 564.1 [M+H]$^+$. $^1$H NMR (600 MHz, CDCl$_3$): 8.85-8.82 (m, 2H), 8.17 (s, 2H), 7.75 (s, 0.66H), 7.72 (s, 1.34H), 7.68 (s, 1.34H), 7.64 (s, 0.66H), 7.45-7.42 (m, 4H), 7.31-7.26 (m, 4H), 6.09 (d, J=2.1 Hz, 4H), 4.36 (q, J=7.1 Hz, 4H), 3.67-3.62 (m, 4H), 3.49-3.42 (m, 4H), 3.31 (d, J=1.9, 6H), 1.38 (t, J=7.1 Hz, 6H).

Step C: 1-[6-chloro-5-mercapto-1-(2-methoxy-ethoxymethyl)-1H-benzoimidazol-2-yl]-1H-pyrazole-4-carboxylic acid ethyl ester. To a stirred cooled (0° C.) solution of 1-[6-chloro-1-(2-methoxy-ethoxymethyl)-5-(2-nitro-phenyldisulfanyl)-1H-benzoimidazol-2-yl]-1H-pyrazole-4-carboxylic acid ethyl ester (2.99 g, 5.29 mmol) and EtOH (24 mL) was added dropwise a solution of NaBH$_4$ (0.729 g, 19.3 mmol), EtOH (24 mL), and water (10 mL) over 10 minutes. The reaction mixture was stirred for 15 min and additional NaBH$_4$ (0.486 g, 12.8 mmol) in EtOH (16 mL) and water (6.7 mL) was added. The reaction mixture was stirred for an additional 30 min and then partitioned between DCM (200 mL) and water (200 mL). The aqueous layer was acidified to pH 5 with 1M HCl and the product was extracted with DCM (3×300 mL). The organic layers were combined, dried, filtered, and concentrated under reduced pressure. The residue was purified (FCC) (5-80% EtOAc/hexanes) to yield the titled compound (1.27 g, 48%) as a 2:1 mixture of regioisomers. MS (ESI/CI): mass calcd. for $C_{17}H_{19}ClN_4O_4S$, 410.1; m/z found, 411.1 [M+H]$^+$. $^1$H NMR (600 MHz, CDCl$_3$): 8.85-8.84 (m, 2H), 8.17 (s, 2H), 7.75 (s, 0.67H), 7.72 (s, 1.33H), 7.68 (s, 1.33H), 7.64 (s, 0.67H), 6.10-6.09 (m, 4H), 4.36 (q, J=7.1 Hz, 4H), 4.02 (s, 0.67H), 3.93 (s, 1.33H), 3.66-3.62 (m, 4H), 3.47-3.44 (m, 4H), 3.31-3.30 (m, 6H), 1.38 (t, J=7.1 Hz, 6H). Large-scale synthesis of the titled compound also provided a dimer by-product, where the dimer linkage is thru the sulfur bond forming a disulfide intermediate of 1-[6-chloro-5-mercapto-1-(2-methoxy-ethoxymethyl)-1H-benzoimidazol-2-yl]-1H-pyrazole-4-carboxylic acid ethyl ester, this by-product was isolated but not tested: MS (ESI/CI): mass calcd. for $C_{34}H_{36}Cl_2N_8O_8S_2$, 818.1; m/z found, 819.1 [M+H]$^+$.

Step D: 1-[5-benzylsulfanyl-6-chloro-1-(2-methoxy-ethoxymethyl)-1H-benzoimidazol-2-yl]-1H-pyrazole-4-carboxylic acid ethyl ester. To a solution of 1-[6-chloro-5-mercapto-1-(2-methoxy-ethoxymethyl)-1H-benzoimidazol-2-yl]-1H-pyrazole-4-carboxylic acid ethyl ester (0.300 g, 0.730 mmol), benzyl bromide (0.130 mL, 1.10 mmol) and DMF (20 mL) was added potassium carbonate (0.151 g, 1.10 mmol). The reaction mixture was stirred for 15 min at 23° C. and poured onto water (40 mL). The product was extracted with EtOAc (3×50 mL). The organic layers were combined, dried, filtered, and concentrated under reduced pressure. The residue was purified (FCC) (2-50% EtOAc/hexanes) to yield the titled compound (0.330 g, 90%). MS (ESI/CI): mass calcd. for $C_{24}H_{25}ClN_4O_4S$, 500.1; m/z found, 501.1 [M+H]$^+$.

Step E: 1-(5-benzylsulfanyl-6-chloro-1H-benzoimidazol-2-yl)-1H-pyrazole-4-carboxylic acid ethyl ester. To a mixture of 1-[5-benzylsulfanyl-6-chloro-1-(2-methoxy-ethoxymethyl)-1H-benzoimidazol-2-yl]-1H-pyrazole-4-carboxylic acid ethyl ester (160 mg, 0.319 mmol) and EtOH (3.2 mL) was added 4M HCl in dioxane (3.21 mL, 12.8 mmol). The mixture stirred for 18 h at 23° C. The reaction mixture was concentrated and the resulting residue was triturated in Et$_2$O. The suspension was filtered and washed with Et$_2$O to yield the titled compound (0.125 g, 95%) MS (ESI/CI): mass calcd. for $C_{20}H_{17}ClN_4O_2S$, 412.1; m/z found, 413.1 [M+H]$^+$. $^1$H NMR (600 MHz, DMSO-d$_6$); 13.53 (d, J=12.3 Hz, 1H), 8.95 (s, 1H), 8.35 (s, 1H), 7.78 (s, 0.5H), 7.65 (s, 0.5H), 7.55 (s, 0.5H), 7.44 (s, 0.5H), 7.38 (d, J=7.2 Hz, 2H), 7.31 (t, J=7.4 Hz, 2H), 7.25 (s, 1H), 4.32-4.26 (m, 4H), 1.32 (t, J=7.1 Hz, 3H).

Step F: 1-(5-benzylsulfanyl-6-chloro-1H-benzoimidazol-2-yl)-1H-pyrazole-4-carboxylic acid. To a mixture of 1-(5- benzylsulfanyl-6-chloro-1H-benzoimidazol-2-yl)-1H-pyrazole-4-carboxylic acid ethyl ester (0.115 g, 0.256 mmol), THF (4.8 mL), and water (1.2 mL) was added LiOH.H$_2$O (0.107 g, 2.56 mmol). The mixture was stirred for 18 h at 23° C. The solvent was evaporated, water (3 mL) was added and the mixture acidified to pH 3 with 1M HCl. The resulting white precipitate was filtered and dried to yield the titled compound (97.0 mg, 99%). MS (ESI/CI): mass calcd. for C$_{18}$H$_{13}$ClN$_4$O$_2$S, 384.0; m/z found, 385.0 [M+H]$^+$. $^1$H NMR (600 MHz, DMSO-d$_6$): 8.86 (s, 1H), 8.29 (s, 1H), 7.67 (s, 1H), 7.53 (s, 1H), 7.39 (d, J=7.4 Hz, 2H), 7.31 (t, J=7.4 Hz, 2H), 7.25 (t, J=7.1 Hz, 1H), 4.29 (s, 2H).

Example 67: 1-[5-(4-tert-Butyl-benzylsulfanyl)-6-chloro-1H-benzoimidazol-2-yl]-1H-pyrazole-4-carboxylic Acid

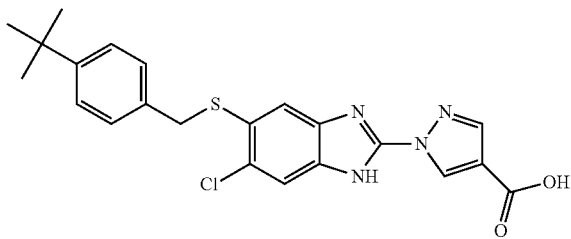 [SMILES: CC(C)(C)c1ccc(CSc2cc3nc(-n4cc(C(=O)O)cn4)[nH]c3cc2Cl)cc1]

The titled compound was prepared in a manner analogous to EXAMPLE 66, Method A, substituting (4-tert-butyl-phenyl)-methanethiol for phenyl-methanethiol in Step A. MS (ESI/CI): mass calcd. for C$_{22}$H$_{21}$ClN$_4$O$_2$S, 440.1; m/z found, 441.1 [M+H]$^+$. $^1$H NMR (600 MHz, DMSO-d$_6$): 8.80 (s, 1H), 8.21 (s, 1H), 7.64 (s, 1H), 7.59 (s, 1H), 7.34-7.23 (m, 4H), 4.21 (s, 2H), 1.26 (s, 9H).

Example 68: 1-[6-Chloro-5-(4-fluoro-benzylsulfanyl)-1H-benzoimidazol-2-yl]-1H-pyrazole-4-carboxylic Acid

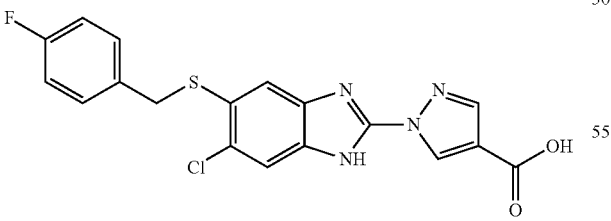

The titled compound was prepared in a manner analogous to EXAMPLE 66, Method A, substituting (4-fluoro-phenyl)-methanethiol for phenyl-methanethiol in Step A. MS (ESI/CI): mass calcd. for C$_{18}$H$_{12}$ClFN$_4$O$_2$S, 402.0; m/z found, 403.0 [M+H]$^+$. $^1$H NMR (600 MHz, DMSO-d$_6$): 8.85 (s, 1H), 8.28 (s, 1H), 7.67 (s, 1H), 7.60-7.46 (m, 1H), 7.39 (dd, J=8.7, 5.5 Hz, 2H), 7.19-7.06 (m, 2H), 4.27 (s, 2H).

Example 69: 1-[6-Chloro-5-(2-chloro-benzylsulfanyl)-1H-benzoimidazol-2-yl]-1H-pyrazole-4-carboxylic Acid

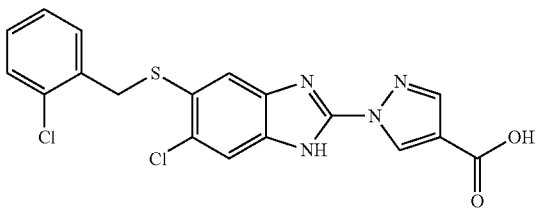 [SMILES: O=C(O)c1cnn(-c2nc3cc(SCc4ccccc4Cl)c(Cl)cc3[nH]2)c1]

The titled compound was prepared in a manner analogous to EXAMPLE 66, Method A, substituting (2-chloro-phenyl)-methanethiol for phenyl-methanethiol in Step A. MS (ESI/CI): mass calcd. for C$_{18}$H$_{12}$Cl$_2$N$_4$O$_2$S, 418.0; m/z found, 419.0 [M+H]$^+$. $^1$H NMR (600 MHz, DMSO-d$_6$): 8.84 (s, 1H), 8.26 (s, 1H), 7.68 (s, 1H), 7.52 (s, 1H), 7.46 (dd, J=7.9, 1.2 Hz, 1H), 7.34 (dd, J=7.5, 1.7 Hz, 1H), 7.29 (td, J=7.6, 1.8 Hz, 1H), 7.24 (td, J=7.4, 1.3 Hz, 1H), 4.31 (s, 2H).

Example 70: 1-(6-Chloro-5-phenethylsulfanyl-1H-benzoimidazol-2-yl)-1H-pyrazole-4-carboxylic Acid

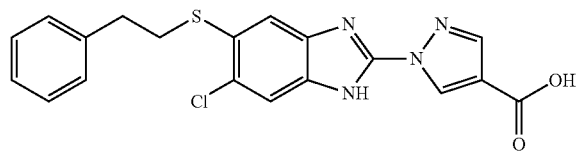 [SMILES: O=C(O)c1cnn(-c2nc3cc(SCCc4ccccc4)c(Cl)cc3[nH]2)c1]

The titled compound was prepared in a manner analogous to EXAMPLE 66, Method A, substituting 2-phenyl-ethanethiol for phenyl-methanethiol in Step A. MS (ESI/CI): mass calcd. for C$_{19}$H$_{15}$ClN$_4$O$_2$S, 398.1; m/z found, 399.0 [M+H]$^+$. $^1$H NMR (600 MHz, DMSO-d$_6$): 13.26 (s, 1H), 8.86 (s, 1H), 8.28 (s, 1H), 7.69 (s, 1H), 7.60 (s, 1H), 7.34-7.29 (m, 4H), 7.24-7.21 (m, 1H), 3.30-3.25 (m, 2H), 2.95-2.90 (m, 2H).

Example 71: 1-(6-Methylsulfanyl-5-trifluoromethyl-1H-benzoimidazol-2-yl)-1H-pyrazole-4-carboxylic Acid

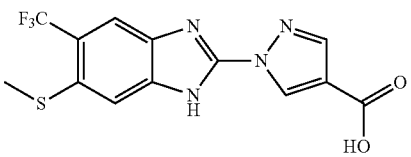 [SMILES: CSc1cc2[nH]c(-n3cc(C(=O)O)cn3)nc2cc1C(F)(F)F]

Step A: 5-Methylsulfanyl-2-nitro-4-trifluoromethyl-phenylamine. To a solution of 5-chloro-2-nitro-4-trifluoromethyl-phenylamine (2.02 g, 8.40 mmol) and DMF (40 mL) was added sodium thiomethoxide (0.618 g, 8.82 mmol). The mixture was heated to 90° C. for 50 min, then poured into brine. Water was added to bring the total volume to 300 mL and the orange precipitate was collected to yield the titled compound (2.02 g, 95%). $^1$H NMR (400 MHz, CDCl$_3$): 8.42 (s, 1H), 6.51 (s, 1H), 6.39 (br s, 2H), 2.53 (s, 3H).

Step B: 1-[1-(2-Methoxy-ethoxymethyl)-6-methylsulfanyl-5-trifluoromethyl-1H-benzoimidazol-2-yl]-1H-pyrazole-4-carboxylic acid ethyl ester. The titled compound was prepared in a manner analogous to EXAMPLE 27, Steps A-E, substituting 5-methylsulfanyl-2-nitro-4-trifluoromethyl-phenylamine for 3-chloro-2-nitro-phenylamine in Step A. The resulting product was recovered as a 1:1 mixture of regioisomers. MS (ESI/CI): mass calcd. for $C_{19}H_{21}F_3N_4O_4S$, 458.1; m/z found, 459.1 [M+H]$^+$. $^1$H NMR (400 MHz, CDCl$_3$): 8.91 (s, 1H), 8.88 (s, 1H), 8.21-8.19 (m, 2H), 8.03 (s, 1H), 7.96 (s, 1H), 7.76 (s, 1H), 7.65 (s, 1H), 6.22-6.19 (m, 4H), 4.37 (q, J=7.1 Hz, 4H), 3.70-3.63 (m, 4H), 3.49-3.45 (m, 4H), 3.32-3.30 (m, 6H), 2.61-2.57 (m, 6H), 1.39 (t, J=7.1 Hz, 6H).

Step C: 1-(6-Methylsulfanyl-5-trifluoromethyl-1H-benzoimidazol-2-yl)-1H-pyrazole-4-carboxylic acid. To a stirred solution of 1-[1-(2-methoxy-ethoxymethyl)-6-methylsulfanyl-5-trifluoromethyl-1H-benzoimidazol-2-yl]-1H-pyrazole-4-carboxylic acid ethyl ester (0.200 g, 0.436 mmol) and acetic acid (1.3 mL) was added 6M aq. hydrochloric acid (1.3 mL). The reaction mixture was heated to 100° C. for 18 h and then cooled to 23° C. The precipitate was collected to yield the titled compound as the HCl salt (0.118 g, 71% yield). MS (ESI/CI): mass calcd. for $C_{13}H_9F_3N_4O_2S$, 342.0; m/z found, 343.0 [M+H]$^+$. $^1$H NMR (400 MHz, DMSO-d$_6$): 8.92 (d, J=0.6 Hz, 1H), 8.33 (d, J=0.4 Hz, 1H), 7.90 (s, 1H), 7.68 (s, 1H), 2.59 (s, 3H).

Example 72: 1-(6-Propylsulfanyl-5-trifluoromethyl-1H-benzoimidazol-2-yl)-1H-pyrazole-4-carboxylic Acid

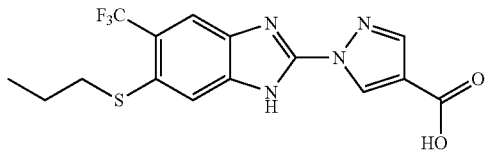 [SMILES: CCCSc1cc2[nH]c(-n3cc(C(=O)O)cn3)nc2cc1C(F)(F)F]

Step A: 2-Nitro-5-propylsulfanyl-4-trifluoromethyl-phenylamine. To a mixture of 5-chloro-2-nitro-4-trifluoromethyl-phenylamine (1.50 g, 6.26 mmol), potassium carbonate (1.72 g, 12.5 mmol), and DMF (31 mL) was added 1-propanethiol (0.620 mL, 6.86 mmol). The reaction mixture was heated at 90° C. for 16 h, then allowed to cool to 23° C. and poured into ice/brine (300 mL). The resulting yellow precipitate was collected to yield the titled compound (1.67 g, 95%). MS (ESI/CI): mass calcd. for $C_{10}H_{11}F_3N_2O_2S$, 280.1; m/z found, 281.0 [M+H]$^+$. $^1$H NMR (400 MHz, CDCl$_3$): 8.41 (s, 1H), 6.58 (s, 1H), 6.36 (br s, 2H), 2.97 (t, J=7.3 Hz, 2H), 1.87-1.72 (m, 2H), 1.10 (t, J=7.4 Hz, 3H).

Step B: 1-(6-Propylsulfanyl-5-trifluoromethyl-1H-benzoimidazol-2-yl)-1H-pyrazole-4-carboxylic acid. The titled compound was prepared in a manner analogous to EXAMPLE 71, Steps B-C. The residue was purified by reverse-phase HPLC to yield the titled compound. MS (ESI/CI): mass calcd. for $C_{15}H_{13}F_3N_4O_2S$, 370.1; m/z found, 371.1 [M+H]$^+$. $^1$H NMR (400 MHz, DMSO-d$_6$, tautomeric broadening): 13.77 (s, 1H), 13.02 (s, 1H), 8.92 (d, J=0.6 Hz, 1H), 8.34 (d, J=0.6 Hz, 1H), 8.17-7.54 (m, 2H), 3.02 (t, J=7.1 Hz, 2H), 1.68-1.52 (m, 2H), 0.98 (t, J=7.3 Hz, 3H).

Example 73: 1-(6-Isopropylsulfanyl-5-trifluoromethyl-1H-benzoimidazol-2-yl)-1H-pyrazole-4-carboxylic Acid

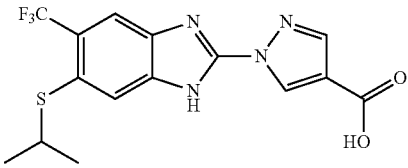 [SMILES: CC(C)Sc1cc2[nH]c(-n3cc(C(=O)O)cn3)nc2cc1C(F)(F)F]

The titled compound was prepared in a manner analogous to EXAMPLE 72, substituting 2-propanethiol for 1-propanethiol in Step A. MS (ESI/CI): mass calcd. for $C_{15}H_{13}F_3N_4O_2S$, 370.1; m/z found, 371.1 [M+H]$^+$. $^1$H NMR (400 MHz, CD$_3$OD, tautomeric broadening): 8.94 (s, 1H), 8.21 (s, 1H), 8.03-7.78 (m, 2H), 3.53-3.38 (m, 1H), 1.29 (d, J=6.7 Hz, 6H).

Example 74: 1-(5-Fluoro-6-methylsulfanyl-1H-benzoimidazol-2-yl)-1H-pyrazole-4-carboxylic Acid

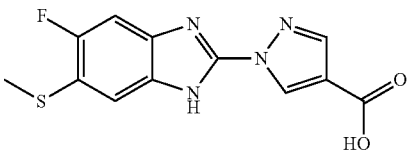 [SMILES: CSc1cc2[nH]c(-n3cc(C(=O)O)cn3)nc2cc1F]

The titled compound was prepared in a manner analogous to EXAMPLE 71, substituting 4,5-difluoro-2-nitro-phenylamine for 5-chloro-2-nitro-4-trifluoromethyl-phenylamine in Step A. MS (ESI/CI): mass calcd. for $C_{12}H_9FN_4O_2S$, 292.0; m/z found, 293.0 [M+H]$^+$. $^1$H NMR (400 MHz, DMSO-d$_6$): 8.87 (s, 1H), 8.29 (s, 1H), 7.48 (d, J=6.7 Hz, 1H), 7.43 (d, J=10.1 Hz, 1H), 2.52 (s, 3H).

Example 75: 1-(5-Chloro-6-methylsulfanyl-1H-benzoimidazol-2-yl)-1H-pyrazole-4-carboxylic Acid

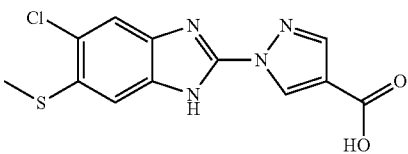 [SMILES: CSc1cc2[nH]c(-n3cc(C(=O)O)cn3)nc2cc1Cl]

The titled compound was prepared in a manner analogous to EXAMPLE 71, substituting 4,5-dichloro-2-nitro-phenylamine for 5-chloro-2-nitro-4-trifluoromethyl-phenylamine in Step A. MS (ESI/CI): mass calcd. for $C_{13}H_9ClN_4O_2S$, 308.0; m/z found, 309.0 [M+H]$^+$. $^1$H NMR (400 MHz, DMSO-d$_6$): 8.87 (d, J=0.6 Hz, 1H), 8.30 (d, J=0.5 Hz, 1H), 7.67 (s, 1H), 7.43 (s, 1H), 2.54 (s, 3H).

Example 76: 1-(5-Chloro-6-ethylsulfanyl-1H-benzoimidazol-2-yl)-1H-pyrazole-4-carboxylic Acid

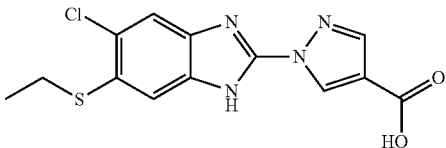 [SMILES: CCSc1cc2[nH]c(-n3cc(C(=O)O)cn3)nc2cc1Cl]

The titled compound was prepared in a manner analogous to EXAMPLE 71, substituting 4,5-dichloro-2-nitro-phenylamine for 5-chloro-2-nitro-4-trifluoromethyl-phenylamine and sodium thioethoxide for sodium thiomethoxide in Step A. MS (ESI/CI): mass calcd. for $C_{13}H_{11}ClN_4O_2S$, 322.0; m/z found, 323.0 $[M+H]^+$. $^1$H NMR (600 MHz, DMSO-$d_6$): 8.85 (s, 1H), 8.27 (s, 1H), 7.65 (s, 1H), 7.53 (s, 1H), 2.99 (q, J=7.3 Hz, 2H), 1.25 (t, J=7.3 Hz, 3H).

Example 77: 1-(5-Chloro-6-isopropylsulfanyl-1H-benzoimidazol-2-yl)-1H-pyrazole-4-carboxylic Acid

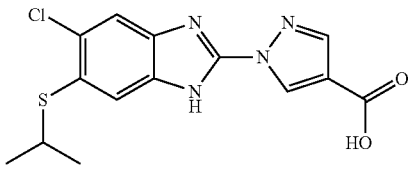 [SMILES: CC(C)Sc1cc2[nH]c(-n3cc(C(=O)O)cn3)nc2cc1Cl]

The titled compound was prepared in a manner analogous to EXAMPLE 71, substituting 4,5-dichloro-2-nitro-phenylamine for 5-chloro-2-nitro-4-trifluoromethyl-phenylamine and sodium thioisopropoxide for sodium thiomethoxide in Step A. MS (ESI/CI): mass calcd. for $C_{14}H_{13}ClN_4O_2S$, 336.0; m/z found, 337.0 $[M+H]^+$. $^1$H NMR (600 MHz, DMSO-$d_6$): 8.89 (s, 1H), 8.30 (s, 1H), 7.70 (s, 1H), 7.68 (s, 1H), 3.56-3.48 (m, 1H), 1.27 (d, J=6.6 Hz, 6H).

Example 78: 1-(5-Chloro-6-propylsulfanyl-1H-benzoimidazol-2-yl)-1H-pyrazole-4-carboxylic Acid

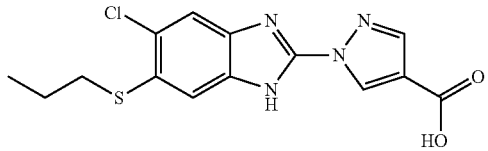

The titled compound was prepared in a manner analogous to EXAMPLE 72, substituting 4,5-dichloro-2-nitro-phenylamine for 5-chloro-2-nitro-4-trifluoromethyl-phenylamine in Step A; and precipitating the final compound in Step B without purification by reverse-phase HPLC. MS (ESI/CI): mass calcd. for $C_{14}H_{13}ClN_4O_2S$, 336.0; m/z found, 337.0 $[M+H]^+$. $^1$H NMR (600 MHz, DMSO-$d_6$): 8.88 (s, 1H), 8.30 (s, 1H), 7.68 (s, 1H), 7.55 (s, 1H), 2.98 (t, J=7.2 Hz, 2H), 1.64 (h, J=7.3 Hz, 2H), 1.02 (t, J=7.3 Hz, 3H).

Example 79: 1-(6-Methylsulfanyl-5-trifluoromethoxy-1H-benzoimidazol-2-yl)-1H-pyrazole-4-carboxylic Acid

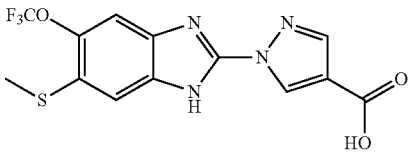 [SMILES: CSc1cc2[nH]c(-n3cc(C(=O)O)cn3)nc2cc1OC(F)(F)F]

The titled compound was prepared in a manner analogous to EXAMPLE 71, substituting 5-chloro-2-nitro-4-trifluoromethoxy-phenylamine for 5-chloro-2-nitro-4-trifluoromethyl-phenylamine in Step A. MS (ESI/CI): mass calcd. for $C_{13}H_9F_3N_4O_3S$, 358.0; m/z found, 359.0 $[M+H]^+$. $^1$H NMR (400 MHz, DMSO-$d_6$, tautomeric broadening): 13.00 (br s, 1H), 8.88 (s, 1H), 8.32 (s, 1H), 7.81-7.12 (m, 2H), 2.54 (s, 3H).

Example 80: 1-(6-Isopropylsulfanyl-5-trifluoromethoxy-1H-benzoimidazol-2-yl)-1H-pyrazole-4-carboxylic Acid

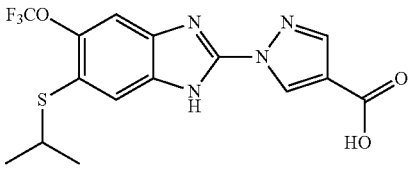 [SMILES: CC(C)Sc1cc2[nH]c(-n3cc(C(=O)O)cn3)nc2cc1OC(F)(F)F]

The titled compound was prepared in a manner analogous to EXAMPLE 72, substituting 5-chloro-2-nitro-4-trifluoromethoxy-phenylamine for 5-chloro-2-nitro-4-trifluoromethyl-phenylamine and 2-propanethiol for 1-propanethiol in Step A. MS (ESI/CI): mass calcd. for $C_{15}H_{13}F_3N_4O_3S$, 386.1; m/z found, 387.1 $[M+H]^+$. $^1$H NMR (400 MHz, DMSO-$d_6$, tautomeric broadening): 13.65 (s, 1H), 13.00 (s, 1H), 8.89 (d, J=0.5 Hz, 1H), 8.32 (d, J=0.5 Hz, 1H), 7.65 (br s, 2H), 3.57-3.44 (br m, 1H), 1.24 (d, J=6.6 Hz, 6H).

Example 81: 1-(6-Propylsulfanyl-5-trifluoromethoxy-1H-benzoimidazol-2-yl)-1H-pyrazole-4-carboxylic Acid

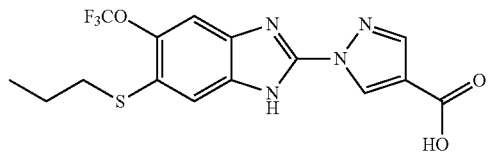 [SMILES: CCCSc1cc2[nH]c(-n3cc(C(=O)O)cn3)nc2cc1OC(F)(F)F]

The titled compound was prepared in a manner analogous to EXAMPLE 72, substituting 5-chloro-2-nitro-4-trifluoromethoxy-phenylamine for 5-chloro-2-nitro-4-trifluoromethyl-phenylamine in Step A. MS (ESI/CI): mass calcd. for $C_{15}H_{13}F_3N_4O_3S$, 386.1; m/z found, 387.1 $[M+H]^+$. $^1$H NMR (400 MHz, DMSO-$d_6$, tautomeric broadening): 13.80-12.75 (m, 2H), 8.88 (d, J=0.6 Hz, 1H), 8.32 (d, J=0.6 Hz, 1H), 7.57 (s, 2H), 2.98 (t, J=7.2 Hz, 2H), 1.68-1.53 (m, 2H), 0.99 (t, J=7.3 Hz, 3H).

Example 82: 1-[6-Chloro-5-(toluene-3-sulfonyl)-1H-benzoimidazol-2-yl]-1H-pyrazole-4-carboxylic Acid

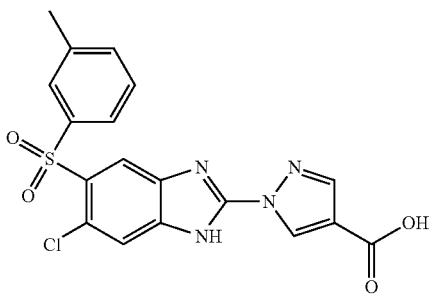 [SMILES: Cc1cccc(S(=O)(=O)c2cc3nc(-n4cc(C(=O)O)cn4)[nH]c3cc2Cl)c1]

Step A: 1-[6-chloro-1-(2-methoxy-ethoxymethyl)-5-(toluene-3-sulfonyl)-1H-benzoimidazol-2-yl]-1H-pyrazole-4-carboxylic acid ethyl ester. To a solution of 1-[6-chloro-1-(2-methoxy-ethoxymethyl)-5-m-tolylsulfanyl-1H-benzoimidazol-2-yl]-1H-pyrazole-4-carboxylic acid ethyl ester (Intermediate from EXAMPLE 60, product from Step F) (0.160 g, 0.319 mmol) and MeOH (1.6 mL) was added a solution of Oxone® (0.412 g, 0.671 mmol) and water (1.7 mL) at 23° C. The reaction mixture was stirred at 23° C. for 16 h. Dichloromethane (30 mL) was added followed by a solution of sodium thiosulfate (0.106 g, 0.670 mmol) in 80% saturated aq. NaHCO₃ (30 mL). The mixture was stirred vigorously until both layers were clear. The organic layer was collected and the water layer extracted with CH₂Cl₂ (2×50 mL). The organic layers were combined, dried, filtered, and concentrated under reduced pressure. The residue was purified (FCC) (0-100% EtOAc/hexanes) to yield the titled compound (0.105 mg, 62%) as a mixture of regioisomers. MS (ESI/CI): mass calcd. for $C_{24}H_{25}ClN_4O_6S$, 532.1; m/z found, 533.1 [M+H]$^+$. $^1$H NMR (400 MHz, CDCl₃): 8.90 (d, J=0.6 Hz, 1.5H), 8.89 (d, J=0.6 Hz, 0.5H), 8.73 (br s, 1.5H), 8.69 (br s, 0.5H), 8.19 (d, J=0.6 Hz, 0.5H), 8.18 (d, J=0.6, 1.5H), 7.79-7.75 (m, 2H), 7.75-7.72 (m, 2H), 7.71 (s, 0.5H), 7.67 (s, 1.5H), 7.39-7.36 (m, 4H), 6.27 (s, 1H), 6.14 (s, 3H), 4.40-4.32 (m, 4H), 3.71-3.67 (m, 1H), 3.66-3.61 (m, 3H), 3.49-3.45 (m, 1H), 3.44-3.39 (m, 3H), 3.28 (s, 1.5H), 3.24 (s, 4.5H), 2.38 (br s, 6H), 1.38-1.33 (m, 6H).

Step B: 1-[6-Chloro-5-(toluene-3-sulfonyl)-1H-benzoimidazol-2-yl]-1H-pyrazole-4-carboxylic acid. The titled compound was prepared in a manner analogous to EXAMPLE 60, steps G-H. MS (ESI/CI): mass calcd. for $C_{18}H_{13}ClN_4O_4S$, 416.0; m/z found, 417.1 [M+H]$^+$. $^1$H NMR (400 MHz, DMSO-d₆): 8.93 (d, J=0.5 Hz, 1H), 8.44 (s, 1H), 8.33 (d, J=0.4 Hz, 1H), 7.75-7.69 (m, 3H), 7.53-7.48 (m, 2H), 2.37 (s, 3H).

Example 83: 1-(5-Benzenesulfonyl-6-chloro-1H-benzoimidazol-2-yl)-1H-pyrazole-4-carboxylic Acid

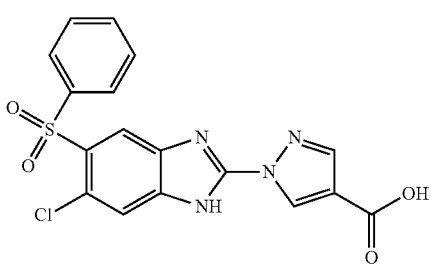 [SMILES: O=C(O)c1cnn(-c2nc3cc(S(=O)(=O)c4ccccc4)c(Cl)cc3[nH]2)c1]

The titled compound was prepared in a manner analogous to EXAMPLE 82, from 1-[6-chloro-1-(2-methoxy-ethoxymethyl)-5-phenylsulfanyl-1H-benzoimidazol-2-yl]-1H-pyrazole-4-carboxylic acid ethyl ester (Intermediate from Example 62). MS (ESI/CI): mass calcd. for $C_{17}H_{11}ClN_4O_4S$, 402.0; m/z found, 403.0 [M+H]$^+$. $^1$H NMR (400 MHz, DMSO-d₆): 8.94 (s, 1H), 8.47 (s, 1H), 8.35 (s, 1H), 7.95-7.89 (m, 2H), 7.76 (br s, 1H), 7.74-7.67 (m, 1H), 7.65-7.58 (m, 2H).

Example 84: 1-[6-Chloro-5-(4-methoxy-benzenesulfonyl)-1H-benzoimidazol-2-yl]-1H-pyrazole-4-carboxylic Acid

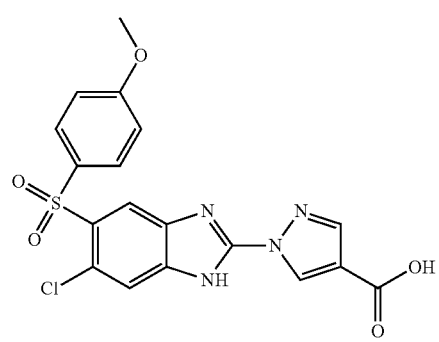 [SMILES: COc1ccc(S(=O)(=O)c2cc3nc(-n4cc(C(=O)O)cn4)[nH]c3cc2Cl)cc1]

The titled compound was prepared in a manner analogous to EXAMPLE 82 from 1-[6-chloro-1-(2-methoxy-ethoxymethyl)-5-(4-methoxy-phenylsulfanyl)-1H-benzoimidazol-2-yl]-1H-pyrazole-4-carboxylic acid ethyl ester (Intermediate from Example 65). MS (ESI/CI): mass calcd. for $C_{18}H_{13}ClN_4O_5S$, 432.0; m/z found, 433.0 [M+H]$^+$. $^1$H NMR (600 MHz, DMSO-d₆): 14.09 (br s, 1H), 13.04 (br s, 1H), 8.94 (s, 1H), 8.42 (s, 1H), 8.35 (s, 1H), 7.89-7.84 (m, 2H), 7.75 (br s, 1H), 7.14-7.10 (m, 2H), 3.84 (s, 3H).

Example 85: 1-[6-Chloro-5-(4-chloro-benzenesulfonyl)-1H-benzoimidazol-2-yl]-1H-pyrazole-4-carboxylic Acid

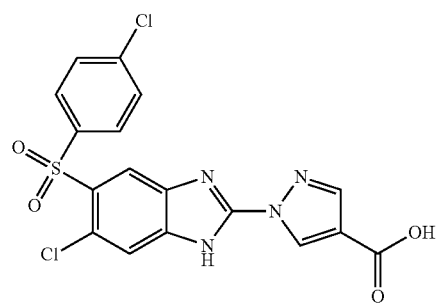 [SMILES: O=C(O)c1cnn(-c2nc3cc(S(=O)(=O)c4ccc(Cl)cc4)c(Cl)cc3[nH]2)c1]

Step A: 1-[6-Chloro-5-(4-chloro-benzenesulfonyl)-1-(2-methoxy-ethoxymethyl)-1H-benzoimidazol-2-yl]-1H-pyrazole-4-carboxylic acid ethyl ester. To a solution of 1-[6-chloro-5-(4-chloro-phenylsulfanyl)-1-(2-methoxy-ethoxymethyl)-1H-benzoimidazol-2-yl]-1H-pyrazole-4-carboxylic acid ethyl ester (Intermediate from Example 61) (2.69 g, 5.16 mmol) and dichloromethane (26 mL) was added mCPBA (2.43 g, 10.8 mmol) at 23° C. The reaction was stirred for 16 h at 23° C. Dichloromethane (30 mL) was added followed by a solution of sodium thiosulfate (1.71 g, 10.8 mmol) in 80% saturated aqueous NaHCO$_3$ (30 mL). The mixture was stirred vigorously until both layers were clear. The organic layer was collected and the aqueous layer extracted with CH$_2$Cl$_2$ (2×80 mL). The organic layers were combined, dried, filtered, and concentrated under reduced pressure. The residue was purified (FCC) (0-100% EtOAc/hexanes) to yield the titled compound (2.55 g, 89%) as a mixture of regioisomers. MS (ESI/CI): mass calcd. for C$_{23}$H$_{22}$Cl$_2$N$_4$O$_6$S, 552.1; m/z found, 553.1 [M+H]$^+$. $^1$H NMR (400 MHz, CDCl$_3$): 8.91-8.89 (m, 2H), 8.73 (s, 1.4H), 8.68 (s, 0.6H), 8.20 (d, J=0.6 Hz, 0.6H), 8.18 (d, J=0.6 Hz, 1.4H), 7.91-7.87 (m, 4H), 7.72 (s, 0.6H), 7.68 (s, 1.4H), 7.48-7.43 (m, 4H), 6.27 (s, 1.2H), 6.15 (s, 2.8H), 4.39-4.32 (m, 4H), 3.71-3.66 (m, 1.2H), 3.67-3.62 (m, 2.8H), 3.48-3.45 (m, 1.2H), 3.44-3.40 (m, 2.8H), 3.28 (s, 1.8H), 3.24 (s, 4.2H), 1.40-1.34 (m, 6H).

Step B: 1-[6-chloro-5-(4-chloro-benzenesulfonyl)-1H-benzoimidazol-2-yl]-1H-pyrazole-4-carboxylic acid ethyl ester. To a mixture of 1-[6-chloro-5-(4-chloro-benzenesulfonyl)-1-(2-methoxy-ethoxymethyl)-1H-benzoimidazol-2-yl]-1H-pyrazole-4-carboxylic acid ethyl ester (2.55 g, 4.61 mmol) and EtOH (11.5 mL) was added 4M HCl in dioxane (11.5 mL). The mixture was stirred for 3 h at 23° C. The reaction mixture was concentrated and Et$_2$O was added. The solids were filtered and washed with Et$_2$O to yield the titled compound (1.92 g, 89%). MS (ESI/CI): mass calcd. for C$_{19}$H$_{14}$Cl$_2$N$_4$O$_4$S, 464.0; m/z found, 465.1 [M+H]$^+$. $^1$H NMR (500 MHz, DMSO-d$_6$): 9.02 (s, 1H), 8.45 (s, 1H), 8.40 (s, 1H), 7.95-7.92 (m, 2H), 7.76 (br s, 1H), 7.70-7.67 (m, 2H), 4.30 (q, J=7.1 Hz, 2H), 1.32 (t, J=7.1 Hz, 3H).

Step C: 1-[6-chloro-5-(4-chloro-benzenesulfonyl)-1H-benzoimidazol-2-yl]-1H-pyrazole-4-carboxylic acid. To a mixture of 1-[6-chloro-5-(4-chloro-benzenesulfonyl)-1H-benzoimidazol-2-yl]-1H-pyrazole-4-carboxylic acid ethyl ester (1.92 g, 4.13 mmol), THF (16 mL), and water (5 mL) was added LiOH.H$_2$O (0.693 g, 16.5 mmol). The mixture was stirred for 18 h at 23° C. The solvent was evaporated, water (10 mL) was added and the mixture acidified with 1M HCl. The resulting precipitate was filtered and dried to yield the titled compound (1.73 g, 94%). MS (ESI/CI): mass calcd. for C$_{17}$H$_{10}$Cl$_2$N$_4$O$_4$S, 436.0; m/z found, 437.0 [M+H]$^+$. $^1$H NMR (500 MHz, DMSO-d$_6$): 8.89 (s, 1H), 8.40 (s, 1H), 8.25 (s, 1H), 7.93-7.90 (m, 2H), 7.69-7.66 (m, 3H).

Example 86: 1-[6-Chloro-5-(4-trifluoromethoxy-benzenesulfonyl)-1H-benzoimidazol-2-yl]-1H-pyrazole-4-carboxylic Acid

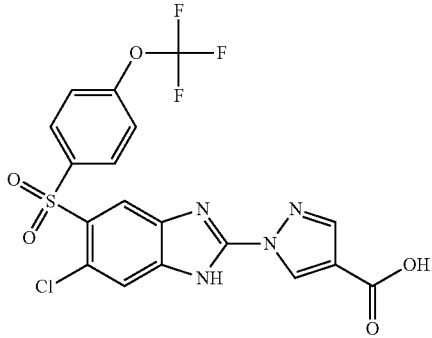 [SMILES: O=C(O)c1cnn(-c2nc3cc(S(=O)(=O)c4ccc(OC(F)(F)F)cc4)c(Cl)cc3[nH]2)c1]

Step A: 1-[6-chloro-1-(2-methoxy-ethoxymethyl)-5-(4-trifluoromethoxy-phenylsulfanyl)-1H-benzoimidazol-2-yl]-1H-pyrazole-4-carboxylic acid ethyl ester. The titled compound was prepared in a manner analogous to Example 60, steps A-F, substituting 4-trifluoromethoxy-benzenethiol for 3-methyl-benzenethiol in Step A.

Step B: 1-[6-Chloro-5-(4-trifluoromethoxy-benzenesulfonyl)-1H-benzoimidazol-2-yl]-1H-pyrazole-4-carboxylic acid. The titled compound was prepared in manner analogous to Example 85. MS (ESI/CI): mass calcd. for C$_{18}$H$_{10}$ClF$_3$N$_4$O$_5$S, 486.0; m/z found, 487.0 [M+H]$^+$. $^1$H NMR (600 MHz, DMSO-d$_6$): 8.77 (s, 1H), 8.29 (s, 1H), 8.02 (s, 1H), 8.01-7.97 (m, 2H), 7.56 (d, J=8.1 Hz, 2H), 7.45 (s, 1H).

Example 87: 1-[6-Chloro-5-(3,4-dichloro-benzenesulfonyl)-1H-benzoimidazol-2-yl]-1H-pyrazole-4-carboxylic Acid

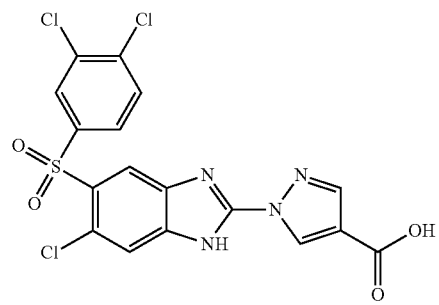 [SMILES: O=C(O)c1cnn(-c2nc3cc(S(=O)(=O)c4ccc(Cl)c(Cl)c4)c(Cl)cc3[nH]2)c1]

The titled compound was prepared in a manner analogous to EXAMPLE 85, from 1-[6-chloro-5-(3,4-dichloro-phenylsulfanyl)-1-(2-methoxy-ethoxymethyl)-1H-benzoimidazol-2-yl]-1H-pyrazole-4-carboxylic acid ethyl ester (Intermediate from Example 63). MS (CI): mass calcd. for C$_{17}$H$_9$Cl$_3$N$_4$O$_4$S, 469.9; m/z found, 468.9 [M−H]$^−$. $^1$H NMR (600 MHz, DMSO-d$_6$): 8.95 (s, 1H), 8.48 (br s, 1H), 8.34 (s, 1H), 8.16 (d, J=1.6 Hz, 1H), 7.92-7.88 (m, 2H), 7.78 (br s, 1H).

Example 88: 1-[6-Chloro-5-(3-methoxy-benzenesulfonyl)-1H-benzoimidazol-2-yl]-1H-pyrazole-4-carboxylic Acid

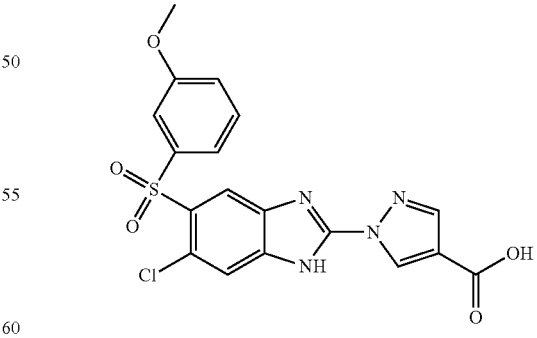

The titled compound was prepared in a manner analogous to EXAMPLE 85, from 1-[6-chloro-1-(2-methoxy-ethoxymethyl)-5-(3-methoxy-phenylsulfanyl)-1H-benzoimidazol-2-yl]-1H-pyrazole-4-carboxylic acid ethyl ester (Intermediate from Example 64). MS (ESI/CI): mass calcd. for C$_{18}$H$_{13}$ClN$_4$O$_5$S, 432.0; m/z found, 433.0 [M+H]$^+$. $^1$H NMR (400 MHz, DMSO-$d_6$): 14.15 (s, 1H), 13.04 (s, 1H), 8.95 (d, J=0.5 Hz, 1H), 8.45 (s, 1H), 8.36 (s, 1H), 7.77 (br s, 1H), 7.53 (t, J=8.0 Hz, 1H), 7.48-7.43 (m, 1H), 7.41-7.38 (m, 1H), 7.27 (ddd, J=8.3, 2.6, 1.0 Hz, 1H), 3.81 (s, 3H).

Example 89: 1-(6-Chloro-5-phenylmethanesulfonyl-1H-benzoimidazol-2-yl)-1H-pyrazole-4-carboxylic Acid

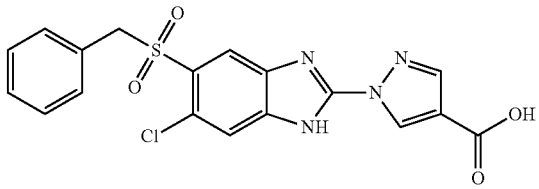 [SMILES: O=C(O)c1cnn(-c2nc3cc(S(=O)(=O)Cc4ccccc4)c(Cl)cc3[nH]2)c1]

The titled compound was prepared in a manner analogous to EXAMPLE 85, from 1-[5-benzylsulfanyl-6-chloro-1-(2-methoxy-ethoxymethyl)-1H-benzoimidazol-2-yl]-1H-pyrazole-4-carboxylic acid ethyl ester (Intermediate from Example 66). MS (ESI/CI): mass calcd. for $C_{18}H_{13}ClN_4O_4S$, 416.0; m/z found, 417.0 [M+H]$^+$. $^1$H NMR (400 MHz, DMSO-$d_6$): 8.92 (s, 1H), 8.33 (s, 1H), 7.98-7.82 (m, 2H), 7.33-7.15 (m, 5H), 4.86 (s, 2H).

Example 90: 1-[6-Chloro-5-(2,4,6-trimethyl-phenylmethanesulfonyl)-1H-benzoimidazol-2-yl]-1H-pyrazole-4-carboxylic Acid

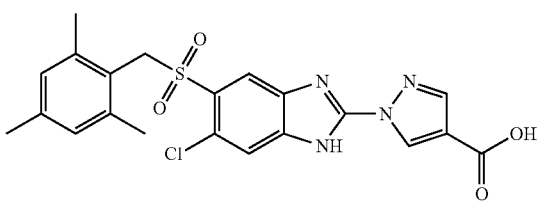 [SMILES: Cc1cc(C)c(CS(=O)(=O)c2cc3nc(-n4cc(C(=O)O)cn4)[nH]c3cc2Cl)c(C)c1]

Step A: 1-[6-Chloro-1-(2-methoxy-ethoxymethyl)-5-(2,4,6-trimethyl-benzylsulfanyl)-1H-benzoimidazol-2-yl]-1H-pyrazole-4-carboxylic acid ethyl ester. The titled compound was prepared in a manner analogous to Example 66, Method A, steps A-B, substituting (2,4,6-trimethyl-phenyl)-methanethiol for phenyl-methanethiol in Step A. MS (ESI/CI): mass calcd. for $C_{27}H_{31}ClN_4O_4S$, 542.2; m/z found, 543.2 [M+H]$^+$.

Step B: 1-[6-Chloro-5-(2,4,6-trimethyl-phenylmethanesulfonyl)-1H-benzoimidazol-2-yl]-1H-pyrazole-4-carboxylic acid. The titled compound was prepared in manner analogous to Example 85. MS (ESI/CI): mass calcd. for $C_{21}H_{19}ClN_4O_4S$, 458.1; m/z found, 459.1 [M+H]$^+$. $^1$H NMR (600 MHz, DMSO-$d_6$): 8.95 (s, 1H), 8.35 (s, 1H), 8.13 (s, 1H), 7.94 (s, 1H), 6.90 (s, 2H), 4.85 (s, 2H), 2.32 (s, 6H), 2.23 (s, 3H).

Example 91: 1-[6-Chloro-5-(4-methoxy-phenylmethanesulfonyl)-1H-benzoimidazol-2-yl]-1H-pyrazole-4-carboxylic Acid

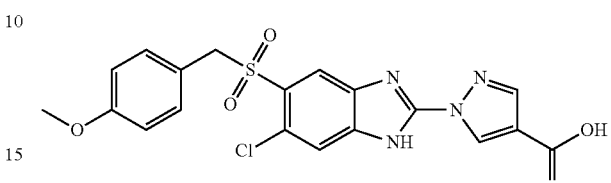

Step A: 1-[6-Chloro-5-(4-methoxy-benzylsulfanyl)-1-(2-methoxy-ethoxymethyl)-1H-benzoimidazol-2-yl]-1H-pyrazole-4-carboxylic acid ethyl ester. The titled compound was prepared in a manner analogous to Example 66, Method A, steps A-B, substituting (4-methoxy-phenyl)-methanethiol for phenyl-methanethiol in Step A. MS (ESI/CI): mass calcd. for $C_{25}H_{27}ClN_4O_5S$, 530.1; m/z found, 531.1 [M+H]$^+$.

Step B: 1-[6-Chloro-5-(4-methoxy-phenylmethanesulfonyl)-1H-benzoimidazol-2-yl]-1H-pyrazole-4-carboxylic acid. The titled compound was prepared in manner analogous to Example 85. MS (ESI/CI): mass calcd. for $C_{19}H_{15}ClN_4O_5S$, 446.1; m/z found, 447.0 [M+H]$^+$. $^1$H NMR (600 MHz, DMSO-$d_6$): 8.92 (s, 1H), 8.34 (s, 1H), 8.03 (s, 0.6H), 7.92 (s, 0.4H), 7.83 (s, 0.6H), 7.74 (s, 0.4H), 7.11 (d, J=8.7 Hz, 2H), 6.82 (d, J=8.4 Hz, 2H), 4.79 (s, 2H), 3.68 (s, 3H).

Example 92: 1-[6-Chloro-5-(4-fluoro-phenylmethanesulfonyl)-1H-benzoimidazol-2-yl]-1H-pyrazole-4-carboxylic Acid

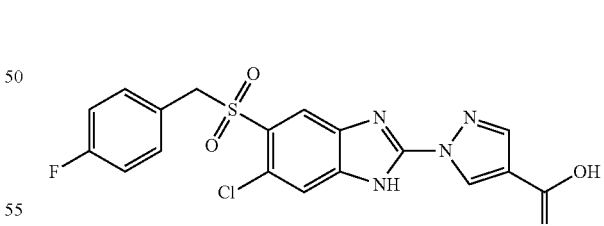

The titled compound was prepared in a manner analogous to EXAMPLE 85, from 1-[6-chloro-5-(4-fluoro-benzylsulfanyl)-1-(2-methoxy-ethoxymethyl)-1H-benzoimidazol-2-yl]-1H-pyrazole-4-carboxylic acid ethyl ester (Intermediate from Example 68. MS (ESI/CI): mass calcd. for $C_{18}H_{12}ClFN_4O_4S$, 434.0; m/z found, 435.0 [M+H]$^+$. $^1$H NMR (600 MHz, DMSO-$d_6$): 8.92 (s, 1H), 8.32 (s, 1H), 7.95-7.83 (m, 2H), 7.26-7.21 (m, 2H), 7.11 (t, J=8.8 Hz, 2H), 4.87 (s, 2H).

Example 93: 1-[6-Chloro-5-(2-chloro-phenylmethanesulfonyl)-1H-benzoimidazol-2-yl]-1H-pyrazole-4-carboxylic Acid

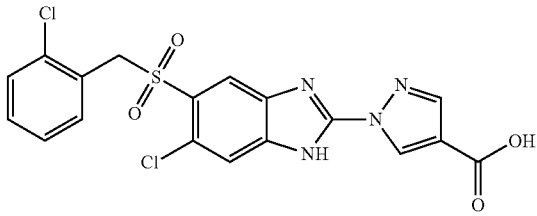 [SMILES: O=C(O)c1cnn(-c2nc3cc(S(=O)(=O)Cc4ccccc4Cl)c(Cl)cc3[nH]2)c1]

The titled compound was prepared in a manner analogous to EXAMPLE 85, from 1-[6-chloro-5-(2-chloro-benzylsulfanyl)-1-(2-methoxy-ethoxymethyl)-1H-benzoimidazol-2-yl]-1H-pyrazole-4-carboxylic acid ethyl ester (Intermediate from Example 69). MS (ESI/CI): mass calcd. for $C_{18}H_{12}Cl_2N_4O_4S$, 450.0; m/z found, 451.0 [M+H]$^+$. $^1$H NMR (600 MHz, DMSO-d$_6$): 14.05 (s, 1H), 13.02 (s, 1H), 8.94 (s, 1H), 8.34 (s, 1H), 8.04-7.83 (m, 2H), 7.43 (dd, J=7.2 Hz, 2.1 Hz, 1H), 7.40 (dd, J=7.7 Hz, 1.5, 1H), 7.34 (pd, J=7.3 Hz, 1.8 Hz, 2H), 5.02 (s, 2H).

Example 94: 1-[6-Chloro-5-(2-phenyl-ethanesulfonyl)-1H-benzoimidazol-2-yl]-1H-pyrazole-4-carboxylic Acid

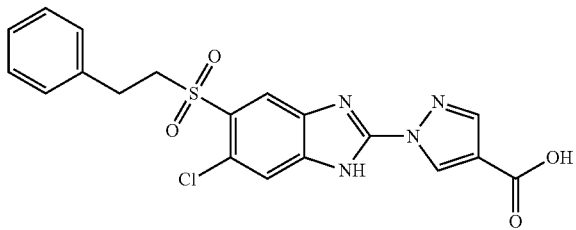 [SMILES: O=C(O)c1cnn(-c2nc3cc(S(=O)(=O)CCc4ccccc4)c(Cl)cc3[nH]2)c1]

The titled compound was prepared in a manner analogous to EXAMPLE 85, from 1-[6-chloro-1-(2-methoxy-ethoxymethyl)-5-phenethylsulfanyl-1H-benzoimidazol-2-yl]-1H-pyrazole-4-carboxylic acid ethyl ester (Intermediate from Example 70). MS (ESI/CI): mass calcd. for $C_{19}H_{15}ClN_4O_4S$, 430.1; m/z found, 431.0 [M+H]$^+$. $^1$H NMR (600 MHz, DMSO-d$_6$): 8.95 (s, 1H), 8.35 (s, 1H), 8.16 (s, 1H), 7.84 (s, 1H), 7.22-7.16 (m, 4H), 7.15-7.11 (m, 1H), 3.88-3.82 (m, 2H), 2.96-2.87 (m, 2H).

Example 95: 1-(5-Chloro-6-ethanesulfinyl-1H-benzoimidazol-2-yl)-1H-pyrazole-4-carboxylic Acid

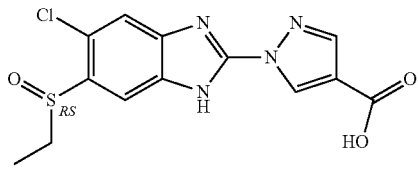 [SMILES: CCS(=O)c1cc2[nH]c(-n3cc(C(=O)O)cn3)nc2cc1Cl]

Step A: 1-[1-(2-Methoxy-ethoxymethyl)-6-ethylsulfanyl-5-trifluoromethyl-1H-benzoimidazol-2-yl]-1H-pyrazole-4-carboxylic acid ethyl ester. The titled compound was prepared in a manner analogous to EXAMPLE 71, Steps A-B, substituting 4,5-dichloro-2-nitro-phenylamine for 5-chloro-2-nitro-4-trifluoromethyl-phenylamine and sodium thioethoxide for sodium thiomethoxide in Step A. A 1:1 mixture of regioisomers was observed. $^1$H NMR (600 MHz, CDCl$_3$): 8.86 (d, J=0.6 Hz, 1H), 8.85 (d, J=0.6 Hz, 1H), 8.18 (s, 2H), 7.75 (s, 1H), 7.68 (s, 1H), 7.67 (s, 1H), 7.56 (s, 1H), 6.14 (s, 2H), 6.10 (s, 2H), 4.36 (q, J=7.1 Hz, 4H), 3.68-3.63 (m, 4H), 3.48-3.44 (m, 4H), 3.31 (s, 3H), 3.31 (s, 3H), 3.02 (p, J=7.3 Hz, 4H), 1.41-1.36 (m, 12H).

Step B: 1-[1-(2-methoxy-ethoxymethyl)-6-ethylsulfinyl-5-trifluoromethyl-1H-benzoimidazol-2-yl]-1H-pyrazole-4-carboxylic acid ethyl ester. To a mixture of 1-[1-(2-methoxy-ethoxymethyl)-6-ethylsulfanyl-5-trifluoromethyl-1H-benzoimidazol-2-yl]-1H-pyrazole-4-carboxylic acid ethyl ester (0.501 g, 1.14 mmol) and MeOH (5.7 mL) was added a solution of Oxone®/potassium peroxymonosulfate (1.47 g, 2.40 mmol) in water (5.7 mL). The mixture was stirred for 44 h at 23° C. EtOAc (50 mL) and water (30 mL) were added and the biphasic mixture stirred. The layers were separated and the aqueous layer was further extracted with EtOAc (50 mL). The combined organic layers were washed with brine, dried, filtered, and concentrated under reduced pressure. The residue was purified (FCC) (10-80% EtOAc/hex) to yield the titled compound (0.232 g, 45% yield, 2:1 mixture of regioisomers) and 1-[1-(2-methoxy-ethoxymethyl)-6-ethylsulfonyl-5-trifluoromethyl-1H-benzoimidazol-2-yl]-1H-pyrazole-4-carboxylic acid ethyl ester (0.260 g, 48% yield, 5:2 mixture of regioisomers). MS (ESI/CI): mass calcd. for $C_{13}H_{23}ClN_4O_5S$, 454.1; m/z found, 455.1 [M+H]$^+$. $^1$H NMR (400 MHz, CDCl$_3$): 8.90 (d, J=0.6 Hz, 1H), 8.20 (d, J=0.6 Hz, 1H), 8.13 (s, 1H), 7.74 (s, 1H), 6.25-6.16 (m, 2H), 4.37 (q, J=7.1 Hz, 2H), 3.68-3.62 (m, 2H), 3.46-3.41 (m, 2H), 3.27 (s, 3H), 3.26-3.13 (m, 1H), 2.94-2.83 (m, 1H), 1.39 (t, J=7.1 Hz, 3H), 1.27 (t, J=7.4 Hz, 3H).

Step C: 1-(5-Chloro-6-ethanesulfinyl-1H-benzoimidazol-2-yl)-1H-pyrazole-4-carboxylic acid ethyl ester. To a solution of 1-[1-(2-methoxy-ethoxymethyl)-6-ethylsulfinyl-5-trifluoromethyl-1H-benzoimidazol-2-yl]-1H-pyrazole-4-carboxylic acid ethyl ester (0.191 g, 0.420 mmol) in ethanol (2 mL) was added 4M HCl in dioxane (2 mL). The reaction mixture was stirred at 23° C. for 2 h. The resulting precipitate was collected and rinsed with diethyl ether to yield the titled compound (0.103 g, 67% yield). MS (ESI/CI): mass calcd. for $C_{15}H_{15}ClN_4O_3S$, 366.1; m/z found, 367.0 [M+H]$^+$. $^1$H NMR (400 MHz, DMSO-d$_6$): 9.02 (d, J=0.6 Hz, 1H), 8.40 (d, J=0.6 Hz, 1H), 7.87 (s, 1H), 7.80 (s, 1H), 4.30 (q, J=7.1 Hz, 2H), 3.17 (dq, J=14.6, 7.3 Hz, 1H), 2.84 (dq, J=14.6, 7.4 Hz, 1H), 1.32 (t, J=7.1 Hz, 3H), 1.08 (t, J=7.3 Hz, 3H).

Step D: 1-(5-Chloro-6-ethanesulfinyl-1H-benzoimidazol-2-yl)-1H-pyrazole-4-carboxylic acid. To a solution of 1-(5-chloro-6-ethanesulfinyl-1H-benzoimidazol-2-yl)-1H-pyrazole-4-carboxylic acid ethyl ester (100 mg, 0.273 mmol), THF (1.0 mL), and water (0.33 mL) was added lithium hydroxide (31.3 mg, 0.818 mmol). The mixture was sonicated briefly, and stirred at 23° C. for 56 h. The solvent was evaporated, water was added, and the resulting solution was acidified to pH 1 with 1M aq. HCl. The precipitate was collected to yield the titled compound (79.1 mg, 85% yield). MS (ESI/CI): mass calcd. for $C_{13}H_{11}ClN_4O_3S$, 338.0; m/z found, 339.0 [M+H]$^+$. $^1$H NMR (400 MHz, DMSO-d$_6$, tautomeric broadening): 13.88 (br s, 1H), 13.01 (br s, 1H), 8.94 (s, 1H), 8.40 (s, 1H), 8.03-7.55 (m, 2H), 3.23-3.11 (m, 1H), 2.89-2.78 (m, 1H), 1.08 (t, J=7.4 Hz, 3H).

Example 96: 1-(5-Chloro-6-ethanesulfonyl-1H-benzoimidazol-2-yl)-1H-pyrazole-4-carboxylic Acid

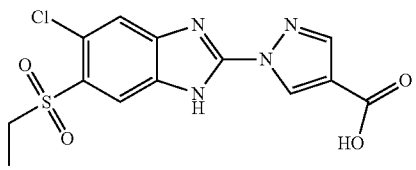 [SMILES: CCS(=O)(=O)c1cc2[nH]c(-n3cc(C(=O)O)cn3)nc2cc1Cl]

Step A: 1-[1-(2-methoxy-ethoxymethyl)-6-ethylsulfonyl-5-trifluoromethyl-1H-benzoimidazol-2-yl]-1H-pyrazole-4-carboxylic acid ethyl ester. To a mixture of 1-[1-(2-methoxy-ethoxymethyl)-6-ethylsulfanyl-5-trifluoromethyl-1H-benzoimidazol-2-yl]-1H-pyrazole-4-carboxylic acid ethyl ester (EXAMPLE 95, product from Step A) (0.501 g, 1.14 mmol) and methanol (5.7 mL) was added a solution of Oxone®/potassium peroxymonosulfate (1.47 g, 2.40 mmol) in water (5.7 mL). The mixture was stirred for 44 h at 23° C. EtOAc (50 mL) and water (30 mL) were added and the biphasic mixture was stirred. The layers were separated and the aqueous layer was further extracted with EtOAc (50 mL). The combined organic layers were washed with brine, dried, filtered, and concentrated under reduced pressure. The residue was purified (FCC) (10-80% EtOAc/hexanes) to yield the titled compound (0.260 g, 48% yield, 5:2 mixture of regioisomers) and 1-[1-(2-methoxy-ethoxymethyl)-6-ethylsulfinyl-5-trifluoromethyl-1H-benzoimidazol-2-yl]-1H-pyrazole-4-carboxylic acid ethyl ester (0.232 g, 45% yield, 2:1 mixture of regioisomers). MS (ESI/CI): mass calcd. for $C_{13}H_{23}ClN_4O_6S$, 470.1; m/z found, 471.1 [M+H]$^+$. $^1$H NMR (400 MHz, CDCl$_3$): 8.91 (d, J=0.6 Hz, 1H), 8.53 (s, 1H), 8.20 (d, J=0.6 Hz, 1H), 7.82 (s, 1H), 6.21 (s, 2H), 4.37 (q, J=7.1 Hz, 2H), 3.72-3.67 (m, 2H), 3.53-3.42 (m, 4H), 3.29 (s, 3H), 1.39 (t, J=7.1 Hz, 3H), 1.30 (t, J=7.4 Hz, 3H).

Step B: 1-(5-Chloro-6-ethanesulfonyl-1H-benzoimidazol-2-yl)-1H-pyrazole-4-carboxylic acid. The titled compound was prepared in a manner analogous to EXAMPLE 95, Steps C-D from 1-[1-(2-methoxy-ethoxymethyl)-6-ethylsulfonyl-5-trifluoromethyl-1H-benzoimidazol-2-yl]-1H-pyrazole-4-carboxylic acid ethyl ester. MS (ESI/CI): mass calcd. for $C_{13}H_{11}ClN_4O_4S$, 354.0; m/z found, 355.0 [M+H]$^+$. $^1$H NMR (400 MHz, DMSO-d$_6$, tautomeric broadening): 13.02 (br s, 1H), 8.95 (d, J=0.6 Hz, 1H), 8.36 (d, J=0.5 Hz, 1H), 8.18 (s, 1H), 7.90 (br s, 1H), 3.53 (q, J=7.4 Hz, 2H), 1.14 (t, J=7.4 Hz, 3H).

Example 97: 1-(6-Methanesulfonyl-5-trifluoromethyl-1H-benzoimidazol-2-yl)-1H-pyrazole-4-carboxylic Acid

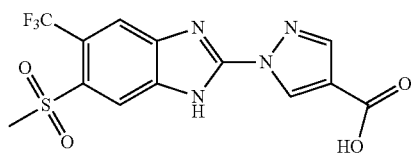 [SMILES: CS(=O)(=O)c1cc2[nH]c(-n3cc(C(=O)O)cn3)nc2cc1C(F)(F)F]

The titled compound was prepared in a manner analogous to EXAMPLE 95, substituting 5-chloro-2-nitro-4-trifluoromethyl-phenylamine for 4,5-dichloro-2-nitro-phenylamine in Step A. MS (ESI/CI): mass calcd. for $C_{13}H_9F_3N_4O_4S$, 374.0; m/z found, 375.0 [M+H]$^+$. $^1$H NMR (400 MHz, DMSO-de, tautomeric broadening): 14.41 (br s, 1H), 13.08 (br s, 1H), 8.99 (s, 1H), 8.60-7.85 (m, 3H), 3.33 (s, 3H).

Example 98: 1-(5-Fluoro-6-methanesulfonyl-1H-benzoimidazol-2-yl)-1H-pyrazole-4-carboxylic Acid

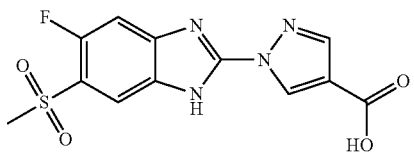 [SMILES: CS(=O)(=O)c1cc2[nH]c(-n3cc(C(=O)O)cn3)nc2cc1F]

The titled compound was prepared in a manner analogous to Example 95, substituting 4,5-difluoro-2-nitro-phenylamine for 5-chloro-2-nitro-4-trifluoromethyl-phenylamine in Step A. MS (ESI/CI): mass calcd. for $C_{12}H_9FN_4O_4S$, 324.0; m/z found, 325.0 [M+H]$^+$. $^1$H NMR (400 MHz, DMSO-d$_6$, tautomeric broadening): 14.03 (br s, 1H), 13.04 (br s, 1H), 8.95 (d, J=0.4 Hz, 1H), 8.36 (s, 1H), 8.15-7.41 (m, 2H), 3.35 (s, 3H).

Example 99: 1-(5-Chloro-6-methanesulfonyl-1H-benzoimidazol-2-yl)-1H-pyrazole-4-carboxylic Acid

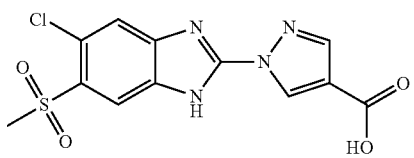 [SMILES: CS(=O)(=O)c1cc2[nH]c(-n3cc(C(=O)O)cn3)nc2cc1Cl]

The titled compound was prepared in a manner analogous to Example 95, substituting 4,5-dichloro-2-nitro-phenylamine for 5-chloro-2-nitro-4-trifluoromethyl-phenylamine in Step A. MS (ESI/CI): mass calcd. for $C_{12}H_9ClN_4O_4S$, 340.0; m/z found, 341.0 [M+H]$^+$. $^1$H NMR (400 MHz, DMSO-de, tautomeric broadening): 14.10 (br s, 1H), 13.05 (br s, 1H), 8.96 (s, 1H), 8.37 (s, 1H), 8.32-7.63 (m, 2H), 3.40 (s, 3H).

Example 100: 1-(6-Methanesulfonyl-5-trifluoromethoxy-1H-benzoimidazol-2-yl)-1H-pyrazole-4-carboxylic Acid

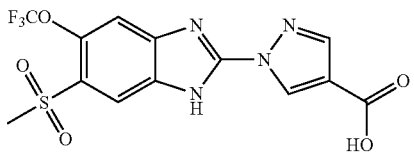 [SMILES: CS(=O)(=O)c1cc2[nH]c(-n3cc(C(=O)O)cn3)nc2cc1OC(F)(F)F]

The titled compound was prepared in a manner analogous to Example 95, substituting 5-chloro-2-nitro-4-trifluoromethoxy-phenylamine for 5-chloro-2-nitro-4-trifluoromethyl-phenylamine in Step A. MS (ESI/CI): mass calcd. for $C_{13}H_9F_3N_4O_5S$, 390.0; m/z found, 391.0 [M+H]$^+$. $^1$H NMR (400 MHz, DMSO-d$_6$, tautomeric broadening): 14.19 (br s, 1H), 13.07 (br s, 1H), 8.95 (s, 1H), 8.38 (s, 1H), 8.11 (br s, 1H), 7.81 (br s, 1H), 3.33 (s, 3H).

Example 101: 1-[5-Chloro-6-(propane-2-sulfonyl)-1H-benzoimidazol-2-yl]-1H-pyrazole-4-carboxylic Acid

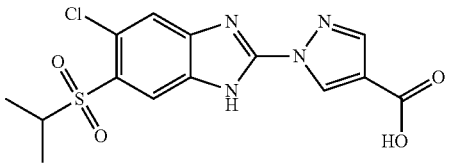

Step A: 4-chloro-5-isopropylsulfanyl-2-nitro-phenylamine. To a solution of 4,5-dichloro-2-nitro-phenylamine (3 g, 14.5 mmol) and DMF (73 mL) was added sodium thioisopropoxide (4.95 g, 45.6 mmol). The solution was heated to 100° C. for 4 days, cooled, and poured into brine (300 mL). The aqueous layer was extracted with EtOAc (3×200 mL) and the combined organic layers were washed with water (3×200 mL) and brine (1×200 mL), dried, filtered, and concentrated under reduced pressure. The crude product was used in the next step without further purification. MS (ESI/CI): mass calcd. for $C_9H_{11}ClN_2O_2S$, 246.0; m/z found, 247.0 [M+H]$^+$.

Step B: 1-[5-Chloro-1-(2-methoxy-ethoxymethyl)-6-(propane-2-sulfanyl)-1H-benzoimidazol-2-yl]-1H-pyrazole-4-carboxylic acid ethyl ester. The titled compound was prepared in a manner analogous to EXAMPLE 27, Steps A-E, substituting 4-chloro-5-isopropylsulfanyl-2-nitro-phenylamine 3-chloro-2-nitro-phenylamine in Step A. A 1:1 mixture of regioisomers resulted. MS (ESI/CI): mass calcd. for $C_{20}H_{25}ClN_4O_4S$, 452.1; m/z found, 453.1 [M+H]$^+$. $^1$H NMR (600 MHz, CDCl$_3$): 8.87-8.86 (m, 2H), 8.18 (d, J=0.4 Hz, 2H), 7.81 (s, 1H), 7.77 (s, 1H), 7.72 (s, 1H), 7.70 (s, 1H), 6.14 (s, 2H), 6.11 (s, 2H), 4.36 (q, J=7.1 Hz, 4H), 3.69-3.62 (m, 4H), 3.55-3.43 (m, 6H), 3.31 (s, 3H), 3.30 (s, 3H), 1.38 (t, J=7.1 Hz, 6H), 1.35 (dd, J=6.7, 2.0 Hz, 12H).

Step C: 1-[5-Chloro-1-(2-methoxy-ethoxymethyl)-6-(propane-2-sulfonyl)-1H-benzoimidazol-2-yl]-1H-pyrazole-4-carboxylic acid ethyl ester. To a solution of 1-[5-chloro-1-(2-methoxy-ethoxymethyl)-6-(propane-2-sulfanyl)-1H-benzoimidazol-2-yl]-1H-pyrazole-4-carboxylic acid ethyl ester (0.249 g, 0.550 mmol) and dichloromethane (2.8 mL) was added m-CPBA (0.259 g, 1.15 mmol, 77% w/w). The reaction mixture stirred for 2.5 days at 23° C. Ethyl acetate (20 mL) and a solution of sodium thiosulfate (0.182 g, 1.15 mmol) in 80% saturated aqueous sodium carbonate (10 mL) were added and the layers were stirred vigorously for 10 minutes, until clear. The layers were separated and the aqueous layer was extracted with EtOAc (2×30 mL). The combined organic layers were washed with brine (10 mL), dried, and concentrated under reduced pressure. The residue was purified (FCC) (10-60% EtOAc/hexanes) to yield the titled compound (0.254 g, 95% yield) as a 10:9 mixture of regioisomers. MS (ESI/CI): mass calcd. for $C_{20}H_{25}ClN_4O_6S$, 484.1; m/z found, 485.1 [M+H]$^+$. $^1$H NMR (600 MHz, CDCl$_3$): 8.91 (d, J=0.5 Hz, 1H), 8.51 (s, 1H), 8.20 (d, J=0.5 Hz, 1H), 7.81 (s, 1H), 6.21 (s, 2H), 4.37 (q, J=7.1 Hz, 2H), 3.90-3.83 (m, 1H), 3.72-3.68 (m, 2H), 3.49-3.45 (m, 2H), 3.29 (s, 3H), 1.39 (t, J=7.1 Hz, 3H), 1.35 (d, J=6.8 Hz, 6H).

Step D: 1-[5-Chloro-6-(propane-2-sulfonyl)-1H-benzoimidazol-2-yl]-1H-pyrazole-4-carboxylic acid ethyl ester. To a solution of 1-[5-chloro-1-(2-methoxy-ethoxymethyl)-6-(propane-2-sulfonyl)-1H-benzoimidazol-2-yl]-1H-pyrazole-4-carboxylic acid ethyl ester (0.243 g, 0.501 mmol) in ethanol (1.8 mL) was added 4M HCl in dioxane (1.8 mL). The reaction mixture was stirred at 23° C. for 1.5 h. Diethyl ether was added and the precipitate collected to yield the titled compound (0.183 g, 92% yield). MS (ESI/CI): mass calcd. for $C_{16}H_{17}ClN_4O_4S$, 369.1; m/z found, 397.1 [M+H]$^+$. $^1$H NMR (400 MHz, DMSO): 9.03 (d, J=0.6 Hz, 1H), 8.42 (d, J=0.6 Hz, 1H), 8.16 (s, 1H), 7.90 (s, 1H), 4.31 (q, J=7.1 Hz, 2H), 3.89-3.76 (m, 1H), 1.33 (t, J=7.1 Hz, 3H), 1.21 (d, J=6.8 Hz, 6H).

Step E: 1-[5-Chloro-6-(propane-2-sulfonyl)-1H-benzoimidazol-2-yl]-1H-pyrazole-4-carboxylic acid. To a solution of 1-[5-Chloro-6-(propane-2-sulfonyl)-1H-benzoimidazol-2-yl]-1H-pyrazole-4-carboxylic acid ethyl ester (0.179 mg, 0.451 mmol), THF (1.7 mL), and water (0.55 mL) was added LiOH.H$_2$O (56.8 mg, 1.35 mmol). The mixture was sonicated briefly, and stirred at 23° C. for 56 h. The solvent was evaporated, water was added, and the resulting solution was acidified to pH 1 with 1M aq. HCl. The precipitate was collected to yield the titled compound (0.146 g, 86% yield). MS (ESI/CI): mass calcd. for $C_{14}H_{13}ClN_4O_4S$, 368.0; m/z found, 369.0 [M+H]$^+$. $^1$H NMR (600 MHz, DMSO-d$_6$, tautomeric broadening): 14.07 (s, 1H), 13.03 (s, 1H), 8.95 (d, J=0.4 Hz, 1H), 8.36 (s, 1H), 8.16 (s, 1H), 8.09-7.64 (m, 1H), 3.88-3.76 (m, 1H), 1.22 (d, J=7.9 Hz, 6H).

Example 102: 1-[5-Chloro-6-(propane-1-sulfonyl)-1H-benzoimidazol-2-yl]-1H-pyrazole-4-carboxylic Acid

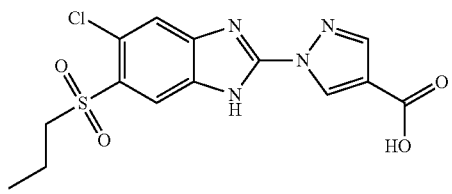 [SMILES: CCCS(=O)(=O)c1cc2[nH]c(-n3cc(C(=O)O)cn3)nc2cc1Cl]

Step A: 4-Chloro-2-nitro-5-propylsulfanyl-phenylamine. To a mixture of 4,5-dichloro-2-nitro-phenylamine (3.50 g, 16.9 mmol), potassium carbonate (4.67 g, 33.8 mmol), and DMF (85 mL) was added 1-propanethiol (2.30 mL, 25.4 mmol). The reaction mixture was heated at 90° C. for 1.5 h, and allowed to cool to 23° C. The mixture was poured into ice/brine (600 mL) and the resulting precipitate was collected to yield the titled compound (4.09 g, 98%). $^1$H NMR (600 MHz, CDCl$_3$): 8.11 (s, 1H), 6.46 (s, 1H), 6.10 (br s, 2H), 2.91 (t, J=7.3 Hz, 2H), 1.85-1.76 (m, 2H), 1.12 (t, J=7.4 Hz, 3H).

Step B: 1-[5-Chloro-6-(propane-1-sulfonyl)-1H-benzoimidazol-2-yl]-1H-pyrazole-4-carboxylic acid. The titled compound was prepared in a manner analogous to EXAMPLE 101, Steps B-E. MS (ESI/CI): mass calcd. for $C_{14}H_{13}ClN_4O_4S$, 368.0; m/z found, 369.0 [M+H]$^+$. $^1$H NMR (600 MHz, DMSO-d$_6$, tautomeric broadening): 14.05 (s, 1H), 13.02 (s, 1H), 8.95 (s, 1H), 8.36 (s, 1H), 8.30-8.08 (m, 1H), 8.07-7.64 (m, 1H), 3.57-3.44 (m, 2H), 1.64-1.55 (m, 2H), 0.94 (t, J=7.4 Hz, 3H).

Example 103: 1-[6-(Propane-2-sulfonyl)-5-trifluoromethyl-1H-benzoimidazol-2-yl]-1H-pyrazole-4-carboxylic Acid

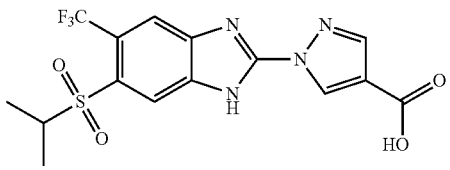 [SMILES: CC(C)S(=O)(=O)c1cc2[nH]c(-n3cc(C(=O)O)cn3)nc2cc1C(F)(F)F]

The titled compound was prepared in a manner analogous to EXAMPLE 102, substituting 5-chloro-2-nitro-4-trifluoromethyl-phenylamine for 4,5-dichloro-2-nitro-phenylamine and 2-propanethiol for 1-propanethiol in Step A. MS (ESI/CI): mass calcd. for $C_{15}H_{13}F_3N_4O_4S$, 402.1; m/z found, 403.0 [M+H]$^+$. $^1$H NMR (400 MHz, DMSO-d$_6$, tautomeric broadening): 13.68-12.50 (m, 1H), 8.99 (s, 1H), 8.39 (s, 1H), 8.29 (s, 1H), 8.18 (s, 1H), 3.59-3.47 (m, 1H), 1.22 (d, J=6.8 Hz, 6H).

Example 104: 1-[6-(Propane-1-sulfonyl)-5-trifluoromethyl-1H-benzoimidazol-2-yl]-1H-pyrazole-4-carboxylic Acid

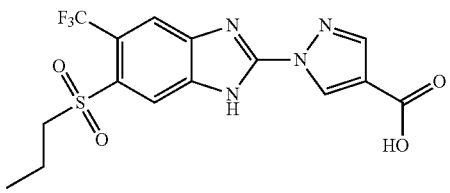 [SMILES: CCCS(=O)(=O)c1cc2[nH]c(-n3cc(C(=O)O)cn3)nc2cc1C(F)(F)F]

The titled compound was prepared in a manner analogous to EXAMPLE 102, substituting 5-chloro-2-nitro-4-trifluoromethyl-phenylamine for 4,5-dichloro-2-nitro-phenylamine in Step A. MS (ESI/CI): mass calcd. for $C_{15}H_{13}F_3N_4O_4S$, 402.1; m/z found, 403.0 [M+H]$^+$. $^1$H NMR (400 MHz, DMSO-d$_6$, tautomeric broadening): 14.37 (s, 1H), 13.08 (s, 1H), 8.99 (s, 1H), 8.51-7.88 (m, 3H), 3.40-3.32 (m, 2H), 1.75-1.57 (m, 2H), 0.95 (t, J=7.4 Hz, 3H).

Example 105: 1-[6-(Propane-2-sulfonyl)-5-trifluoromethoxy-1H-benzoimidazol-2-yl]-1H-pyrazole-4-carboxylic Acid

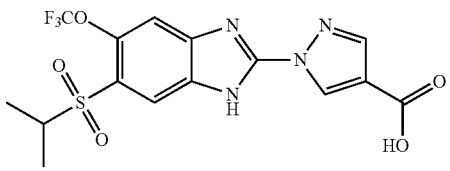 [SMILES: CC(C)S(=O)(=O)c1cc2[nH]c(-n3cc(C(=O)O)cn3)nc2cc1OC(F)(F)F]

The titled compound was prepared in a manner analogous to EXAMPLE 102, substituting 5-chloro-2-nitro-4-trifluoromethoxy-phenylamine for 4,5-dichloro-2-nitro-phenylamine and 2-propanethiol for 1-propanethiol in Step A. MS (ESI/CI): mass calcd. for $C_{15}H_{13}F_3N_4O_5S$, 418.1; m/z found, 419.0 [M+H]$^+$. $^1$H NMR (400 MHz, DMSO-d$_6$, tautomeric broadening): 14.17 (s, 1H), 13.07 (s, 1H), 8.95 (s, 1H), 8.40-8.35 (m, 1H), 8.08 (s, 1H), 7.78 (s, 1H), 3.59-3.45 (m, 1H), 1.20 (d, J=6.8 Hz, 6H).

Example 106: 1-[6-(Propane-1-sulfonyl)-5-trifluoromethoxy-1H-benzoimidazol-2-yl]-1H-pyrazole-4-carboxylic Acid

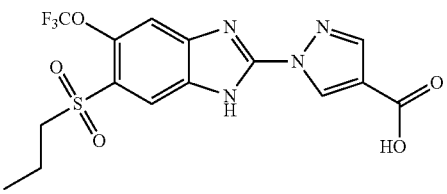

The titled compound was prepared in a manner analogous to EXAMPLE 102, substituting 5-chloro-2-nitro-4-trifluoromethoxy-phenylamine for 4,5-dichloro-2-nitro-phenylamine in Step A. MS (ESI/CI): mass calcd. for $C_{15}H_{13}F_3N_4O_5S$, 418.1; m/z found, 419.0 [M+H]$^+$. $^1$H NMR (400 MHz, DMSO-d$_6$, tautomeric broadening): 14.17 (s, 1H), 13.06 (s, 1H), 8.95 (s, 1H), 8.37 (s, 1H), 8.09 (s, 1H), 7.78 (s, 1H), 3.44-3.34 (m, 2H), 1.67-1.51 (m, 2H), 0.93 (t, J=7.4 Hz, 3H).

Example 107: 1-(5-Benzenesulfinyl-6-chloro-1H-benzoimidazol-2-yl)-1H-pyrazole-4-carboxylic Acid

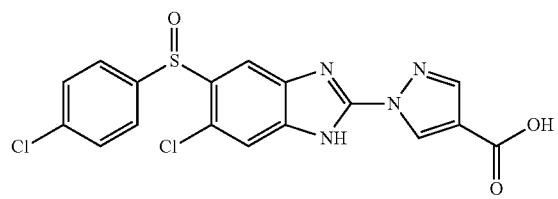 [SMILES: O=C(O)c1cnn(-c2nc3cc(S(=O)c4ccc(Cl)cc4)c(Cl)cc3[nH]2)c1]

The titled compound was prepared in a manner analogous to EXAMPLE 82, from 1-[6-chloro-5-(4-chloro-phenylsulfanyl)-1-(2-methoxy-ethoxymethyl)-1H-benzoimidazol-2-yl]-1H-pyrazole-4-carboxylic acid ethyl ester (Intermediate from Example 61). MS (ESI/CI): mass calcd. for $C_{17}H_{10}Cl_2N_4O_3S$, 420.0; m/z found, 421.0 [M+H]$^+$. $^1$H NMR (600 MHz, DMSO-d$_6$): 13.94 (br s, 1H), 13.05 (br s, 1H), 8.93 (s, 1H), 8.34 (s, 1H), 8.06 (br s, 1H), 7.78 (br s, 1H), 7.76 (d, J=8.6 Hz, 2H), 7.65-7.58 (m, 2H). The enantiomers were separated on a Kromasil® DMB 250× 21.2 mm (L×I.D.) preparatory SFC column at 40° C. using 8.5 mL/min of MeOH containing 0.2% diisopropyl amine and 34 g/min CO$_2$, with UV detection at 214 nm. The two enantiomers were isolated as the diisopropyl amine salt. MS (ESI/CI): mass calcd. for $C_{17}H_{10}Cl_2N_4O_3S$, 420.0; m/z found, 421.0 [M+H]$^+$. $^1$H NMR (500 MHz, DMSO-d$_6$): 8.56 (s, 1H), 7.85 (s, 1H), 7.71 (s, 1H), 7.70-7.66 (m, 2H), 7.60-7.56 (m, 2H), 7.39 (s, 1H), 1.11 (d, J=6.4 Hz, 12H).

Example 108: 1-(6-Methanesulfinyl-5-trifluoromethyl-1H-benzoimidazol-2-yl)-1H-pyrazole-4-carboxylic Acid

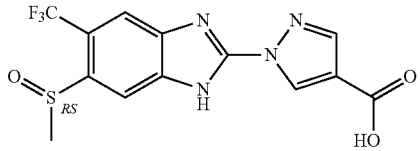 [SMILES: CS(=O)c1cc2[nH]c(-n3cc(C(=O)O)cn3)nc2cc1C(F)(F)F]

Step A: 1-[1-(2-Methoxy-ethoxymethyl)-6-methylsulfinyl-5-trifluoromethyl-1H-benzoimidazol-2-yl]-1H-pyrazole-4-carboxylic acid ethyl ester. To a mixture of 1-[1-(2-methoxy-ethoxymethyl)-6-methylsulfanyl-5-trifluoromethyl-1H-benzoimidazol-2-yl]-1H-pyrazole-4-carboxylic acid ethyl ester (Intermediate from EXAMPLE 71, product from Step B) (0.300 g, 0.654 mmol) and methanol (3.3 mL) was added a solution of OXONE®/potassium peroxymonosulfate (0.402 g, 0.654 mmol) in water (3.3 mL). The mixture was allowed to stir for 4 h at 23° C. EtOAc (40 mL) and water (20 mL) were added and the biphasic mixture was stirred. The layers were separated and the aqueous layer was further extracted with EtOAc (30 mL). The combined organic layers were washed with brine (15 mL), dried, filtered, and concentrated under reduced pressure. The residue was purified (FCC) (20-100% EtOAc/hexanes) to yield the titled compound (0.249 g, 80% yield) as a 10:9 mixture of regioisomers. MS (ESI/CI): mass calcd. for $C_{19}H_{21}F_3N_4O_5S$, 474.1; m/z found, 475.1 [M+H]+. $^1$H NMR (400 MHz, CDCl$_3$): 8.94 (d, J=0.6 Hz, 1H), 8.58 (s, 1H), 8.22 (s, 1H), 8.08 (s, 1H), 6.34-6.23 (m, 2H), 4.38 (q, J=7.1 Hz, 2H), 3.74-3.66 (m, 2H), 3.51-3.41 (m, 2H), 3.28 (s, 3H), 2.81 (s, 3H), 1.40 (t, J=7.1 Hz, 3H).

Step B: 1-(6-methanesulfinyl-5-trifluoromethyl-1H-benzoimidazol-2-yl)-1H-pyrazole-4-carboxylic acid. The titled compound was prepared in a manner analogous to EXAMPLE 27, Steps F-G. MS (ESI/CI): mass calcd. for $C_{13}H_9F_3N_4O_3S$, 358.0; m/z found, 359.0 [M+H]+. $^1$H NMR (400 MHz, DMSO-d$_6$, tautomeric broadening): 14.25 (br s, 1H), 13.06 (br s, 1H), 8.98 (s, 1H), 8.38 (d, J=0.5 Hz, 1H), 8.34 (br s, 1H), 8.05 (br s, 1H), 2.79 (s, 3H).

The resulting enantiomers were isolated as the respective isopropylamine salts using preparative chiral SFC. The separation was performed using a Chiralpak® AD-H column at 40° C., with a flow rate of 8.6 mL/min of methanol with 0.2% isopropylamine and 33 mL/min CO$_2$, and a column pressure of 37 bar. Absolute stereochemistry was not assigned for these compounds. MS (ESI/CI): mass calcd. for $C_{13}H_9F_3N_4O_3S$, 358.0; m/z found, 359.0 [M+H]+. $^1$H NMR (600 MHz, DMSO-d$_6$): 8.78 (s, 1H), 8.26-7.14 (br s, 3H), 8.16 (s, 1H), 8.04 (s, 1H), 7.77 (s, 1H), 3.29 (m, 1H), 2.70 (s, 3H), 1.17 (d, J=6.5 Hz, 6H).

Example 109: 1-(6-Bromo-5-fluoro-1H-benzoimidazol-2-yl)-1H-pyrazole-4-carboxylic Acid

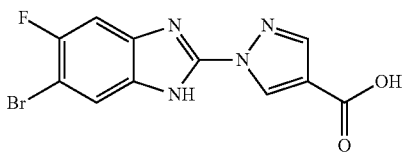 [SMILES: O=C(O)c1cnn(-c2nc3cc(F)c(Br)cc3[nH]2)c1]

Step A: 5-Bromo-4-fluoro-2-nitro-phenylamine. A mixture of 1-bromo-2,5-difluoro-4-nitro-benzene (1.50 g, 6.30 mmol) and 7M ammonia in methanol (25 mL) was heated in a sealed tube at 60° C. for 15 h. The reaction mixture was transferred to a round bottom flask, washing the sealed tube with EtOAc. The reaction mixture was concentrated, and the crude material was used in the next step without further purification.

Step B: 1-(6-Bromo-5-fluoro-1H-benzoimidazol-2-yl)-1H-pyrazole-4-carboxylic acid. The titled compound was prepared in a manner analogous to EXAMPLE 60, Steps B-H substituting 5-bromo-4-fluoro-2-nitro-phenylamine for 4-chloro-2-nitro-5-m-tolylsulfanyl-phenylamine in Step B and lithium diisopropylamide for butyllithium in Step E. MS (ESI/CI): mass calcd. for $C_{11}H_6BrFN_4O_2$, 324.0; m/z found, 325.0 [M+H]+. $^1$H NMR (400 MHz, DMSO-d$_6$): 12.92 (s, 1H), 8.88 (s, 1H), 8.29 (s, 1H), 7.84 (br s, 1H), 7.57 (br s, 1H).

Example 110: 1-(4-Fluoro-1H-benzoimidazol-2-yl)-1H-pyrazole-4-carboxylic Acid

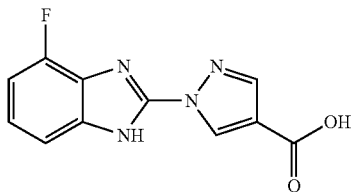 [SMILES: O=C(O)c1cnn(-c2nc3c(F)cccc3[nH]2)c1]

The titled compound was prepared in a manner analogous to EXAMPLE 60, Steps B-H substituting 2-fluoro-6-nitro-phenylamine for 4-chloro-2-nitro-5-m-tolylsulfanyl-phenylamine in Step B and lithium diisopropylamide for butyllithium in Step E. MS (ESI/CI): mass calcd. for $C_{11}H_7FN_4O_2$, 246.1; m/z found, 247.1 [M+H]+. $^1$H NMR (400 MHz, DMSO-d$_6$): 8.91 (d, J=0.5 Hz, 1H), 8.28 (d, J=0.4 Hz, 1H), 7.35 (d, J=8.0 Hz, 1H), 7.22 (td, J=8.1, 4.9 Hz, 1H), 7.06 (dd, J=11.0, 8.1 Hz, 1H).

Example 111: 1-(4,5-Difluoro-1H-benzoimidazol-2-yl)-1H-pyrazole-4-carboxylic Acid

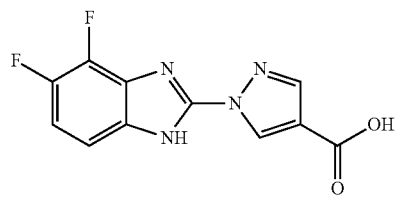 [SMILES: O=C(O)c1cnn(-c2nc3c(F)c(F)ccc3[nH]2)c1]

The titled compound was prepared in a manner analogous to EXAMPLE 60, Steps D-H substituting 4,5-difluorobenzoimidazole for 6-chloro-5-m-tolylsulfanyl-1H-benzoimidazole in Step B and lithium diisopropylamide for butyllithium in Step E. MS (ESI/CI): mass calcd. for $C_{11}H_6F_2N_4O_2$, 264.1; m/z found, 265.1 [M+H]+. $^1$H NMR (500 MHz, DMSO-d$_6$): 13.76 (br s, 1H), 12.97 (br s, 1H), 8.94 (s, 1H), 8.31 (d, J=0.6 Hz, 1H), 7.38-7.21 (m, 2H).

Example 112: 1-(4,6-Difluoro-1H-benzoimidazol-2-yl)-1H-pyrazole-4-carboxylic Acid

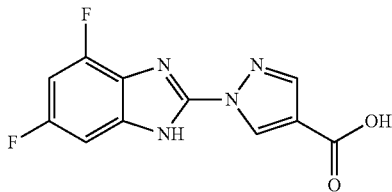 [SMILES: O=C(O)c1cnn(-c2nc3c(F)cc(F)cc3[nH]2)c1]

The titled compound was prepared in a manner analogous to EXAMPLE 60, Steps C-H substituting 3,5-difluoro-benzene-1,2-diamine for 4-chloro-5-m-tolylsulfanyl-benzene-1,2-diamine in Step C and lithium diisopropylamide for butyllithium in Step E. MS (ESI/CI): mass calcd. for $C_{11}H_6F_2N_4O_2$, 264.1; m/z found, 265.1 [M+H]$^+$. $^1$H NMR (500 MHz, DMSO-$d_6$): 13.84 (br s, 1H), 12.95 (br s, 1H), 8.91 (s, 1H), 8.30 (s, 1H), 7.19-7.11 (m, 2H).

Example 113: 1-(6-Chloro-5-trifluoromethoxy-1H-benzoimidazol-2-yl)-1H-pyrazole-4-carboxylic Acid

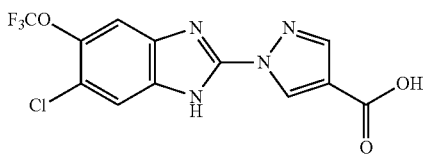 [SMILES: O=C(O)c1cnn(-c2nc3cc(OC(F)(F)F)c(Cl)cc3[nH]2)c1]

Method A:

The titled compound was prepared in a manner analogous to EXAMPLE 27 substituting 5-chloro-2-nitro-4-trifluoromethoxy-phenylamine for 3-chloro-2-nitro-phenylamine in Step A. MS (ESI/CI): mass calcd. for $C_{12}H_6ClF_3N_4O_3$, 346.0; m/z found, 347.0 [M+H]$^+$. $^1$H NMR (500 MHz, DMSO-$d_6$): 13.37 (s, 1H), 8.88 (s, 1H), 8.29 (s, 1H), 7.80 (s, 1H), 7.71 (s, 1H).

Method B:

Step A: 6-Chloro-5-trifluoromethoxy-1H-benzoimidazole. A mixture of 5-chloro-2-nitro-4-trifluoromethoxy-phenylamine (2.00 g, 7.80 mmol), sodium dithionite (7.06 g, 40.5 mmol), trimethyl orthoformate (23.1 mL, 210 mmol), DMF (23 mL), and acetic acid (4.0 mL) was heated in a sealed tube for 15 h at 100° C. The reaction mixture was cooled to 23° C. and partitioned between EtOAc (100 mL) and saturated aq. NaHCO$_3$ (100 mL). The organic layer was collected and the aqueous layer was extracted with EtOAc (2×80 mL). The combined organic layers were dried, filtered, and concentrated under reduced pressure. The residue was purified (FCC) (0-15% MeOH/DCM) to yield the titled compound (1.46 g, 78%). MS (ESI/CI): mass calcd. for $C_8H_4ClF_3N_2O$, 236.0; m/z found, 237.0 [M+H]. $^1$H NMR (500 MHz, CDCl$_3$): 8.11 (s, 1H), 7.74 (s, 1H), 7.64 (s, 1H).

Step B: 1-(6-Chloro-5-trifluoromethoxy-1H-benzoimidazol-2-yl)-1H-pyrazole-4-carboxylic acid. The titled compound was prepared in a manner analogous to EXAMPLE 60, Steps D-H. MS (ESI/CI): mass calcd. for $C_{12}H_6ClF_3N_4O_2$, 346.0; m/z found, 347.0 [M+H]$^+$. $^1$H NMR (600 MHz, DMSO-$d_6$): 8.90 (s, 1H), 8.32 (s, 1H), 7.83 (br s, 1H), 7.74 (br s, 1H).

Method C:

Step A: 4-Chloro-5-trifluoromethoxy-benzene-1,2-diamine. 5-Chloro-2-nitro-4-trifluoromethoxy-phenylamine (180 g, 0.7 mol, 1.0 equiv.) was dissolved in dry DMF (1 L) and then 5% Pt/C containing 50.2% water (4.0 g) was added. The reaction solution was hydrogenated (50 psi) at room temperature for 16 hours. HPLC analysis indicated complete reaction. MS [M+H]$^+$ found 225.2. The reaction solution was used on the next step without isolation.

Step B: 5-Chloro-6-trifluoromethoxy-1,3-dihydro-benzoimidazol-2-one. The Pt/C from Step A was filtered off and washed with dry DMF (250 mL). The filtrate solution was concentrated to 750 mL. Activated 3 A molecular sieves (100 g) was added and the solution was stirred at room temperature for 3 hours. The molecular sieves was filtered off and washed with dry DMF (250 mL). To the dried DMF solution, was added as solid CDI (125 g, 0.77 mol, 1.1 equiv.), (slightly exothermic), at room temperature. After stirring at room temperature for 30 minutes. Water (1.8 L) was added. The resulting suspension was stirred at room temperature overnight. The precipitated white solid was collected by filtration, washed with water, dried thoroughly to afford the title compound (154.6 g, 87%). MS [M+H]$^+$ found 253.1.

Step C: 2,6-Dichloro-5-trifluoromethoxy-1H-benzoimidazole. Thoroughly dried 5-chloro-6-trifluoromethoxy-1,3-dihydro-benzoimidazol-2-one (154.6 g, 0.61 mol, 1.0 equiv.) was suspended in POCl$_3$ (450 mL, 8.0 equiv.). The reaction solution was heated to reflux temperature for 6 hours and cooled to room temperature. The solution was poured into crushed ice/water (~3 L) slowly with sufficient stirring. The solution was neutralized to pH=6.0 with NaOH. The precipitated solid was collected by filtration, washed with water, and dried to afford the title compound (159.97 g, 96%). The crude product was used in the following reaction without further purification.

The next 3 steps were performed in a one-pot fashion. The intermediates were not isolated.

Step D: 1-(6-Chloro-5-trifluoromethoxy-1H-benzoimidazol-2-yl)-1H-pyrazole-4-carboxylic acid. 2,6-Dichloro-5-trifluoromethoxy-1H-benzoimidazole (160 g, 0.59 mol, 1.0 equiv.) was dissolved in dry DMF (1.5 L) and then K$_2$CO$_3$ (98 g, 0.71 mol, 1.2 equiv.) and dimethylsulfamoyl chloride (85 g, 0.59 mol, 1.0 equiv.) were added sequentially. The reaction mixture was stirred at room temperature for 16 hours to afford 2,6-dichloro-5-trifluoromethoxy-benzoimidazole-1-sulfonic acid dimethylamide. Without isolation of 2,6-dichloro-5-trifluoromethoxy-benzoimidazole-1-sulfonic acid dimethylamide, 1H-pyrazole-4-carboxylic acid ethyl ester (91 g, 0.65 mol, 1.1 equiv.) and K$_2$CO$_3$ (98 g, 0.71 mol, 1.2 equiv.) were added to the reaction mixture. The reaction mixture was stirred at 70° C. for 10 hours and cooled to room temperature, to afford 1-(6-chloro-1-dimethylsulfamoyl-5-trifluoromethoxy-1H-benzoimidazol-2-yl)-1H-pyrazole-4-carboxylic acid ethyl ester. To crude reaction mixture was added LiOH H$_2$O (124 g, 2.95 mol, 5.0 equiv.) in 2.5 L water. The reaction solution was heated at 70° C. for 6 hours and then cooled to room temperature. Concentrated HCl was added to adjust pH=4.0. The precipitated solid was collected by filtration, washed with water and dried. The solid was recrystallized from hot EtOAc (~3 L). After cooling to room temperature and filtration, the pure compound was obtained as a white solid (109 g, 0.31 mol, 54% over 3 steps). MS (ESI/CI): mass calcd. for $C_{12}H_6ClF_3N_4O_2$, 346.0; m/z found, 347.0 [M+H]$^+$. $^1$H NMR (500 MHz, DMSO-d$_6$): 13.79 (s, 1H), 13.06 (s, 1H), 8.91 (s, 1H), 8.33 (s, 1H), 7.79 (br d, 2H).

Example 114: 1-(1H-Naphtho[2,3-d]imidazol-2-yl)-1H-pyrazole-4-carboxylic Acid

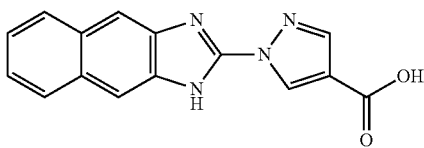 [SMILES: O=C(O)c1cnn(-c2nc3cc4ccccc4cc3[nH]2)c1]

The titled compound was prepared in a manner analogous to EXAMPLE 60 Steps C-H, substituting 4-chloro-5-m-tolylsulfanyl-benzene-1,2-diamine for naphthalene-2,3-diamine in Step C. MS (ESI/CI): mass calcd. for C$_{15}$H$_{10}$N$_4$O$_2$, 278.1; m/z found, 279.2 [M+H]$^+$. $^1$H NMR (400 MHz, DMSO-d$_6$): 13.12-12.83 (m, 1H), 9.00 (d, J=0.6 Hz, 1H), 8.34 (d, J=0.6 Hz, 1H), 8.06 (s, 2H), 8.01 (dd, J=6.3, 3.3 Hz, 2H), 7.40 (dd, J=6.4, 3.2 Hz, 2H).

Example 115: 1-(3H-Naphtho[1,2-d]imidazol-2-yl)-1H-pyrazole-4-carboxylic Acid

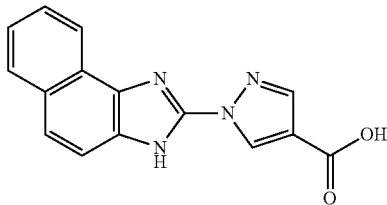 [SMILES: O=C(O)c1cnn(-c2nc3c(ccc4ccccc43)[nH]2)c1]

The titled compound was prepared in a manner analogous to EXAMPLE 60 Steps C-H, substituting 4-chloro-5-m-tolylsulfanyl-benzene-1,2-diamine for naphthalene-1,2-diamine in Step C. MS (ESI/CI): mass calcd. for C$_{15}$H$_{10}$N$_4$O$_2$, 278.1; m/z found, 279.2 [M+H]$^+$. $^1$H NMR (400 MHz, DMSO-d$_6$): 12.92 (s, 1H), 8.95 (d, J=0.6 Hz, 1H), 8.51 (d, J=8.0 Hz, 1H), 8.32 (d, J=0.5 Hz, 1H), 8.02 (d, J=8.0 Hz, 1H), 7.75 (q, J=8.8 Hz, 2H), 7.67-7.59 (m, 1H), 7.51 (ddd, J=8.2, 6.9, 1.2 Hz, 1H).

Example 116: 1-(5-Fluoro-4-methyl-1H-benzoimidazol-2-yl)-1H-pyrazole-4-carboxylic Acid

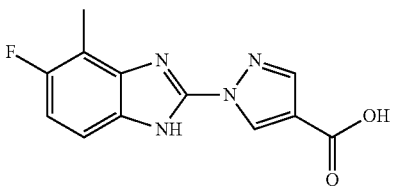 [SMILES: Cc1c(F)ccc2[nH]c(-n3cc(C(=O)O)cn3)nc12]

Step A: 1-[5-fluoro-1-(2-methoxy-ethoxymethyl)-4-methyl-1H-benzoimidazol-2-yl]-1H-pyrazole-4-carboxylic acid ethyl ester. The titled compound was prepared in a manner analogous to EXAMPLE 60, Steps B-F substituting 3-fluoro-2-methyl-6-nitro-phenylamine for 4-chloro-2-nitro-5-m-tolylsulfanyl-phenylamine in Step B and lithium diisopropylamide for butyllithium in Step E. MS (ESI/CI): mass calcd. for C$_{18}$H$_{21}$FN$_4$O$_4$, 376.2; m/z found, 377.1 [M+H]$^+$.

Step B: 1-(5-Fluoro-4-methyl-1H-benzoimidazol-2-yl)-1H-pyrazole-4-carboxylic acid. A mixture of 1-[5-fluoro-1-(2-methoxy-ethoxymethyl)-4-methyl-1H-benzoimidazol-2-yl]-1H-pyrazole-4-carboxylic acid ethyl ester (0.131 g, 0.481 mmol), glacial acetic acid (4.8 mL), and 6M aqueous HCl (4.8 mL) was heated at 100° C. for 4 h in a sealed tube. The reaction mixture was cooled to 23° C. and then 0° C. The resulting precipitate was filtered and washed with cold water to yield the titled compound (75.0 mg, 60%). MS (ESI/CI): mass calcd. for C$_{12}$H$_9$FN$_4$O$_2$, 260.1; m/z found, 261.1 [M+H]$^+$. $^1$H NMR (500 MHz, DMSO-d$_6$): 8.88 (s, 1H), 8.29 (s, 1H), 7.35 (dd, J=8.7, 4.5 Hz, 1H), 7.06 (dd, J=10.4, 8.8 Hz, 1H), 2.46 (d, J=1.3 Hz, 3H).

Example 117: 1-(5-Piperidin-1-yl-6-trifluoromethoxy-1H-benzoimidazol-2-yl)-1H-pyrazole-4-carboxylic Acid

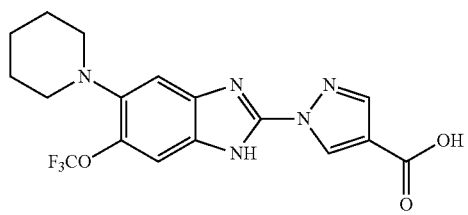 [SMILES: O=C(O)c1cnn(-c2nc3cc(N4CCCCC4)c(OC(F)(F)F)cc3[nH]2)c1]

Step A: 2-nitro-5-piperidin-1-yl-4-trifluoromethoxy-phenylamine. Piperidine (1.2 mL) was added to 5-chloro-2-nitro-4-trifluoromethoxy-phenylamine (0.757 g, 2.94 mmol) in a sealed tube and the mixture was heated to 100° C. for 2 h. The mixture was cooled to 23° C., poured into water (50 mL) and extracted with EtOAc (3×80 mL). The combined organic layers were washed with brine (50 mL), dried, filtered, and concentrated under reduced pressure to yield the titled compound (0.900 g, 99.9%). MS (ESI/CI): mass calcd. for C$_{12}$H$_{14}$F$_3$N$_3$O$_3$, 305.1; m/z found, 306.1 [M+H]$^+$.

Step B: 5-piperidin-1-yl-6-trifluoromethoxy-1H-benzoimidazole. A mixture of 2-nitro-5-piperidin-1-yl-4-trifluoromethoxy-phenylamine (0.900 g, 2.94 mmol), sodium dithionite (2.67 g, 15.3 mmol), trimethyl orthoformate (8.72 mL, 79.6 mmol), DMF (8.56 mL), and acetic acid (1.45 mL) was heated in a sealed tube for 15 h at 100° C. The reaction mixture was cooled to 23° C. and partitioned between EtOAc (80 mL) and saturated aqueous NaHCO$_3$ (80 mL). The organic layer was collected and the aqueous layer was extracted with EtOAc (2×80 mL). The combined organic layers were dried, filtered, and concentrated under reduced pressure. The residue was purified (FCC) (0-15% MeOH/DCM) to yield the titled compound (0.589 g, 71%). MS (ESI/CI): mass calcd. for C$_{13}$H$_{14}$F$_3$N$_3$O, 285.1; m/z found, 286.1 [M+H]$^+$.

Step C: 1-[1-(2-methoxy-ethoxymethyl)-5-piperidin-1-yl-6-trifluoromethoxy-1H-benzoimidazol-2-yl]-1H-pyrazole-4-carboxylic acid ethyl ester. The titled compound was prepared as a 1:1 mixture of regioisomers in a manner analogous to EXAMPLE 60, Steps D-F substituting lithium diisopropylamide for butyllithium in Step E. MS (ESI/CI): mass calcd. for C$_{23}$H$_{28}$F$_3$N$_5$O$_5$, 511.2; m/z found, 512.2 [M+H]$^+$. $^1$H NMR (400 MHz, CDCl$_3$): 8.82 (d, J=0.6 Hz, 1H), 8.80 (d, J=0.6 Hz, 1H), 8.17-8.15 (m, 2H), 7.56-7.55

(m, 1H), 7.48-7.46 (m, 1H), 7.36 (s, 1H), 7.19 (s, 1H), 6.08 (s, 2H), 6.07 (s, 2H), 4.39-4.32 (m, 4H), 3.67-3.61 (m, 4H), 3.48-3.42 (m, 4H), 3.31 (s, 3H), 3.30 (s, 3H), 3.05-2.95 (m, 8H), 1.79-1.70 (m, 8H), 1.63-1.55 (m, 4H), 1.41-1.34 (m, 6H).

Step D: 1-(5-Piperidin-1-yl-6-trifluoromethoxy-1H-benzoimidazol-2-yl)-1H-pyrazole-4-carboxylic acid. A mixture of 1-[1-(2-methoxy-ethoxymethyl)-5-piperidin-1-yl-6-trifluoromethoxy-1H-benzoimidazol-2-yl]-1H-pyrazole-4-carboxylic acid ethyl ester (0.300 g, 0.586 mmol), glacial acetic acid (5.9 mL), and 6M aqueous HCl (6.9 mL) was heated at 100° C. for 4.5 h in a sealed tube. The reaction mixture was cooled to 23° C. and then 0° C. The resulting precipitate was filtered and washed with cold water to yield the titled compound (60.0 mg, 26%). MS (ESI/CI): mass calcd. for $C_{17}H_{16}F_3N_5O_3$, 395.1; m/z found, 396.1 [M+H]$^+$. $^1$H NMR (400 MHz, DMSO-d$_6$): 8.84 (d, J=0.6 Hz, 1H), 8.27 (d, J=0.6 Hz, 1H), 7.47 (br s, 1H), 7.21 (br s, 1H), 2.98-2.89 (m, 4H), 1.71-1.59 (m, 4H), 1.58-1.47 (m, 2H).

Example 118: 1-(5-Fluoro-6-piperidin-1-yl-1H-benzoimidazol-2-yl)-1H-pyrazole-4-carboxylic Acid

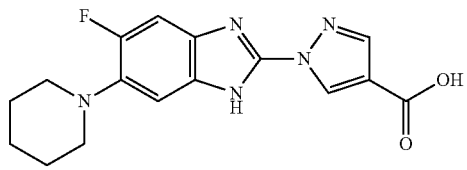 [SMILES: O=C(O)c1cnn(-c2nc3cc(F)c(N4CCCCC4)cc3[nH]2)c1]

The titled compound was prepared in a manner analogous to EXAMPLE 117, substituting 2-nitro-4,5-difluoroaniline for 2-nitro-4-trifluoromethoxy-5-chloroaniline in Step A. MS (ESI/CI): mass calcd. for $C_{16}H_{16}FN_5O_2$, 329.1; m/z found, 330.1 [M+H]$^+$. $^1$H NMR (400 MHz, DMSO-d$_6$): 8.88 (s, 1H), 8.28 (s, 1H), 7.99 (br s, 1H), 7.56 (d, J=12.2 Hz, 1H), 3.39 (br s, 4H), 1.93 (br s, 4H), 1.64 (br m, 2H).

Example 119: 1-(6-Ethoxy-5-fluoro-1H-benzoimidazol-2-yl)-1H-pyrazole-4-carboxylic Acid

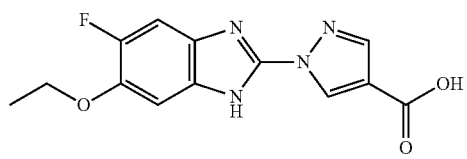 [SMILES: CCOc1cc2[nH]c(-n3cc(C(=O)O)cn3)nc2cc1F]

The titled compound was in a manner analogous to EXAMPLE 117, substituting 2-nitro-4,5-difluoroaniline for 2-nitro-4-trifluoromethoxy-5-chloroaniline and sodium ethoxide (21 wt % solution in ethanol) for piperidine in Step A. MS (ESI/CI): mass calcd. for $C_{13}H_{11}FN_4O_3$, 290.1; m/z found, 291.1 [M+H]$^+$. $^1$H NMR (400 MHz, DMSO-d$_6$): 13.63-12.41 (m, 2H), 8.82 (s, 1H), 8.25 (s, J=0.5 Hz, 1H), 7.61-6.97 (m, 2H), 4.13 (q, J=7.0 Hz, 2H), 1.38 (t, J=6.9 Hz, 3H).

Example 120: 1-(5-Phenylcarbamoyl-1H-benzoimidazol-2-yl)-1H-pyrazole-4-carboxylic Acid

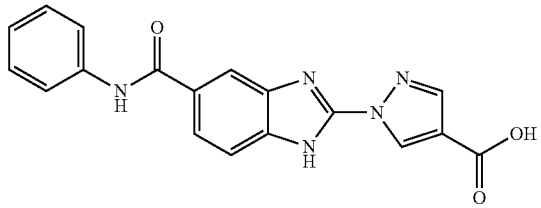 [SMILES: O=C(O)c1cnn(-c2nc3cc(C(=O)Nc4ccccc4)ccc3[nH]2)c1]

Step A: 2-oxo-2,3-dihydro-1H-benzoimidazole-5-carboxylic acid methyl ester. To a solution of 3,4-diamino-benzoic acid methyl ester (5.00 g, 30.1 mmol) and THF (40 mL), was added carbonyl diimidazole (7.32 g, 45.1 mmol) at 0° C. The mixture stirred for 16 h, and allowed to warm to 23° C. A solution of 1M aq. HCl (50 mL) was added at 0° C., followed by water (70 mL) and the mixture was stirred for 1 h. The resulting precipitate was filtered and dried under reduced pressure for 18 h to yield the titled compound, which was used in the next step without further purification (5.45 g, 94%). MS (ESI/CI): mass calcd. for $C_9H_8N_2O_3$, 192.1; m/z found, 193.1 [M+H]$^+$. $^1$H NMR (400 MHz, CDCl$_3$): 11.01 (s, 1H), 10.84 (s, 1H), 7.63 (dd, J=8.2, 1.6 Hz, 1H), 7.47 (s, 1H), 7.02 (d, J=8.2 Hz, 1H), 3.82 (s, 3H).

Step B: 2-chloro-1H-benzoimidazole-5-carboxylic acid methyl ester. 2-oxo-2,3-dihydro-1H-benzoimidazole-5-carboxylic acid methyl ester (3.00 g, 15.6 mmol) and phosphorus oxychloride (30 mL) were combined and heated to 100° C. for 48 h. The mixture was cooled to 23° C. and concentrated under reduced pressure. The residue was cooled to 0° C., and cold, saturated aqueous NaHCO$_3$ (60 mL) was added cautiously. After stirring at 23° C. for 15 min, the mixture was sonicated and the resulting residue was filtered to yield the titled compound (3.13 g, 95%), which was used in the next step without further purification. MS (ESI/CI): mass calcd. for $C_9H_7ClN_2O_2$, 210.02; m/z found, 211.0 [M+H]$^+$.

Step C: 2-chloro-1-(2-methoxy-ethoxymethyl)-1H-benzoimidazole-5-carboxylic acid methyl ester. To a mixture of 2-chloro-1H-benzoimidazole-5-carboxylic acid methyl ester (2.00 g, 9.50 mmol) and THF (17 mL) was added DIPEA (2.46 mL, 14.3 mmol) followed by 1-chloromethoxy-2-methoxy-ethane (1.30 mL, 11.4 mmol) at 23° C. After stirring for 18 h the reaction mixture was concentrated under reduced pressure. The residue was purified (FCC) (5-50% EtOAc/hexanes) to yield the titled compound as a mixture of regioisomers (1.71 g, 60%). MS (ESI/CI): mass calcd. for $C_{13}H_{15}ClN_2O_4$, 298.1; m/z found, 299.1 [M+H]$^+$. $^1$H NMR (400 MHz, DMSO-d$_6$): 8.34-8.31 (m, 1H), 8.21-8.20 (m, 1H), 7.98 (dd, J=8.6, 1.6 Hz, 1H), 7.91 (dd, J=8.5, 1.6 Hz, 1H), 7.83 (dd, J=8.6, 0.5 Hz, 1H), 7.74 (dd, J=8.5, 0.5 Hz, 1H), 5.78 (s, 1H), 5.73 (s, 1H), 3.89 (d, J=6.3 Hz, 6H), 3.64-3.60 (m, 5H), 3.43-3.39 (m, 5H), 3.17 (d, J=2.6 Hz, 6H).

Step D: 2-chloro-1-(2-methoxy-ethoxymethyl)-1H-benzoimidazole-5-carboxylic acid. To a mixture of 2-chloro-1-(2-methoxy-ethoxymethyl)-1H-benzoimidazole-5-carboxylic acid methyl ester (0.600 g, 0.200 mmol), THF (10 mL), and water (3.33 mL), was added LiOH.H$_2$O (47.0 mg, 1.96 mmol). The mixture was stirred 18 h at 23° C. The solvent was evaporated, water (5 mL) was added and the mixture acidified to with 1 M HCl. The resulting white precipitate was filtered and dried to yield the titled compound (0.490 g, 86%). MS (ESI/CI): mass calcd. for $C_{12}H_{13}ClN_2O_4$, 284.1; m/z found, 285.1 [M+H]$^+$. $^1$H NMR (400 MHz, DMSO-d$_6$): 12.93 (s, 2H), 8.30 (s, 1H), 8.18 (d, J=1.4 Hz, 1H), 7.96 (dd, J=8.6, 1.5 Hz, 1H), 7.90 (dd, J=8.5, 1.6 Hz, 1H), 7.80 (d, J=8.6 Hz, 1H), 7.71 (d, J=8.5 Hz, 1H), 5.74 (d, J=17.5 Hz, 4H), 3.64-3.60 (m, 4H), 3.43-3.39 (m, 4H), 3.18 (d, J=0.6 Hz, 6H).

Step E: 2-chloro-1-(2-methoxy-ethoxymethyl)-1H-benzoimidazole-5-carboxylic acid phenylamide. To a solution of 2-chloro-1-(2-methoxy-ethoxymethyl)-1H-benzoimidazole-5-carboxylic acid (0.235 g, 0.825 mmol) and acetonitrile (4 mL) was added HATU (0.408 g, 1.07 mmol). The resulting suspension was stirred at 23° C. for 5 min, treated with DIPEA (0.428 mL, 2.48 mmol) and stirred for an additional 20 minutes. The reaction mixture was then treated with aniline (90.0 μL, 0.990 mmol) and stirred for 2 h. The reaction mixture was diluted with water (10 mL) and extracted with EtOAc (3×20 mL). The combined organic layers were washed with brine, dried, filtered, and concentrated under reduced pressure. The residue was purified (FCC) (5-70% EtOAc/hexanes) to yield the titled compound (0.265 g, 89%) as a mixture of regioisomers. MS (ESI/CI): mass calcd. for $C_{18}H_{18}ClN_3O_3$, 359.1; m/z found, 360.1 [M+H]$^+$. $^1$H NMR (400 MHz, DMSO-d$_6$): 10.26 (d, J=7.5 Hz, 2H), 8.32 (dd, J=3.6, 1.5 Hz, 2H), 7.99 (dd, J=8.6, 1.6 Hz, 1H), 7.94 (dd, J=8.5, 1.6 Hz, 1H), 7.87-7.73 (m, 6H), 7.41-7.32 (m, 4H), 7.16-7.02 (m, 2H), 5.75 (d, J=8.6 Hz, 4H), 3.67-3.61 (m, 4H), 3.43 (ddd, J=6.3, 4.7, 3.1 Hz, 4H), 3.19 (d, J=1.5 Hz, 6H).

Step F: 1-(5-phenylcarbamoyl-1H-benzoimidazol-2-yl)-1H-pyrazole-4-carboxylic acid. The titled compound was prepared in a manner analogous to EXAMPLE 27, Steps E-G. MS (ESI/CI): mass calcd. for $C_{18}H_{13}N_5O_3$, 347.1; m/z found, 348.1 [M+H]$^+$. $^1$H NMR (400 MHz, DMSO-d$_6$): 13.73 (s, 1H), 12.93 (s, 1H), 10.25 (s, 1H), 8.94 (s, 1H), 8.32 (s, 1H), 8.24 (s, 1H), 7.90 (d, J=8.4 Hz, 1H), 7.81 (d, J=8.1 Hz, 1H), 7.68 (s, 1H), 7.36 (t, J=7.9 Hz, 2H), 7.10 (t, J=7.2 Hz, 1H).

Example 121: 1-(5-Benzylcarbamoyl-1H-benzoimidazol-2-yl)-1H-pyrazole-4-carboxylic Acid

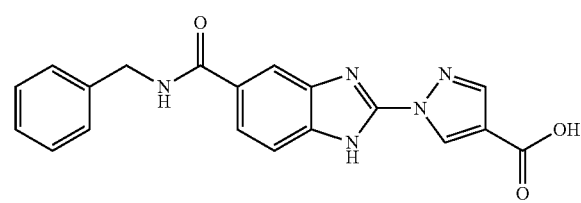 [SMILES: O=C(O)c1cnn(-c2nc3cc(C(=O)NCc4ccccc4)ccc3[nH]2)c1]

The titled compound was prepared in a manner analogous to EXAMPLE 120, substituting benzylamine for aniline in Step E. MS (ESI/CI): mass calcd. for $C_{19}H_{15}N_5O_3$, 361.1; m/z found, 362.1 [M+H]$^+$. $^1$H NMR (500 MHz, DMSO-d$_6$): 13.63 (s, 1H), 12.93 (s, 1H), 9.08 (s, 1H), 8.92 (s, 1H), 8.31 (s, 1H), 8.22 (s, 0.5H), 8.05 (s, 0.5H), 7.85 (s, 1H), 7.70 (s, 0.5H), 7.55 (s, 0.5H), 7.44-7.27 (m, 4H), 7.25 (s, 1H), 4.51 (d, J=5.9 Hz, 2H).

Example 122: 1-[5-(Morpholin-4-ylcarbamoyl)-1H-benzoimidazol-2-yl]-1H-pyrazole-4-carboxylic Acid

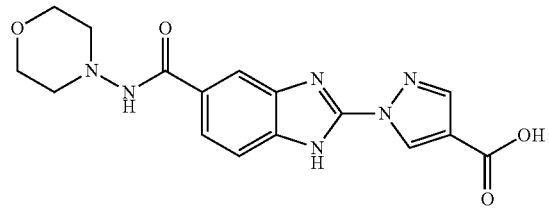 [SMILES: O=C(O)c1cnn(-c2nc3cc(C(=O)NN4CCOCC4)ccc3[nH]2)c1]

The titled compound was prepared in a manner analogous to EXAMPLE 120, substituting morpholin-4-ylamine for aniline in Step E. MS (ESI/CI): mass calcd. for $C_{16}H_{16}N_6O_4$, 356.1; m/z found, 357.1 [M+H]$^+$. $^1$H NMR (600 MHz, DMSO-d$_6$): 12.95 (s, 1H), 9.56 (s, 1H), 8.92 (s, 1H), 8.31 (s, 1H), 8.02 (s, 1H), 7.71 (d, J=8.4 Hz, 1H), 7.59 (d, J=8.0 Hz, 1H), 3.68 (s, 6H), 2.93 (s, 5H).

Example 123: 1-(5-Benzyloxymethyl-1H-benzoimidazol-2-yl)-1H-pyrazole-4-carboxylic Acid

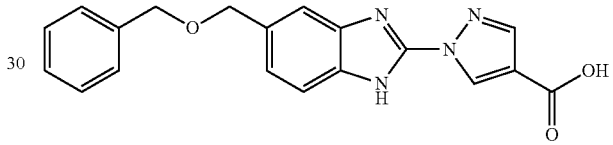

Step A: [2-chloro-1-(2-methoxy-ethoxymethyl)-1H-benzoimidazol-5-yl]-methanol. To a stirred solution of 2-chloro-1-(2-methoxy-ethoxymethyl)-1H-benzoimidazole-5-carboxylic acid methyl ester (Intermediate from EXAMPLE 120, product of Step C) (0.500 g, 1.67 mmol) and THF (30 mL) was added lithium aluminum hydride (2M in THF, 0.836 mL) dropwise over 10 min at 0° C. The reaction mixture was stirred for 48 h, warming to 23° C. The reaction mixture was cooled to 0° C., water (20 mL) was added and the resulting mixture was acidified with 1M HCl. The product was extracted with EtOAc (3×40 mL) and the combined organic layers were washed with brine, dried, filtered, and concentrated under reduced pressure. The residue was purified (FCC) (5-80% EtOAc/hexanes) to yield the titled compound (0.356 g, 78%) as a 1:1 mixture of regioisomers. MS (ESI/CI): mass calcd. for $C_{12}H_{15}ClN_2O_3$, 270.1; m/z found, 271.1 [M+H]$^+$. $^1$H (600 MHz, CDCl$_3$): 7.65-7.61 (m, 2H), 7.52 (s, J=0.7 Hz, 1H), 7.45 (d, J=8.3 Hz, 1H), 7.35 (dd, J=8.3 Hz, 1.5 Hz, 1H), 7.27 (dd, J=8.2 Hz, 1.5 Hz, 1H), 5.63 (s, 2H), 5.62 (s, 2H), 4.81 (s, 2H), 4.77 (s, 2H), 3.64-3.60 (m, 4H), 3.49 (dd, J=5.4 Hz, 3.6 Hz, 4H), 3.35 (s, 3H), 3.34 (s, 3H), 2.59 (s, 1H), 2.50 (s, 1H).

Step B: 5-Benzyloxymethyl-2-chloro-1-(2-methoxy-ethoxymethyl)-1H-benzoimidazole. To a solution of [2-chloro-1-(2-methoxy-ethoxymethyl)-1H-benzoimidazol-5-yl]-methanol (100 mg, 0.370 mmol) and DMF (3 mL) was added NaH (30.0 mg, 0.740 mmol, 60% suspension in mineral oil) at 0° C. The reaction mixture was stirred for 1 h at 0° C., then treated with benzyl bromide (52.0 μL, 0.440 mmol). The reaction mixture was stirred for 16 h. Water (5 mL) was added and the product was extracted with EtOAc (3×20 mL). The combined organic layers were washed with brine, dried, filtered, and concentrated under reduced pressure. The residue was purified (FCC) (5-50% EtOAc/hexanes) to provide the titled compound (100 mg, 75%). MS (ESI/CI): mass calcd. for $C_{19}H_{21}ClN_2O_3$, 360.1; m/z found, 361.1 [M+H]$^+$ Step C: Preparation of 1-(5-benzyloxymethyl-1H-benzoimidazol-2-yl)-1H-pyrazole-4-carboxylic acid. The titled compound was prepared in a manner analogous to EXAMPLE 27 Steps E-G. MS (ESI/CI): mass calcd. for $C_{19}H_{16}N_4O_3$, 348.1; m/z found, 349.1 [M+H]' $^1$H NMR (600 MHz, DMSO-$d_6$): 13.31 (s, 1H), 12.93 (s, 1H), 8.88 (s, 1H), 8.27 (s, 1H), 7.62 (s, 1H), 7.48 (s, 1H), 7.39-7.35 (m, 4H), 7.32-7.21 (m, 2H), 4.64 (s, 2H), 4.55 (s, 2H).

Example 124: 1-(4-Bromo-6-fluoro-1H-benzoimidazol-2-yl)-1H-pyrazole-4-carboxylic Acid

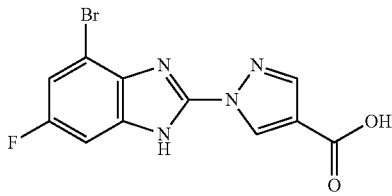 [SMILES: O=C(O)c1cnn(-c2nc3c(Br)cc(F)cc3[nH]2)c1]

Step A: 1-Benzoyl-3-(2,6-dibromo-4-fluoro-phenyl)-thiourea. A mixture of 2,6-dibromo-4-fluoro-phenylamine (1.00 g, 3.72 mmol), benzoyl isothiocyanate (0.600 ml, 4.46 mmol), dimethyl-pyridin-4-yl-amine (45.0 g, 0.370 mmol), and toluene (5 ml) was stirred at 23° C. for 16 hours. The resulting precipitate was collected by filtration and washed with hexane to yield titled compound (1.37 g, 85%). MS (ESI/CI): mass calcd. for $C_{14}H_9Br_2FN_2OS$, 429.9; m/z found, 430.9 [M+H]$^+$. $^1$H NMR (400 MHz, CD$_3$OD-$d_4$): 8.05-7.98 (m, 2H), 7.73-7.66 (m, 1H), 7.62-7.55 (m, 4H).

Step B: (2,6-Dibromo-4-fluoro-phenyl)-thiourea. To a solution of 1-benzoyl-3-(2,6-dibromo-4-fluoro-phenyl)-thiourea (1.37 g, 3.17 mmol) in MeOH (12 mL) was added dropwise a sodium methoxide solution (5.4M in MeOH, 1.29 mL, 6.96 mmol) at 0° C. The mixture was warmed to 23° C. and stirred for 16 hours. MeOH was concentrated under reduced pressure. The residue was dissolved in water, cooled to 0° C., and acidified to pH 4 with 1M HCl. The resulting precipitate was collected by filtration and washed with hexanes to yield titled compound (1.04 g, 99%). MS (ESI/CI): mass calcd. for $C_7H_5Br_2FN_2S$, 325.9; m/z found, 326.9 [M+H]$^+$. $^1$H NMR (400 MHz, CD$_3$OD-$d_4$): 8.05-8.01 (m, 2H).

Step C: 2,6-Dibromo-4-fluoro-phenyl-cyanamide. A solution of (2,6-dibromo-4-fluoro-phenyl)-thiourea (0.300 g, 0.920 mmol) and 1M aq. KOH (7.23 mL) was heated to 100° C. Lead (II) acetate trihydrate (0.400 g, 1.05 mmol) in water (2 mL) was then added. The mixture was heated at 100° C. for another 10 minutes while a precipitate was observed. The mixture was cooled to 0° C. and filtered to provide a clear colorless solution. The filtrate was acidified to pH 5 with acetic acid. The precipitate was collected by filtration to yield titled compound (0.170 g, 63%). $^1$H NMR (400 MHz, DMSO-$d_6$): 7.80-7.78 (m, 2H).

Step D: 1-[N-(2,6-Dibromo-4-fluoro-phenyl)-carbamimidoyl]-1H-pyrazole-4-carboxylic acid ethyl ester. A mixture of 2,6-dibromo-4-fluoro-phenyl-cyanamide (0.167 g, 0.570 mmol), ethyl pyrazole-4-carboxylate (80.0 mg, 0.570 mmol), 4M HCl in dioxane (0.156 mL, 0.630 mmol), and 1,4-dioxane (2 mL) was heated to reflux for 2 h, during which time a precipitate formed. The mixture was allowed to cool to 23° C. Et$_2$O (10 mL) was added to the mixture. The resulting precipitate was collected by filtration, washed with Et$_2$O, and dried to yield the titled compound (0.134 g, 50%) as the HCl salt. MS (ESI/CI): mass calcd. for $C_{13}H_{11}Br_2FN_4O_2$, 431.9; m/z found, 432.9 [M+H]$^+$. $^1$H NMR (400 MHz, DMSO-$d_6$): 8.20 (s, 1H), 7.43 (s, 1H), 6.82 (d, J=7.9 Hz, 2H), 3.56 (q, J=7.1 Hz, 2H), 2.85 (s, 3H), 0.57 (t, J=7.1 Hz, 3H).

Step E: 1-(4-Bromo-6-fluoro-1H-benzoimidazol-2-yl)-1H-pyrazole-4-carboxylic acid ethyl ester. A mixture of 1-[N-(2,6-dibromo-4-fluoro-phenyl)-carbamimidoyl]-1H-pyrazole-4-carboxylic acid ethyl ester (0.134 g, 0.290 mmol), CuI (6.00 mg, 0.0290 mmol), Cs$_2$CO$_3$ (0.464 g, 1.43 mmol), and DMF (2 mL) was heated to 80° C. for 1 h. The mixture was cooled to 23° C., diluted with EtOAc (3 mL), filtered through Celite®, and rinsed with EtOAc. The filtrate was washed with aqueous 1M HCl and water, dried (MgSO$_4$), filtered, and concentrated under reduced pressure. Dichloromethane was added and the resulting precipitate was collected by filtration to yield the titled compound (17.0 mg, 17%). MS (ESI/CI): mass calcd. for $C_{13}H_{10}BrFN_4O_2$, 353.2; m/z found, 354.2 [M+H]$^+$. $^1$H NMR (400 MHz, DMSO-$d_6$): 13.86 (s, 1H), 8.95 (s, 1H), 8.36 (s, 1H), 7.45 (dd, J=9.6, 2.3 Hz, 1H), 7.32 (s, 1H), 4.30 (q, J=7.1 Hz, 2H), 1.33 (t, J=7.1 Hz, 3H).

Step F: 1-(4-Bromo-6-fluoro-1H-benzoimidazol-2-yl)-1H-pyrazole-4-carboxylic acid. A mixture of 1-(4-bromo-6-fluoro-1H-benzoimidazol-2-yl)-1H-pyrazole-4-carboxylic acid ethyl ester (16.0 mg, 45.0 mmol), LiOH (10.0 mg, 0.230 mmol), THF (0.5 mL), and H$_2$O (0.17 mL) was stirred at 23° C. for 16 h. THF was removed under reduced pressure and then aqueous HCl was added. The resulting precipitate was collected and washed with water to yield the titled compound (10.0 mg, 67%). MS (ESI/CI): mass calcd. for $C_{11}H_6BrFN_4O_2$, 325.1; m/z found, 326.0 [M+H]$^+$. $^1$H NMR (400 MHz, DMSO-$d_6$): 13.82 (s, 1H), 12.94 (s, 1H), 8.87 (s, 1H), 8.30 (d, J=0.5 Hz, 1H), 7.45 (dd, J=9.6, 2.3 Hz, 1H), 7.32 (s, 1H).

Example 125: 1-(8H-Imidazo[4',5':3,4]benzo[2,1-d]thiazol-7-yl)-1H-pyrazole-4-carboxylic Acid

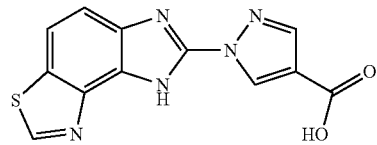 [SMILES: O=C(O)c1cnn(-c2nc3ccc4scnc4c3[nH]2)c1]

The titled compound was prepared in a manner analogous to EXAMPLE 124, Steps A-E, substituting 4-bromo-benzothiazol-5-ylamine for 2,6-dibromo-4-fluoro-phenylamine in Step A. The following modifications were made in Step E:

Step E: 1-(8H-imidazo[4',5':3,4]benzo[2,1-d]thiazol-7-yl)-1H-pyrazole-4-carboxylic acid ethyl ester. The hydrochloride salt of 1-[N-(4-bromo-benzothiazol-5-yl)-carbamimidoyl]-1H-pyrazole-4-carboxylic acid ethyl ester (0.128 g, 0.297 mmol), 1,10-phenanthroline (10.7 mg, 59.4 µmol), cesium carbonate (0.290 g, 0.891 mmol), and DME (5.5 mL) were combined in a sealable microwave tube. The tube was sparged with dry nitrogen and copper (I) iodide (5.70 mg, 29.7 µmol) was added. The reaction mixture was further sparged and the tube was sealed and heated at 80° C. for 1.75 h. The reaction mixture was partitioned between 1M aq. HCl (15 mL) and EtOAc (25 mL). The aqueous layer was further extracted with EtOAc (2×20 mL) and the combined organic layers were washed with brine (10 mL), dried, filtered, and concentrated under reduced pressure. The residue was purified (FCC) (10-60% EtOAc/hexanes, dry-loaded), the clean fractions were concentrated and the residue triturated with diethyl ether to yield the titled compound (19.5 mg, 21% yield). MS (ESI/CI): mass calcd. for $C_{14}H_{11}N_5O_2S$, 313.1; m/z found, 314.1 [M+H]$^+$. $^1$H NMR (400 MHz, DMSO-$d_6$): 13.75 (s, 1H), 9.45 (s, 1H), 9.05 (s, 1H), 8.37 (s, 1H), 8.00 (d, J=8.6 Hz, 1H), 7.65 (d, J=6.0 Hz, 1H), 4.31 (q, J=7.0 Hz, 2H), 1.34 (t, J=7.1 Hz, 3H).

Step F: 1-(8H-Imidazo[4',5':3,4]benzo[2,1-d]thiazol-7-yl)-1H-pyrazole-4-carboxylic acid. The titled compound was prepared in a manner analogous to EXAMPLE 124, Step F. MS (ESI/CI): mass calcd. for $C_{12}H_7N_5O_2S$, 285.0; m/z found, 286.0 [M+H]$^+$. $^1$H NMR (400 MHz, DMSO-$d_6$): 12.94 (br s, 1H), 9.46 (s, 1H), 8.98 (d, J=0.47 Hz, 1H), 8.31 (s, 1H), 8.00 (d, J=8.6 Hz, 1H), 7.69 (d, J=8.5 Hz, 1H).

Example 126: 1-(5,6-Bis-trifluoromethyl-1H-benzo-imidazol-2-yl)-1H-pyrazole-4-carboxylic Acid

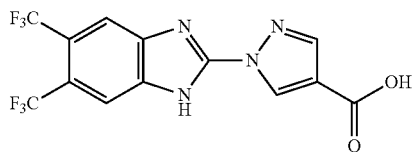 [SMILES: O=C(O)c1cnn(-c2nc3cc(C(F)(F)F)c(C(F)(F)F)cc3[nH]2)c1]

The titled compound was prepared in a manner analogous to EXAMPLE 124, substituting 2-bromo-4,5-bis-trifluoromethyl-phenylamine for 2,6-dibromo-4-fluoro-phenylamine in Step A. MS (ESI/CI): mass calcd. for $C_{13}H_6F_6N_4O_2$, 364.0; m/z found, 365.0 [M+H]$^+$. $^1$H NMR (500 MHz, DMSO-$d_6$): 14.29 (s, 1H), 13.06 (s, 1H), 8.97 (d, J=0.4 Hz, 1H), 8.37 (s, 1H), 8.15 (s, 2H).

Example 127: 1-(4,5,6-Trichloro-1H-benzoimidazol-2-yl)-1H-pyrazole-4-carboxylic Acid

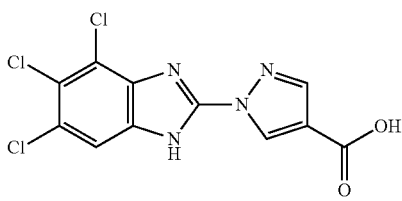 [SMILES: O=C(O)c1cnn(-c2nc3c(Cl)c(Cl)c(Cl)cc3[nH]2)c1]

Step A: 2,3,4-Trichloro-6-nitro-phenylamine. A mixture of 4,5-dichloro-2-nitro-phenylamine (0.500 g, 2.42 mmol), N-chlorosuccinimide (0.403 g, 3.02 mmol), and DMF (5 mL) was heated to 100° C. for 1 h. After cooling to 23° C., the solution was poured into ice water. The yellow precipitate was collected by filtration and dissolved in dichloromethane. The organic phase was washed with water, dried (MgSO$_4$), filtered, and concentrated to yield the titled compound (0.468 g, 81%). $^1$H NMR (400 MHz, CDCl$_3$): 8.28 (s, 1H), 6.70 (s, 2H). The compound did not yield MS data.

Step B: 4,5,6-Trichloro-1H-benzoimidazole. A mixture of 2,3,4-trichloro-6-nitro-phenylamine (0.250 g, 1.04 mmol), sodium dithionite (0.907 g, 5.21 mmol), trimethyl orthoformate (4 ml), DMF (4 mL), and acetic acid (0.5 mL) was heated in a sealed tube for 15 h at 100° C. The reaction mixture was cooled to 23° C. and partitioned between EtOAc and saturated aqueous NaHCO$_3$. The organic layer was collected and the aqueous layer was extracted with EtOAc. The combined organic layers were dried (MgSO$_4$), filtered, and concentrated to yield the titled compound (0.098 g, 43%). MS (ESI/CI): mass calcd. for $C_7H_3Cl_3N_2$, 219.9; m/z found, 221.0 [M+H]$^+$. $^1$H NMR (400 MHz, DMSO-$d_6$): 13.16 (s, 1H), 8.43 (s, 1H), 7.90 (s, 1H).

Step C: 4,5,6-Trichloro-1-(2-methoxy-ethoxymethyl)-1H-benzoimidazole. To a mixture of 4,5,6-trichloro-1H-benzoimidazole (0.098 g, 0.446 mmol) and THF (2.5 mL) was added DIPEA (0.155 mL, 0.892 mmol), followed by 1-chloromethoxy-2-methoxy-ethane (0.057 ml, 0.49 mmol) at 23° C. After stirring for 18 h, EtOAc was added. The organic layer was washed with saturated aqueous NaHCO$_3$. The aqueous layer was further extracted with EtOAc. The organic layer was dried over MgSO$_4$, filtered, and concentrated under reduced pressure. The residue was purified (FCC) to yield the titled compound as a mixture of regioisomers (0.084 g, 61%). MS (ESI/CI): mass calcd. for $C_{11}H_{11}Cl_3N_2O_2$, 308.0; m/z found, 309.0 [M+H]$^+$. $^1$H NMR (400 MHz, DMSO-$d_6$): 8.59 (s, 1H), 8.58 (s, 1H), 8.09 (s, 1H), 8.04 (d, J=8.5 Hz, 1H), 5.84 (s, 2H), 5.71 (s, 2H), 3.59-3.57 (m, 2H), 3.56-3.53 (m, 2H), 3.42-3.38 (m, 4H), 3.18 (s, 3H), 3.17 (s, 3H).

Step D: 2,4,5,6-Tetrachloro-1-(2-methoxy-ethoxymethyl)-1H-benzoimidazole. A solution of 4,5,6-trichloro-1-(2-methoxy-ethoxymethyl)-1H-benzoimidazole (0.388 g, 1.26 mmol) and THF (6 mL) was cooled to −78° C. in an acetone/dry ice bath. Lithium diisopropylamide (1.0 M solution in THF, 2.52 mL, 2.52 mmol) was added dropwise and the reaction mixture was stirred at −78° C. for 1 h. A solution of N-chlorosuccinimide (0.336 g, 2.52 mmol) and THF (2 mL) was added. The reaction mixture was warmed to 23° C. and stirred for 2 h. Saturated aqueous NH$_4$Cl was added and the crude product was extracted with EtOAc. The combined organic layers were dried, filtered, and concentrated under reduced pressure. The residue was purified (FCC) to yield the titled compound as a mixture of regioisomers (0.267 g, 62%). MS (ESI/CI): mass calcd. for $C_{11}H_{10}Cl_4N_2O_2$, 342.0; m/z found, 343.0 [M+H]$^+$. $^1$H NMR (400 MHz, DMSO-$d_6$): 8.18 (s, 1H), 8.03 (s, 1H), 5.88 (d, J=5.8 Hz, 2H), 5.71 (s, 2H), 3.71-3.66 (m, 2H), 3.64-3.61 (m, 2H), 3.44-3.38 (m, 4H), 3.17 (t, J=1.7 Hz, 6H).

Step E: 1-[4,5,6-Trichloro-1-(2-methoxy-ethoxymethyl)-1H-benzoimidazol-2-yl]-1H-pyrazole-4-carboxylic acid ethyl ester. A mixture of 2,4,5,6-tetrachloro-1-(2-methoxy-ethoxymethyl)-1H-benzoimidazole (0.275 g, 0.80 mmol), Cs$_2$CO$_3$ (0.524 g, 1.61 mmol), 1H-pyrazole-4-carboxylic acid ethyl ester (0.124 g, 0.89 mmol), and DMF (4 mL) was heated to 80° C. for 2 h. The mixture was cooled to 23° C. EtOAc was added and the mixture was washed with brine. The organic layer was dried (MgSO$_4$), filtered, and concentrated under reduced pressure. The residue was purified (FCC) to yield the titled compound as a mixture of regioisomers (0.166 g, 46%). MS (ESI/CI): mass calcd. for $C_{17}H_{17}Cl_3N_4O_4$, 446.0; m/z found, 447.0 [M+H]$^+$. $^1$H NMR (400 MHz, DMSO-$d_6$): 9.01-8.97 (m, 2H), 8.40 (t, J=2.3 Hz, 1H), 8.37 (s, 1H), 8.21 (s, 1H), 8.13 (s, 1H), 6.09 (s, 2H), 6.01 (s, 2H), 4.30 (qd, J=7.1 Hz, 2.9, 8H), 3.58-3.51 (m, 2H), 3.44 (d, J=4.9 Hz, 2H), 3.11 (s, 3H), 3.08 (s, 3H), 1.32 (tt, J=7.1 Hz, 1.7 Hz, 6H).

Step F: 1-(4,5,6-Trichloro-1H-benzoimidazol-2-yl)-1H-pyrazole-4-carboxylic acid. To a stirred solution of 1-[4,5, 6-trichloro-1-(2-methoxy-ethoxymethyl)-1H-benzoimidazol-2-yl]-1H-pyrazole-4-carboxylic acid ethyl ester (0.166 g, 0.372 mmol) and acetic acid (6 mL) was added 6M aq. hydrochloric acid (6 mL). The reaction mixture was heated to 100° C. for 18 h and then cooled to 23° C. The precipitate was collected to yield the titled compound as the HCl salt (0.91 g, 74% yield). MS (ESI/CI): mass calcd. for $C_{11}H_5Cl_3N_4O_2$, 330.0; m/z found, 331.0 [M+H]+. 1H NMR (400 MHz, DMSO-$d_6$): 8.92 (s, 1H), 8.34 (s, 1H), 7.74 (s, 1H).

Example 128: 1-(4-Bromo-5,6-dichloro-1H-benzoimidazol-2-yl)-1H-pyrazole-4-carboxylic Acid

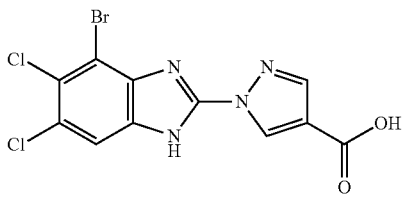 [SMILES: O=C(O)c1cnn(-c2nc3c(Br)c(Cl)c(Cl)cc3[nH]2)c1]

Step A: 1-[4-Bromo-5,6-dichloro-1-(2-methoxyethoxymethyl)-1H-benzoimidazol-2-yl]-1H-pyrazole-4-carboxylic acid ethyl ester. The titled compound was prepared in a manner analogous to EXAMPLE 127, Steps A-E, substituting N-chlorosuccinimide with N-bromosuccinimide in Step A. MS (ESI/CI): mass calcd. for $C_{17}H_{17}BrCl_2N_4O_4$, 490.0; m/z found, 491.0 [M+H]+.

Step B: 1-(4-Bromo-5,6-dichloro-1H-benzoimidazol-2-yl)-1H-pyrazole-4-carboxylic acid ethyl ester. To a mixture of 1-[4-bromo-5,6-dichloro-1-(2-methoxy-ethoxymethyl)-1H-benzoimidazol-2-yl]-1H-pyrazole-4-carboxylic acid ethyl ester (0.132 g, 0.27 mmol) and EtOH (2 mL) was added 4M HCl in dioxane (2 mL). The mixture was stirred for 18 h at 23° C. The resulting white precipitate was filtered and washed with EtOH to yield the titled compound (0.088 g, 81%). MS (ESI/CI): mass calcd. for $C_{13}H_9BrCl_2N_4O_4$, 402.9; m/z found, 403.9 [M+H]+. 1H NMR (500 MHz, DMSO-$d_6$): 14.22-13.94 (m, 1H), 8.98 (s, 1H), 8.40 (s, 1H), 7.74 (s, 1H), 4.30 (q, J=7.1 Hz, 2H), 1.33 (t, J=7.1 Hz, 3H).

Step C: 1-(4-Bromo-5,6-dichloro-1H-benzoimidazol-2-yl)-1H-pyrazole-4-carboxylic acid. LiOH.H2O (0.046 g, 1.09 mmol) was added to a mixture of 1-(4-Bromo-5,6-dichloro-1H-benzoimidazol-2-yl)-1H-pyrazole-4-carboxylic acid ethyl ester (0.088 g, 0.22 mmol), THF (1 mL), and water (0.33 mL), and the mixture was stirred 18 h at 23° C. The solvent was evaporated, water (3 mL) was added and the mixture acidified with 1M HCl. The resulting white precipitate was filtered and dried to yield the titled compound (0.068 g, 83%). MS (ESI/CI): mass calcd. for $C_{11}H_5BrCl_2N_4O_2$, 374.9; m/z found, 375.9 [M+H]+. 1H NMR (500 MHz, DMSO-$d_6$): 8.89 (s, 1H), 8.32 (s, 1H), 7.74 (s, 1H).

Example 129: 1-(6-Fluoro-5-trifluoromethyl-1H-benzoimidazol-2-yl)-1H-pyrazole-4-carboxylic Acid

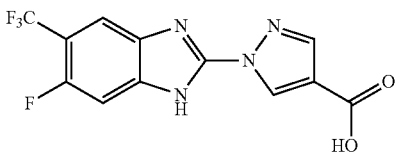

Step A: N-(3-Fluoro-4-trifluoromethyl-phenyl)-acetamide. To a mixture of 3-fluoro-4-trifluoromethyl-phenylamine (16.9 g, 92.6 mmol), N,N-dimethyl-4-aminopyridine (1.13 g, 9.26 mmol), and toluene (230 mL) was added acetic anhydride (13.1 mL, 0.139 mol). The reaction mixture was heated at reflux for 3 h, and stirred at 23° C. for 16 h. The reaction mixture was concentrated and the crude product was dissolved in EtOAc (100 mL). The organic layer was washed with water (40 mL) and brine (40 mL), dried, filtered, and concentrated under reduced pressure. The crude solid was triturated from DCM/hexanes to yield the titled compound (16.5 g, 81% yield). MS (ESI/CI): mass calcd. for $C_9H_7F_4NO$, 221.1; m/z found, 222.0 [M+H]+. 1H NMR (400 MHz, CDCl3): 7.68 (d, J=12.5 Hz, 1H), 7.52 (t, J=8.3 Hz, 1H), 7.45 (br s, 1H), 7.19 (d, J=8.5 Hz, 1H), 2.22 (s, 3H).

Step B: N-(5-Fluoro-2-nitro-4-trifluoromethyl-phenyl)-acetamide. To a vigorously stirred solution of N-(3-fluoro-4-trifluoromethyl-phenyl)-acetamide (0.663 g, 3.00 mmol) and sulfuric acid (3 mL) was added dropwise a solution of potassium nitrate (0.607 g, 6.00 mmol) and conc. sulfuric acid (3 mL) at 0° C. The reaction mixture was stirred for 1 h at 0° C. and then slowly pipetted into ice/water with stirring. The resulting precipitate was collected and dried in vacuo to yield the titled compound (0.648 g, 81% yield) as a single regioisomer. The compound did not yield MS data. 1H NMR (600 MHz, CDCl3): 10.67 (br s, 1H), 8.86 (d, J=12.9 Hz, 1H), 8.57 (d, J=7.2 Hz, 1H), 2.35 (s, 3H).

Step C: 5-Fluoro-2-nitro-4-trifluoromethyl-phenylamine. A suspension of N-(5-fluoro-2-nitro-4-trifluoromethyl-phenyl)-acetamide (17.8 g, 67.0 mmol) in aqueous HCl (3M, 400 mL) was heated at reflux for 3 h. The resulting suspension was cooled to 0° C. and brought to pH 8 with NaHCO3. The resulting solid was collected to yield the titled compound (13.7 g, 91% yield). The compound did not yield MS data. 1H NMR (400 MHz, CDCl3): 8.48 (d, J=7.3 Hz, 1H), 6.75-6.18 (m, 3H).

Step D: 1-(6-Fluoro-5-trifluoromethyl-1H-benzoimidazol-2-yl)-1H-pyrazole-4-carboxylic acid. The titled compound was prepared in a manner analogous to EXAMPLE 71, Steps B-C. MS (ESI/CI): mass calcd. for $C_{12}H_6F_4N_4O_2$, 314.0; m/z found, 315.1 [M+H]+. 1H NMR (400 MHz, CD3OD, tautomeric broadening): 8.93 (s, 1H), 8.20 (s, 1H), 7.87 (br s, 1H), 7.49 (br s, 1H).

Example 130: 1-(6-Chloro-5-ethylamino-1H-benzoimidazol-2-yl)-1H-pyrazole-4-carboxylic Acid

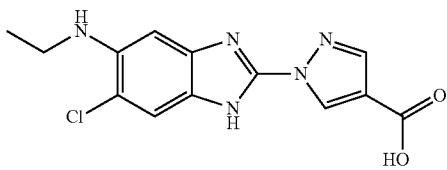 [SMILES: CCNc1cc2nc(-n3cc(C(=O)O)cn3)[nH]c2cc1Cl]

Step A: 1-[6-Chloro-5-ethylamino-1-(2-methoxyethoxymethyl)-1H-benzoimidazol-2-yl]-1H-pyrazole-4-carboxylic acid ethyl ester. To a slurry of 4 Å molecular sieves (1.2 g) and 1-[5-amino-6-chloro-1-(2-methoxy-ethoxymethyl)-1H-benzoimidazol-2-yl]-1H-pyrazole-4-carboxylic acid ethyl ester (Intermediate from Example 41, product from Step A) (0.300 g, 0.762 mmol), and ethanol (3 mL) was added acetaldehyde (0.500 mL, 8.91 mmol) at 0° C. in a sealable microwave tube. The tube was sealed and the reaction mixture was allowed to warm to 23° C. over 16 h.

The reaction mixture was heated at 60° C. for 1 h. The molecular sieves were removed from the resulting solution by filtration and the filtrate was concentrated under reduced pressure. Sodium triacetoxy borohydride (0.242 g, 1.14 mmol), THF (3 mL), and glacial acetic acid (0.04 mL) were added to the residue and the resulting suspension was stirred for 7.5 h at 23° C. The reaction mixture was concentrated and the residue partitioned between saturated aqueous sodium bicarbonate and EtOAc (35 mL). The aqueous layer was further extracted with EtOAc (2×35 mL) and the combined organic layers were washed with brine (15 mL), dried, filtered, and concentrated under reduced pressure. The residue was purified (FCC) (10-45% EtOAc/hexanes) to yield the titled compound (0.169 g, 47% crude yield). This compound was used without further purification in subsequent reactions. MS (ESI/CI): mass calcd. for $C_{19}H_{24}ClN_5O_4$, 421.2; m/z found, 422.1 $[M+H]^+$.

Step B: 1-(6-Chloro-5-ethylamino-1H-benzoimidazol-2-yl)-1H-pyrazole-4-carboxylic acid. The titled compound was prepared in a manner analogous to EXAMPLE 27, Steps F-G. MS (ESI/CI): mass calcd. for $C_{13}H_{12}ClN_5O_2$, 305.1; m/z found, 306.1 $[M+H]^+$. $^1$H NMR (400 MHz, DMSO-$d_6$, tautomeric broadening): 8.84 (s, 1H), 8.27 (s, 1H), 7.60 (s, 1H), 7.03 (br s, 1H), 3.22 (q, J=6.9 Hz, 2H), 1.25 (t, J=7.1 Hz, 3H).

Example 131: 1-(6-Chloro-5-propylamino-1H-benzoimidazol-2-yl)-1H-pyrazole-4-carboxylic Acid

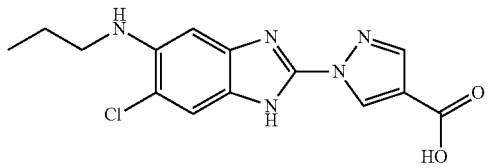 [SMILES: CCCNc1cc2nc(-n3cc(C(=O)O)cn3)[nH]c2cc1Cl]

Step A: 1-[6-Chloro-5-ethylamino-1-(2-methoxy-ethoxymethyl)-1H-benzoimidazol-2-yl]-1H-pyrazole-4-carboxylic acid ethyl ester. To a solution of 1-[5-amino-6-chloro-1-(2-methoxy-ethoxymethyl)-1H-benzoimidazol-2-yl]-1H-pyrazole-4-carboxylic acid ethyl ester (Intermediate from Example 41, product from Step A) (0.300 g, 0.762 mmol) and propionaldehyde (61.0 μL, 0.838 mmol) in THF (3 mL) was added sodium triacetoxyborohydride (0.226 g, 1.07 mmol) followed by acetic acid (40.9 μL, 0.762 mmol). The reaction mixture was stirred at 23° C. for 22 h. Molecular sieves (4 Å, 1.2 g) were added, and the reaction was kept at 40-50° C. for 24 h. Over the next 48 h, two additional portions of both propionaldehyde and sodium triacetoxyborohydride were added. The reaction was quenched with saturated aqueous sodium bicarbonate (10 mL). The aqueous layer was extracted with EtOAc (3×35 mL) and the combined organic layers were washed with brine (25 mL), dried, filtered, and concentrated under reduced pressure. The residue was purified (FCC) (10-45% EtOAc/hexanes) to yield the titled compound (0.178 g, 54% yield) as a 1:1 mixture of regioisomers. $^1$H NMR (400 MHz, CDCl$_3$): 8.83 (s, 1H), 8.76 (s, 1H), 8.15 (s, 2H), 7.63 (s, 1H), 7.55 (s, 1H), 6.94 (s, 1H), 6.76 (s, 1H), 6.03 (s, 4H), 4.42 (br s, 1H), 4.35 (q, J=7.1 Hz, 2H), 4.27 (br s, 1H), 3.65-3.59 (m, 4H), 3.49-3.41 (m, 4H), 3.33 (s, 3H), 3.32 (s, 3H), 3.23-3.12 (m, 4H), 1.82-1.69 (m, 4H), 1.37 (t, J=7.1 Hz, 6H), 1.11-1.01 (m, 6H).

Step B: 1-(6-Chloro-5-ethylamino-1H-benzoimidazol-2-yl)-1H-pyrazole-4-carboxylic acid. The titled compound was prepared in a manner analogous to EXAMPLE 27, Steps F-G. MS (ESI/CI): mass calcd. for $C_{14}H_{14}ClN_5O_2$, 319.1; m/z found, 320.1 $[M+H]^+$. $^1$H NMR (400 MHz, DMSO-$d_6$, tautomeric broadening): 12.91 (br s, 1H), 8.80 (s, 1H), 8.24 (s, 1H), 7.51 (br s, 1H), 6.71 (br s, 1H), 3.10 (t, J=7.1 Hz, 2H), 1.69-1.59 (m, 2H), 0.96 (t, J=7.4 Hz, 3H).

Example 132: 1-(5-Benzylamino-6-chloro-1H-benzoimidazol-2-yl)-1H-pyrazole-4-carboxylic Acid

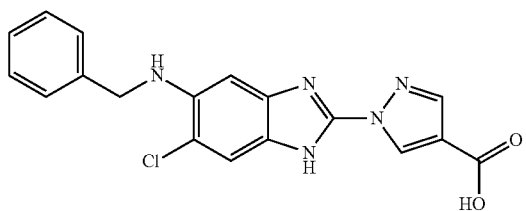 [SMILES: O=C(O)c1cnn(-c2nc3cc(NCc4ccccc4)c(Cl)cc3[nH]2)c1]

Step A: 1-[5-(Benzylidene-amino)-6-chloro-1-(2-methoxy-ethoxymethyl)-1H-benzoimidazol-2-yl]-1H-pyrazole-4-carboxylic acid ethyl ester. Benzaldehyde (93.0 mg, 0.876 mmol), 1-[5-amino-6-chloro-1-(2-methoxy-ethoxymethyl)-1H-benzoimidazol-2-yl]-1H-pyrazole-4-carboxylic acid ethyl ester (Intermediate from Example 41, product from Step A) (0.300 g, 0.762 mmol), THF (3 mL), and 4 Å molecular sieves (0.910 g) were combined and stirred for 18 h at 23° C. Sodium triacetoxyborohydride (0.242 g, 1.14 mmol) was added and stirring was continued for 4 days. The reaction was quenched with saturated aqueous sodium bicarbonate (15 mL) and stirred with dichloromethane (25 mL). This mixture was filtered and the layers were separated. The aqueous layer was extracted with dichlormethane (2×25 mL) and the combined organic layers were washed with brine (20 mL), dried, filtered, and concentrated under reduced pressure. The residue was purified (FCC) (10-45% EtOAc/hexanes) to yield the titled compound (0.288 g, 78% yield) as a 4:3 mixture of regioisomers. The titled compound was not stable enough to obtain a mass spectrum. $^1$H NMR (400 MHz, CDCl$_3$): 8.87 (s, 1H), 8.48 (s, 1H), 8.19 (s, 1H), 8.03-7.94 (m, 2H), 7.73 (s, 1H), 7.58-7.48 (m, 3H), 7.39 (s, 1H), 6.12 (s, 2H), 4.36 (q, J=7.1 Hz, 2H), 3.7-3.6 (m, 2H), 3.5-3.4 (m, 2H), 3.32 (s, 3H), 1.39 (t, J=7.1 Hz, 3H).

Step B: 1-[5-Benzylamino-6-chloro-1-(2-methoxy-ethoxymethyl)-1H-benzoimidazol-2-yl]-1H-pyrazole-4-carboxylic acid ethyl ester. To a slurry of 1-[5-(benzylidene-amino)-6-chloro-1-(2-methoxy-ethoxymethyl)-1H-benzoimidazol-2-yl]-1H-pyrazole-4-carboxylic acid ethyl ester (0.177 g, 0.366 mmol) in ethanol (7 mL) was added sodium borohydride (41.6 mg, 1.10 mmol) at 0° C. The yellow slurry was warmed to 23° C. over 24 h. The reaction mixture was concentrated and saturated aqueous sodium bicarbonate (25 mL) was added to the residue. The reaction mixture was extracted with EtOAc (3×25 mL) and the combined organic layers were washed with brine (20 mL), dried, filtered, and concentrated under reduced pressure. The residue was purified (FCC) (10-45% EtOAc/hexanes) to yield the titled compound as a 6:5 mixture of regioisomers (0.144 g, 81% yield). MS (ESI/CI): mass calcd. for $C_{24}H_{26}ClN_5O_4$, 483.2; m/z found, 484.2 $[M+H]^+$. $^1$H NMR (400 MHz, CDCl$_3$): 8.79 (s, 1H), 8.14 (s, 1H), 7.58 (s, 1H), 7.43-7.27 (m, 5H), 6.92 (s, 1H), 6.03 (s, 2H), 4.75 (t, J=6.0

Hz, 1H), 4.49-4.43 (m, 2H), 4.34 (q, J=7.2 Hz, 2H), 3.65-3.61 (m, 2H), 3.47-3.44 (m, 2H), 3.32 (s, 1H), 1.36 (t, J=7.1 Hz, 3H).

Step C: 1-(5-Benzylamino-6-chloro-1H-benzoimidazol-2-yl)-1H-pyrazole-4-carboxylic acid. The titled compound was prepared in a manner analogous to EXAMPLE 27, Steps F-G. MS (ESI/CI): mass calcd. for $C_{18}H_{14}ClN_5O_2$, 367.1; m/z found, 368.0 [M+H]$^+$. $^1$H NMR (400 MHz, DMSO-d$_6$, tautomeric broadening): 12.87 (br s, 1H), 8.76 (d, J=0.5 Hz, 1H), 8.20 (s, 1H), 7.52 (br s, 1H), 7.40-7.31 (m, 4H), 7.25-7.20 (m, 1H), 6.56 (br s, 1H), 6.00 (br s, 1H), 4.44 (s, 2H).

Example 133: 1-(6-Chloro-5-phenylamino-1H-benzoimidazol-2-yl)-1H-pyrazole-4-carboxylic Acid

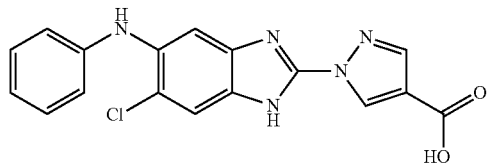 [SMILES: O=C(O)c1cnn(-c2nc3cc(Nc4ccccc4)c(Cl)cc3[nH]2)c1]

Step A: 1-[6-Chloro-1-(2-methoxy-ethoxymethyl)-5-phenylamino-1H-benzoimidazol-2-yl]-1H-pyrazole-4-carboxylic acid ethyl ester. An oven-dried flask was charged with 1-[5-amino-6-chloro-1-(2-methoxy-ethoxymethyl)-1H-benzoimidazol-2-yl]-1H-pyrazole-4-carboxylic acid ethyl ester (Intermediate from Example 41, product from Step A) (0.100 g, 0.254 mmol), bromobenzene (43.8 mg, 0.279 mmol), Pd(dba)$_2$ (1.50 mg, 2.50 µmol), Q-Phos (3.60 mg, 5.10 µmol), and sodium tert-butoxide (36.6 mg, 0.381 mmol). The flask was purged with N$_2$. Dry toluene (0.5 mL) was added and the slurry was briefly sonicated. The reaction mixture was heated at 50° C. for 18 h. The reaction mixture was then diluted with dichloromethane and filtered through a pad of Celite®. The filter cake was rinsed with EtOAc and the filtrate was concentrated under reduced pressure. The residue was purified (FCC) (10-45% EtOAc/hexanes) to yield the titled compound (7.1 mg, 6% yield), which was used in the next step without further purification. MS (ESI/CI): mass calcd. for $C_{23}H_{24}ClN_5O_4$, 469.2; m/z found, 470.1 [M+H]$^+$.

Step B: 1-(6-Chloro-5-phenylamino-1H-benzoimidazol-2-yl)-1H-pyrazole-4-carboxylic acid. The titled compound was prepared in a manner analogous to EXAMPLE 27, Steps F-G. MS (ESI/CI): mass calcd. for $C_{17}H_{12}ClN_5O_2$, 353.1; m/z found, 354.1 [M+H]$^+$. $^1$H NMR (400 MHz, DMSO-d$_6$, tautomeric broadening): 12.94 (br s, 1H), 8.86 (s, 1H), 8.28 (s, 1H), 7.74-7.69 (m, 2H), 7.40 (s, 1H), 7.24-7.18 (m, 2H), 6.95 (d, J=7.8 Hz, 2H), 6.81 (t, J=7.3 Hz, 1H).

Example 134: 1-[6-Chloro-5-(2-morpholin-4-yl-ethylamino)-1H-benzoimidazol-2-yl]-1H-pyrazole-4-carboxylic Acid

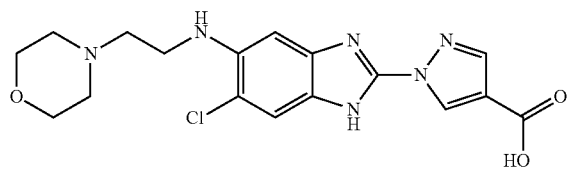 [SMILES: O=C(O)c1cnn(-c2nc3cc(NCCN4CCOCC4)c(Cl)cc3[nH]2)c1]

Step A: 1-[6-Chloro-1-(2-methoxy-ethoxymethyl)-5-(2-morpholin-4-yl-ethylamino)-1H-benzoimidazol-2-yl]-1H-pyrazole-4-carboxylic acid ethyl ester. To a slurry of 4 Å molecular sieves (0.9 g), 1-[5-amino-6-chloro-1-(2-methoxy-ethoxymethyl)-1H-benzoimidazol-2-yl]-1H-pyrazole-4-carboxylic acid ethyl ester (Intermediate from Example 41, product from Step A) (0.187 g, 0.475 mmol), sodium 1-hydroxy-2-morpholin-4-yl-ethanesulfonate (0.122 g, 0.523 mmol) and THF (2.5 mL) was added triethylamine (0.300 mL, 2.15 mmol). The slurry was stirred at 23° C. for 24 h, and sodium triacetoxyborohydride (0.282 g, 1.33 mmol) was added. The reaction mixture was stirred for an additional 24 h. Additional sodium 1-hydroxy-2-morpholin-4-yl-ethanesulfonate (62.0 mg, 0.270 mmol) was added and the reaction was allowed to continue for another 24 h at 23° C. The reaction mixture was diluted with EtOAc, filtered, and washed with saturated aqueous NaHCO$_3$. The aqueous layer was further extracted with EtOAc (2×30 mL). The combined organic layers were washed with brine, dried, filtered, and concentrated under reduced pressure. The residue was purified (FCC) (EtOAc/hexanes) to yield the titled compound (30 mg, 12% crude yield). This compound was used without further purification in subsequent reactions. MS (ESI/CI): mass calcd. for $C_{23}H_{31}ClN_6O_5$, 506.2; m/z found, 507.2 [M+H]$^+$.

Step B: 1-[6-Chloro-5-(2-morpholin-4-yl-ethylamino)-1H-benzoimidazol-2-yl]-1H-pyrazole-4-carboxylic acid. The titled compound was prepared in a manner analogous to EXAMPLE 27, Steps F-G. MS (ESI/CI): mass calcd. for $C_{17}H_{19}ClN_6O_3$, 390.1; m/z found, 391.1 [M+H]$^+$. $^1$H NMR (600 MHz, CD$_3$OD-d$_4$, tautomeric broadening): 8.77 (s, 1H), 8.12 (s, 1H), 7.50 (br s, 1H), 6.86 (br s, 1H), 3.79-3.74 (m, 4H), 3.38 (t, J=6.3 Hz, 2H), 2.89-2.82 (br m, 2H), 2.69 (br s, 4H).

Example 135: 1-(6-Chloro-5-cyclopropanesulfonylamino-1H-benzoimidazol-2-yl)-1H-pyrazole-4-carboxylic Acid

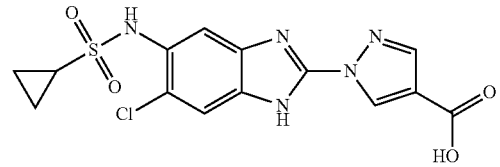 [SMILES: O=C(O)c1cnn(-c2nc3cc(NS(=O)(=O)C4CC4)c(Cl)cc3[nH]2)c1]

Step A: 1-[6-Chloro-5-cyclopropanesulfonylamino-1-(2-methoxy-ethoxymethyl)-1H-benzoimidazol-2-yl]-1H-pyrazole-4-carboxylic acid ethyl ester. To a stirred solution of 1-[5-amino-6-chloro-1-(2-methoxy-ethoxymethyl)-1H-benzoimidazol-2-yl]-1H-pyrazole-4-carboxylic acid ethyl ester (Intermediate from Example 41, product from Step A) (0.100 g, 0.254 mmol) in pyridine (1.5 mL) was added dropwise cyclopropanesulfonyl chloride (71.0 mg, 0.510 mmol) at 0° C. The reaction mixture was slowly warmed to 23° C., and maintained at this temperature for 42 h. The reaction was quenched with sat. aq. sodium bicarbonate (10 mL) and extracted with EtOAc (3×15 mL). The combined organic layers were washed with brine (10 mL), dried, filtered, and concentrated under reduced pressure. The residue was purified (FCC) (10-55% EtOAc/hexanes) to yield the titled compound (96.0 mg, 76%), which was recovered as a 5:4 mixture of regioisomers. MS (ESI/CI): mass calcd. for $C_{20}H_{24}ClN_5O_6S$, 497.1; m/z found, 498.1 [M+H]$^+$. $^1$H NMR (400 MHz, CDCl₃): 8.83 (s, 1H), 8.19 (s, 1H), 8.03 (s, 1H), 7.71 (s, 1H), 6.73 (s, 1H), 6.14 (s, 2H), 4.31-4.28 (m, 2H), 3.71-3.64 (m, 2H), 3.51-3.45 (m, 2H), 3.32 (s, 3H), 2.54-2.44 (m, 1H), 1.43-1.35 (m, 3H), 1.21-1.11 (m, 2H), 1.00-0.92 (m, 2H).

Step B: Preparation of 1-(6-Chloro-5-cyclopropanesulfonylamino-1H-benzoimidazol-2-yl)-1H-pyrazole-4-carboxylic acid. The titled compound was prepared in a manner analogous to EXAMPLE 71, Step C. MS (ESI/CI): mass calcd. for C₁₄H₁₂ClN₅O₄S, 381.0; m/z found, 382.1 [M+H]⁺. ¹H NMR (400 MHz, DMSO-d₆, tautomeric broadening): 13.55 (br s, 1H), 12.97 (br s, 1H), 9.46 (br s, 1H), 8.89 (s, 1H), 8.31 (s, 1H), 7.94-7.45 (m, 2H), 2.69-2.59 (m, 1H), 0.98-0.79 (m, 4H).

Example 136: 1-(6-Chloro-5-methanesulfonylamino-1H-benzoimidazol-2-yl)-1H-pyrazole-4-carboxylic Acid

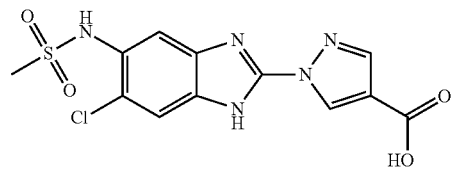 [SMILES: CS(=O)(=O)Nc1cc2nc(-n3cc(C(=O)O)cn3)[nH]c2cc1Cl]

The titled compound was prepared in a manner analogous to EXAMPLE 135, substituting methanesulfonyl chloride for cyclopropanesulfonyl chloride in Step A. MS (ESI/CI): mass calcd. for C₁₂H₁₀ClN₅O₄, 355.0; m/z found, 356.0 [M+H]⁺. ¹H NMR (400 MHz, DMSO-d₆): 9.48 (s, 1H), 8.90 (s, 1H), 8.31 (s, 1H), 7.72 (s, 1H), 7.61 (s, 1H), 3.01 (s, 3H).

Example 137: 1-(6-Chloro-5-ethanesulfonylamino-1H-benzoimidazol-2-yl)-1H-pyrazole-4-carboxylic Acid

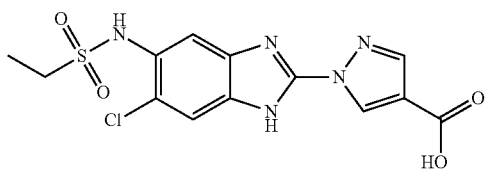 [SMILES: CCS(=O)(=O)Nc1cc2nc(-n3cc(C(=O)O)cn3)[nH]c2cc1Cl]

The titled compound was prepared in a manner analogous to EXAMPLE 135, substituting ethanesulfonyl chloride for cyclopropanesulfonyl chloride in Step A. A 5:4 mixture of tautomers was observed in the ¹H NMR spectrum. MS (ESI/CI): mass calcd. for C₁₃H₁₂ClN₅O₄S, 369.0; m/z found, 370.0 [M+H]⁺. ¹H NMR (400 MHz, DMSO-d₆): 13.60-13.48 (m, 1H), 12.97 (br s, 1H), 9.46 (s, 1H), 8.89 (s, 1H), 8.31 (s, 1H), 7.85-7.52 (m, 2H), 3.18-3.04 (m, 2H), 1.35-1.20 (m, 3H).

Example 138: 1-(5-Benzenesulfonylamino-6-chloro-1H-benzoimidazol-2-yl)-1H-pyrazole-4-carboxylic Acid

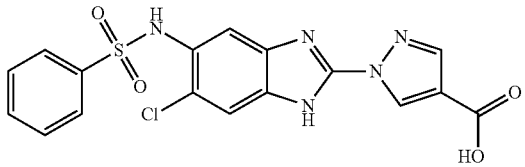 [SMILES: O=C(O)c1cnn(-c2nc3cc(NS(=O)(=O)c4ccccc4)c(Cl)cc3[nH]2)c1]

The titled compound was prepared in a manner analogous to EXAMPLE 135, substituting benzenesulfonyl chloride for cyclopropanesulfonyl chloride in Step A. MS (ESI/CI): mass calcd. for C₁₇H₁₂ClN₅O₄S, 417.0; m/z found, 418.0 [M+H]⁺. ¹H NMR (400 MHz, DMSO-d₆): 13.58-13.46 (m, 1H), 12.97 (br s, 1H), 10.02-9.90 (m, 1H), 8.93-8.81 (m, 1H), 8.29 (s, 1H), 7.70-7.42 (m, 6H), 7.34 (s, 1H).

Example 139: 1-(5-Acetylamino-6-chloro-1H-benzoimidazol-2-yl)-1H-pyrazole-4-carboxylic Acid

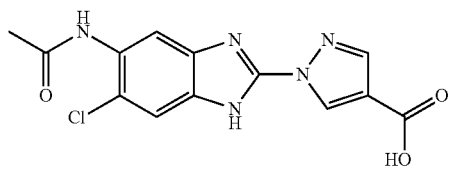 [SMILES: CC(=O)Nc1cc2nc(-n3cc(C(=O)O)cn3)[nH]c2cc1Cl]

Step A: 1-[5-Acetylamino-6-chloro-1-(2-methoxyethoxymethyl)-1H-benzoimidazol-2-yl]-1H-pyrazole-4-carboxylic acid ethyl ester. To a stirred suspension of 1-[5-amino-6-chloro-1-(2-methoxy-ethoxymethyl)-1H-benzoimidazol-2-yl]-1H-pyrazole-4-carboxylic acid ethyl ester (Intermediate from Example 41, product from Step A) (0.300 g, 0.762 mmol) and THF (4 mL) was added diisopropylethylamine (0.330 mL, 1.90 mmol) at 0° C. Acetyl chloride (57.0 µL, 0.800 mmol) was then added. After 3 h, the reaction was quenched with water (10 mL) and extracted with EtOAc (3×35 mL). The combined organic layers were washed with brine (15 mL), dried, filtered, and concentrated under reduced pressure. The residue was purified (FCC) (5-65% EtOAc/hexanes) to yield the titled compound (0.270 g, 81%) as a 2:1 mixture of regioisomers. MS (ESI/CI): mass calcd. for C₁₉H₂₂ClN₅O₅, 435.1; m/z found, 436.1 [M+H]⁺. ¹H NMR (400 MHz, CDCl₃): 8.83 (s, 1H), 8.71 (s, 1H), 8.18 (s, 1H), 7.79 (br s, 1H), 7.74 (s, 1H), 6.10 (s, 1H), 4.36 (q, J=7.1 Hz, 2H), 3.66-3.62 (m, 2H), 3.48-3.43 (m, 2H), 3.29 (s, 3H), 2.29 (s, 3H), 1.38 (t, J=7.1 Hz, 3H).

Step B: 1-(5-Acetylamino-6-chloro-1H-benzoimidazol-2-yl)-1H-pyrazole-4-carboxylic acid. The titled compound was prepared in a manner analogous to EXAMPLE 27, Steps F-G. MS (ESI/CI): mass calcd. for C₁₃H₁₀ClN₅O₃, 319.1; m/z found, 320.1 [M+H]⁺. ¹H NMR (400 MHz, DMSO-d₆): 9.54 (s, 1H), 8.89 (s, 1H), 8.94 (s, 1H), 8.30 (s, 1H), 7.82 (s, 1H), 7.69 (s, 1H), 2.11 (s, 3H).

Example 140: 1-(6-Chloro-5-propionylamino-1H-benzoimidazol-2-yl)-1H-pyrazole-4-carboxylic Acid

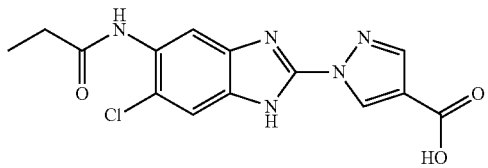 [SMILES: CCC(=O)Nc1cc2nc(-n3cc(C(=O)O)cn3)[nH]c2cc1Cl]

The titled compound was prepared) in a manner analogous to EXAMPLE 139, substituting propionyl chloride for acetyl chloride in Step A. MS (ESI/CI): mass calcd. for $C_{14}H_{12}ClN_5O_3$, 333.1; m/z found, 334.1 [M+H]$^+$. $^1$H NMR (400 MHz, DMSO-de, tautomeric broadening): 13.48 (br s, 1H), 12.96 (br s, 1H), 9.41 (s, 1H), 8.88 (s, 1H), 8.30 (s, 1H), 7.93-7.43 (m, 2H), 2.46-2.35 (m, 2H), 1.11 (t, J=7.6 Hz, 3H).

Example 141: 1-(5-Benzoylamino-6-chloro-1H-benzoimidazol-2-yl)-1H-pyrazole-4-carboxylic Acid

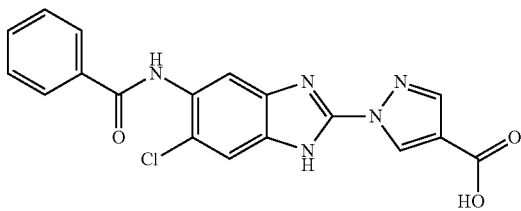 [SMILES: O=C(O)c1cnn(-c2nc3cc(NC(=O)c4ccccc4)c(Cl)cc3[nH]2)c1]

The titled compound was prepared in a manner analogous to EXAMPLE 139, substituting benzoyl chloride for acetyl chloride in Step A. MS (ESI/CI): mass calcd. for $C_{18}H_{12}ClN_5O_3$, 381.1; m/z found, 382.1 [M+H]$^+$. $^1$H NMR (400 MHz, DMSO-d$_6$): 12.96 (br s, 1H), 10.10 (s, 1H), 8.93 (s, 1H), 8.32 (s, 1H), 8.06-8.00 (m, 2H), 7.78-7.72 (m, 2H), 7.65-7.51 (m, 3H).

Example 142: 1-[6-Chloro-5-(2-morpholin-4-yl-acetylamino)-1H-benzoimidazol-2-yl]-1H-pyrazole-4-carboxylic Acid

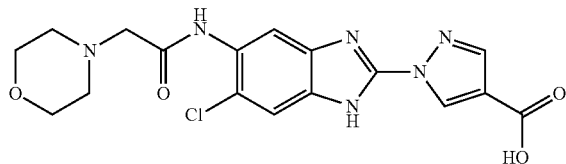 [SMILES: O=C(CN1CCOCC1)Nc1cc2nc(-n3cc(C(=O)O)cn3)[nH]c2cc1Cl]

Step A: 1-[5-(2-Bromo-acetylamino)-6-chloro-1-(2-methoxy-ethoxymethyl)-1H-benzoimidazol-2-yl]-1H-pyrazole-4-carboxylic acid ethyl ester. To a solution of diisopropylethylamine (0.86 mL, 4.95 mmol), 1-[5-amino-6-chloro-1-(2-methoxy-ethoxymethyl)-1H-benzoimidazol-2-yl]-1H-pyrazole-4-carboxylic acid ethyl ester (Intermediate from Example 41, product from Step A) (0.650 g, 1.65 mmol), and THF (8 mL) at 0° C., was added bromoacetyl bromide (0.244 mL, 2.81 mmol). The reaction mixture was allowed to slowly warm to 23° C. A second aliquot of bromoacetyl bromide (0.244 mL, 2.81 mmol) was added and the reaction mixture was kept at 23° C. for an additional 25 min. Water was added (20 mL) and the aqueous layer was extracted with EtOAc (2×75 mL). The combined organic layers were washed with brine (25 mL), dried, filtered, and concentrated under reduced pressure. The residue was purified (FCC) (10-45% EtOAc/hexanes) to yield the titled compound (0.361 g, 42% yield) after trituration with EtOAc. A 3:2 mixture of regioisomers was observed in the $^1$H NMR spectrum. MS (ESI/CI): mass calcd. for $C_{19}H_{21}BrClN_5O_5$, 513.0; m/z found, 514.0 [M+H]$^+$. $^1$H NMR (400 MHz, CDCl$_3$): 8.89 (s, 1H), 8.87 (br s, 1H), 8.71 (s, 1H), 8.18 (s, 1H), 7.70 (s, 1H), 6.13 (s, 2H), 4.36 (q, J=7.2 Hz, 2H), 4.13 (s, 2H), 3.68-3.62 (m, 2H), 3.49-3.43 (m, 2H), 3.31 (s, 3H), 1.38 (t, J=7.1 Hz, 3H).

Step B: 1-[6-Chloro-1-(2-methoxy-ethoxymethyl)-5-(2-morpholin-4-yl-acetylamino)-1H-benzoimidazol-2-yl]-1H-pyrazole-4-carboxylic acid ethyl ester. To a suspension of 1-[5-(2-bromo-acetylamino)-6-chloro-1-(2-methoxy-ethoxymethyl)-1H-benzoimidazol-2-yl]-1H-pyrazole-4-carboxylic acid ethyl ester (0.100 g, 0.194 mmol) and dichloromethane (1 mL) was added morpholine (51.0 µL, 0.580 mmol). The reaction mixture was stirred at 23° C. for 50 min. The reaction mixture was partitioned between EtOAc (15 mL) and water (10 mL), and the aqueous layer was further extracted with EtOAc (2×15 mL). The combined organic layers were washed with brine (15 mL), dried, filtered, and concentrated under reduced pressure, to yield the titled compound (97 mg, 96% yield) as a 3:1 mixture of regioisomers. MS (ESI/CI): mass calcd. for $C_{23}H_{29}ClN_6O_6$, 520.2; m/z found, 521.2 [M+H]$^+$. $^1$H NMR (400 MHz, CDCl$_3$): 10.00 (s, 1H), 8.89 (s, 1H), 8.85 (s, 1H), 8.18 (s, 1H), 7.68 (s, 1H), 6.12 (s, 2H), 4.36 (q, J=7.1 Hz, 2H), 3.87-3.80 (m, 4H), 3.67-3.60 (m, 2H), 3.48-3.42 (m, 2H), 3.32 (s, 2H), 3.24 (s, 3H), 2.73-2.67 (m, 4H), 1.38 (t, J=7.1 Hz, 3H).

Step C: 1-[6-Chloro-5-(2-morpholin-4-yl-acetylamino)-1H-benzoimidazol-2-yl]-1H-pyrazole-4-carboxylic acid. The titled compound was prepared in a manner analogous to EXAMPLE 27, Steps F-G. MS (ESI/CI): mass calcd. for $C_{17}H_{17}ClN_6O_4$, 404.1; m/z found, 405.1 [M+H]$^+$. $^1$H NMR (400 MHz, DMSO-d$_6$, tautomeric broadening): 13.46 (br s, 1H), 12.95 (br s, 1H), 10.04-9.86 (m, 1H), 8.88 (s, 1H), 8.46 (s, 1H), 8.29 (s, 1H), 7.96-7.43 (m, 1H), 3.73-3.65 (m, 4H), 3.21 (s, 2H), 2.64-2.56 (m, 4H).

Example 143: 1-[6-Chloro-5-(2-piperidin-1-yl-acetylamino)-1H-benzoimidazol-2-yl]-1H-pyrazole-4-carboxylic Acid

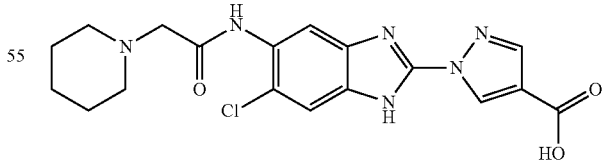

The titled compound was prepared in a manner analogous to EXAMPLE 142, substituting piperidine for morpholine in Step B, and was recovered as the hydrochloride salt. MS (ESI/CI): mass calcd. for $C_{18}H_{19}ClN_6O_3$, 402.1; m/z found, 403.1 [M+H]$^+$. $^1$H NMR (400 MHz, DMSO-d$_6$, tautomeric broadening): 13.68 (br s, 1H), 13.00 (br s, 1H), 10.47 (s, 1H), 10.02 (br s, 1H), 8.91 (s, 1H), 8.32 (s, 1H), 7.89-7.62

(m, 2H), 4.32-4.13 (m, 2H), 3.60-3.45 (m, 2H), 3.21-3.02 (m, 2H), 1.90-1.61 (m, 5H), 1.50-1.33 (m, 1H).

Example 144: 1-{6-Chloro-5-[2-(4-methyl-piperazin-1-yl)-acetylamino]-1H-benzoimidazol-2-yl}-1H-pyrazole-4-carboxylic Acid

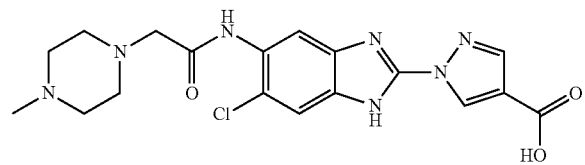 [SMILES: CN1CCN(CC(=O)Nc2cc3nc(-n4cc(C(=O)O)cn4)[nH]c3cc2Cl)CC1]

The titled compound was prepared in a manner analogous to EXAMPLE 142, substituting N-methylpiperazine for morpholine in Step B. The titled compound was recovered as the hydrochloride salt. MS (ESI/CI): mass calcd. for $C_{18}H_{20}ClN_7O_3$, 417.1; m/z found, 418.1 [M+H]$^+$. $^1$H NMR (400 MHz, DMSO-d$_6$, tautomeric broadening): 13.53 (br s, 1H), 12.98 (br s, 1H), 10.67 (br s, 1H), 9.77 (s, 1H), 8.89 (s, 1H), 8.33-8.23 (m, 2H), 7.77 (br s, 1H), 3.50-3.35 (m, 4H), 3.18-3.03 (m, 4H), 2.85-2.70 (m, 5H).

Example 145: 1-[6-Chloro-5-(4-methoxy-phenoxy)-1H-benzoimidazol-2-yl]-1H-pyrazole-4-carboxylic Acid

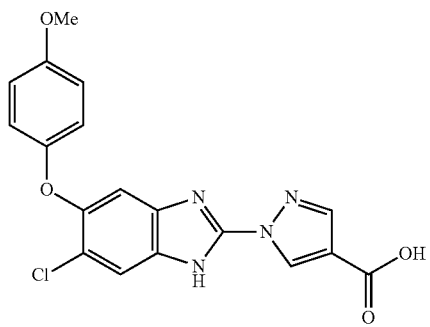 [SMILES: COc1ccc(Oc2cc3nc(-n4cc(C(=O)O)cn4)[nH]c3cc2Cl)cc1]

The titled compound was prepared in a manner analogous to EXAMPLE 50, substituting 4-methoxy-phenol for 3,4-dichloro-phenol and 4,5-dichloro-2-nitro-phenylamine for 5-chloro-2-nitro-4-trifluoromethyl-phenylamine in Step A. MS (ESI/CI): mass calcd. for $C_{18}H_{13}ClN_4O_4$, 384.1; m/z found, 385.0 [M+H]$^+$. $^1$H NMR (500 MHz, DMSO-d$_6$): 13.23 (s, 2H), 8.86 (d, J=0.5 Hz, 1H), 8.28 (d, J=0.5 Hz, 1H), 7.75 (s, 1H), 7.13 (s, 1H), 6.95 (s, 4H), 3.75 (s, 3H).

Example 146: 1-[6-Chloro-5-(4-chloro-2-fluoro-phenoxy)-1H-benzoimidazol-2-yl]-1H-pyrazole-4-carboxylic Acid

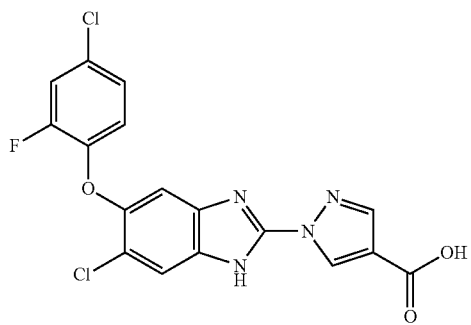 [SMILES: O=C(O)c1cnn(-c2nc3cc(Oc4ccc(Cl)cc4F)c(Cl)cc3[nH]2)c1]

The titled compound was prepared in a manner analogous to EXAMPLE 50, substituting 4-chloro-2-fluoro-phenol for 3,4-dichloro-phenol and 4,5-dichloro-2-nitro-phenylamine for 5-chloro-2-nitro-4-trifluoromethyl-phenylamine in Step A. MS (ESI/CI): mass calcd. for $C_{17}H_9Cl_2FN_4O_3$, 406.0; m/z found, 407.0 [M+H]$^+$. $^1$H NMR (500 MHz, DMSO-d$_6$): 13.33 (s, 1H), 8.87 (s, 1H), 8.29 (s, 1H), 7.79 (s, 1H), 7.65 (dd, J=10.9 Hz, 2.5 Hz, 1H), 7.36 (s, 1H), 7.23 (dd, J=8.8 Hz, 1.6 Hz, 1H), 6.91 (t, J=8.9 Hz, 1H).

Example 147: 1-[6-Chloro-5-(4-trifluoromethoxy-phenoxy)-1H-benzoimidazol-2-yl]-1H-pyrazole-4-carboxylic Acid

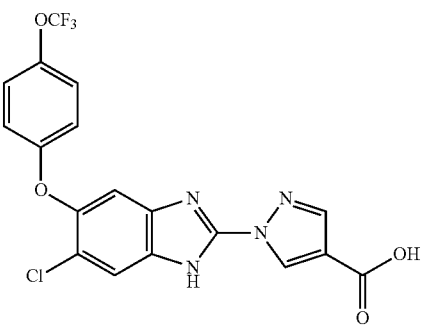 [SMILES: O=C(O)c1cnn(-c2nc3cc(Oc4ccc(OC(F)(F)F)cc4)c(Cl)cc3[nH]2)c1]

The titled compound was prepared in a manner analogous to EXAMPLE 50, substituting 4-trifluoromethoxy-phenol for 3,4-dichloro-phenol and 4,5-dichloro-2-nitro-phenylamine for 5-chloro-2-nitro-4-trifluoromethyl-phenylamine in Step A. MS (ESI/CI): mass calcd. for $C_{18}H_{10}ClF_3N_4O_4$, 438.0; m/z found, 439.0 [M+H]$^+$. $^1$H NMR (mixture of tautomers, 500 MHz, DMSO-d$_6$): 13.64 (s, 0.5H), 13.58 (s, 0.5H), 12.97 (s, 1H), 8.89 (s, 1H), 8.31 (s, 1H), 7.92 (s, 0.5H), 7.67 (s, 0.5H), 7.59 (s, 0.5H), 7.37 (d, J=7.6, 2H), 7.28 (s, 0.5H), 7.03 (s, 2H).

Example 148: 1-[6-Chloro-5-(3-chloro-4-fluoro-phenoxy)-1H-benzoimidazol-2-yl]-1H-pyrazole-4-carboxylic Acid

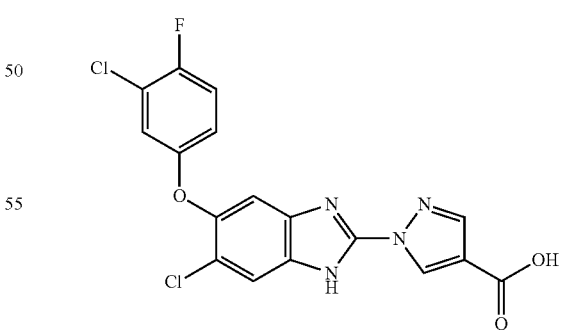

The titled compound was prepared in a manner analogous to EXAMPLE 50, substituting 3-chloro-4-fluoro-phenol for 3,4-dichloro-phenol and 4,5-dichloro-2-nitro-phenylamine for 5-chloro-2-nitro-4-trifluoromethyl-phenylamine in Step A. MS (ESI/CI): mass calcd. for $C_{17}H_9Cl_2FN_4O_3$, 406.0; m/z found, 407.0 [M+H]$^+$. $^1$H NMR (500 MHz, DMSO-d$_6$):

8.88 (s, 1H), 8.31 (d, J=0.4 Hz, 1H), 7.79 (s, 1H), 7.41 (t, J=9.0 Hz, 2H), 7.19 (d, J=2.8 Hz, 1H), 6.94 (d, J=9.0 Hz, 1H).

Example 149: 1-(5-Ethylsulfanyl-6-trifluoromethyl-1H-benzoimidazol-2-yl)-1H-pyrazole-4-carboxylic Acid

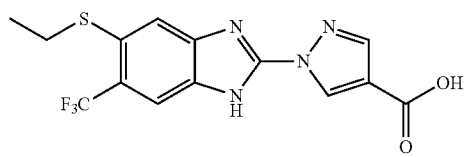 [SMILES: CCSc1cc2nc(-n3cc(C(=O)O)cn3)[nH]c2cc1C(F)(F)F]

Step A: 4-chloro-5-ethylsulfanyl-2-nitro-phenylamine. To a solution of 5-chloro-2-nitro-4-trifluoromethyl-phenylamine (2.23 g, 9.25 mmol) and DMF (46 mL) was added sodium thioethoxide (2.16 g, 23.1 mmol). The reaction mixture was heated at 100° C. for 18 h, cooled, and poured into ice/brine (350 mL). The resulting precipitate was collected to yield the titled compound (2.10 g, 85% yield). This compound did not yield MS data. $^1$H NMR (400 MHz, CDCl$_3$): 8.41 (s, 1H), 6.59 (s, 1H), 6.38 (s, 3H), 3.02 (q, J=7.4 Hz, 2H), 1.43 (t, J=7.4 Hz, 3H).

Step B: 1-(5-Ethylsulfanyl-6-trifluoromethyl-1H-benzoimidazol-2-yl)-1H-pyrazole-4-carboxylic acid. The titled compound was prepared in a manner analogous to EXAMPLE 27. MS (ESI/CI): mass calcd. for C$_{14}$H$_{11}$F$_3$N$_4$O$_2$S, 356.1; m/z found, 357.0 [M+H]$^+$. $^1$H NMR (400 MHz, DMSO-d$_6$): 13.02 (s, 1H), 8.92 (d, J=0.6 Hz, 1H), 8.34 (d, J=0.6 Hz, 1H), 7.91 (s, 1H), 7.79 (s, 1H), 3.06 (q, J=7.3 Hz, 2H), 1.23 (t, J=7.3 Hz, 3H).

Example 150: 1-(5-Ethylsulfanyl-6-trifluoromethoxy-1H-benzoimidazol-2-yl)-1H-pyrazole-4-carboxylic Acid

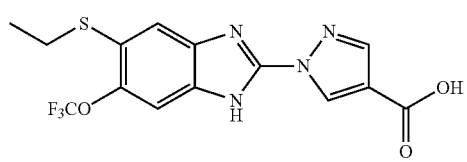 [SMILES: CCSc1cc2nc(-n3cc(C(=O)O)cn3)[nH]c2cc1OC(F)(F)F]

The titled compound was prepared in a manner analogous to EXAMPLE 149, substituting 5-chloro-2-nitro-4-trifluoromethoxy-phenylamine for 5-chloro-2-nitro-4-trifluoromethyl-phenylamine in Step A. MS (ESI/CI): mass calcd. for C$_{14}$H$_{11}$F$_3$N$_4$O$_3$S, 372.1; m/z found, 373.0 [M+H]$^+$. $^1$H NMR (400 MHz, DMSO-d$_6$, tautomeric broadening): 13.60 (s, 1H), 12.99 (s, 1H), 8.88 (d, J=0.6 Hz, 1H), 8.32 (d, J=0.6 Hz, 1H), 7.83-7.36 (m, 2H), 3.02 (q, J=7.3 Hz, 2H), 1.25 (t, J=7.3 Hz, 3H).

Example 151: 1-(5-Ethylsulfanyl-6-fluoro-1H-benzoimidazol-2-yl)-1H-pyrazole-4-carboxylic Acid

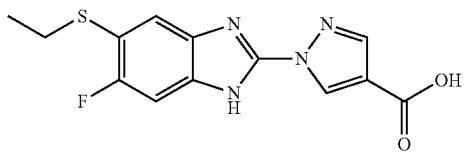 [SMILES: CCSc1cc2nc(-n3cc(C(=O)O)cn3)[nH]c2cc1F]

The titled compound was prepared in a manner analogous to EXAMPLE 149, substituting 4,5-difluoro-2-nitro-phenylamine for 5-chloro-2-nitro-4-trifluoromethyl-phenylamine in Step A. MS (ESI/CI): mass calcd. for C$_{13}$H$_{11}$FN$_4$O$_2$S, 306.1; m/z found, 307.0 [M+H]$^+$. $^1$H NMR (400 MHz, DMSO-d$_6$): 13.46 (s, 1H), 12.97 (s, 1H), 8.87 (d, J=0.6 Hz, 1H), 8.30 (d, J=0.6 Hz, 1H), 7.58 (s, 1H), 7.44 (s, 1H), 2.95 (q, J=7.3 Hz, 2H), 1.21 (t, J=7.3 Hz, 3H).

Example 152: 1-(6-Fluoro-5-propylsulfanyl-1H-benzoimidazol-2-yl)-1H-pyrazole-4-carboxylic Acid

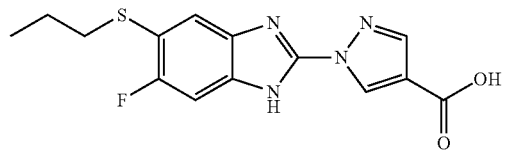 [SMILES: CCCSc1cc2nc(-n3cc(C(=O)O)cn3)[nH]c2cc1F]

Step A: 4-Fluoro-2-nitro-5-propylsulfanyl-phenylamine. To a mixture of 4,5-difluoro-2-nitro-phenylamine (1.51 g, 8.67 mmol), potassium carbonate (2.40 g, 17.3 mmol), and DMF (43 mL) was added 1-propanethiol (0.865 mL, 9.54 mmol). The reaction mixture was heated at 90° C. for 1.5 h, and allowed to cool to 23° C. The mixture was poured into ice/brine (400 mL) and the resulting precipitate was collected to yield the titled compound (1.97 g, 98% yield). MS (ESI/CI): mass calcd. for C$_9$H$_{11}$FN$_2$O$_2$S, 230.1; m/z found, 231.1 [M+H]$^+$. $^1$H NMR (400 MHz, CDCl$_3$): 7.78 (d, J=10.3 Hz, 1H), 6.52 (d, J=6.3 Hz, 1H), 6.04 (s, 2H), 2.93 (t, J=7.3 Hz, 2H), 1.84-1.70 (m, 2H), 1.09 (t, J=7.4 Hz, 3H).

Step B: 1-(6-Fluoro-5-propylsulfanyl-1H-benzoimidazol-2-yl)-1H-pyrazole-4-carboxylic acid. The titled compound was prepared in a manner analogous to EXAMPLE 27. MS (ESI/CI): mass calcd. for C$_{14}$H$_{13}$F$_3$N$_4$O$_2$S, 320.1; m/z found, 321.1 [M+H]$^+$. $^1$H NMR (400 MHz, DMSO-d$_6$, tautomeric broadening): 13.99-12.55 (m, 2H), 8.87 (d, J=0.6 Hz, 1H), 8.30 (d, J=0.6 Hz, 1H), 7.87-7.18 (m, 2H), 2.91 (t, J=7.1 Hz, 2H), 1.66-1.48 (m, 2H), 0.98 (t, J=7.3 Hz, 3H).

Example 153: 1-(6-Fluoro-5-isopropylsulfanyl-1H-benzoimidazol-2-yl)-1H-pyrazole-4-carboxylic Acid

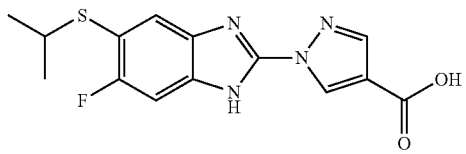 [SMILES: CC(C)Sc1cc2nc(-n3cc(C(=O)O)cn3)[nH]c2cc1F]

The titled compound was prepared in a manner analogous to EXAMPLE 152, substituting 2-propanethiol for 1-propanethiol in Step A. MS (ESI/CI): mass calcd. for $C_{14}H_{13}FN_4O_2S$, 320.1; m/z found, 321.1 [M+H]⁺. ¹H NMR (400 MHz, DMSO-d₆, tautomeric broadening): 13.88-13.19 (m, 1H), 12.97 (s, 1H), 8.88 (d, J=0.6 Hz, 1H), 8.30 (d, J=0.6 Hz, 1H), 7.87-7.22 (m, 2H), 3.46-3.33 (m, 1H), 1.21 (d, J=6.4 Hz, 6H).

Example 154: 1-(5-Ethylsulfonyl-6-trifluoromethyl-1H-benzoimidazol-2-yl)-1H-pyrazole-4-carboxylic Acid

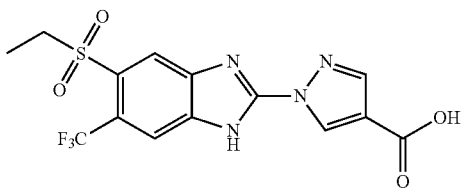 [SMILES: CCS(=O)(=O)c1cc2nc(-n3cc(C(=O)O)cn3)[nH]c2cc1C(F)(F)F]

The titled compound was prepared in a manner analogous to EXAMPLE 101, substituting 5-chloro-2-nitro-4-trifluoromethyl-phenylamine for 4,5-dichloro-2-nitro-phenylamine and sodium thioethoxide for sodium thioisopropoxide in Step A. MS (ESI/CI): mass calcd. for $C_{14}H_{11}F_3N_4O_4S$, 388.0; m/z found, 389.0 [M+H]⁺. ¹H NMR (400 MHz, DMSO-d₆, tautomeric broadening): 14.38 (s, 1H), 13.08 (s, 1H), 8.99 (s, 1H), 8.39 (d, J=0.6 Hz, 1H), 8.38-7.94 (m, 2H), 3.39 (q, J=7.4 Hz, 2H), 1.18 (t, J=7.4 Hz, 3H).

Example 155: 1-(5-Ethylsulfonyl-6-trifluoromethoxy-1H-benzoimidazol-2-yl)-1H-pyrazole-4-carboxylic Acid

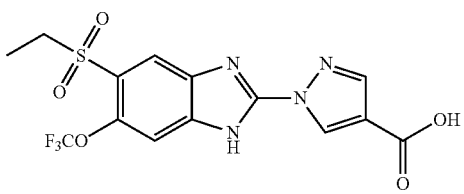 [SMILES: CCS(=O)(=O)c1cc2nc(-n3cc(C(=O)O)cn3)[nH]c2cc1OC(F)(F)F]

The titled compound was prepared in a manner analogous to EXAMPLE 101, substituting 5-chloro-2-nitro-4-trifluoromethoxy-phenylamine for 4,5-dichloro-2-nitro-phenylamine and sodium thioethoxide for sodium thioisopropoxide in Step A. MS (ESI/CI): mass calcd. for $C_{14}H_{11}F_3N_4O_5S$, 404.0; m/z found, 405.0 [M+H]⁺. ¹H NMR (400 MHz, DMSO-d₆): 14.19 (s, 1H), 13.07 (s, 1H), 8.95 (s, 1H), 8.38 (s, 1H), 8.09 (s, 1H), 7.80 (s, 1H), 3.40 (q, J=7.4 Hz, 2H), 1.13 (t, J=7.4 Hz, 3H).

Example 156: 1-(5-Ethylsulfonyl-6-fluoro-1H-benzoimidazol-2-yl)-1H-pyrazole-4-carboxylic Acid

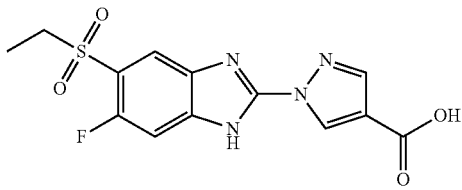 [SMILES: CCS(=O)(=O)c1cc2nc(-n3cc(C(=O)O)cn3)[nH]c2cc1F]

The titled compound was prepared in a manner analogous to EXAMPLE 101, substituting 4,5-difluoro-2-nitro-phenylamine for 4,5-dichloro-2-nitro-phenylamine and sodium thioethoxide for sodium thioisopropoxide in Step A. MS (ESI/CI): mass calcd. for $C_{13}H_{11}FN_4O_4S$, 338.1; m/z found, 339.0 [M+H]⁺. ¹H NMR (400 MHz, DMSO-d₆, tautomeric broadening): 14.04 (s, 1H), 13.04 (s, 1H), 8.95 (d, J=0.5 Hz, 1H), 8.36 (s, 1H), 8.09-7.35 (m, 2H), 3.42 (q, J=7.4 Hz, 2H), 1.15 (t, J=7.3 Hz, 3H).

Example 157: 1-(6-Fluoro-5-propylsulfonyl-1H-benzoimidazol-2-yl)-1H-pyrazole-4-carboxylic Acid

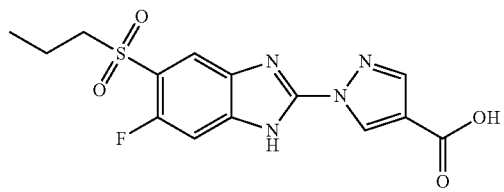 [SMILES: CCCS(=O)(=O)c1cc2nc(-n3cc(C(=O)O)cn3)[nH]c2cc1F]

The titled compound was prepared in a manner analogous to EXAMPLE 102, substituting 4,5-difluoro-2-nitro-phenylamine for 4,5-dichloro-2-nitro-phenylamine in Step A. MS (ESI/CI): mass calcd. for $C_{14}H_{13}FN_4O_4S$, 352.1; m/z found, 353.1 [M+H]⁺. ¹H NMR (400 MHz, DMSO-d₆, tautomeric broadening): 14.04 (s, 1H), 13.04 (s, 1H), 8.94 (d, J=0.6 Hz, 1H), 8.36 (s, 1H), 8.09-7.46 (m, 2H), 3.44-3.37 (m, 2H), 1.72-1.53 (m, 2H), 0.94 (t, J=7.4 Hz, 3H).

Example 158: 1-(6-Fluoro-5-isopropylsulfonyl-1H-benzoimidazol-2-yl)-1H-pyrazole-4-carboxylic Acid

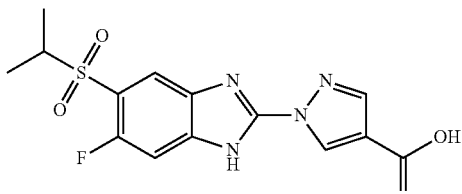

The titled compound was prepared in a manner analogous to EXAMPLE 102, substituting 4,5-difluoro-2-nitro-phenylamine for 4,5-dichloro-2-nitro-phenylamine and 2-propanethiol for 1-propanethiol in Step A. MS (ESI/CI): mass calcd. for $C_{14}H_{13}FN_4O_4S$, 352.1; m/z found, 353.1 [M+H]⁺. ¹H NMR (400 MHz, DMSO-d₆, tautomeric broadening):

14.03 (s, 1H), 13.04 (s, 1H), 8.94 (d, J=0.6 Hz, 1H), 8.36 (s, 1H), 8.08-7.45 (m, 2H), 3.61-3.46 (m, 1H), 1.22 (d, J=6.8 Hz, 6H).

Example 159: 1-(5-Phenylsulfanyl-6-trifluoromethyl-1H-benzoimidazol-2-yl)-1H-pyrazole-4-carboxylic Acid

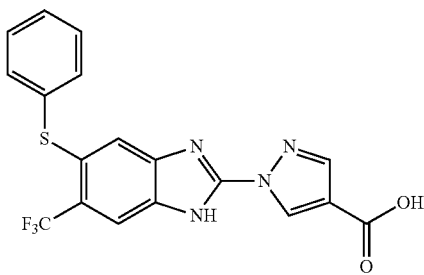 [SMILES: O=C(O)c1cnn(-c2nc3cc(Sc4ccccc4)c(C(F)(F)F)cc3[nH]2)c1]

The titled compound was prepared in a manner analogous to EXAMPLE 60, substituting benzenethiol for 3-methyl-benzenethiol and 5-chloro-2-nitro-4-trifluoromethyl-phenylamine for 4,5-dichloro-2-nitro-phenylamine in Step A. MS (ESI/CI): mass calcd. for $C_{18}H_{11}F_3N_4O_2S$, 404.1; m/z found, 405.0 [M+H]$^+$. $^1$H NMR (600 MHz, DMSO): 8.80 (d, J=0.5 Hz, 1H), 8.11 (s, 1H), 7.92 (s, 1H), 7.63 (s, 1H), 7.31-7.26 (m, 2H), 7.20-7.16 (m, 1H), 7.12-7.09 (m, 2H).

Example 160: 1-[5-(4-Methoxy-phenylsulfanyl)-6-trifluoromethyl-1H-benzoimidazol-2-yl]-1H-pyrazole-4-carboxylic Acid

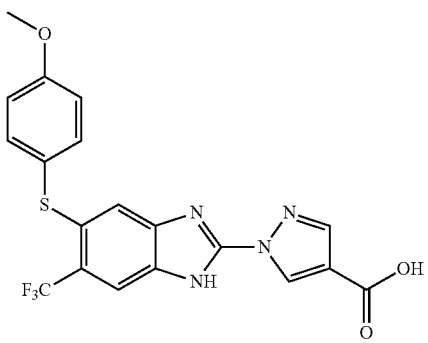 [SMILES: COc1ccc(Sc2cc3nc(-n4cc(C(=O)O)cn4)[nH]c3cc2C(F)(F)F)cc1]

The titled compound was prepared in a manner analogous to EXAMPLE 60, substituting 4-methoxy-benzenethiol for 3-methyl-benzenethiol and 5-chloro-2-nitro-4-trifluoromethyl-phenylamine for 4,5-dichloro-2-nitro-phenylamine in Step A. MS (ESI/CI): mass calcd. for $C_{19}H_{13}F_3N_4O_3S$, 434.1; m/z found, 435.1 [M+H]$^+$. $^1$H NMR (500 MHz, DMSO): 8.79 (s, 1H), 8.15 (s, 1H), 7.87 (s, 1H), 7.36 (s, 1H), 7.32 (d, J=8.6 Hz, 2H), 6.98 (d, J=8.7 Hz, 2H), 3.76 (s, 3H).

Example 161: 1-(5-Benzenesulfonyl-6-trifluoromethyl-1H-benzoimidazol-2-yl)-1H-pyrazole-4-carboxylic Acid

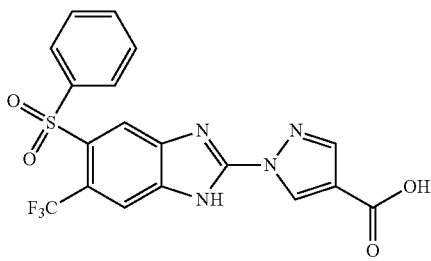 [SMILES: O=C(O)c1cnn(-c2nc3cc(S(=O)(=O)c4ccccc4)c(C(F)(F)F)cc3[nH]2)c1]

The titled compound was prepared in a manner analogous to EXAMPLE 85, from 1-[1-(2-methoxy-ethoxymethyl)-5-phenylsulfanyl-6-trifluoromethyl-1H-benzoimidazol-2-yl]-1H-pyrazole-4-carboxylic acid ethyl ester (Intermediate from Example 159). MS (ESI/CI): mass calcd. for $C_{18}H_{11}F_3N_4O_4S$, 436.0; m/z found, 437.0 [M+H]$^+$. $^1$H NMR (600 MHz, DMSO): 14.40 (s, 1H), 13.03 (s, 1H), 8.98 (s, 1H), 8.61 (s, 1H), 8.38 (s, 1H), 8.11 (s, 1H), 7.85 (d, J=7.7 Hz, 2H), 7.70-7.66 (m, 1H), 7.63-7.58 (m, 2H).

Example 162: 1-[5-(4-Methoxy-benzenesulfonyl)-6-trifluoromethyl-1H-benzoimidazol-2-yl]-1H-pyrazole-4-carboxylic Acid

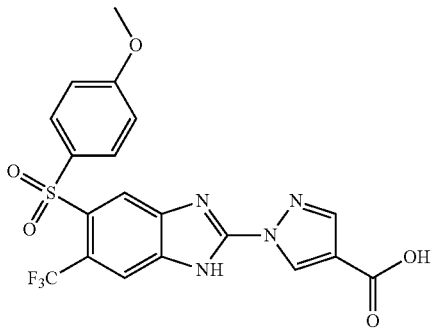

The titled compound was prepared in a manner analogous to EXAMPLE 85, from 1-[1-(2-methoxy-ethoxymethyl)-5-(4-methoxy-phenylsulfanyl)-6-trifluoromethyl-1H-benzoimidazol-2-yl]-1H-pyrazole-4-carboxylic acid ethyl ester (Intermediate from Example 160). MS (ESI/CI): mass calcd. for $C_{19}H_{13}F_3N_4O_5S$, 466.1; m/z found, 467.1 [M+H]$^+$. $^1$H NMR (600 MHz, DMSO): 14.35 (s, 1H), 13.05 (s, 1H), 8.97 (s, 1H), 8.55 (s, 1H), 8.38 (s, 1H), 8.11 (br s, 1H), 7.81 (d, J=7.9 Hz, 2H), 7.16-7.07 (m, 2H), 3.83 (s, 3H).

Example 163: 1-[6-Chloro-5-(4-chloro-benzylsulfanyl)-1H-benzoimidazol-2-yl]-1H-pyrazole-4-carboxylic Acid

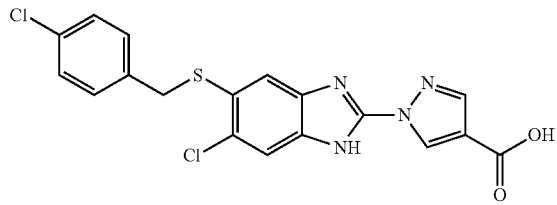 [SMILES: O=C(O)c1cnn(-c2nc3cc(SCc4ccc(Cl)cc4)c(Cl)cc3[nH]2)c1]

The titled compound was prepared in a manner analogous to EXAMPLE 66, Method B, substituting 1-bromomethyl-4-chloro-benzene for benzyl bromide in Step D. MS (ESI/CI): mass calcd. for $C_{18}H_{12}Cl_2N_4O_2S$, 418.0; m/z found, 419.0 [M+H]$^+$. $^1$H NMR (600 MHz, DMSO-d$_6$): 13.50 (s, 1H), 12.95 (s, 1H), 8.87 (s, 1H), 8.29 (s, 1H), 7.84-7.49 (m, 2H), 7.37 (q, J=8.6 Hz, 4H), 4.29 (s, 2H).

Example 164: 1-[6-Chloro-5-(3-chloro-benzylsulfanyl)-1H-benzoimidazol-2-yl]-1H-pyrazole-4-carboxylic Acid

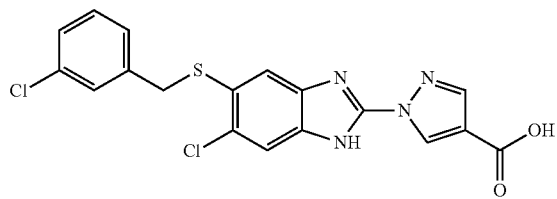 [SMILES: O=C(O)c1cnn(-c2nc3cc(SCc4cccc(Cl)c4)c(Cl)cc3[nH]2)c1]

The titled compound was prepared in a manner analogous to EXAMPLE 66, Method B, substituting 1-bromomethyl-3-chloro-benzene for benzyl bromide in Step D. MS (ESI/CI): mass calcd. for $C_{18}H_{12}Cl_2N_4O_2S$, 418.0; m/z found, 419.0 [M+H]$^+$. $^1$H NMR (600 MHz, DMSO-d$_6$): 8.86 (d, J=0.5, 1H), 8.28 (d, J=0.5 Hz, 1H), 7.67 (s, 1H), 7.53 (s, 1H), 7.44 (s, 1H), 7.34-7.29 (m, 3H), 4.30 (s, 2H).

Example 165: 1-(6-Chloro-5-cyclohexylmethylsulfanyl-1H-benzoimidazol-2-yl)-1H-pyrazole-4-carboxylic Acid

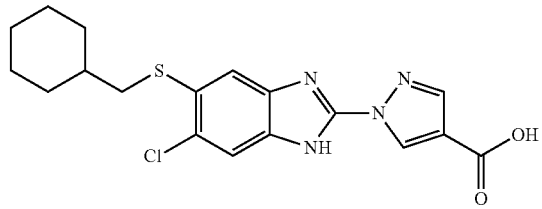 [SMILES: O=C(O)c1cnn(-c2nc3cc(SCC4CCCCC4)c(Cl)cc3[nH]2)c1]

The titled compound was prepared in a manner analogous to EXAMPLE 66, Method B, substituting bromomethyl-cyclohexane for benzyl bromide in Step D. MS (ESI/CI): mass calcd. for $C_{18}H_{19}ClN_4O_2S$, 390.1; m/z found, 391.1 [M+H]$^+$. $^1$H NMR (600 MHz, DMSO-d$_6$) 8.87 (d, J=0.5 Hz, 1H), 8.29 (d, J=0.5 Hz, 1H), 7.67 (s, 1H), 7.53 (s, 1H), 2.90 (d, J=6.7 Hz, 2H), 1.88 (d, J=12.3 Hz, 2H), 1.69 (dd, J=9.6 Hz, 3.1 Hz, 2H), 1.61 (d, J=10.9 Hz, 1H), 1.57-1.47 (m, 1H), 1.25-1.10 (m, 3H), 1.10-1.00 (m, 2H).

Example 166: 1-[6-Chloro-5-(2-morpholin-4-yl-ethylsulfanyl)-1H-benzoimidazol-2-yl]-1H-pyrazole-4-carboxylic Acid

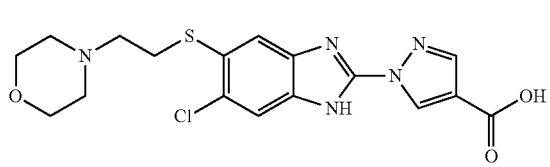 [SMILES: O=C(O)c1cnn(-c2nc3cc(SCCN4CCOCC4)c(Cl)cc3[nH]2)c1]

The titled compound was prepared in a manner analogous to EXAMPLE 66, Method B, substituting 4-(2-bromo-ethyl)-morpholine for benzyl bromide in Step D. MS (ESI/CI): mass calcd. for $C_{17}H_{18}ClN_5O_3S$, 407.1; m/z found, 408.1 [M+H]$^+$. $^1$H NMR (600 MHz, DMSO-d$_6$): 13.62 (s, 1H), 12.99 (s, 1H), 8.86 (s, 1H), 8.32 (s, 1H), 7.86 (s, 1H), 7.61 (s, 1H), 3.97 (s, 2H), 3.71 (s, 2H), 3.50 (s, 2H), 3.41 (s, 2H), 3.35 (s, 2H), 3.12 (s, 2H).

Example 167: 1-[6-Chloro-5-(3,4-dichloro-benzylsulfanyl)-1H-benzoimidazol-2-yl]-1H-pyrazole-4-carboxylic Acid

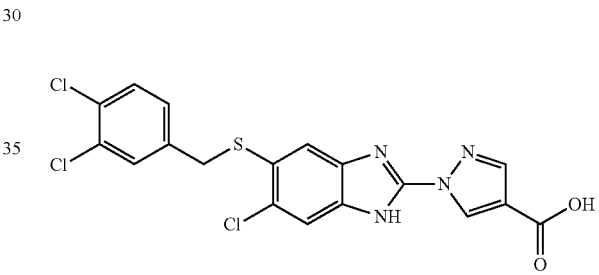

The titled compound was prepared in a manner analogous to EXAMPLE 66, Method B, substituting 4-bromomethyl-1,2-dichloro-benzene for benzyl bromide in Step D. MS (ESI/CI): mass calcd. for $C_{18}H_{11}Cl_3N_4O_2S$, 452.0; m/z found, 452.9 [M+H]$^+$. $^1$H NMR (600 MHz, DMSO-d$_6$): 13.52 (s, 1H), 12.95 (s, 1H), 8.87 (s, 1H), 8.29 (d, J=0.5 Hz, 1H), 7.86-7.28 (m, 5H), 4.30 (s, 2H).

Example 168: 1-[6-Chloro-5-(2,6-dichloro-benzylsulfanyl)-1H-benzoimidazol-2-yl]-1H-pyrazole-4-carboxylic Acid

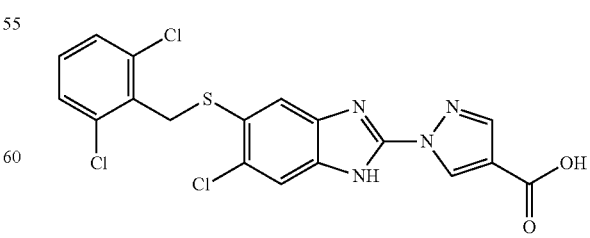

The titled compound was prepared in a manner analogous to EXAMPLE 66, Method B, substituting 2-bromomethyl-1,3-dichloro-benzene for benzyl bromide in Step D. MS (ESI/CI): mass calcd. for $C_{18}H_{11}Cl_3N_4O_2S$, 452.0; m/z found, 452.9 [M+H]⁺. ¹H NMR (600 MHz, DMSO-d₆): 8.89 (s, 1H), 8.31 (s, 1H), 7.72 (s, 1H), 7.57 (s, 1H), 7.45 (d, J=8.0 Hz, 2H), 7.33 (dd, J=8.4 Hz, 7.8 Hz, 1H), 4.38 (s, 2H).

Example 169: 1-[6-Chloro-5-(4-methyl-benzylsulfanyl)-1H-benzoimidazol-2-yl]-1H-pyrazole-4-carboxylic Acid

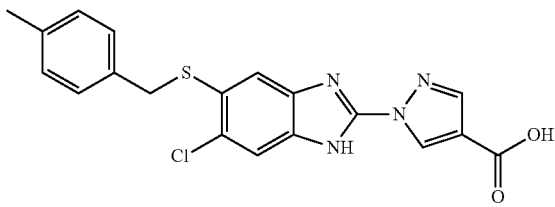 [SMILES: Cc1ccc(CSc2cc3nc(-n4cc(C(=O)O)cn4)[nH]c3cc2Cl)cc1]

The titled compound was prepared in a manner analogous to EXAMPLE 66, Method B, substituting 1-bromomethyl-4-methyl-benzene for benzyl bromide in Step D. MS (ESI/CI): mass calcd. for $C_{19}H_{15}ClN_4O_2S$, 398.1; m/z found, 399.1 [M+H]⁺. ¹H NMR (400 MHz, DMSO-d₆): 8.86 (d, J=0.5 Hz, 1H), 8.29 (d, J=0.5 Hz, 1H), 7.67 (s, 1H), 7.53 (s, 1H), 7.27 (d, J=8.0 Hz, 2H), 7.12 (d, J=7.8 Hz, 2H), 4.25 (s, 2H), 2.26 (s, 3H).

Example 170: 1-[6-Chloro-5-(4-trifluoromethyl-benzylsulfanyl)-1H-benzoimidazol-2-yl]-1H-pyrazole-4-carboxylic Acid

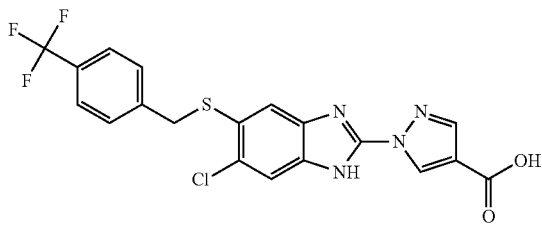 [SMILES: O=C(O)c1cnn(-c2nc3cc(SCc4ccc(C(F)(F)F)cc4)c(Cl)cc3[nH]2)c1]

The titled compound was prepared in a manner analogous to EXAMPLE 66, Method B, substituting 1-bromomethyl-4-trifluoromethyl-benzene for benzyl bromide in Step D. MS (ESI/CI): mass calcd. for $C_{19}H_{12}ClF_3N_4O_2S$, 452.0; m/z found, 453.1 [M+H]⁺. ¹H NMR (400 MHz, DMSO-d₆): 13.25 (s, 2H), 8.86 (d, J=0.4 Hz, 1H), 8.29 (d, J=0.5 Hz, 1H), 7.70-7.47 (m, 6H), 4.40 (s, 2H).

Example 171: 1-[5-(2,4-Bis-trifluoromethyl-benzylsulfanyl)-6-chloro-1H-benzoimidazol-2-yl]-1H-pyrazole-4-carboxylic Acid

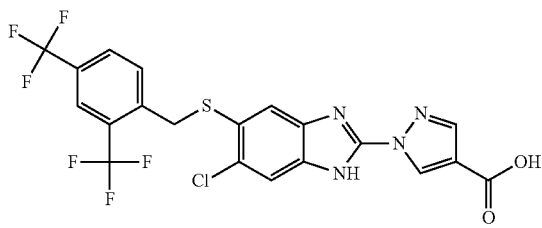 [SMILES: O=C(O)c1cnn(-c2nc3cc(SCc4ccc(C(F)(F)F)cc4C(F)(F)F)c(Cl)cc3[nH]2)c1]

The titled compound was prepared in a manner analogous to EXAMPLE 66, Method B, substituting 1-bromomethyl-2,4-bis-trifluoromethyl-benzene for benzyl bromide in Step D. MS (ESI/CI): mass calcd. for $C_{20}H_{11}ClF_6N_4O_2S$, 520.0; m/z found, 521.0 [M+H]⁺. ¹H NMR (400 MHz, DMSO-d₆): 13.56 (s, 2H), 12.99 (s, 1H), 8.88 (s, 1H), 8.31 (s, 1H), 8.05-7.99 (m, 2H), 7.90-7.33 (m, 5H), 4.45 (s, 2H).

Example 172: 1-[6-Chloro-5-(2'-cyano-biphenyl-4-ylmethylsulfanyl)-1H-benzoimidazol-2-yl]-1H-pyrazole-4-carboxylic Acid

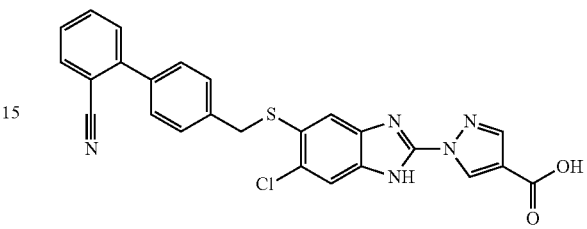

The titled compound was prepared in a manner analogous to EXAMPLE 66, Method B, substituting 4'-bromomethyl-biphenyl-2-carbonitrile for benzyl bromide in Step D. MS (ESI/CI): mass calcd. for $C_{25}H_{16}ClN_5O_2S$, 485.1; m/z found, 486.1 [M+H]⁺. ¹H NMR (400 MHz, DMSO-d₆): 13.50 (s, 1H), 12.98 (s, 1H), 8.88 (s, 1H), 8.30 (s, 1H), 7.95 (dd, J=7.7 Hz, 1.0 Hz, 1H), 7.78 (td, J=7.7 Hz, 1.3 Hz, 1H), 7.74-7.50 (m, 8H), 4.40 (s, 2H).

Example 173: 1-[6-Chloro-5-(4-chloro-phenylmethanesulfonyl)-1H-benzoimidazol-2-yl]-1H-pyrazole-4-carboxylic Acid

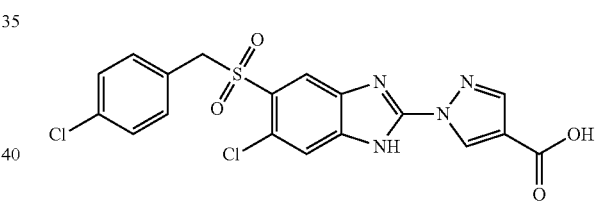

The titled compound was prepared in a manner analogous to EXAMPLE 85, from 1-[6-chloro-5-(4-chloro-benzylsulfanyl)-1-(2-methoxy-ethoxymethyl)-1H-benzoimidazol-2-yl]-1H-pyrazole-4-carboxylic acid ethyl ester (Intermediate from Example 163). MS (ESI/CI): mass calcd. for $C_{18}H_{12}Cl_2N_4O_4S$, 450.0; m/z found, 451.0 [M+H]⁺. ¹H NMR (600 MHz, DMSO-d₆): 14.01 (s, 1H), 13.02 (s, 1H), 8.96-8.90 (m, 1H), 8.34 (s, 1H), 7.87 (s, 2H), 7.35 (d, J=8.5 Hz, 2H), 7.25-7.20 (m, 2H), 4.90 (s, 2H).

Example 174: 1-[6-Chloro-5-(3-chloro-phenylmethanesulfonyl)-1H-benzoimidazol-2-yl]-1H-pyrazole-4-carboxylic Acid

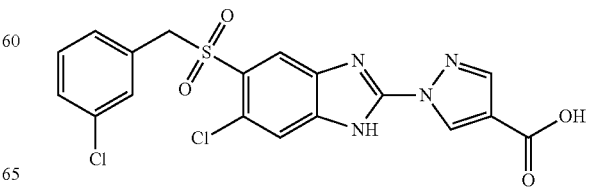

The titled compound was prepared in a manner analogous to EXAMPLE 85, from 1-[6-chloro-5-(3-chloro-benzylsulfanyl)-1-(2-methoxy-ethoxymethyl)-1H-benzoimidazol-2-yl]-1H-pyrazole-4-carboxylic acid ethyl ester (Intermediate from Example 164). MS (ESI/CI): mass calcd. for $C_{18}H_{12}Cl_2N_4O_4S$, 450.0; m/z found, 451.0 [M+H]$^+$. $^1$H NMR (600 MHz, DMSO-d$_6$): 14.03 (s, 1H), 13.03 (s, 1H), 8.93 (s, 1H), 8.33 (s, 1H), 7.96-7.86 (m, 2H), 7.37 (ddd, J=8.0 Hz, 2.1 Hz, 0.9 Hz, 1H), 7.34-7.28 (m, 2H), 7.14 (d, J=7.8 Hz, 1H), 4.91 (s, 2H).

Example 175: 1-(6-Chloro-5-cyclohexylmethanesulfonyl-1H-benzoimidazol-2-yl)-1H-pyrazole-4-carboxylic Acid

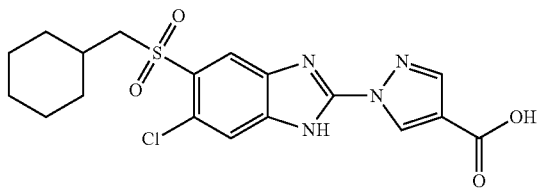 [SMILES: O=C(O)c1cnn(-c2nc3cc(S(=O)(=O)CC4CCCCC4)c(Cl)cc3[nH]2)c1]

The titled compound was prepared in a manner analogous to EXAMPLE 85, from 1-[6-chloro-5-cyclohexylmethylsulfanyl-1-(2-methoxy-ethoxymethyl)-1H-benzoimidazol-2-yl]-1H-pyrazole-4-carboxylic acid ethyl ester (Intermediate from Example 165). MS (ESI/CI): mass calcd. for $C_{18}H_{19}ClN_4O_4S$, 422.1; m/z found, 423.1 [M+H]$^+$. $^1$H NMR (600 MHz, DMSO-d$_6$): 14.06 (s, 1H), 13.02 (s, 1H), 8.95 (s, 1H), 8.35 (s, 1H), 8.19 (s, 1H), 7.90 (s, 1H), 3.44 (d, J=6.2 Hz, 2H), 1.89-1.81 (m, 1H), 1.75 (d, J=10.0 Hz, 2H), 1.60 (dd, J=9.3 Hz, 3.4 Hz, 2H), 1.53 (d, J=11.9 Hz, 1H), 1.22-1.05 (m, 5H).

Example 176: 1-[6-Chloro-5-(3,4-dichloro-phenylmethanesulfonyl)-1H-benzoimidazol-2-yl]-1H-pyrazole-4-carboxylic Acid

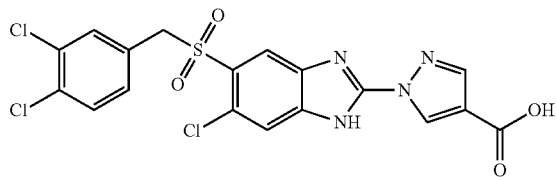 [SMILES: O=C(O)c1cnn(-c2nc3cc(S(=O)(=O)Cc4ccc(Cl)c(Cl)c4)c(Cl)cc3[nH]2)c1]

The titled compound was prepared in a manner analogous to EXAMPLE 85, from 1-[6-chloro-5-(3,4-dichloro-benzylsulfanyl)-1-(2-methoxy-ethoxymethyl)-1H-benzoimidazol-2-yl]-1H-pyrazole-4-carboxylic acid ethyl ester (Intermediate from Example 167). MS (ESI/CI): mass calcd. for $C_{18}H_{11}Cl_3N_4O_4S$, 484.0; m/z found, 484.9 [M+H]$^+$. $^1$H NMR (600 MHz, DMSO-d$_6$): 14.05 (s, 1H), 13.02 (s, 1H), 8.94-8.93 (m, 1H), 8.35 (s, 1H), 8.10-7.82 (m, 2H), 7.57 (d, J=8.3 Hz, 1H), 7.52 (d, J=2.0 Hz, 1H), 7.16 (dd, J=8.3 Hz, 2.0 Hz, 1H), 4.93 (s, 2H).

Example 177: 1-[6-Chloro-5-(2,6-dichloro-phenylmethanesulfonyl)-1H-benzoimidazol-2-yl]-1H-pyrazole-4-carboxylic Acid

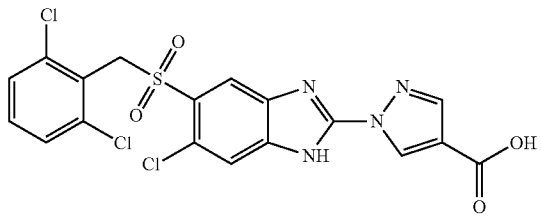 [SMILES: O=C(O)c1cnn(-c2nc3cc(S(=O)(=O)Cc4c(Cl)cccc4Cl)c(Cl)cc3[nH]2)c1]

The titled compound was prepared in a manner analogous to EXAMPLE 85, from 1-[6-chloro-5-(2,6-dichloro-benzylsulfanyl)-1-(2-methoxy-ethoxymethyl)-1H-benzoimidazol-2-yl]-1H-pyrazole-4-carboxylic acid ethyl ester (Intermediate from Example 168). MS (ESI/CI): mass calcd. for $C_{18}H_{11}Cl_3N_4O_4S$, 484.0; m/z found, 484.9 [M+H]$^+$. $^1$H NMR (600 MHz, DMSO-d$_6$): 8.95 (d, J=0.5 Hz, 1H), 8.35 (d, J=0.5 Hz, 1H), 8.03-7.85 (m, 2H), 7.50 (d, J=7.9 Hz, 2H), 7.41 (dd, J=8.7 Hz, 7.5 Hz, 1H), 5.16 (s, 2H).

Example 178: 1-(6-Chloro-5-p-tolylmethanesulfonyl-1H-benzoimidazol-2-yl)-1H-pyrazole-4-carboxylic Acid

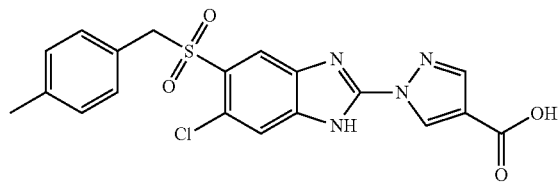 [SMILES: Cc1ccc(CS(=O)(=O)c2cc3nc(-n4cc(C(=O)O)cn4)[nH]c3cc2Cl)cc1]

The titled compound was prepared in a manner analogous to EXAMPLE 85, from 1-[6-chloro-1-(2-methoxy-ethoxymethyl)-5-(4-methyl-benzylsulfanyl)-1H-benzoimidazol-2-yl]-1H-pyrazole-4-carboxylic acid ethyl ester (Intermediate from Example 169). MS (ESI/CI): mass calcd. for $C_{19}H_{15}ClN_4O_4S$, 430.1; m/z found, 431.0 [M+H]$^+$. $^1$H NMR (500 MHz, DMSO-d$_6$): 13.98 (s, 1H), 13.02 (s, 1H), 8.93 (s, 1H), 8.34 (s, 1H), 8.03 (s, 1H), 7.85 (s, 1H), 7.07 (s, 4H), 4.82 (s, 2H), 2.22 (s, 3H).

Example 179: 1-[6-Chloro-5-(4-trifluoromethylphenylmethanesulfonyl)-1H-benzoimidazol-2-yl]-1H-pyrazole-4-carboxylic Acid

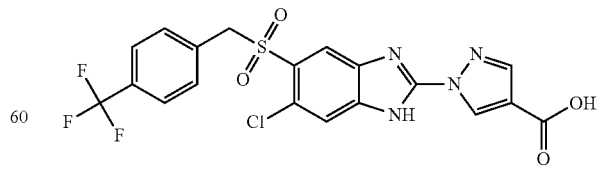

The titled compound was prepared in a manner analogous to EXAMPLE 85, from 1-[6-chloro-1-(2-methoxyethoxymethyl)-5-(4-trifluoromethyl-benzylsulfanyl)-1H-benzoimidazol-2-yl]-1H-pyrazole-4-carboxylic acid ethyl ester (Intermediate from Example 170). MS (ESI/CI): mass calcd. for $C_{19}H_{12}ClF_3N_4O_4S$, 484.0; m/z found, 485.0 $[M+H]^+$. $^1H$ NMR (500 MHz, DMSO-$d_6$): 14.05 (d, J=57.4 Hz, 1H), 13.03 (s, 1H), 8.93 (s, 1H), 8.35 (s, 1H), 8.10-7.74 (m, 3H), 7.69 (d, J=8.1 Hz, 2H), 7.46 (d, J=8.1 Hz, 2H), 5.02 (s, 2H).

Example 180: 1-[5-(2,4-Bis-trifluoromethyl-phenylmethanesulfonyl)-6-chloro-1H-benzoimidazol-2-yl]-1H-pyrazole-4-carboxylic Acid

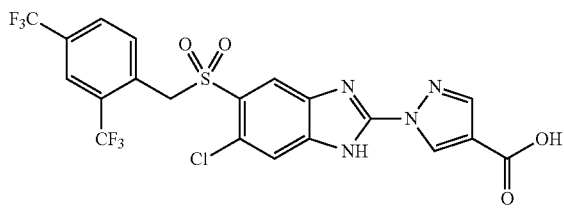 [SMILES: O=C(O)c1cnn(-c2nc3cc(S(=O)(=O)Cc4ccc(C(F)(F)F)cc4C(F)(F)F)c(Cl)cc3[nH]2)c1]

The titled compound was prepared in a manner analogous to EXAMPLE 85, from 1-[5-(2,4-bis-trifluoromethyl-benzylsulfanyl)-6-chloro-1-(2-methoxy-ethoxymethyl)-1H-benzoimidazol-2-yl]-1H-pyrazole-4-carboxylic acid ethyl ester (Intermediate from Example 171). MS (ESI/CI): mass calcd. for $C_{20}H_{11}ClF_6N_4O_4S$, 552.0; m/z found, 553.0 $[M+H]^+$. $^1H$ NMR (500 MHz, DMSO-$d_6$): 14.10 (s, 1H), 13.04 (s, 1H), 8.96 (s, 1H), 8.36 (s, 1H), 8.16 (d, J=8.2 Hz, 1H), 8.13-7.98 (m, 3H), 7.87 (d, J=8.0 Hz, 1H), 5.16 (s, 2H).

Example 181: 1-[6-Chloro-5-(2'-cyano-biphenyl-4-ylmethanesulfonyl)-1H-benzoimidazol-2-yl]-1H-pyrazole-4-carboxylic Acid

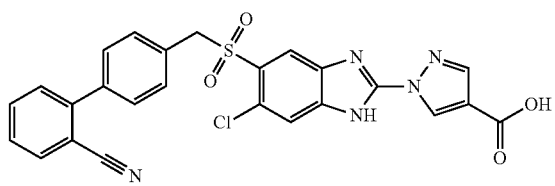 [SMILES: N#Cc1ccccc1-c1ccc(CS(=O)(=O)c2cc3nc(-n4cc(C(=O)O)cn4)[nH]c3cc2Cl)cc1]

The titled compound was prepared in a manner analogous to EXAMPLE 85, from 1-[6-chloro-5-(2'-cyano-biphenyl-4-ylmethylsulfanyl)-1-(2-methoxy-ethoxymethyl)-1H-benzoimidazol-2-yl]-1H-pyrazole-4-carboxylic acid ethyl ester (Intermediate from Example 172). MS (ESI/CI): mass calcd. for $C_{25}H_{16}ClN_5O_4S$, 517.1; m/z found, 518.0 $[M+H]^+$. $^1H$ NMR (500 MHz, DMSO-$d_6$): 13.97 (s, 1H), 13.03 (s, 1H), 8.93 (s, 1H), 8.34 (s, 1H), 7.96 (s, 1H), 7.94-7.83 (m, 2H), 7.76 (td, J=7.9 Hz, 1.3 Hz, 1H), 7.60-7.55 (m, 2H), 7.52 (d, J=8.3 Hz, 2H), 7.39 (d, J=8.3 Hz, 2H), 4.97 (s, 2H).

Example 182: 1-(1H-Imidazo[4,5-b]quinoxalin-2-yl)-1H-pyrazole-4-carboxylic Acid

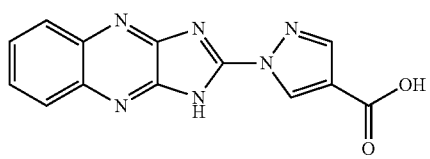 [SMILES: O=C(O)c1cnn(-c2nc3nc4ccccc4nc3[nH]2)c1]

Step A: 1-Carbamimidoyl-1H-pyrazole-4-carboxylic acid ethyl ester hydrochloride. To a solution of 1H-pyrazole-4-carboxylic acid ethyl ester (5.00 g, 35.7 mmol), cyanamide (1.50 g, 35.7 mmol), and dioxane (25 mL) was added a solution of 4M HCl in dioxane (9.80 mL, 39.3 mmol). The reaction mixture was heated to 100° C. for 3 h. The reaction was cooled to 23° C. and $Et_2O$ (20 mL) was added. The resulting white precipitate was filtered to yield the titled compound (7.26 g, 93%). $^1H$ NMR (400 MHz, DMSO-$d_6$): 9.65 (br m, 4H), 9.29 (s, 1H), 8.43 (s, 1H), 4.31 (q, J=7.1 Hz, 2H), 1.31 (t, J=7.1 Hz, 3H).

Step B: 1-(1H-Imidazo[4,5-b]quinoxalin-2-yl)-1H-pyrazole-4-carboxylic acid ethyl ester. A solution of 1-carbamimidoyl-1H-pyrazole-4-carboxylic acid ethyl ester hydrochloride (0.220 g, 1.00 mmol), 2,3-dichloro-quinoxaline (200 mg, 1.00 mmol), and $Cs_2CO_3$ (1.63 g, 5.00 mmol) in DMF (2 mL) was stirred for 4 h. $H_2O$ (3 mL) was added and the mixture was acidified to pH 2 with aqueous 1M HCl to form a white precipitate. The precipitate was filtered, triturated with anhydrous EtOH (2 mL), and filtered to yield the titled compound (0.130 g, 43%). MS (CI): mass calcd. for $C_{15}H_{12}N_6O_2$, 308.1; m/z found, 309.1 $[M+H]^+$. $^1H$ NMR (400 MHz, DMSO-$d_6$): 9.08 (s, 1H), 8.23 (s, 1H), 7.92 (d, J=8.1 Hz, 1H), 7.87 (d, J=8.2 Hz, 1H), 7.75 (t, J=7.1 Hz, 1H), 7.59 (t, J=7.5 Hz, 1H), 4.31 (q, J=7.1 Hz, 2H), 1.32 (t, J=7.1 Hz, 3H).

Step C: 1-(1H-Imidazo[4,5-b]quinoxalin-2-yl)-1H-pyrazole-4-carboxylic acid. A mixture of 1-(1H-Imidazo[4,5-b]quinoxalin-2-yl)-1H-pyrazole-4-carboxylic acid ethyl ester (0.110 g, 0.360 mmol), aqueous KOH (1 M, 3.0 mL) and THF (3.0 mL) was stirred for 4 h. The mixture was concentrated and the aqueous residue was acidified to pH 2 with 1 M aqueous HCl. The resulting precipitate was collected by filtration to yield the titled compound (89.0 mg, 89%). MS (ESI/CI): mass calcd. for $C_{13}H_8N_6O_2$, 280.2; m/z found, 281.1 $[M+H]^+$. $^1H$ NMR (500 MHz, DMSO-$d_6$): 13.32-12.37 (br m, 1H), 9.03 (s, 1H), 8.19 (s, 1H), 7.94 (d, J=8.2 Hz, 1H), 7.89 (d, J=8.3 Hz, 1H), 7.76 (t, J=7.6 Hz, 1H), 7.61 (t, J=7.0 Hz, 1H).

Example 183: 1-(6,7-Dichloro-1H-imidazo[4,5-b]quinoxalin-2-yl)-1H-pyrazole-4-carboxylic Acid

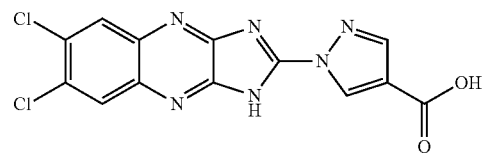 [SMILES: O=C(O)c1cnn(-c2nc3nc4cc(Cl)c(Cl)cc4nc3[nH]2)c1]

The titled compound was prepared in a manner analogous to EXAMPLE 182, substituting 2,3,6,7-tetrachloro-quinoxaline for 2,3-dichloro-quinoxaline in Step B. MS (CI): mass calcd. for $C_{13}H_6Cl_2N_6O_2$, 349.1; m/z found, 349.0 $[M]^+$. $^1H$ NMR (500 MHz, $CD_3OD$-$d_4$): 9.23 (s, 1H), 8.20 (s, 1H), 8.12 (s, 1H), 8.03 (s, 1H).

Example 184: 1-(1H-Imidazo[4,5-b]pyrazin-2-yl)-1H-pyrazole-4-carboxylic Acid

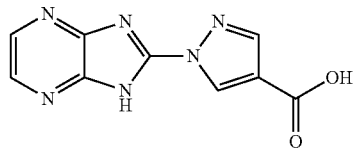 [SMILES: O=C(O)c1cnn(-c2nc3nccnc3[nH]2)c1]

The titled compound was prepared in a manner analogous to EXAMPLE 182, substituting 2,3-dichloro-pyrazine for 2,3-dichloro-quinoxaline in Step B. MS (ESI): mass calcd. for $C_9H_6N_6O_2$, 230.2; m/z found, 229.2 [M–H]$^-$. $^1$H NMR (500 MHz, DMSO-d$_6$): 13.21-12.59 (br m, 1H), 8.93 (s, 1H), 8.41 (s, 1H), 8.25 (s, 1H), 8.21 (s, 1H).

Example 185: 1-(6-Chloro-9H-purin-8-yl)-1H-pyrazole-4-carboxylic Acid

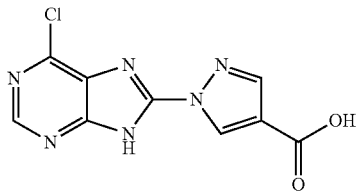

The titled compound was prepared in a manner analogous to EXAMPLE 182, substituting 4,5,6-trichloro-pyrimidine for 2,3-dichloro-quinoxaline in Step B. MS (ESI/CI): mass calcd. for $C_9H_5ClN_6O_2$, 264.6; m/z found, 265.0 [M+H]$^+$. $^1$H NMR (500 MHz, DMSO-d$_6$): 8.76 (s, 1H), 8.51 (s, 1H), 8.19 (s, 1H).

Example 186: 1-(6-Chloro-5-phenylsulfamoyl-1H-benzoimidazol-2-yl)-1H-pyrazole-4-carboxylic Acid

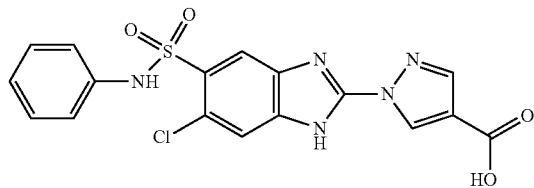 [SMILES: O=C(O)c1cnn(-c2nc3cc(S(=O)(=O)Nc4ccccc4)c(Cl)cc3[nH]2)c1]

Step A: 1-[6-Chloro-5-chlorosulfonyl-1-(2-methoxy-ethoxymethyl)-1H-benzoimidazol-2-yl]-1H-pyrazole-4-carboxylic acid ethyl ester. N-chlorosuccinimide (97.7 mg, 0.732 mmol) was added to a suspension of disulfide (Example 66, Method B, Step C, large scale synthesis by-product) (0.100 g, 0.122 mmol) in aqueous 2M HCl (0.15 mL, 0.305 mmol) and acetonitrile (0.75 mL) at 0° C. The reaction mixture was stirred for 75 min. At this point it was diluted with EtOAc (20 mL), washed with brine (10 mL), dried, filtered, and concentrated. The residue was purified via FCC (5-40% EtOAc/hexanes) to yield the titled compound (77.0 mg, 66% yield) as a 1:1 mixture of regioisomers. MS (ESI/CI): mass calcd. for $C_{17}H_{18}Cl_2N_4O_6S$, 476.0; m/z found, 477.0 [M+H]$^+$. $^1$H NMR (400 MHz, CDCl$_3$): 8.96 (d, J=0.6 Hz, 1H), 8.92 (d, J=0.6 Hz, 1H), 8.54 (s, 1H), 8.50 (s, 1H), 8.23 (d, J=0.5 Hz, 1H), 8.22 (d, J=0.5 Hz, 1H), 7.92 (s, 1H), 7.90 (s, 1H), 6.29 (s, 2H), 6.25 (s, 2H), 4.38 (q, J=7.1 Hz, 4H), 3.75-3.67 (m, 4H), 3.51-3.43 (m, 4H), 3.29 (s, 3H), 3.29 (s, 3H), 1.43-1.37 (m, 6H).

Step B: 1-[6-Chloro-1-(2-methoxy-ethoxymethyl)-5-phenylsulfamoyl-1H-benzoimidazol-2-yl]-1H-pyrazole-4-carboxylic acid ethyl ester. Aniline (15.8 µL, 0.173 mmol) was added to a solution of 1-[6-chloro-5-chlorosulfonyl-1-(2-methoxy-ethoxymethyl)-1H-benzoimidazol-2-yl]-1H-pyrazole-4-carboxylic acid ethyl ester (75.0 mg, 0.157 mmol) in pyridine (0.79 mL) and the reaction mixture was allowed to stir at 23° C. for 1.5 h. At this point it was partitioned between EtOAc (20 mL) and water (20 mL). The aqueous layer was further extracted with EtOAc (20 mL) and the combined organic layers were washed with brine (10 mL), dried, filtered, and concentrated. The residue was purified via FCC (5-80% EtOAc/hexanes) to yield the titled compound (36.0 mg, 43% yield). MS (ESI/CI): mass calcd. for $C_{23}H_{24}ClN_5O_8S$, 533.1; m/z found, 534.1 [M+H]$^+$.

Step C: 1-(6-Chloro-5-phenylsulfamoyl-1H-benzoimidazol-2-yl)-1H-pyrazole-4-carboxylic acid ethyl ester. Hydrochloric acid in dioxane (4M, 0.241 mL) was added to 1-[6-chloro-1-(2-methoxy-ethoxymethyl)-5-phenylsulfamoyl-1H-benzoimidazol-2-yl]-1H-pyrazole-4-carboxylic acid ethyl ester (35.0 mg, 65.5 µmol) in ethanol (0.50 mL) and allowed to stir at 23° C. for 2.5 h. The solvent was evaporated and the residue was purified via FCC (5-100% EtOAc/hexanes) to yield the titled compound (28.7 mg, 98% yield). MS (ESI/CI): mass calcd. for $C_{19}H_{16}ClN_5O_4S$, 445.1; m/z found, 446.0 [M+H]$^+$.

Step D: 1-(6-Chloro-5-phenylsulfamoyl-1H-benzoimidazol-2-yl)-1H-pyrazole-4-carboxylic acid. Lithium hydroxide monohydrate (7.90 mg, 0.188 mmol), 1-(6-chloro-5-phenylsulfamoyl-1H-benzoimidazol-2-yl)-1H-pyrazole-4-carboxylic acid ethyl ester (28.0 mg, 62.8 µmol), THF (0.24 mL), and water (79 µL) were combined, briefly sonicated, and left to stir at 23° C. for 18 h. Solvent was evaporated and 2 mL water was added. This solution was brought to pH 1 with aqueous 1M HCl and the resulting precipitate was collected and dried to yield the titled compound (20.6 mg, 75% yield). MS (ESI/CI): mass calcd. for $C_{17}H_{12}ClN_5O_4S$, 417.0; m/z found, 418.0 [M+H]$^+$. $^1$H NMR (400 MHz, DMSO-de, tautomeric broadening): 13.96 (s, 1H), 13.02 (s, 1H), 10.55 (s, 1H), 8.91 (s, 1H), 8.33 (s, 1H), 8.31-8.08 (m, 1H), 7.95-7.53 (m, 1H), 7.26-7.04 (m, 4H), 6.96 (t, J=7.2 Hz, 1H).

Biological Protocols:

As indicated herein (see table above), the biological activity of the exemplified compounds was determined according to the following protocols.

Expression and Purification of PHD2$_{181-417}$

The human PHD2 expression construct containing amino acids 181-417 of GenBank Accession ID NM_022051 was cloned into a pBAD vector (Invitrogen), incorporating both an N-terminal histidine tag and a Smt3-tag, both of which are cleaved by Ulp1. Protein production was achieved by expression in BL21 cells grown in Terrific Broth containing 100 µg/ml ampicillin. Cell cultures were inoculated at 37° C. and grown to an OD$_{600}$ of 0.8. Cultures were induced with 0.1% arabinose and grown overnight at 20° C. with continuous shaking at 225 rpm. Cells were then harvested by centrifugation and stored at −80° C. Cell pellets were suspended in Buffer A (50 mM Tris-HCl pH 7.2, 100 mM NaCl, 100 mM L-arginine, 1 mM TCEP, 0.05% (w/v) NP-40, 50 mM imidazole) followed by the addition of lysozyme and benzonase. Cells were lysed by sonication and the lysate was cleared by centrifugation (15,000 rpm, 90 min, 4° C.). The protein was purified by nickel affinity chromatography using a HisTrap Crude FF column (GE Healthcare). Samples were eluted in Buffer A with a 50-200 mM imidazole gradient. Cleavage of the Smt tag with Ulp1 protease was achieved via overnight incubation with dialyzing against Buffer A. The PHD2$_{181-417}$ sample was then passed over a second HisTrap Crude FF column (GE Healthcare) to remove uncleaved protein. The flow-through was then dialyzed into 50 mM MES pH 6.0, 1 mM TCEP, 5 mM NaCl for ion exchange chromatography on a HiTrap SP Cation Exchange column (GE Healthcare). The PHD2$_{181-417}$ protein was eluted with a 0-0.2 M NaCl gradient. Fractions were pooled for further purification by size exclusion chromatography over a Superdex 75 Size Exclusion Column (GE Healthcare). Final protein was concentrated to 4 mg/ml and dialyzed in 10 mM PIPES pH 7.0, 100 mM NaCl, 0.5 mM TCEP. The protein was determined to have a purity of >95% by gel electrophoresis.

Enzyme Activity Assay

The PHD2$_{181-417}$ polypeptide (3 μg) was pre-incubated for 30 minutes with test compound prior to assessing the enzymatic activity of the polypeptide. The PHD enzymatic assay was then performed by transferring the purified PHD2$_{181-417}$ polypeptide (3 μg) mixture with compound to 0.5 ml of reaction mixture containing the following: synthetic HIF-1α peptide comprising residues [KNPFSTGDT-DLDLEMLAPYIPMDDDFQLRSFDQLS] (10 μM, California Peptide Research Inc., Napa, Calif.), and [5-$^{14}$C]-2-oxoglutaric acid (50 mCi/mmol, Moravek Chemicals, Brea, Calif.) in reaction buffer (40 mM Tris-HCl, pH 7.5, 0.4 mg/ml catalase, 0.5 mM DTT, 1 mM ascorbate) for 10 minutes in the presence of compound. The reaction was stopped by addition of 50 μl of 70 mM H$_3$PO$_4$ and 50 μl of 500 mM NaH$_2$PO$_4$, pH 3.2. Detection of [$^{14}$C]-succinic acid was achieved by separating from [5-$^{14}$C]-2-oxoglutaric acid by incubating the reaction mixture with 100 μl of 0.16 M DNP prepared in 30% perchloric acid. Next, 50 μl of unlabeled 20 mM 2-oxoglutaric acid/20 mM succinic acid, serving as carrier for the radioactivity, was added to the mixture, and was allowed to proceed for 30 minutes at room temperature. The reaction was then incubated with 50 μl of 1 M 2-oxoglutaric acid for 30 additional minutes at room temperature to precipitate the excess DNP. The reaction was then centrifuged at 2800×g for 10 minutes at room temperature to separate [$^{14}$C]-succinic acid in the supernatant from the precipitated [$^{14}$C]-dinitrophenylhydrazone. Fractions of the supernatant (400 μl) were counted using a beta counter (Beckman Coulter, Fullerton, Calif.). Inhibition of PHD2$_{181-417}$ activity was measured as a decrease in [$^{14}$C]-succinic acid production. The IC$_{50}$ values were estimated by fitting the data to a three-parameter logistic function using GraphPad Prism, version 4.02 (Graph Pad Software, San Diego, Calif.). IC$_{50}$ values up to 10 μM were quantified otherwise were noted as >10 μM. All compounds were diluted at 10 mM in 100% DMSO (w/v) and tested from 10 μM to 3 nM at half-log serial dilutions, with a final concentration of 2% DMSO (w/v) in the assay.

Cellular Assay

Hep-3B cells (ATCC, Manassas, Va.) were plated in 96-well plates at 20,000 cells per well in 100 μl of DMEM containing 10% fetal bovine serum, 1% non-essential amino acids, 50 IU/mL of penicillin and 50 μg/mL of streptomycin (all cell culture reagents from Invitrogen, Carlsbad, Calif.). Twenty-four hours after plating, compounds were added and incubated for an additional 24 hours. All test compounds were dissolved at 10 mM in 100% DMSO (w/v) and were tested under saturating conditions with final compound concentrations at 100 μM in 1% DMSO (w/v). Fifty microliters of the supernatant was then transferred to a human Hypoxia assay kit (Meso-Scale Discovery, Gaithersburg, Md.). Erythropoietin in the supernatant was detected according to the manufacturer's instructions as follows. EPO detection plates were blocked with 3% BSA in PBS overnight and 50 μl of the supernatant was incubated at room temperature in an orbital shaker for 2 h. Twenty-five microliters of 0.5 μg/ml anti-EPO detection antibody was added for 2 hours at room temperature in an orbital shaker. After 3 washes in PBS, 150 μl of 1× read buffer is added and the plate is then read on the MSD SECTOR instrument. Data was then analyzed by determining the percent of EPO secretion in the presence of 10 μM or 100 μM compound relative to an assay control compound, 7-[(4-Chloro-phenyl)-(5-methyl-isoxazol-3-ylamino)-methyl]-quinolin-8-ol. Data is reported as a percentage of EPO secretion of the control compound and shows to be reproducible within 10%.

While the invention has been illustrated by reference to exemplary and preferred embodiments, it will be understood that the invention is intended not to be limited to the foregoing detailed description.

What is claimed is:

1. A compound having PHD inhibitor activity of the formula (I):

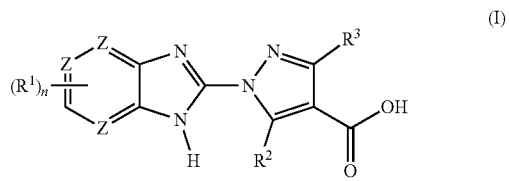

wherein:

n is 2-4;

each R$^1$ is independently selected from H, halo, —C$_{1-4}$perhaloalkyl, trifluoroC$_{1-4}$-alkoxy, and —SC$_{1-4}$alkyl;

R$^2$ and R$^3$ are both H, —CF$_3$, or C$_{1-3}$alkyl;

each Z is C; or an enantiomer, a diastereomer, a racemate, or a pharmaceutically acceptable salt thereof.

2. The compound according to claim 1, wherein R$^2$ and R$^3$ are both H.

3. The compound according to claim 1, wherein R$^2$ and R$^3$ are both —CF$_3$.

4. The compound according to claim 1, wherein R$^2$ and R$^3$ are both C$_{1-3}$alkyl.

* * * * *